(12) United States Patent
Coleman

(10) Patent No.: US 7,273,751 B2
(45) Date of Patent: Sep. 25, 2007

(54) VASCULAR ENDOTHELIAL GROWTH FACTOR-2

(75) Inventor: Timothy A. Coleman, Gaithersburg, MD (US)

(73) Assignee: Human Genome Science, Inc., Rockville, MD (US)

(*) Notice: Subject to any disclaimer, the term of this patent is extended or adjusted under 35 U.S.C. 154(b) by 483 days.

(21) Appl. No.: 09/921,143

(22) Filed: Aug. 3, 2001

(65) Prior Publication Data

US 2003/0215921 A1 Nov. 20, 2003

Related U.S. Application Data

(60) Provisional application No. 60/223,276, filed on Aug. 4, 2000.

(51) Int. Cl.
*C12N 15/63* (2006.01)

(52) U.S. Cl. .............. 435/320.1; 435/325; 435/455

(58) Field of Classification Search .............. 536/23.1; 435/320.1, 325, 455
See application file for complete search history.

(56) References Cited

U.S. PATENT DOCUMENTS

| | | |
|---|---|---|
| 5,073,492 A | 12/1991 | Chen et al. |
| 5,194,596 A | 3/1993 | Tischer et al. |
| 5,219,739 A | 6/1993 | Tischer et al. |
| 5,234,908 A | 8/1993 | Szabo et al. |
| 5,240,848 A | 8/1993 | Keck et al. |
| 5,283,354 A | 2/1994 | Lemischka |
| 5,326,695 A | 7/1994 | Andersson et al. |
| 5,607,918 A | 3/1997 | Eriksson et al. |
| 5,633,147 A | 5/1997 | Meissner et al. |
| 5,652,225 A | 7/1997 | Isner |
| 5,661,133 A | 8/1997 | Leiden and Barr |
| 5,693,622 A | 12/1997 | Wolff et al. |
| 5,776,755 A | 7/1998 | Alitalo et al. |
| 5,792,453 A | 8/1998 | Hammond et al. |
| 5,840,693 A | 11/1998 | Eriksson et al. |
| 5,861,301 A | 1/1999 | Terman et al. |
| 5,932,540 A | 8/1999 | Hu et al. |
| 5,935,820 A | 8/1999 | Hu et al. |
| 6,040,157 A | 3/2000 | Hu et al. |
| 6,121,246 A | 9/2000 | Isner |
| 6,130,071 A | 10/2000 | Alitalo et al. |
| 6,221,839 B1 | 4/2001 | Alitalo et al. |
| 6,245,530 B1 | 6/2001 | Alitalo et al. |
| 6,297,238 B1 | 10/2001 | Doyle et al. |
| 6,361,946 B1 | 3/2002 | Alitalo and Joukov |
| 6,403,088 B1 | 6/2002 | Alitalo et al. |
| 6,451,764 B1 | 9/2002 | Lee and Wood |
| 6,515,105 B1 | 2/2003 | Alitalo et al. |
| 6,645,933 B1 | 11/2003 | Alitalo and Joukov |
| 6,660,744 B1 | 12/2003 | Hirst et al. |
| 6,713,474 B2 | 3/2004 | Hirst et al. |
| 6,764,820 B2 | 7/2004 | Ferrell et al. |
| 6,824,777 B1 | 11/2004 | Alitalo et al. |
| 2002/0013261 A1 | 1/2002 | Pawliuk et al. |
| 2002/0019350 A1 | 2/2002 | Levine et al. |
| 2002/0034501 A1 | 3/2002 | Pawliuk et al. |
| 2002/0086004 A1 | 7/2002 | Adnot et al. |
| 2002/0111362 A1 | 8/2002 | Rubinfeld |
| 2002/0151489 A1 | 10/2002 | Gravereaux et al. |
| 2002/0155421 A1 | 10/2002 | Kearney et al. |
| 2002/0156081 A1 | 10/2002 | Hirst et al. |
| 2003/0103943 A1 | 6/2003 | Rosengart et al. |
| 2003/0125523 A1 | 7/2003 | Alitalo et al. |
| 2003/0153752 A1 | 8/2003 | Hirst et al. |
| 2003/0165464 A1 | 9/2003 | Enholm et al. |
| 2003/0180286 A1 | 9/2003 | Carmeliet et al. |
| 2003/0187001 A1 | 10/2003 | Calderwood et al. |
| 2003/0211988 A1 | 11/2003 | Epstein |
| 2004/0002140 A1 | 1/2004 | Gilbert et al. |
| 2004/0006083 A1 | 1/2004 | Hirst et al. |
| 2004/0031067 A1 | 2/2004 | Herlyn et al. |
| 2004/0248781 A1 | 12/2004 | Kerbel |
| 2005/0118180 A1 | 6/2005 | Rubinfeld |
| 2006/0014252 A1 | 1/2006 | Lyman |

FOREIGN PATENT DOCUMENTS

AU  710696  9/1999

(Continued)

OTHER PUBLICATIONS

Vale, P et al. Percutaneous electromechanical mapping demonstrates efficacy of pVGI.1(VEGF2) in an animal model of chronic myocardial ischemia. Circulation, Nov. 2, 1999. vol. 100, No. 18 suppl., pp. I.22.*

(Continued)

*Primary Examiner*—Celine Qian
(74) *Attorney, Agent, or Firm*—Sterne, Kessler, Goldstein & Fox P.L.L.C.

(57) ABSTRACT

Disclosed are human VEGF-2 polypeptides, biologically active, diagnostically or therapeutically useful fragments, analogs, or derivatives thereof, and DNA(RNA) encoding such VEGF-2 polypeptides. Also provided are procedures for producing such polypeptides by recombinant techniques and antibodies and antagonists against such polypeptides. Such polypeptides and polynucleotides may be used therapeutically for stimulating wound healing and for vascular tissue repair. Also provided are methods of using the antibodies and antagonists to inhibit tumor angiogenesis and thus tumor growth, inflammation, diabetic retinopathy, rheumatoid arthritis, and psoriasis.

6 Claims, 68 Drawing Sheets

FOREIGN PATENT DOCUMENTS

| | | |
|---|---|---|
| EP | 0 186 084 A2 | 7/1986 |
| EP | 0 399 816 A1 | 11/1990 |
| EP | 0 476983 | 3/1992 |
| EP | 0-476983 | 3/1992 |
| EP | 0476983 A1 | 3/1992 |
| EP | 0-506477 | 9/1992 |
| JP | 64-38100 A | 2/1989 |
| JP | 2-117698 A | 5/1990 |
| WO | WO-91/02058 | 2/1991 |
| WO | WO92/14748 | 9/1992 |
| WO | 94/11506 A1 | 5/1994 |
| WO | WO95/19985 | 7/1995 |
| WO | WO95/24414 | 9/1995 |
| WO | WO-95/24473 | 9/1995 |
| WO | WO95/24473 | 12/1995 |
| WO | WO96/05856 | 2/1996 |
| WO | WO 96/39515 | 12/1996 |
| WO | WO96/39515 | 12/1996 |
| WO | WO-97/00271 | 1/1997 |
| WO | WO97/05250 | 2/1997 |
| WO | WO97/09427 | 3/1997 |
| WO | 97/17442 A1 | 5/1997 |
| WO | WO-97/19694 | 6/1997 |
| WO | WO98/06844 | 2/1998 |
| WO | WO98/07832 | 2/1998 |
| WO | WO98/24811 | 6/1998 |
| WO | WO98/33917 | 6/1998 |
| WO | WO98/39035 | 9/1998 |
| WO | WO98/49300 | 11/1998 |
| WO | WO-98/55619 | 12/1998 |
| WO | WO98/56936 | 12/1998 |
| WO | WO-99/02545 | 1/1999 |
| WO | WO99/08522 | 2/1999 |
| WO | WO-99/20749 | 4/1999 |
| WO | WO99/21590 | 5/1999 |
| WO | WO99/46364 | 9/1999 |
| WO | 00/21560 A1 | 4/2000 |
| WO | 00/24412 A2 | 5/2000 |
| WO | 00/45835 A1 | 8/2000 |
| WO | 00/58511 A1 | 10/2000 |
| WO | 00/61186 A1 | 10/2000 |
| WO | 00/62798 A2 | 10/2000 |
| WO | WO-00/73430 | 12/2000 |
| WO | WO 00/75163 | 12/2000 |
| WO | 01/52904 A2 | 7/2001 |
| WO | WO-01/57226 | 8/2001 |
| WO | WO-01/58956 | 8/2001 |
| WO | 02/11769 A1 | 2/2002 |
| WO | 02/083704 A1 | 10/2002 |
| WO | 02/083849 A2 | 10/2002 |
| WO | 02/083850 A2 | 10/2002 |
| WO | 03/000009 A2 | 1/2003 |
| WO | 03/015755 A1 | 2/2003 |
| WO | 03/097660 A1 | 11/2003 |
| WO | WO-97/08320 | 3/2004 |
| ZA | 9-403464 | 1/1996 |

OTHER PUBLICATIONS

Verma et al. (1997, Nature, vol. 389, pp. 239-242).*
Anderson et al.(1998, Nature, vol. 392, pp. 25-30).*
Manniatis et al. Molecular Cloning: A Laboratory Manual. 1982. Cold Spring Harbor Laboratory. Chapter 8, pp. 248-251.*
International Search Report, Application No. PCT/US02/26246, mailed May 21, 2003.
Statutory Declaration of Kari Alitalo, executed on Aug. 14, 2002, and accompanying Exhibits KA-1 and KA-2.
Statutory Declaration of Peter Adrian Walton Rogers, executed on Aug. 9, 2002.
Statutory Declaration of Francis John Ballard, executed on Jul. 16, 2002.
Statutory Declaration of Kari Alitalo, executed on Jul. 16, 2002, and accompanying Exhibit 1.
Statutory Declaration of Susan Power, executed on Mar. 22, 2002, and accompanying Appendices I to IV.
Statutory Declaration of Nicholas Kim Hayward, executed on Mar. 26, 2002.
Statutory Declaration of Stuart A. Aaronson, executed on Mar. 22, 2002, and accompanying Appendices I to III.
Statutory Declaration of Gary Baxter Cox, executed on Mar. 22, 2002, and accompanying Exhibit GBC24 (Statutory Declaration of Peter Adrian Walters, executed on Oct. 26, 2001).
Statutory Declaration of Frances John Ballard, executed on Dec. 12, 2001, and accompanying Exhibit 1.
Statutory Declaration of Kari Alitalo, executed on Sep. 24, 2001, and accompanying Exhibits 1 and 2.
Statutory Declaration of Peter Adrian Walton Rogers, executed on Nov. 12, 2001, and accompanying Exhibits PAWR1 to PAWR14.
Statutory Declaration of John Stanley Mattick, executed on Dec. 12, 2000, and accompanying Exhibits JSM1 to JSM4.
Statutory Declaration of Nicholas Kim Hayward, executed on Dec. 8, 2000, and accompanying Exhibits NKH1 and 2.
Statutory Declaration of Jennifer Ruth Gamble, executed on Dec. 12, 2000, and accompany Exhibits JRG 1 to 3.
Statutory Declaration of Tom Rapoport, executed on Dec. 13, 2000, and accompanying Exhibits TP 1 and 2.
Statutory Declaration of Stuart A. Aaronson, executed on Dec. 14, 2000, and accompanying CV.
Statutory Declaration of Susan Power, executed on Dec. 13, 2000, and accompanying Appendices 1 to 2 and F161.
Statutory Declaration of Gary Baxter Cox, executed on Dec. 13, 2000, and accompanying Exhibits GBC 1 to 23.
Statutory Declaration of Peter Adrian Walton Rogers, executed on Feb. 16, 2000, and accompanying Exhibits 1.
Statutory Declaration of Frances John Ballard, executed on Feb. 16, 2000, and accompanying Exhibit 1.
Statutory Declaration of Kari Alitalo, executed on Feb. 15, 2000, and accompanying Exhibits 1 to 3.
U.S. Appl. No. 08/510,133, filed Aug. 1995.
U.S. Appl. No. 08/585,895, filed Jan. 1996.
U.S. Appl. No. 08/601,132, filed Feb. 1996.
U.S. Appl. No. 08/671,573, filed Jun. 1996.
U.S. Appl. No. 60/003,491, filed Sep. 1995.
U.S. Appl. No. 08/554,374, filed Nov. 1995.
Achen et al., "Vacular endothelial growth factor D (VEGF-D) is a ligand for the tyrosine kinases (VEGF) receptor-2 (Flk1) and VEGF receptor 3 (Flt4)," Proc. Natl. Acad. Sci. (USA), 95(2): 548-553 (1998).
Alderson, et al. (1999) Vascular endothelial cell growth factor (VEGF)-2 enhances the development of rat photoreceptor cells in vitro. Keystone Symposia, Ocular Cell and Molecular Biology, 202. (Abstract provided).
Andersson et al., "Assignment of interchain disulfide bonds in platelet-derived growth factor (PDGF) and evidence for agonist activity of monomeric PDGF," J. Biol. Chem., 267(16): 11260-11266 (1992).
Andersson W.F., "Human gene therapy," Science, 256:808-813 (1992).
Aprelikova et al., "FLT4, a novel class III receptor tyrosine kinase in chromosome 5q33-qter," Cancer Research, 52:746-748 (1992).
Dignam et al., "Balbiani ring 3 in *chironomus tentans* encodes a 185-kDa secretory protein which is synthesized throughout the fourth larval instar," *Gene* 88:133-140 (1990).
Ferrara et al., "Molecular and biological properties of the vascular endothelial growth factor family of proteins," *Endocrine Rev.* 13(1): 18-32 (1992).
Finnerty et al., "Molecular cloning of murine FLT and FLT4,"*Oncogene* 8(11): 2293-2298 (1993).
Heldin et al., "Structure of platelet-derived growth factor: implications for funcational properties," *Growth Factors* 8:245-252 (1993).
Eichmann et al., "Avian VEGF-C: cloning, embryonic expression pattern and stimulation of the differentiation of VEGFR2-expressing endothelial cell precursors," *Development* 125(4): 743-752 (1998).

Pajusola et al., "FLT4 receptor tyrosine kinase contains seven immunoglobulin-like loops and is expressed in multiple human tissues and cell lines," *Cancer Research* 52:5738-5743 (1992).

Leung et al., "Vascular endothelial growth factor is a secreted angiogenic mitogen," *Science* 246:1306-1309 (1989).

Breier et al., "Expression of vascular andothelial growth factor during embryonic angiogenesis and endothelial cell differentiation," *Development* 114:521-532 (1992).

Bell et al., "Human epidermal growth factor precursor: cDNA sequence, expression in vitro and gene organization," *Nucl. Acids Res.* 14(21): 8427-8446 (1986).

Berse et al., Vascular permeability factor (vascular endothelial growth factor) gene is expressed differentially in normal tissues, macrophages, and tumors, *Mol. Biol. Cell.* 3:211-220 (1992).

Betsholtz et al., "cDNA sequence and chromosomal localization of human platelet-derived growth factor A-chain and its expression in tumor cell lines," *Nature* 320:695-699 (1986).

Claffey et al., "Vascular endothelial growth factor," *J. Biol. Chem.* 267(23): 16317-16322 (1992).

Corson et al., "Fibrillin binds calcium and is coded by cDNAs that reveal a multidomain structure and alternatively spliced exons at the 5' end," *Genomics* 17:476-484 (1993).

Ferrara et al., "The vascular endothelial growth factor family of polypeptides," *J. Cellular Biochemistry* 47:211-218 (1991).

George et al., "Current Methods in Sequence Comparison and Analysis," Macromolecular Seq. and Syn. Selected Meth—Application (Alan R. Liss), pp. 127-149 (1988).

Hu et al., "A novel regulatory function of proteolytically cleaved VEGF-2 for vascular endothelial smooth muscle cells," *FASEB J.*, 11:498-504 (1997).

Joukov et al., "A novel vascular endothelial growth factor, VEGF-C, is a ligand for the Flt4 (VEGFR-3) and KDR (VEGFR-2) receptor tyrosine kinases," *EMBO J.* 15(2): 290-298 (1996).

Joukov et al., "Proteolytic processing regulates receptor specificity and activity of VEGF-C," *EMBO J.* 16(13): 3898-3911 (1997).

Kaipainen et al., "The related FLT4, FLT1 and KDR receptor tyrosine kinases show distinct expression patterns in human fetal endothelial cells," *J. Exp. Med.* 178:2077-2088 (1993).

Keck et al., "Vascular permeability factor, an endothelial cell mitogen related to PDGF," *Science* 246: 1309 (1989).

Kingsley, D., "The TGF-β superfamily: new members, new receptors, and new genetic tests of function in different organisms," *Genes & Development* 8: 133-146 (1994).

Kukk et al., "VEGF-C receptor binding and pattern of expression with VEGFR-3 suggests a role in lymphatic vascular development," *Development* 122: 3829-37 (1996).

Lee et al., "Vascular endothelial growth factor-related protein: a ligand and specific activator of the tyrosine kinase receptor Flt4," *Proc. Natl. Acad. Sci. (USA)*, 93:1988-1992 (1996).

Maglione et al., "Two alternative mRNAs coding for the angiogenic factor, placenta growth factor (PlGF), are transcribed from a single gene of chromosome 14," *Oncogene* 8:925-931 (1993).

Maglione et al., "Isolation of a human placenta cDNA coding for a protein related to the vascular permeability factor," *Proc. Natl. Acad. Sci. (USA)*, 88:9267-9271 (1991).

Massague, J., "The transforming growth factor-beta family," *Annu. Rev. Cell Biol.* 6:597-641 (1990).

Matthews et al., "A receptor tyrosine kinase cDNA isolated from a population of enriched primitive hematopoietic cells and exhibiting close genetic linkage to c-kit," *Proc. Natl. Acad. Sci. (USA)*, 88:9026-9030 (1991).

Millauer et al., "High affinity VEGF binding and developmental expression suggest FLK-1 as a major regulator of vasculogenesis and angiogenesis," *Cell* 72:835-846 (1993).

Millauer et al., "Glioblastoma growth inhibited in vivo by a dominant-negative Flk-1 mutant," *Nature* 367:576-579 (1994).

Oltvai et al., "Bcl-2 heterodimerizes in vivo with a conserved homolog, bax, that accelerates programmed cell death," *Cell* 74:609-619 (1993).

Paulsson et al., "The balbani ring 3 gene in *chironomus tentans* has a diverged repetitive structure split by many introns," *J. Mol. Biol.* 211:331-349 (1990).

Pajusola et al., "Two human FLT4 receptor tyrosine kinase isoforms with distinct carboxy terminal tails are produced by alternative processing of primary transcripts," *Oncogene* 8:2931-2937 (1993).

Tischer et al., "Vascular endothelial growth factor: A new member of the platelet-derived growth factor gene family," *Biochem. & Biophys.Res. Comms.* 165(3): 1198-1206 (1989).

Tanaka et al., "DNA sequence encoding the amino-terminal region of the human c-*src* protein: implications of sequence divergence among *src*-type kinase oncogenes," *Mol. Cell Biol.* 7(5): 1978-1983 (1987).

Terman et al., "Identification of a new endothelial cell growth factor receptor tyrosine kinase," *Oncogene* 6:1677-1683 (1991).

Terman et al., "Identification of the kdr tyrosine kinase as a receptor for vascular endothelial cell growth factor," *Biochem. Biophys. Res. Commun.* 187(3): 1579-1586 (1992).

Tsujimoto et al., "Analysis of the structure, transcripts, and protein products of *bcl-2*, the gene involved in human follicular lymphoma," *Proc. Natl. Acad. Sci (USA)*, 83:5214-5218 (1986).

Tischer et al., "The Human Gene for Vascular Endothelial Growth Factor," *J. Biol.Chem.* 266(18): 11947-11954 (1991).

Friedman, T., "A brief history of gene therapy," *Nat. Genetics* 2:93-98 (1992).

Williams, R.S. "Southwestern internal medicine conference: prospects for gene therapy of ischemic heart disease," *Am. J. Med. Sci.* 306(2): 129-136 (1993).

Hockel et al., "Therapeutic angiogenesis," *Arch. Surg.* 128:423-429 (1993).

Guzman et al. "Efficient gene transfer into myocardium by direct injection of adenovirus vectors," *Circ. Res.* 73:1202-1207 (1993).

Bellomo et al., "Mice Lacking the Vascular Endothelial Growth Factor-B Gene (Vegfb) Have Smaller Hearts, Dysfunctional Coronary Vasculature, and Impaired Recovery From Cardiac Ischemia," *Circ. Research* 89(2): e29-e35 (2000).

Cockerill et al., "Angiogenesis: Models and Modulators" *Intl. Rev. Cytology* 159:113-160 (1995).

Gamble et al., "Regulation of In Vitro Capillary Tube Formation by Anti-Integrin Antibodies," *J. Cell. Bio.* 121(4): 931-943 (1993).

Goldspiel et al., "Human Gene Therapy," *Clinical Pharmacy* 12: 488-505 (1993).

Grimmond et al., "Cloning and Characterization of a Novel Human Gene Related to Vascular Endothelial Growth Factor," *Genome Research* 6:124-131 (1996).

Hyde et al., "Correction of the ion transport defect in cystic fibrosis transgenic mice by gene therapy," *Nature* 362: 250-255 (1993).

Kay et al., "In Vivo Gene Therapy of Hemophilia B: Sustained Partial Correction in Factor IX-Deficient Dogs," *Science* 262:117-119 (1993).

Kolodka et al., "Hepatic Gene Therapy: Efficient Retroviral-Mediated Gene Transfer into Rat Hepatocytes in Vivo," *Somatic Cell and Molecular Genetics* 19(5): 491-497 (1993).

Litwin et al., "Role of Cytokines in Endothelial Cell Functions," *Human Cytokines* 101-129.

Shibuya et al., "Nucleotide sequence and expression of a novel human receptor-type tyrosine kinase gene (*flt*) closely related to the *fms* family," *Oncogene* 519-524 (1990).

Silins et al., "Analysis of the Promoter Region of the Human VEGF-Related Factor Gene," *Biochem. Biophys. Res. Comm.* 230: 413-418 (1997).

Stewart et al., "Insulin delivery by somatic cell gene therapy," *J of Mol. Endocrinology* 11:335-341 (1993).

Townson et al., "Characterization of the Murine VEGF-Related Factor Gene," *Biocyhem. & Biophys. Res. Comms.* 220: 922-928 (1996).

Walsh et al., "Gene Therapy for Human Hemoglobinopathies," P.S.E.B.M. 204: 289-300.

Yourey, et al. (2000) Vascular Endothelial Cell Growth Factors Promote the In Vitro Development of Rat Photoreceptor Cells. J. N euroscience, 20: 6781-6788.

Yourey, et al. (1999) Vascular Endothelial Cell Growth Factor (VEGF)-2 Enhances the Development of Rat Photoreceptor Cells In Vitro. Soc. Cell Biology, 227. (Abstract provided).

GenBank Accession No. X68203, Aprelikova et al., "H.sapiens mRNA for FLT4, class III receptor tyrosine kinase," Nov. 30, 1993.

GenBank Accession No. M95200, Claffey et al., "Mouse vacular endothelial growth factor mRNA, complete cds," Apr. 27, 1993.
GenBank Accession No. M24160, Dignam et al., "C.tentans 185-kd secretory protein (sp185) mRNA, partial cds, clone pCt185," Apr. 26, 1993.
GenBank Accession No. M24276, Dignam et al., "C.tentans 140-kd secretory protein (sp140) mRNA, partial cds, clone pCt140.1," Apr. 26, 1993.
GenBank Accession No. M24277, Dignam et al., "C.tentans 140-kd secretory protein (sp140) mRNA, partial cds, clone pCt140.2," Apr. 26, 1993.
GenBank Accession No. D88689, Finnerty et al., "Mus musculus mRNA for flt-1, complete cds," Apr. 14, 2000.
GenBank Accession No. L07296, Finnerty et al., "Mus musculus receptor tyrosine kinase (FLT4) mRNA, complete cds," Aug. 9, 1993.
GenBank Accession No. X54936, Maglione et al., "H.sapiens mRNA for placenta growth factor (PIGF)," Nov. 12, 1991.
GenBank Accession No. S57152, Maglione et al., "Homo sapiens placenta growth factor 2 (PIGF-2) gene, partial cds," Mar. 5, 2001.
GenBank Accession No. X59397, Matthews et al., "Mouse Flk-1 mRNA for a tyrosine kinase receptor," Nov. 6, 1991.
GenBank Accession No. X52263, Paulsson et al., "C.tentans balbiani ring 3 (BR3) gene," Dec. 18, 1992.
GenBank Accession No. M63971, Tischer et al., "Human vascular endothelial growth factor gene, exon 1," Aug., 1993.
GenBank Accession No. M63972, Tischer et al., "Human vascular endothelial growth factor gene, exon 2," Aug. 3, 1993.
GenBank Accession No. M63973, Tischer et al., "Human vascular endothelial growth factor gene, exon 3," Aug. 3, 1993.
GenBank Accession No. M63974, Tischer et al., "Human vascular endothelial growth factor gene, exon 4," Aug. 3, 1993.
GenBank Accession No. M63975, Tischer et al., "Human vascular endothelial growth factor gene, exon 5," Aug. 3, 1993.
GenBank Accession No. M63976, Tischer et al., "Human vascular endothelial growth factor gene, exon 6," Aug. 3, 1993.
GenBank Accession No. M63977, Tischer et al., "Human vascular endothelial growth factor gene, exon 7," Aug. 3, 1993.
GenBank Accession No. M63978, Tischer et al., "Human vascular endothelial growth factor gene, exon 8," Aug. 3, 1993.
GenBank Accession No. M27281, Keck et al., "Human vascular permeability factor mRNA, complete cds," Aug. 3, 1993.
GenBank Accession No. X04571, Bell et al., "Human mRNA for kidney epidermal growth factor (EGF) precursor," Mar. 21, 1995.
GenBank Accession No. X63556, Corson et al., "H. sapiens mRNA for fibrillin," Feb. 17, 1997.
GenBank Accession No. L19896, Corson et al., "Human fibrillin (FBN1) gene, 5'end including alternative exons A, B, and C, and exon M," Nov. 8, 1994.
GenBank Accession No. L04947, Terman et al., "Homo sapiens (clonoes BT3.081.8, BT3.129.5 and BT4.169," Jan. 6, 1995.
GenBank Accession No. M16237, Tanaka et al., "Human c-src-1 proto-oncogene, exono 2," Jan. 13, 1995.
GenBank Accession No. M16243, Tanaka et al., "Human c-src-1 proto-oncogene, exon 3," Jan. 13, 1995.
GenBank Accession No. M16244, Tanaka et al., Human c-src-1 proto-oncogene, exon 4, Jan. 13, 1995.
GenBank Accession No. M16245, Tanaka et al., "Human c-src-1 proto-oncogene, exon 5," Jan. 13, 1995.
GenBank Accession No. K03212, Anderson et al., "Human c-src-1 proto-oncogene, exon 6," Jan. 13, 1995.
GenBank Accession No. K03213, Anderson et al., "Human c-src-1 proto-oncogene, exon 7," Jan. 13, 1995.
GenBank Accession No. K03214, Anderson et al., "Human c-src-1 proto-oncogene, exono 8", Jan. 13, 1995.
GenBank Accession No. K03215, Anderson et al., "Human c-src-1 proto-oncogene, exon 9," Jan. 13, 1995.
GenBank Accession No. K03216, Tanaka et al., Human c-src-1 proto-oncogene, exon 10, Jan. 13, 1995.
GenBank Accession No. K03217, Tanaka et al., "Human c-src-1 proto-oncogene, exon 11," Jan. 13, 1995.
GenBank Accession No. K03218, Tanaka et al., "Human c-src-1 proto-oncogene, exon 12," Jan. 13, 1995.

GenBank Accession No. M13994, Tsujimoto et al., "Human B-cell leukemia/lymphoma 2 (bcl-2) proto-oncogene mRNA encoding bcl-2-alpha protein, complete cds," Oct. 31, 1994.
GenBank Accession No. M13995, Tsujimoto et al., "Human B-cell leukemia/lymphoma 2 (bcl-2) proto-oncogene mRNA encoding bcl-3-beta protein, complete cds," Oct. 31, 1994.
GenBank Accession No. L22473, Oltvai et al., "Human Bax alpha mRNA, complete cds, "Dec. 15, 1993.
GenBank Accession No. L22474, Oltvai et al., "Human Bax beta mRNA, complete cds," Dec. 13, 1993.
GenBank Accession No. AJ000185, Achen et al., "Homo Sapiens mRNA for vascular endothelial growth factor-D," Feb. 11, 1998.
International Search Report, Application No. PCT/US99/05021.
International Search Report, Application No. PCT/US94/05291.
International Search Report, Application No. PCT/US01/24658 mailed on Dec. 12, 2001.
EBI Accessioni No. AAW27553, Knappik et al., "Human Ab heavy chain variable region VH3 consensus" (Jan. 23, 1998).
Yang et al., "Flk-1, a Receptor for Vascular Endothelial Growth Factor (VEGF), Is Expressed by Reginal Progenitor Cells," *J. Neuroscience*, 16(19):6089-6099 (Oct. 1, 1996).
Gerhardinger, et al., "Expression of Vascular Endothelial Growth Factor in the Human Retina and in Nonproliferative Diabetic Retinopathy," *Am. J. Pathol.*, 152(6):1453-1462 (Jun. 6, 1998).
Yourey et al., "Vascular Endothelial Cell Growth Factors Promote the In Vitro Development of Rat Photoreceptor Cells," *J. Neuroscience*, 20(18.):6781-6788 (Sep. 15, 2000).
Yourey et al., "Vascular Endothelial Cell Growth Factors Promote the In Vitro Development of Rat Photoreceptor Cells," *Molecul. Biol. Cell*, 10(Suppl.):39a (Nov. 1999) and 39th Ann. Mtg. Am. Soc. Cell Biol., Wash, DC, (Dec. 11-15, 1999) (abstract (227) only).
Supplementary European Search Report, Application No. EP 02 72 6730, mailed Oct. 25, 2004.
Supplementary European Search Report, Application No. EP 00 90 5992, mailed Nov. 8, 2004.
Litwin et al., "Role of Cytokines in Endothelial Cell Functions," *Human Cytokines* 101-129 (1995).
Walsh et al., "Gene Therapy for Human Hemoglobinopathies," P.S.E.B.M. 204:289-300 (1993).
Schratzberger et al., "Reversal of experimental diabetic neuropathy by VEGF gene transfer," *J. Clin. Invest.*, 107(9):1083-1092 (May 2001).
Vale et al., "Randomized, Single-Blind, Placebo-Controlled Pilot Study of Catheter-Based Myocardial Gene Transfer for Therapeutic Angiognesis Using Left Ventricular Electromechanical Mapping in Patients with Chronic Myocardial Ischemia," *Circulation*, 103:17:2138-2143 (May 1, 2001).
European Supplementary Search Report, Application No. EP 01 96 3814, mailed Jul. 14, 2004.
U.S. Appl. No. 08/340,011, filed Nov. 14, 1994, Alitalo et al.
Altshuler et al., "Taurine promotes the differentiation of a vertebrate retinal cell type in vitro," *Development*, 119:1317-1328 (1993).
Bocker-Meffert et al., "Erythropoietin and VEGF Promote Neural Outgrowth from Retinal Explants in Postnatal Rats," *Invest. Ophthalmol. Vis. Sci.*, 43(6):2021-2026 (2002).
Gail M. Seigel, "The golden age of retinal cell culture," *Molec. Vis.* 5:4 (1999).
Hanniink et al., "Deletions in the C-Terminal Coding Region of the v-sis Gene: Dimerization Is Required for Transformation" *Mol. And Cellular Biol.* 1304-1314 (1986).
Hirai et al., "Expression of Vascular Endothelial Growth Factors (VEGF-A/VEGF-1 and VEGF-C/VEFG-2) in Postmenopausal Uterine Endometrial Carcinoma," *Gynecol. Oncol.* 80:181-188 (2001).
Kelley et al., "Regulation of a Proliferation and Protoreceptor Differentiation in Fetal Human Reginal Cell Cultures," *Invest. Ophthalmol. Vis. Sci.* 36(7):1280-1289 (1995).
Maglione et al., "Two alternative mRNAs coding for the angiogenic factor, placenta growth factor (PIGF), are transcribed from a single gene of chromosome 14," *Oncogene* 8:925-931 (1993).
Ngo et al., The Protein Folding Problem and Tertiary Structure Prediction, Kenneth Merz, Jr. and Scoott LeGrand, eds., Birkhauser, Boston, pp. 492-495 (1994).

Rudikoff et al., "Single amino acid substitution altering antigen-binding specificity," *Proc. Natl. Acad. Sci. USA*, 79(6):1979-1983 (Mar. 1982).

Schulz-Key et al., "Ciliary Neurotrophic Factor as a Transient Negative Regulator of Rod Development in Rat Retina," *Invest. Ophthalmol. Vis. Sci.* 43(9):3099-3108 (2002).

Stacker et al., "The Vascular Endothelial Growth Factor Family: Signalling for Vascular Development," *Growth Factors*, vol. 17, pp. 1-11 (1999).

Joosten et al., "The production of antibody fragments and antibody fusion proteins by yeasts and filamentous fungi," *Microbial Cell Factories* 2:1 (Jan. 30, 2003).

Skerra et al., "Assembly of a functional immunoglobulin Fv fragment in *Escherichia coli,*" *Science* 240(4855):1038-1041 (May 20, 1988).

Better et al., "*Escherichia coli* secretion of an active chimeric antibody fragment," *Science* 240(4855):1041-1043 (May 20, 1988).

Houck, et al., "The vascular endothelial growth factor family: identification of a fourth molecular species and characterization of alternative splicing of RNA." Molecular Endocrinology. 5(12):1806-14 (1991).

Colwell, et al., "Method for generating a high frequency of hybridomas producing monoclonal IgA antibodies." Methods Enzymol. 121:42-51 (1986).

GenBank Accession No. S08167, Paulsson et al., 1990.

Supplementary Partial European Search Report, Application No. EP 02 72 6730, mailed Aug. 4, 2004.

Supplementary Partial European Search Report, Application No. EP 02 72 1715, mailed Jan. 10, 2005.

Supplementary Partial European Search Report, Application No. EP 02 72 1715, mailed Oct. 22, 2004.

Danis, R.P., et al., "Anti-angiogenic therapy of proliferative diabetic retinopathy," *Exp. Opin. Pharma.* 2:395-407. Ashley Publications Ltd. (Mar. 2001).

Enholm, B., et al., "Vascular Endothelial Growth Factor-C: A Growth Factor for Lymphatic and Blood," *Trends Cardiovascular Med.* 8:292-297, Elsevier Science, Inc. (Oct. 1998).

Ferrara, N., "Vascular Endothelial Growth Factor and the Regulation of angiogenesis," *Recent Prog. Hormone Res.* 55:15-36, The Endocrine Society (Mar. 2000).

Halin, C. and Neri, D., "Antibody-Based Targeting of Angiogenesis," *Crit. Rev. Ther. Drug Carrier Syst.* 18:299-339, Begell House, Inc. (Aug. 2001).

Longo, R., et al., "Anti-angiogenic therapy: Rationale, challenges and clinical studies," *Angiogenesis* 5:237-256, Kluwer Academic Publishers (Dec. 2002).

Schlaeppi, J.-M., et al., "Characterization of a new potent, in vivo neutralizing monoclonal antibody to human vascular endothelial growth factor," *J. Cancer Res. Clin. Oncol.* 125:336-342, Springer-Verlag (May 1999).

van der Flier, M., et al., "Antibody neutralization of vascular endothelial growth factor (VEGF) fails to attenuate vascular permeability and brain edema in experimental pneumococcal meningitis," *J. Neuroimmunol.* 160:170-177, Elsevier B.V. (Mar. 2005).

Walsh, D.A., "Angiogenesis and arthritis," *Rheumatology* 38:103-112, British Society for Rheumatology (Feb. 1999).

Winkler, K., et al., "Changing the Antigen Binding Specificity by Single Point Mutations of a Anti-p24 (HIV-1) Antibody," *J. Immunol.* 165:4505-4514, The American Association of Immunologists (Oct. 2000).

NCBI Entrez, GenBank Report, Accession No. AF010302, Mandriota S.J. and Pepper, M.S., Entry date Jul. 1997.

Anderson, W.F., "Human gene therapy," *Nature* 392:25-30, Macmillan Magazines Ltd. (Apr. 1998).

Borg, J.-P., et al., "Biochemical characterization of two isoforms of FLT4, a VEGF receptor-related tyrosine kinase," *Oncogene* 10:973-984, Stockton Press (Mar. 1995).

Capogrossi, M.C., "Gene Therapy of Coronary Artery Disease," Project No. Z01AG00811-01, Abstract (Jan. 1994).

Capogrossi, M.C., "Gene Therapy of Coronary Artery Disease," Project No. A01AG00811-05, Abstract (Jan. 1995).

Choi, I.H., et al., "Angiogenesis and Mineralization During Distraction Osteogenesis," *J. Korean Med. Sci.* 17:435-447, The Korean Academy of Medical Sciences (Aug. 2002).

Declaration of Dr. Karl Alitalo, In re of: U.S. Appl. No. 08/585,895, Alitalo et al., filed Jan. 12, 1996, submitted Nov. 26, 1997.

Dias, S., et al., "Vascular endothelial growth factor (VEGF)-C signaling FLT-4 (VEGFR-3) mediates leukemic cell proliferation, survival, and resistance to chemotherapy," *Blood* 99:2179-2184, The American Society of Hematology (Mar. 2002).

English language abstract of JP 64-38100A, cited as document FP2 on Form PTO/SB/08A, Derwent Accession No. 1989-088700/198912.

English language abstract of Kp 2-117698 A, cited as document FP3 on Form PTO/SB/08A, Derwent Accession No. 1990-181364/199024.

Fan, T.-P., et al., "Controlling the vasculare: angiogenesis, anti-angiogenesis and vascular targeting of gene therapy," *Trends Pharmaco. Sci.* 16:57-66, Elsevier Science Ltd. (Feb. 1995).

Isner, J.M., et al., "Arterial Gene Therapy for Therapeutic Angiogenesis in Patients With Peripheral Artery Disease," *Circulation* 91:2687-2692, American Heart Association, Inc. (Jun. 1995).

Isner, J.M., et al., "Gene therapy for arterial disease," *Lancet* 344:1653-1654, The Lancet Ltd. (Dec. 1994).

Isner, J.M., et al., "Physiologic Assessment of Angiogenesis by Arterial Gene Therapy with Vascular Endothelial Growth," *J. Cell. Biochem. (Suppl. 21A):378*, Abstract C6-215, Wiley-Liss (Mar.-Apr. 1995).

Isner, J.M., et al., "Therapeutic Angiogenesis in Vascular Medicine," Project No. R01 HL5335401, Abstract (Mar. 1995).

Kubo, H., et al., "Blockade of vascular endotherlial growth factor receptor-3 signaling ingibits fibroblasts growth factor-2-induced lymphangiogenesis in mouse cornea," *Proc. Natl. Acad. Sci.* 99:8868-8873, The National Academy of Science (Jun. 2002).

Kuzuya, M. and Kinsella, J.L., "Induction of Endothelial Cell differentiation In Vitro by Fibroblast-Derived Soluble Factors," *Exp. Cell Res.* 215:310-318, Academic Press, Inc.(Dec. 1994).

Maher, P.A., "Stimulation of Endothelial Cell Proliferation by Vanadate Is Specific for Microvascular Endothelial Cells," *J. Cell. Physiol.* 151:549-554, Wiley-Liss, Inc. (1992).

Maynard, J. and Georgiou, G., "Antibody Engineering," *Annu. Rev. Biomed. Eng.* 2:339-376, Annual Reviews (Aug. 2000).

Mesri, E.A., et al., "Expression of Vascular Endothelial Growth Factor From a Defective Herpes Simplex Virus Type I Amplicon Vector Induces Angiogenesis in Mice," *Circulation Res.* 76:161-167, American Heart Association, Inc. (Feb. 1995).

Morea, V., et al., "Antibody Modeling: Implications for Engineering and Design," *Methods* 20:267-279, Academic Press (Mar. 2000).

Mülhauser, J., et al., "In Vivo Gene Transfer into Porcine Cardiac Cells with a Replication-Deficient Recombinant Adenovirus Vector," *Circulation* 88:I-475, Abstract No. 2558, American Heart Association (Oct. 1993).

Mülhauser, J., et al., "VEGF $_{165}$Expressed by a Replication-Deficient Recombinant Adenovirus Vector Induces Angiogenesis In Vivo," *Circulation Res.* 77:1077-1086, American Heart Association, Inc. (Dec. 1995).

Oikawa, T., et al., "Three Isoforms of Platelet-Derived Growth Factors All Have the Capacity to Induce Angiogenesis In Vivo," *Biol. Pharm. Bull.* 17:1686-1688, Pharmaceutical Society of Japan (Dec. 1994).

Pajusola, K., et al., "Signalling properties of FLT4, a proteolytically processed receptor tyrosine kinase related to two VEGF receptors," *Oncogene* 9:3545-3555, Stockton Press Ltd. (Dec. 1994).

Pepper, M.S., et al., "In Vitro Angiogenci and Proteolytic Properties of Bovine Lymphatic Endothelial Cells," *Exp. Cell Res.* 210:298-305, Academic Press, Inc. (Feb. 1994).

Plate, K.H., "From Angiogenesis to lymphangiogenesis," *Nat. Med.* 7:151-152, Nature America, Inc. (Feb. 2001).

Spranger, J. and Pfeiffer, A.F.H., "New concepts in pathogenesis and treatment of diabetic retinopathy," *Exp. Clin. Endocrinol. Diabetes* 109(Suppl. 2):S438-S450, J.A. Barth Verlag (2001).

Stacker, S.A. and Achen, M.G., "The Vascular Endothelial Growth Factor Family: Signalling for Vascular Development," *Growth Factors* 17:1-11, Taylor & Francis (1999).

Symes, J.F., et al., "Angiogenesis: potential therapy for ischaemic disease," *Curr. Opin. Lipidol.* 5:305-312, Current Science Ltd. (Aug. 1994).

Takeshita, S. et al., "In Vivo Evidence of Enhanced Angiogenesis Following Direct Arterial Gene Transfer of the Plasmid Encoding Vascular Endothelial Growth Factor," *Circulation 88*, Abstract No. 2565, American Heart Association, Inc. (Oct. 1993).

Takeshita, S., et al., "Therapeutic Angiogenesis. A Single Intraarterial Bolus of Vascular Endothelial Growth Factor Augments Revascularization in a Rabbit Ischemic Hind Limb Model," *J. Clin. Invest. 93:662-670*, The American Society for Clinical Investigation, Inc. (Feb. 1994).

Vale, P.R., et al., "Percutaneous Electromechanical Mapping Demonstrates Efficacy of pVGI.1 (VEGF2) in an Animal Model of Chronic Myocardial Ischemia," *Circulation (Suppl 1.)100:I-22*, Lipponcott Williams & Wilkins (Nov. 1999).

Verma, I. and Somia, N., "Gene therapy—promises, problems and prospects," *Nature 389:239-242*, Macmillan Magazines Ltd. (Sep. 1997).

Walsh, D.A. and Pearson, C.I., "Angiogenesis in the pathogenesis of inflammatory joint and lung diseases," *Arthritis Res. 3:147-153*, BioMed Central Ltd. (Feb. 2001).

Williams, R.S., "Southwestern Internal Medicine Conference: Prospects for Gene Therapy of Ischemic Heart Disease," *Am. J. Med. Sci. 306:129-136*, Lippincott Williams & Wilkins (Aug. 1993).

Witzenbichler, B., et al., "Vascular Endothelial Growht Factor-C (VEGF-C/VEGF-2) Promotes Angiogenesis in the Setting of Tissue Ischemia," *Am. J. Pathol. 153:381-394*, American Society for Investigative Pathology, Inc. (Aug. 1998).

Yeung, P.K.F., "VEGF-2 St Elizabeth's Medical Center," *Curr. Opin. Invest. Drugs 2:796-8000*, PharmaPress Ltd. (Jun. 2001).

Letter from John J. Chicca II, Ph.D., Molecular Diagnostic Services, Inc. regarding a third progress report for a project entitled "Cloning and expression of VEGF-2 gene and the efficacy fof VEGF-2 protein utilizing the 3-D collagen angiogenesis assay and proliferation," dated Feb. 16, 2006.

Letter from John J. Chicca II, Ph.D., Molecular Diagnostic Services, Inc. regarding a fourth progress report for a project entitled "Cloning and expression of VEGF-2 protein utilizing the 3-D collagen angiogenesis assay and proliferation," dated Mar. 14, 2006.

Lee et al., "Improved Expression of Vascular Endothelial Growth Factor by Naked DNA in Mouse Skeletal Muscles: Implication for Gene Therapy of Ischemic Diseases," *Biochem. Biophys. Res. Comm.* 272:230-235, Academic Press (May 2000).

Walter et al., "Local Gene Transfer of phVEGF-2 Plasmid by Gene-Eluting Stents," *Circulation* 110:36-45, American Heart Association, Inc. (Jun. 2004).

\* cited by examiner

```
   1  GTCCTTCCACCATGCACTCGCTGGGCTTCTCTCTGTGGCGTGTTCTCTGCTCGCCGCTG    60
      ---------+---------+---------+---------+---------+---------+
      CAGGAAGGTGGTACGTGAGCGACCCGAAGAGAGACACCGCACAGAGACGAGCGGCGAC
                M  H  S  L  G  F  S  L  W  R  V  L  C  S  A  A

61  CGCTGCTCCCGGGTCCTCGGAGGCGCCCGCGCCCGCGCCTTCGAGTCCGGACTCG          120
      ---------+---------+---------+---------+---------+---------+
      GCGACGAGGGCCCAGGAGCGCTCCGCGGGCGCGGGCGCGGAAGCTCAGGCCTGAGC
         L  L  P  G  P  R  E  A  P  A  A  A  A  F  E  S  G  L  D

121  ACCTCTCGACGCGGAGCCCGACGCGGGCGAGGCCACGGCTTATGCAAGCAAAGATCTGG    180
      ---------+---------+---------+---------+---------+---------+
      TGGAGAGCCTGCGCCTCGGGCTGCGCCCGCTCCGGTGCCGAATACGTTCGTTTCTAGACC
         L  S  D  A  E  P  D  A  G  E  A  T  A  Y  A  S  K  D  L  E

181  AGGAGCAGTTACGGTCTCTGTGTCCAGTGTAGATGAACTCATGACTACTGTACTCTACCCAGAAT    240
      ---------+---------+---------+---------+---------+---------+
      TCCTCGTCAATGCCAGACACAGTCACATCTACTTGAGTACTGACATGAGATGGGTCTTA
         E  Q  L  R  S  V  S  V  D  E  L  M  T  V  L  Y  P  E  Y

241  ATTGGAAAAATGTACAAGTGTCAGCTAAGGAAAGAGGCTGGCAACATAACAGAGAACAGG    300
      ---------+---------+---------+---------+---------+---------+
      TAACCTTTTACATGTTCACAGTCGATTCCTTCCTCCGACCGTTGTATTGTCTCTTGTCC
         W  K  M  Y  K  C  Q  L  R  K  G  G  W  Q  H  N  R  E  Q  A

301  CCAACCTCAACTCAAGGACAGAAGAGACTATAAAATTGCTGCAGCACATTATAATACAG    360
      ---------+---------+---------+---------+---------+---------+
      GGTTGGAGTTGAGTTCCTGTCTTCTCTGATATTTAAACGACGTCGTGTAATATTATGTC
         N  L  N  S  R  T  E  E  T  I  K  F  A  A  H  Y  N  T  E

FIG. 1A
```

```
361  AGATCTTGAAAAGTATTGATAATGAGTGGAGAAAGACTCAATGCCATGCCACGGGAGGTGT
     ------+---------+---------+---------+---------+---------+    420
     TCTAGAACTTTTCATAACTATTACTCACCTCTTTCTGAGTTACGTACGGTGCCCTCCACA
      I  L  K  S  I  D  N  E  W  R  K  T  Q  C  M  P  R  E  V  C

421  GTATAGATGTGGGGAAGGAGTTTGGAGTCGGCGACAAACACCTTCTTTAAACCTCCATGTG
     ------+---------+---------+---------+---------+---------+    480
     CATATCTACACCCCTTCCTCAAACCTCAGCCGCTGTTTGTGGAAGAAATTTGGAGGTACAC
      I  D  V  G  K  E  F  G  V  A  T  N  T  F  F  K  P  P  C  V

481  TGTCCGTCTACAGATGTGGGGGTTGCTGCAATAGTGAGGGGCTGCAGTGCATGAACACCA
     ------+---------+---------+---------+---------+---------+    540
     ACAGGCAGATGTCTACACCCCCAACGACGTTATCACTCCCCGACGTCACGTACTTGTGGT
      S  V  Y  R  C  G  G  C  N  S  E  G  L  Q  C  M  N  T  S

541  GCACGAGCTACCTCAGCAAGACGTTATTTGAAATTACAGTGCCTCTCTCTCAAGGCCCCA
     ------+---------+---------+---------+---------+---------+    600
     CGTGCTCGATGGAGTCGTTCTGCAATAAACTTTAATGTCACGGAGAGAGAGTTCCGGGGT
      T  S  Y  L  S  K  T  L  F  E  I  T  V  P  L  S  Q  G  P  K

601  AACCAGTAACAATCAGTTTGCCAATCACACTTCCTGCCGATGCATGTCTAAACTGGATG
     ------+---------+---------+---------+---------+---------+    660
     TTGGTCATTGTTAGTCAAAACGGTTAGTGTGAAGGACGGCTACGTACAGATTTGACCTAC
      P  V  T  I  S  F  A  N  H  T  S  C  R  C  M  S  K  L  D  V
```

FIG. 1B

```
      TTTACAGACAAGTTCATTCCATTATTAGACGTTCCCTGCCAGCAACACTACCACAGTGTC
661   ------+---------+---------+---------+---------+---------+   720
      AAATGTCTGTTCAAGTAAGGTAATAATCTGCAAGGACGGTCGTTGTGATGGTGTCACAG
       Y  R  Q  V  H  S  I  R  R  S  L  P  A  T  L  P  Q  C  Q

AGGCAGCGAACAAGACCTGCCCCACCAATTACACATGTGGAATAATCACATCTGCAGATGCC
721   ------+---------+---------+---------+---------+---------+   780
      TCCGTCGCTTGTTCTGGACGGGGTGGTTAATGTACACCTTATTAGTGTAGACGTCTACGG
       A  A  N  K  T  C  P  T  N  Y  M  W  N  N  H  I  C  R  C  L

TGGCTCAGGAAGATTTATGTTTCCTCGGATGCTGGAGATGACTCAACAGATGGATTCC
781   ------+---------+---------+---------+---------+---------+   840
      ACCGAGTCCTTCTAAATACAAAGGAGCCTACGACCTCTACTGAGTTGTCTACCTAAGG
       A  Q  E  D  F  M  F  S  S  D  A  G  D  D  S  T  D  G  F  H

ATGACATCTGTGGACCAAACAAGGAGCTGGATGAAGAGACCTGTCAGTGTGTCTGCAGAG
841   ------+---------+---------+---------+---------+---------+   900
      TACTGTAGACACCTGGTTTGTTCCTCGACCTACTTCTCTGGACAGTCACACAGACGTCTC
       D  I  C  G  P  N  K  E  L  D  E  E  T  C  Q  C  V  C  R  A

CGGGGCTTCGGCCTGCCAGCTGTGGACCCCACAAAGAACTAGACAGAAACTCATGCCAGT
901   ------+---------+---------+---------+---------+---------+   960
      GCCCCGAAGCCGGACGGTCGACACCTGGGGTGTTTCTTGATCTGTCTTTGAGTACGGTCA
       G  L  R  P  A  S  C  G  P  H  K  E  L  D  R  N  S  C  Q  C
```

FIG. 1C

```
 961  GTGTCTGTAAAAACAAACTCTTCCCCAGCCAATGTGGGGCCAACCGAGAATTTGATGAAA  1020
      ---------+---------+---------+---------+---------+---------+
      CACAGACATTTTGTTTGAGAAGGGTCGGTTACACCCCGGTTGGCTCTTAAACTACTTT
      V  C  K  N  K  L  F  P  S  Q  C  G  A  N  R  E  F  D  E  N

1021  ACACATGCCAGTGTGTATGTAAAAGAACCTGCCCCAGAAATCAACCCCTAAATCCTGAA   1080
      ---------+---------+---------+---------+---------+---------+
      TGTGTACGGTCACACATACATTTTCTTGGACGGGGTCTTTAGTTGGGATTTAGGACCTT
      T  C  Q  C  V  C  K  R  T  C  P  R  N  Q  P  L  N  P  G  K

1081  AATGTGCCTGTGAATGTACAGAAAGTCCACAGAAATGCTTGTTAAAGGAAAGAAGTTCC   1140
      ---------+---------+---------+---------+---------+---------+
      TTACACGGACACTTACATGTCTTTCAGGTGTCTTTACGAACAATTTCCTTTCTTCAAGG
      C  A  C  E  C  T  E  S  P  Q  K  C  L  L  K  G  K  K  F  H

1141  ACCACCAAACATGCAGCTGTTACAGACGGCCATGTCTGCGGTACATGCTTGGCGGTCTCG   1200
      ---------+---------+---------+---------+---------+---------+
      TGGTGGTTTGTACGTCGACAATGTCTGCCGGTACAGACGCCATGTACGAACCGCCAGAGC
      H  Q  T  C  S  C  Y  R  R  P  C  T  N  R  Q  K  A  C  E  P

1201  CAGGATTTTCATATAGTGAAGAAGTGTGTCGTTGTGTCCCTTCATATTGGCAAAGACCAC   1260
      ---------+---------+---------+---------+---------+---------+
      GTCCTAAAAGTATATCACTTCTTCACACAGCAACACAGGAAGTATAACCGTTTCTGGTG
      G  F  S  Y  S  E  E  V  C  R  C  V  P  S  Y  W  Q  R  P  Q
```

FIG. 1D

```
1261  AAATGAGCTAAGATTGTACTGTTTTCCAGTTCATCGATTTTCTATTATGGAAAACTGTGT  1320
      TTTACTCGATTCTAACATGACAAAAGGTCAAGTAGCTAAAAGATAATACCTTTTGACACA
            M  S  *

1321  TGCCACAGTAGAACTGTCTGTGAACAGAGAGACCCTTGTGGGTCCATGCTAACAAAGACA  1380
      ACGGTGTCATCTTGACAGACACTTGTCTCTCTGGGAACACCCAGTACGATTGTTTCTGT

1381  AAAGTCTGTCTTTCCTGAACCATGTGGATAACTTTACAGAAATGGACTGGAGCTCATCTG  1440
      TTTCAGACAGAAAGGACTTGGTACACCTATTGAAATGTCTTTACCTGACCTCGAGTAGAC

1441  CAAAAGGCCTCTTGTAAAGACTGGTTTTCTGCCAATGACCAAACAGCCAAGATTTCCTC   1500
      GTTTTCCGGAGAACATTTCTGACCAAAAGACGGTTACTGGTTTGTCGGTTCTAAAAGGAG

1501  TTGTGATTTCTTTAAAGAATGACTATATAATTTATTCCACTAAAAATATTGTTTCTGC   1560
      AACACTAAAGAAATTTTCTTACTGATATATTAAATAAGGTGATTTTTATAACAAAGACG

1561  ATTCATTTTATAGCAACAACAATTGGTAAAACTCACTGTGATCAATATTTTTATATCAT  1620
      TAAGTAAAAATATCGTTGTTGTTAACCATTTGAGTGACACTAGTTATAAAAATATAGTA

1621  GCAAAATATGTTTAAAATAATAAAAATGAAAATTGTATTTATAAAAAAAAAAAAAAA    1674
      CGTTTTATACAAATTTTATTTTTACTTTTAACATAAATATTTTTTTTTTTTTTT
```

FIG. 1E

```
1   CGAGGCCACGGCTTATGCAAGCAAAGATCTGGAGGAGCAGTTACGGTCTGTGTCCAGTGT

61  AGATGAACTCATGACTGTACTCTACCCAGAATATTGGAAAATGTACAAGTGTCAGCTAAG
         M  T  V  L  Y  P  E  Y  W  K  M  Y  K  C  Q  L  R

121 GAAAGGAGGCTGGCAACATAACAGAGAACAGGCCAACCTCAACTCAAGGACAGAAGAGAC
     K  G  G  W  Q  H  N  R  E  Q  A  N  L  N  S  R  T  E  E  T

181 TATAAAATTTGCTGCAGCACATTATAATACAGAGATCTTGAAAAGTATTGATAATGAGTG
     I  K  F  A  A  A  H  Y  N  T  E  I  L  K  S  I  D  N  E  W

241 GAGAAAGACTCAATGCATGCCACGGGAGGTGTGTATAGATGTGGGGAAGGAGTTTGGAGT
     R  K  T  Q  C  M  P  R  E  V  C  I  D  V  G  K  E  F  G  V

301 CGCGACAAACACCTTCTTTAAACCTCCATGTGTCCGTCTACAGATGTGGGGTTGCTG
     A  T  N  T  F  F  K  P  P  C  V  S  V  Y  R  C  G  G  C  C
```

FIG. 2A

361 CAATAGTGAGGGCTGCAGTGCATGAACACCAGCACGAGCTACCTCAGCAAGACGTTATT
    N  S  E  G  L  Q  C  M  N  T  S  T  S  Y  L  S  K  T  L  F

421 TGAAATTACAGTGCCTCTCTCTCAAGGCCCCAAACCAGTAACAATCAGTTTGCCAATCA
    E  I  T  V  P  L  S  Q  G  P  K  P  V  T  I  S  F  A  N  H

481 CACTTCCTGCCGATGCATGTCTAAACTGGATGTGTTTACAGACAAGTTCATTCCATTATTAG
    T  S  C  R  C  M  S  K  L  D  V  Y  R  Q  V  H  S  I  I  R

541 ACGTTCCCTGCCAGCAACACTACCACAGTGTCAGGCAGCGAACAAGACCTGCCCCACCAA
    R  S  L  P  A  T  L  P  Q  C  Q  A  A  N  K  T  C  P  T  N

601 TTACATGTGGAATAATCACATCTGCAGATGCCTGGCTCAGGAAGATTTTATGTTTTCCTC
    Y  M  W  N  N  H  I  C  R  C  L  A  Q  E  D  F  M  F  S  S

661 GGATGCTGGAGATGACTCAACAGATGGATTCCATGACATCTGTGGACCAAACAAGGAGCT
    D  A  G  D  D  S  T  D  G  F  H  D  I  C  G  P  N  K  E  L

FIG. 2B

```
721  GGATGAAGAGACCTGTCAGTGTGTCTGCAGAGCGGGGCTTCGGCCTGCCAGTGTGGACC
     ---------+---------+---------+---------+---------+---------+
      D  E  E  T  C  Q  C  V  C  R  A  G  L  R  P  A  S  C  G  P

781  CCACAAAGAACTAGACAGAAACTCATGCCAGTGTGTCTGTAAAACAAACTCTTCCCCAG
     ---------+---------+---------+---------+---------+---------+
      H  K  E  L  D  R  N  S  C  Q  C  V  C  K  N  K  L  F  P  S

841  CCAATGTGGGGCCCAACCCGAGAATTTGATGAAAACACATGCCAGTGTGTATGTAAAAGAAC
     ---------+---------+---------+---------+---------+---------+
      Q  C  G  A  N  R  E  F  D  E  N  T  C  Q  C  V  C  K  R  T

901  CTGCCCCCAGAAATCAACCCCCTAAATCCTGGAAAAATGTGCCTGTGAATGTACAGAAAGTCC
     ---------+---------+---------+---------+---------+---------+
      C  P  R  N  Q  P  L  N  P  G  K  C  A  C  E  C  T  E  S  P

961  ACAGAAATGCTTGTTAAAAGGAAAAGAAGTTCCACCACCAAACATGCAGCTGTTACAGACG
     ---------+---------+---------+---------+---------+---------+
      Q  K  C  L  L  K  G  K  K  F  H  H  Q  T  C  S  C  Y  R  R

1021 GCCATGTACGAACCGCCAGAAGGCTTGTGAGCCAGGATTTCATATAGTGAAGAAGTGTG
     ---------+---------+---------+---------+---------+---------+
      P  C  T  N  R  Q  K  A  C  E  P  G  F  S  Y  S  E  E  V  C
```

FIG. 2C

```
1081  TCGTTGTGTCCCTTCATATTGGCAAAGACCACAAATGAGCTAAGATTGTACTGTTTTCCA
      R  C  V  P  S  Y  W  Q  R  P  Q  M  S  *

1141  GTTCATCGATTTTCTATTATGGAAAACTGTGTTGCCACAGTAGAACTGTCTGTGAACAGA

1201  GAGACCCTTGTGGGTCCATGCTAACAAAGACAAAAGTCTGTGTCTTTCCTGAACCATGTGA

1261  TAACTTTACAGAAATGGACTGGAGCTCATCTGCAAAAGGCCTCTTGTAAAGACTGGTTTT

1321  CTGCCAATGACCAAACAGCCAAGATTTCCTCTTGTGATTTCTTTAAAAGAATGACTATA

1381  TAATTTATTTCCACTAAAAAATATTGTTTCTGCATTCATTTTTATAGCAACACAATTGGT

1441  AAAAACTCACTGTGATCAATATTTTTATATCATGCAAAATATGTTTAAAATAAAATGAAAA

1501  TTGTATTATAAAAAAAAAAAAAAA
```

FIG. 2D

```
      1   MRTLACLLL LGCCYLAHVL AEEAEIPREV IERLARSQIH SIRDLQRLLE      50
Pdgfa     MRTLACLLL LGCCYLAHVL AEEAEIPREV IERLARSQIH SIRDLQRLLE
Pdgfb     MNRCWA.LFL SLCCYLRLVS AEGDPIPEEL YEMLSDHSIR SFDDLQRLLH
Vegf      .....MNFLL SWVHWSLALL LY........ .......... .LHHAKWSQA
Vegf2     .....MTV LYPEYWKMYK CQ........ .......... .LRKGGWQHN 51                                                           100
Pdgfa     IDSVGSEDSL DTSLRAHCVH ATKHVPEKRP LPIRRKRSI. .......EEAVP
Pdgfb     GDP.GEEDGA ELDLNMTRSH SGGELES... .LARGRRSLG SLTIAEPAMI
Vegf      APMAE..... ......GGCQ NHHEVKFMD .VYQR..... ..........
Vegf2     REQANLNSRT EETIKFAAAH YNTEILKSID NEWRK..... ..........

101                                                           150
Pdgfa     AVCKTRTVIY EIPRSQVDPT SANFLIWPPC VEVKRCTGCC NTSSVKCQPS
Pdgfb     AECKTRTEVF EISRRLIDRT .......... NANFLVWPPC VEVQRCSGCC NNRNVQCRPT
Vegf      SYCHPIETLV DIFQEYPDEI ..EYIFKPSC VPLMRCGGCC NDEGLEQVPT
Vegf2     TQCMPREVCI DVGKEFGVAT ..NTFFKPPC VSVYRCGGCC NSEGLQCMNT 151                                                           200
Pdgfa     RVHHRSVKVA KVEYVRKKPK LKEVQVRLEE HLECAC.... ..AT...... ..........
Pdgfb     QVQLRPVQVR KIEIVRKKPI FKKATVTLED HLACKC.... ETVAAARPVT
Vegf      EESNITMQIM RIK.PH..QG QHIGEMSFLQ HNKCECRPKK DRARQEKKSV
Vegf2     STSYLSKTLF EIT.VPLSQG PKPVTISFAN HTSCRCMSKL DVYRQVHSII
```

FIG. 3A

```
        201        TSLNPD YREEDTDVR.                                                            250
Pdgfa    RSPGGSQEQR AKTPQTRVTI RTVRVRRPPK GKHRKFKHTH DKTALKETLG
Pdgfb    RGK...... .GKGQKRKRK KSRYKSWSVY VGARCCLMPW SLPGPHP...
Vegf     RRSLPATLPQ CQAANKTCPT NYMWNNHICR CLAQEDFMFS SDAGDDSTDG
Vegf2

251                                                                                     300
Pdgfa    ..........
Pdgfb    A......... .CGP....
Vegf     .......... .......... .......... .....CSE   RRKHLFVQDP QTCKCSCKNT
Vegf2    FHDICGPNKE LDEETCQCVC RAGLRPASCG PHKEL...DR NSCQCVCKNK 301                                                                                     350
Pdgfa    ..........
Pdgfb    ..........
Vegf     .DSRCKARQ LELNERTCRC DKPRR
Vegf2    LFPSQCGANR EFDENTCQC  VCKRTCPRNQ PLNPGKCACE CTESPQKCLL 351                                                     398
Pdgfa    ..........
Pdgfb    ..........
Vegf     ..........
Vegf2    KCKKFHHQTC SCYRRPCTNR QKACEPGFSY SEEVCRCVPS YWQRPQMS

FIG. 3B
```

PERCENTAGE (%) OF AMINO ACID IDENTITIES BETWEEN
EACH PAIR OF GENES IS SHOWN IN THE
FOLLOWING TABLE

|  | PDGFα | PDGFβ | VEGF | VEGF-2 |
|---|---|---|---|---|
| PDGFα |  |  |  |  |
| PDGFβ | 48.0 |  |  |  |
| VEGF | 20.7 | 22.7 |  |  |
| VEGF-2 | 23.5 | 22.4 | 30.0 |  |

FIG. 4

Expression of VEGF-2 mRNA in Human Adult Tissues

| | | | |
|---|---|---|---|
| 1. | Ovary | 6. | Lung |
| 2. | Testes | 7. | Spleen |
| 3. | Gall Blader | 8. | Prostate |
| 4. | Kidney | 9. | Hippocampus |
| 5. | Liver | 10. | Heart |

Lane 1: 14-C and rainbow M.W. marker
Lane 2: FGF control
Lane 3: VEGF2 (M13-reverse & forward primer)
Lane 4: VEGF2 (M13-reverse & VEGF-F4 primer)
Lane 5: VEGF2 (M13-reverse & VEGF-F5 primer)

Lane M: Marker
Lane 1: Vector medium
Lane 2: VEGF2 medium

Lane M: Marker
Lane 1: vector cytoplasm
Lane 2: vector medium
Lane 3: VEGF2 cytoplasm
Lane 4: VEGF2 medium Lane 1: Molelular weight marker
Lane 2: Precipitates containing VEGF2.

1. Molecular weight marker
2. Umbelical vein endothelial cells
3. Aortic smooth muscle cells
4. Dermal fibroblast 1. Molecular weight marker
2. Blank
3. Control protein-HA
4. Vector control
5. VEGF2-HA 1. Molecular weight marker
2. Blank
3. Control protein-HA
4. VEGF2-HA
5. Vector control

```
 1  A A G C T T A A A A A A C T G C A A A A A T A G T TTGACT TGTGAGCGGATAAGAAT
                                                    -35    OPERATOR 1

50 TAAGAT GTACCCA ATTGTGAGCGGATAACAAT TTCACACATTAA
    -10             OPERATOR 2

94 AGAGGAG AAATTA  CATATG
    S/D
```

FIG. 29

HindIII                     NcoI

AAGCTTGACCTTATGCGACTTTCCTACTTGGCAGTACATCTACGTATTAGTCATCGCTATTACCATGGTCATGCG
         +         +         +         +         +         +         +         75
TTCGAACTGGAATACGCTGAAAGGATGAACCGTCATGTAGATGCATAATCAGTAGCGATAATGGTACCACTACGC
                                    ————————— CMV Enhancer —————————

GTTTTGGCAGTACACATCAATGGGCGTGGATAGCGGTTTGACTCACGGGGATTTCCAAGTCTCCACCCCATTGACGT
         +         +         +         +         +         +         +         150
CAAAACCGTCATGTGTAGTTACCCGCACCTATCGCCAAACTGAGTGCCCCTAAAGGTTCAGAGGTGGGGTAACTGCA
————————————————————————————— CMV Enhancer —————————————————————————————

CAATGGGAGTTTGTTTTGGCACCAAAATCAACGAGACTTTCCAAAATGTCGTAACAACTCCGCCCCATTGACGCA
         +         +         +         +         +         +         +         225
GTTACCCTCAAACAAAACCGTGGTTTTAGTTGCTCTGAAAGGTTTTACAGCATTGTTGAGGCGGGGTAACTGCGT
————————————————————————————— CMV Enhancer —————————————————————————————

FIG.31A

```
GAGCAGTTACGGTCTCTGTGTCCAGTGTAGATGAACTCATGACTGTACTCTACCCAGAATATTGGAAAATGTACAAG
     ----+----+----+----+----+----+----+----+----+----+----+----+----+----+---    750
CTCGTCAATGCCAGACACAGGTCACATCTACTGAGTACTGACATGAGAATGGGTCTTATAACCTTTTACATGTTC
```
━━━━━━━━━━━━━━━━━━━━━━━━━━━━━━━━━━━━━━━━━━━━━━━━━━━━━━━━━━━━━━━━━━━━━━━━━━━━
          E  Q  L  R  S  V  S  S  V  D  E  L  M  T  V  L  Y  P  E  Y  W  K  M  Y  K
                                          VEGF-2

```
TGTCAGCTAAGGAGGCTGGCAACATAAACAGAGAACAGGCCAACCTCAACTCAAGGACAGAAGAGACTATA
----+----+----+----+----+----+----+----+----+----+----+----+----+----+----    825
ACAGTCGATTCCTTCCGACCGTTGTATTTGTCTCTTGTCCGGTTGGAGTTGAGTTCCTGTCTTCTCTGATAT
```
━━━━━━━━━━━━━━━━━━━━━━━━━━━━━━━━━━━━━━━━━━━━━━━━━━━━━━━━━━━━━━━━━━━━━━━━
    C  Q  L  R  K  G  G  W  Q  H  N  R  E  Q  A  N  L  N  S  R  T  E  E  T  I
                                          VEGF-2

PstI                      BglII

```
AAATTTGCTGCAGCACATTATAATACAGAGATCTTGAAAAGTATTGATAATGAGTGGAGAAAGACTCAATGCATG
----+----+----+----+----+----+----+----+----+----+----+----+----+----+----    900
TTTAAACGACGTCGTGTAATATTATGTCTCTAGAACTTTTCATAACTATTACTCACCTCTTTCTGAGTTACGTAC
```
━━━━━━━━━━━━━━━━━━━━━━━━━━━━━━━━━━━━━━━━━━━━━━━━━━━━━━━━━━━━━━━━━━━━━━━━━━━━
  K  F  A  A  H  Y  N  T  E  I  L  K  S  I  D  N  E  W  R  K  T  Q  C  M
                                          VEGF-2

FIG.31D

```
CCACGGGGAGGTGTGTATAGATGTGGGGAAGGAGTTTGGAGTCGCGACAAACACCTTCTTTAAACCTCCATGTGTG    975
————————+————————+————————+————————+————————+————————+————————+————————+
GGTGCCCTCCACACATATCTACACCCCTTCCTCAAACCTCAGCGCTGTTTGTGGAAGAAATTTGGAGGTACACAC

P   R   E   V   C   I   D   V   G   K   E   F   G   V   A   T   N   T   F   F   K   P   P   C   V
                                         ├─────── VEGF-2 ──────────────────────────────────────────
                                                                        PstI

TCCGTCTACAGATGTGGGGGTTGCTGCAATAGTGAGGGCTGCAGTGCATGAACACCAGCACGAGCTACCTCAGC    1050
————————+————————+————————+————————+————————+————————+————————+————————+
AGGCAGATGTCTACACCCCCAACGACGTTATCACTCCCGACGTCACGTACTTGTGGTCGTGCTCGATGGAGTCG

S   V   Y   R   C   G   G   C   C   N   S   E   G   L   Q   C   M   N   T   S   T   S   Y   L   S
                             ├─────── VEGF-2 ──────────────────────────────────────────

AAGACGTTATTTGAAATTACAGTGCCTCTCTCTCAAGGCCCCAAACCAGTAACAATCAGTTTTGCCAATCACACT    1125
————————+————————+————————+————————+————————+————————+————————+————————+
TTCTGCAATAAACTTTAATGTCACGGAGAGAGAGTTCCGGGGTTTGGTCATTGTTAGTCAAAACGGTTAGTGTGA

K   T   L   F   E   I   T   V   P   L   S   Q   G   P   K   P   V   T   I   S   F   A   N   H   T
                             ├─────── VEGF-2 ──────────────────────────────────────────
```

FIG. 31E

```
TCCTGCCGATGCATGTCTAAACTGGATGTGTTTACAGACAAGTTCATTCCATTATTAGACGTTCCCTGCCAGCAACA
                                                                              1200
AGGACGGCTACGTACAGATTTGACCTACACAAATGTCTGTTCAAGTAAGGTAATAATCTGCAAGGACGGTCGTTGT

S  C  R  C  M  S  K  L  D  V  Y  R  Q  V  H  S  I  I  R  R  S  L  P  A
    ─────────────────────────────── VEGF-2 ──────────────────────────────────

Pstl
CTACCACAGTGTCAGGCAGGCGAACAAGACCTGCCCCACCAATTACATGTGGAATAATCACATCTGCAGATGCCTG
                                                                              1275
GATGGTGTCACAGTCCGTCCGCTTGTTCTGGACGGGGTGGTTAATGTACACCTTATTAGTGTAGACGTCTACGGAC L  P  Q  Q  A  A  N  K  T  C  P  T  N  Y  M  W  N  N  H  I  C  R  C  L
 ──────────────────────────── VEGF-2 ─────────────────────────────────────

GCTCAGGAAGATTTTATGTTTTCCTCGGATGCTGGAGATGACTCAACAGATGGATTCCATGACATCTGTGGACCA
                                                                              1350
CGAGTCCTTCTAAAATACAAAAGGAGCCTACGACCTCTACTGAGTTGTCTACCTAAGGTACTGTAGACACCTGGT

A  Q  E  D  F  M  F  S  S  D  A  G  D  D  S  T  D  G  F  H  D  I  C  G  P
 ──────────────────────────── VEGF-2 ─────────────────────────────────────
```

```
AGCACCTTTGTGGTTCTCACTTGGTGGAAGCTCTCTACCTGGTGTGTGGGAGCGTGGATTCTTCTACACACCCA
     ----+----|----+----|----+----|----+----|----+----|----+----|----+----|   1875
TCGTGGAAACACCAAGAGTGAACCACCTTCGAGAGATGGACCACACACCCCTCGCACCTAAGAAGATGTGTGGGT
                                ———————— rppi poly A ————————

TGTCCCCGGCGGGGAAGTGGAGGACCCACAAGGTCTCTGCTCCTGAATTCTATCCCAAGTGCTAACTACCCTGT
     ----+----|----+----|----+----|----+----|----+----|----+----|----+----|   1950
ACAGGGGCCGCCCCTTCACCTCCTGGGTGTTCCATTCGAGACGAGGACTTAAGATAGGGTTCACGATTGATGGGACA
                                ———————— rppi poly A ————————

TTGTCTTTCACCCTTGAGACCTTGTAAAATTGTGCCCTAGGTGTGGAGGGTCTCAGGCTAACCAGTGGGGGCACA
     ----+----|----+----|----+----|----+----|----+----|----+----|----+----|   2025
AACAGAAAGTGGGAACTCTGGAACATTTAACACGGGATCCACACCTCCCAGAGTCCGATTGGTCACCCCCGTGT
                                ———————— rppi poly A ————————
```

FIG. 31I

```
TTTCTGTGGGCAGCTAGACATATGTAAACATGGTAGCTGCCAGGAAGGAGTGAGAATCCTTCCTTAAGTCTCCTA  2100
AAAGACACCCGTCGATCTGTATACATTTGTACCATCGACGGTCCTTCCTCACTCTTAGGAAGGAATTCAGAGGAT
                                    ——— rppi poly A ———

KpnI
GGTGGTGACGGGTGGCTAGGCCCCAGGATAGGTACCTATTTGGGGACCCCATAGAGCACTGACTGAGGA  2175
CCACCACTGCCCACCGATCCGGGGTCCTATCCATGGATAAACCCCTGGGTATCTCGTGACTGACTCCCT
                                    ——— rppi poly A ———

TGGTAACAGGATGTGTAGGTTTTGGAGGCCCATATGTCCATTCATGACCAGTGACTTGTCTCACAGCCATGCAAC  2250
ACCATTGTCCTACACATCCAAAACCTCCGGGTATACAGGTAAGTACTGGTCACTGAACAGAGTGTCGGTACGTTG
                                    ——— rppi poly A ———

FIG.31J
```

```
GCCACCACTACCCTGTCCACCCCTCTGCAATGAATAAAACCTTTGAAAGAGCACTACAAGTTGTGTGTACATGC
     +         +         +         +         +         +         +      2625
CGGGTGGTGATGGACAGGTGGGGAGACGTTACTTATTTGGAAACTTTCTCGTGATGTTCAACACACATGTACG

——————————————— rppi poly A ———————————————

GTGCATGTGCATATGTGTGGTGCGGGGGAACATGAGTGGGGCTGGCTGGAGTGGTCGCGGCTTAATCTATCTGGCA
     +         +         +         +         +         +         +      2700
CACGTACACGTATACACCACGCCCCCTTGTACTCACCCCGACCGACCTCACCAGCGCCGAATTAGATAGACCGT

——————————————— rppi poly A ———|

PvuII XbaI
   |  |
GCTGTCTAGACGTAATCATGGTCATAGCTGTTTCCTGTGTGAAATTGTTATCCGCTCACAATTCCACACAACATA
     +         +         +         +         +         +         +      2775
CGACAGATCTGCATTAGTACCAGTATCGACAAAGGACACACTTTAACAATAGGCGAGTGTTAAGGTGTGTTGTAT

CGAGCCCGGAAGCATAAAGTGTAAAGCCTGGGGTGCCTAATGAGTGAGCTAACTCACATTAATTGCGTTGCGCTCA
     +         +         +         +         +         +         +      2850
GCTCGGGCCTTCGTATTTCACATTTCGGACCCCACGGATTACTCACTCGATTGAGTGTAATTAACGCAACGCGAGT
```

FIG.31L

```
                                                                                        2925
CTGCCCGCTTTCCAGTCGGGGAAACCTGTCGTGCCAGCTGCATTAATGAATCGGCCAACGCGCGGGGAGAGGCGGT
----+----+----+----+----+----+----+----+----+----+----+----+----+----+----
GACGGGCGAAAGGTCAGCCCCCTTTGGACAGCACGGTCGACGTAATTACTTAGCCGGTTGCGCGCCCCTCTCCGCCA
     Pvull 3000
TTGCGTATTGGGCGCTCTTCCGCTTCCTCGCTCACTGACTCGCTGCGCTCGGTCGTTCGGCTGCGGCGAGCGGTA
----+----+----+----+----+----+----+----+----+----+----+----+----+----+----
AACGCATAACCCGCGAGAAGGCGAAGGAGCGAGTGACTGAGCGACGCGAGCCAGCAAGCCGACGCCGCTCGCCAT 3075
TCAGCTCACTCAAAGGCGGTAATACGGTTATCCACAGAATCAGGGGATAACGCAGGAAAGAACATGTGAGCAAAA
----+----+----+----+----+----+----+----+----+----+----+----+----+----+----
AGTCGAGTGAGTTTCCGCCATTATGCCAATAGGTGTCTTAGTCCCCTATTGCGTCCTTTCTTGTACACTCGTTTT 3150
GGCCAGCAAAAGGCCAGGAACCGTAAAAAGGCCGCGTTGCTGGCGTTTTTCCATAGGCTCCGCCCCCCTGACGAG
----+----+----+----+----+----+----+----+----+----+----+----+----+----+----
CCGGTCGTTTTCCGGTCCTTGGCATTTTTCCGGCGCAACGACCGCAAAAAGGTATCCGAGGCGGGGGACTGCTC
```

FIG.31M

```
CATCACAAAAATCGACGCTCAAGTCAGAGGTGGGCGAAACCCGACAGGACTATAAAGATACCAGGCGTTTCCCCT   3225
----------+---------+---------+---------+---------+---------+---------+----
GTAGTGTTTTTAGCTGCGAGTTCAGTCTCCACCCGCTTTGGGCTGTCCTGATATTTCTATGGTCCGCAAAGGGGA

GGAAGCTCCCTCGTGCGCTCTCCTGTTCCGACCCTGCCGCTTACCGGATACCTGTCCGCCTTTCTCCCTTCGGGA   3300
----------+---------+---------+---------+---------+---------+---------+----
CCTTCGAGGGAGCACGCGAGAGGACAAGGCTGGGACGGCGAATGGCCTATGGACAGGCGGAAAGAGGGAAGCCCT

AGCGTGGCGCTTTCTCATAGCTCACGCTGTAGGTATCTCAGTTCGGTGTAGGTCGTTCGCTCCAAGCTGGGCTGT   3375
----------+---------+---------+---------+---------+---------+---------+----
TCGCACCGCGAAAGAGTATCGAGTGCGACATCCATAGAGTCAAGCCACATCCAGCAAGCGAGGTTCGACCCGACA

GTGCACGAACCCCCCGTTCAGCCCGACCGCTGCCGCTTATCCGGTAACTATCGTCTTGAGTCCAACCCGGTAAGA   3450
----------+---------+---------+---------+---------+---------+---------+----
CACGTGCTTGGGGGCAAGTCGGGCTGGCGACGGCGGAATAGGCCATTGATAGCAGAACTCAGGTTGGGCCATTCT

CACGACTTATCGCCACTGGCAGCAGCCACTGGTAACAGGATTAGCAGAGCGAGGTATGTAGGCGGTGCTACAGAG   3525
----------+---------+---------+---------+---------+---------+---------+----
GTGCTGAATAGCGGTGACCGTCGTCGGTGACCATTGTCCTAATCGTCTCGCTCCATACATCCGCCACGATGTCTC
```

FIG.31N

```
TTCTTGAAGTGGTGGCCTAACTACGGCTACACTAGAGAACAGTATTTGGTATCTGCGCTCTGCTGAAGCCAGTT    3600
AAGAACTTCACCACCGGATTGATGCCGATGTGATCTTCTTGTCATAAACCATAGACGCGAGACGACTTCGGTCAA

ACCTTCGGAAAAAGAGTTGGTAGCTCTTGATCCGGCAAACAAACCACCGCTGGTAGCGGTGGTTTTTTGTTTGC    3675
TGGAAGCCTTTTCTCAACCATCGAGAACTAGGCCGTTTGTTGGTGGCCGACCATCGGCCACCAAAAACAAACG

AAGCAGCAGATTACGCGCAGAAAAAAAGGATCTCAAGAAGATCCTTTGATCTTTTCTACGGGGTCTGACGCTCAG    3750
TTCGTCGTCTAATGCGCGTCTTTTTTCCTAGAGTTCTTCTAGGAAACTAGAAAAGATGCCCCAGACTGCGAGTC
                                                         SalI

TGGAACGAAAACTCACGTTAAGGGATTTTGGTCATGAGATTATCGTCGACCAAAGCGGCCATCGTGCCTCCCCAC    3825
ACCTTGCTTTTGAGTGCAATTCCCTAAAACCAGTACTCTAATAGCAGCTGGTTCGCCGGTAGCACGGAGGGGTG
```

FIG.31O

```
                                                                            3900
PstI          TCCTGCAGTTCGGGGCATGGATGCGCGGATAGCCGCTGCTGGTTTCCTGGATGCCGACGGATTTGCACTGCCGG
              AGGACGTCAAGCCCCGTACCTACGCGCCTATCGGCGACGACCAAAGGACCTACGGCTGCCTAAACGTGACGGCC

3975
              TAGAACTCCGCGAGGTCGTCCAGCCTCAGGCAGCTGAACCAACTCGCGAGGGATCGAGCCCGGGTGGGCG
                                                    PvuII              SmaI
              ATCTTGAGGCGCTCCAGCAGCAGGTCGGAGTCCGTCGACTTGGTTGAGCGCTCCCTAGCTCGGGCCCACCCGC

4050
              AAGAACTCCAGCATGAGATCCCCGCGCTGGAGGATCATCCAGCCGCGTCCCGGAAAACGATTCCGAAGCCCAAC
              TTCTTGAGGTCGTACTCTAGGGGCGCGACCTCCTAGTAGGTCGGCGCAGGGCCTTTTGCTAAGGCTTCGGGTTG

4125
              CTTTCATAGAAGGCGGTGGAATCGAAATCTCGTGATGGCCAGGTTGGGCGTCGCTTGGTCGGTCATTTCGAAC
              GAAAGTATCTTCCGCCACCTTAGCTTTAGAGCACTACCGGTCCAACCCGCAGCGAACCAGCCAGTAAAGCTTG
```

FIG. 31P

```
CCCAGAGTCCCGCTCAGAAGAACTCGTCAAGAAGGCGATAGAAGGCTGCGAATCGGGAGCGGCGATAC
       +         +         +         +         +         +         + 4200
GGGTCTCAGGGCGAGTCTTCTTGAGCAGTTCTTCCGCTATCTTCCGACGCTTAGCCCTCGCCGCTATG

F  F  E  D  L  L  R  Y  F  A  I  R  Q  S  D  P  A  A  I       G
  ←—————————————————————————————————————————————————————————
                                 kan r CGTAAAGCCACGAGGAAGCGGTCAGCCCATTCGCCCGCCAAGCTCTTCAGCAATATCACGGGTAGCCAACGCTATGT
       +         +         +         +         +         +         + 4275
GCATTTCGTGCTCCTTCGCCAGTCGGGTAAGCGGGCGGTTCGAGAAGTCGTTATAGTGCCCATCGGTTGCGATACA Y  L  V  F  R  D  A  W  E  G  G  L  E  E  A  I  D  R  T  A  L  A  I  D
  ———————————————————————————————————————————————————————————————
                                 kan r CCTGATAGCCGGTCCGCCACACCCAGCCGGGCCACAGTCGATGAATCCAGAAAAAGCGGCCATTTTCCACCATGATAT
       +         +         +         +         +         +         + 4350
GGACTATCGGCCAGGCGGTGTGGGCCGGGTCCAGCTACTTAGGTCTTTTTCGCCGGTAAAAGGTGGTACTATA Q  Y  R  D  A  V  G  L  R  G  C  D  I  F  G  S  F  R  G  N  E  V  M  I  N
  ———————————————————————————————————————————————————————————————
                                 kan r
```

FIG. 31Q

NcoI

```
TCGGCAAGCAGGCATCGGCCATGGGTCACGACGAGATCCTCGCCGTCGGGCATGCGCCCTTGAGCCTGGCGAACA
----+----+----+----+----+----+----+----+----+----+----+----+----+----+----
AGCCGTTCGTCCGTAGCCGGTACCCAGTGCTGCTCTAGGAGCGGCAGCCCGTACGCGGGAACTCGGACCGCTTGT
                                                                          4425
```

P L C A D G H kan r V V L D E G D P M R A K L R A F L

```
GTTCGGCTGGCGCGAGCCCCTGATGCTCTTCGTCCAGATCATCCTGATCGACAAGACCGGCTTCCATCCGAGTAC
----+----+----+----+----+----+----+----+----+----+----+----+----+----+----
CAAGCCGACCGCGCTCGGGGACTACGAGAAGCAGGTCTAGTAGGACTAGTGTTCTGGCCGAAGGTAGGCTCATG
                                                                          4500
```

E A P A L G Q H E E D kan r L D D Q D V L G A E M R I R

```
GTGCTCGCTCGATGCGGATGTTTCGCTTGGGTGGTCGAATGGGTCGAAGGCTAGCCGGATCAAGCCGTATGCAGCCGCCA
----+----+----+----+----+----+----+----+----+----+----+----+----+----+----
CACGAGCGAGCTACGCCTACAAAGCGAACCCACCAGCTTACCCAGCTTCCGATCGGCCTAGTTCGGCATACGTCGGCGGT
                                                                          4575
```

A R E I R H K A Q H D F kan r P C T A P D L T H L R R M

FIG.31R

```
                                                                    4650
TTGCATCAGCCATGATGGATACTTTCTCGGCAGGAGCAAGGTGAGATGACAGGAGATCCTGCCCCGGCACTTCGC
   +    +    +    +    +    +    +
AACGTAGTCGGTACTACCTATGAAAGAGCCGTCCTCGTTCCACTCTACTGTCCTCTAGGACGGGGCCGTGAAGCG

A  D  A  M  I  S  V  K  E  A  P  A  L  H  S  S  L  L  D  Q  G  P  V  E  G
                          ────────────kan r────────────

Pvu II
                                                                    4725
CCAATAGCAGCCAGTCCCTTCCCGCTTCAGTGACAACAGCTGCGCAAGGAACGCCGTCGTGGCCA
   +    +    +    +    +    +    +
GGTTATCGTCGGTCAGGGAAGGGCGAAGTCACTGTTGTCGACGCGTTCCTTGCGGCAGCACCGGT

L  L  L  W  D  R  G  A  E  T  V  V  D  L  V  A  A  C  P  V  G  T  T  A  L
                          ────────────kan r────────────
```

FIG. 31S

```
                                                                                    4800
GCCACGATAGCCGCGCTGCCTCGTCCTGCAGTTCATTCAGGGCACCGGACAGGTCGGTCTTGACAAAAGAACCG
CGGTGCTATCGGCGCGACGGAGACGAGGACGTCAAGTAAGTCCCGTGGCCTGTCCAGCCAGAACTGTTTTCTTGGC
```
W S L R A E D Q L E N L A G S L D T K V F L V P
——————————————————————————kan r——————————————————————————

```
                                                                                    4875
GGCGCCCCTGCGCTGACAGCCGGAACACGGGCATCAGAGCAGCCGATTGTCTGTTGTGCCCAGTCATAGCCGA
CCGCGGGGACGCGACTGTCGGCCTTGTGCCCGTAGTCTCGTCGGCTAACAGACAACACGGGTCAGTATCGGCT
```
R G Q A S L R F V A A D S C G I T Q Q A W D Y G F
——————————————————————————kan r——————————————————————————

```
                                                                                    4950
ATAGCCTCTCCACCAAGCGGCCGGAGAACCTGCCGTGCAATCCATCTTGTTCAATCATGCGAAACGATCCTCATC
TATCGGAGAGGTGGTTCGCCGGCCTCTTGGACGGCACGTTAGGTAGAACAAGTTAGTACGCTTTGCTAGGAGTAG
```
L R E V W A A P S G A H L G D Q E I M
——————————————————————————kan r——————————————————————————

Pstl

FIG.31T

```
                                                                              5025
BglII
CTGTCTCTTGATCAGATCTTGATCCCCTGCGCCATCAGATCCTTGGCGGCAAGAAAGCCATCCAGTTTACTTTGC
GACAGAGAACTAGTCTAGAACTAGGGGACGCGGTAGTCTAGGAACCGCCGTTCTTTCGGTAGGTCAAATGAAACG

5100
                PvuII
AGGGCTTCCCCAACCTTACCAGAGGGCGCCCCAGCTGGCAATTCCGGTTCGCTTGCTGTCCATAAAACCCCCCAGT
TCCCGAAGGGGTTGGAATGGTCTCCCGCGGGGTCGACCGTTAAGGCCAAGCGAACGACAGGTATTTTGGGGGGTCA

5175
CTAGCTATCGCCATGTAAGCCCACTGCAAGCTACCTGCTTTCTCTTTGCGCTTGCGTTTTCCCTTGTCCAGATAG
GATCGATAGCGGTACATTCGGGTGACGTTCGATGGACGTTCGATGGACGAAAGAGAAACGCGAACGCAAAAGGGAACAGGTCTATC

5250
CCCAGTAGCTGACATTCATCCGGGGTCAGCGGGACTGGCTTTCTGCGACTGGCTTTCTACGTGTCCCGCTTCCTTTAGC
GGGTCATCGACTGTAAGTAGGCCCAGTCGTGGCAAAGACGCCTGACCGAAAGATGCACAAGGCGAAGGAAATCG

AGCCCTTGCGCCCTGAGTGCTTGCGGCAGCCGTG   5283
TCGGGAACGCGGGACTCACGAACGCCGTCGCAC
```

FIG.31U

VASCULAR ENDOTHELIAL GROWTH FACTOR-2

This application claims benefit of 35 U.S.C. section 119(e) based on copending U.S. Provisional Application Ser. No. 60/223,276, filed Aug. 4, 2000, herein incorporated by reference in its entirety.

BACKGROUND OF THE INVENTION

The present invention relates to newly identified polynucleotides, polypeptides encoded by such polynucleotides, the use of such polynucleotides and polypeptides, as well as the production of such polynucleotides and polypeptides. The polypeptides of the present invention have been identified as members of the vascular endothelial growth factor family. More particularly, the polypeptides of the present invention are human vascular endothelial growth factor 2 (VEGF-2). The invention also relates to inhibiting the action of such polypeptides.

The formation of new blood vessels, or angiogenesis, is essential for embryonic development, subsequent growth, and tissue repair. Angiogenesis is also an essential part of certain pathological conditions, such as neoplasia (i.e., tumors and gliomas). Abnormal angiogenesis is associated with other diseases such as inflammation, rheumatoid arthritis, psoriasis, and diabetic retinopathy (Folkman, J. and Klagsbrun, M., Science 235:442–447(1987)).

Both acidic and basic fibroblast growth factor molecules are mitogens for endothelial cells and other cell types. Angiotropin and angiogenin can induce angiogenesis, although their functions are unclear (Folkman, J., Cancer Medicine, Lea and Febiger Press, pp. 153–170 (1993)). A highly selective mitogen for vascular endothelial cells is vascular endothelial growth factor or VEGF (Ferrara, N. et al., Endocr. Rev. 13:19–32 (1992)), which is also known as vascular permeability factor (VPF).

Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifunctional regulator of endothelial cell growth and differentiation (Breier, G. et al., Development 114:521–532 (1992)).

VEGF shares sequence homology with human platelet-derived growth factors, PDGFa and PDGFb (Leung, D. W., et al., Science 246:1306–1309, (1989)). The extent of homology is about 21% and 23%, respectively. Eight cysteine residues contributing to disulfide-bond formation are strictly conserved in these proteins. Although they are similar, there are specific differences between VEGF and PDGF. While PDGF is a major growth factor for connective tissue, VEGF is highly specific for endothelial cells. Alternatively spliced mRNAs have been identified for both VEGF, PLGF, and PDGF and these different splicing products differ in biological activity and in receptor-binding specificity. VEGF and PDGF function as homo-dimers or hetero-dimers and bind to receptors which elicit intrinsic tyrosine kinase activity following receptor dimerization.

VEGF has four different forms of 121, 165, 189 and 206 amino acids due to alternative splicing. VEGF121 and VEGF165 are soluble and are capable of promoting angiogenesis, whereas VEGF189 and VEGF-206 are bound to heparin containing proteoglycans in the cell surface. The temporal and spatial expression of VEGF has been correlated with physiological proliferation of the blood vessels (Gajdusek, C. M., and Carbon, S. J., Cell Physiol. 139: 570–579 (1989); McNeil, P. L., et al., J. Cell. Biol. 109: 811–822 (1989)). Its high affinity binding sites are localized only on endothelial cells in tissue sections (Jakeman, L. B., et al., Clin. Invest. 89:244–253 (1989)). The factor can be isolated from pituitary cells and several tumor cell lines, and has been implicated in some human gliomas (Plate, K. H., Nature 359:845–848 (1992)). Interestingly, expression of VEGF121 or VEGF165 confers on Chinese hamster ovary cells the ability to form tumors in nude mice (Ferrara, N. et al., J. Clin. Invest. 91:160–170 (1993)). The inhibition of VEGF function by anti-VEGF monoclonal antibodies was shown to inhibit tumor growth in immune-deficient mice (Kim, K. J., Nature 362:841–844 (1993)). Further, a dominant-negative mutant of the VEGF receptor has been shown to inhibit growth of glioblastomas in mice.

Vascular permeability factor (VPF) has also been found to be responsible for persistent microvascular hyperpermeability to plasma proteins even after the cessation of injury, which is a characteristic feature of normal wound healing. This suggests that VPF is an important factor in wound healing. Brown, L. F. et al., J. Exp. Med. 176:1375–1379 (1992).

The expression of VEGF is high in vascularized tissues, (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sep. 30, 1992.

SUMMARY OF THE INVENTION

The polypeptides of the present invention have been putatively identified as a novel vascular endothelial growth factor based on amino acid sequence homology to human VEGF.

In accordance with one aspect of the present invention, there are provided novel mature polypeptides, as well as biologically active and diagnostically or therapeutically useful fragments, analogs, and derivatives thereof. The polypeptides of the present invention are of human origin.

In accordance with another aspect of the present invention, there are provided isolated nucleic acid molecules comprising polynucleotides encoding full length or truncated VEGF-2 polypeptides having the amino acid sequences shown in SEQ ID NOS:2 or 4, respectively, or the amino acid sequences encoded by the cDNA clones deposited in bacterial hosts as ATCC Deposit Number 97149 on May 12, 1995 or ATCC Deposit Number 75698 on Mar. 4, 1994.

The present invention also relates to biologically active and diagnostically or therapeutically useful fragments, analogs, and derivatives of VEGF-2.

In accordance with still another aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said proteins and subsequent recovery of said proteins.

In accordance with yet a further aspect of the present invention, there are provided processes for utilizing such polypeptides, or polynucleotides encoding such polypeptides for therapeutic purposes, for example, to stimulate angiogenesis, wound-healing, growth of damaged bone and tissue, and to promote vascular tissue repair. In particular, there are provided processes for utilizing such polypeptides, or polynucleotides encoding such polypeptides, for treatment of peripheral artery disease, such as critical limb ischemia and coronary disease.

In accordance with yet another aspect of the present invention, there are provided antibodies against such polypeptides and processes for producing such polypeptides.

In accordance with yet another aspect of the present invention, there are provided antagonists to such polypeptides, which may be used to inhibit the action of such polypeptides, for example, to prevent tumor angiogenesis and thus inhibit the growth of tumors, to treat diabetic retinopathy, inflammation, rheumatoid arthritis and psoriasis.

In accordance with another aspect of the present invention, there are provided nucleic acid probes comprising nucleic acid molecules of sufficient length to specifically hybridize to nucleic acid sequences of the present invention.

In accordance with another aspect of the present invention, there are provided methods of diagnosing diseases or a susceptibility to diseases related to mutations in nucleic acid sequences of the present invention and proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A–1E show the full length nucleotide (SEQ ID NO:1) and the deduced amino acid (SEQ ID NO:2) sequence of VEGF-2. The polypeptide comprises approximately 419 amino acid residues of which approximately 23 represent the leader sequence. The standard one letter abbreviations for amino acids are used. Sequencing was performed using the Model 373 Automated DNA Sequencer (Applied Biosystems, Inc.). Sequencing accuracy is predicted to be greater than 97%.

FIGS. 2A–2D show the nucleotide (SEQ ID NO:3) and the deduced amino acid (SEQ ID NO:4) sequence of a truncated, biologically active form of VEGF-2. The polypeptide comprises approximately 350 amino acid residues of which approximately the first 24 amino acids represent the leader sequence.

FIGS. 3A–3B are an illustration of the amino acid sequence homology between PDGFa (SEQ ID NO:5), PDGFb (SEQ ID NO:6), VEGF (SEQ ID NO:7), and VEGF-2 (SEQ ID NO:4). The boxed areas indicate the conserved sequences and the location of the eight conserved cysteine residues.

FIG. 4 shows, in table-form, the percent homology between PDGFa, PDGFb, VEGF, and VEGF-2.

(FIGS. 26c and d depict the decreased mean arterial pressure (MAP) observed with VEGF-2. Panel E shows the effect of increasing doses of VEGF-2 on the mean arterial pressure (MAP) of SHR rats. Panel F shows the effect of VEGF-2 on the diastolic pressure of SHR rats. Panel G shows the effect of VEGF-2 on the diastolic blood pressure of SHR rats.

FIG. 29 shows the nucleotide sequence of the regulatory elements of the pHE4a promoter (SEQ ID NO:17). The two lac operator sequences, the Shine-Delgarno sequence (S/D), and the terminal HindIII and NdeI restriction sites (italicized) are indicated.

DETAILED DESCRIPTION OF THE PREFERRED EMBODIMENTS

Figure 5:
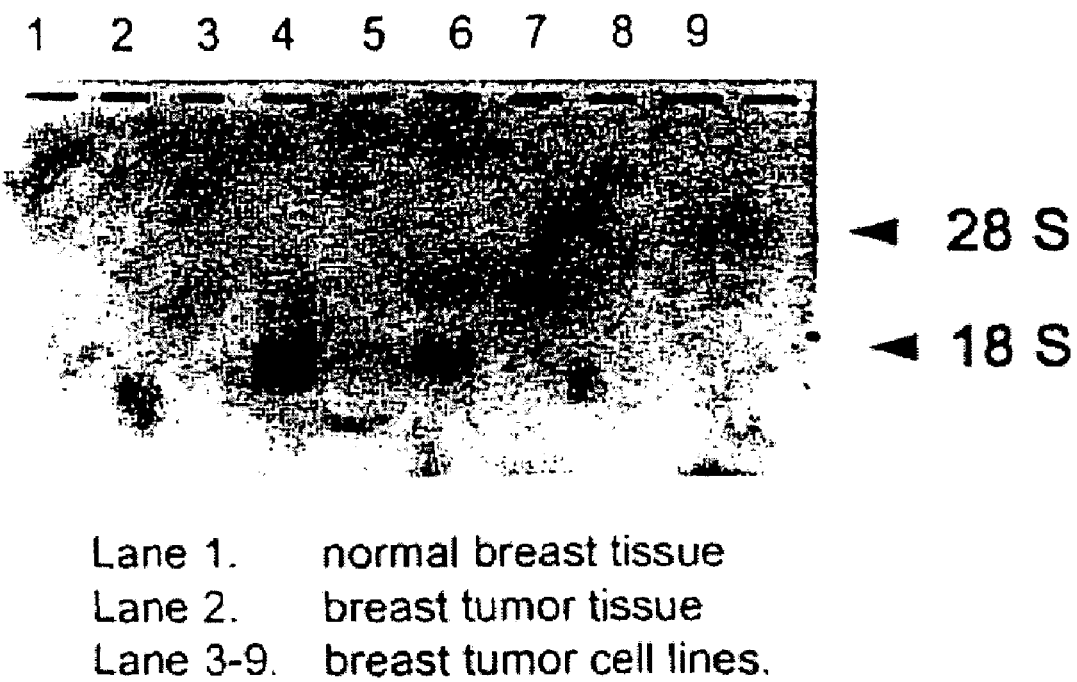
FIG. 5 shows the presence of VEGF-2 mRNA in human breast tumor cell lines.

In accordance with one aspect of the present invention, there are provided isolated nucleic acid molecules comprising a polynucleotide encoding a VEGF-2 polypeptide having the deduced amino acid sequence of FIG. 1 (SEQ ID NO:2), which was determined by sequencing a cloned cDNA. The nucleotide sequence shown in SEQ ID NO:1 was obtained by sequencing a cDNA clone, which was deposited on May 12, 1995 at the American Type Tissue Collection (ATCC), 10801 University Boulevard, Manassas, Va. 20110-2209, and given ATCC Deposit No. 97149.

In accordance with another aspect of the present invention, there are provided isolated nucleic acid molecules comprising a polynucleotide encoding a truncated VEGF-2 polypeptide having the deduced amino acid sequence of FIG. 2 (SEQ ID NO:4), which was determined by sequencing a cloned cDNA. The nucleotide sequence shown in SEQ ID NO:3 was obtained by sequencing a cDNA clone, which was deposited on Mar. 4, 1994 at the American Type Tissue Collection (ATCC), 10801 University Boulevard, Manassas, Va. 20110-2209, and given ATCC Deposit Number 75698.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 419 amino acid residues of which approximately the first 23 amino acid residues are the putative leader sequence such that the mature protein comprises 396 amino acids, and which protein exhibits the highest amino acid sequence homology to human vascular endothelial growth factor (30% identity), followed by PDGFa (24%) and PDGFb (22%). (See FIG. 4). It is particularly important that all eight cysteines are conserved within all four members of the family (see boxed areas of FIG. 3). In addition, the signature for the PDGF/VEGF family, PXCVXXXRCXGCCN, (SEQ ID NO:8) is conserved in VEGF-2 (see FIG. 3). The homology between VEGF-2, VEGF and the two PDGFs is at the protein sequence level. No nucleotide sequence homology can be detected, and therefore, it would be difficult to isolate the VEGF-2 through simple approaches such as low stringency hybridization.

The VEGF-2 polypeptide of the present invention is meant to include the full length polypeptide and polynucleotide sequence which encodes for any leader sequences and for active fragments of the full length polypeptide. Active fragments are meant to include any portions of the full length amino acid sequence which have less than the full 419 amino acids of the full length amino acid sequence as shown in SEQ ID NO:2, but still contain the eight cysteine residues shown conserved in FIG. 3 and that still have VEGF-2 activity.

There are at least two alternatively spliced VEGF-2 mRNA sequences present in normal tissues. The two bands in FIG. 7, lane 5 indicate the presence of the alternatively spliced mRNA encoding the VEGF-2 polypeptide of the present invention.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or FIG. 2, or that of the deposited clones, or may be a different coding sequence which, as a result of the redundancy or degeneracy of the genetic code, encodes the same, mature polypeptide as the DNA of FIG. 1, FIG. 2, or the deposited cDNAs.

The polynucleotide which encodes for the mature polypeptide of FIG. 1 or FIG. 2 or for the mature polypeptides encoded by the deposited cDNAs may include: only the coding sequence for the mature polypeptide; the coding sequence for the mature polypeptide and additional coding sequences such as a leader or secretory sequence or a proprotein sequence; the coding sequence for the mature polypeptide (and optionally additional coding sequences) and non-coding sequences, such as introns or non-coding sequence 5' and/or 3' of the coding sequence for the mature polypeptide.

Thus, the term "polynucleotide encoding a polypeptide" encompasses a polynucleotide which includes only coding sequences for the polypeptide as well as a polynucleotide which includes additional coding and/or non-coding sequences.

The present invention further relates to variants of the hereinabove described polynucleotides which encode for fragments, analogs, and derivatives of the polypeptide having the deduced amino acid sequence of FIG. 1 or 2, or the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or 2 or the same mature polypeptide encoded by the cDNA of the deposited clones as well as variants of such polynucleotides which variants encode for a fragment, derivative, or analog of the polypeptides of FIG. 1 or 2, or the polypeptide encoded by the cDNA of the deposited clones. Such nucleotide variants include deletion variants, substitution variants, and addition or insertion variants.

As hereinabove indicated, the polynucleotide may have a coding sequence which is a naturally occurring allelic variant of the coding sequence shown in FIG. 1 or 2, or of the coding sequence of the deposited clones. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell* 37:767 (1984)).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 396 in SEQ ID NO:2; (d) a nucleotide sequence encoding the polypeptide having the amino acid sequence encoded by the cDNA clone contained in ATCC Deposit No.97149; (e) a nucleotide sequence encoding the mature VEGF-2 polypeptide having the amino acid sequence encoded by the cDNA clone contained in ATCC Deposit No.97149; or (f) a nucleotide sequence complementary to any of the nucleotide sequences in (a), (b), (c), (d), or (e).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:4; (b) a nucleotide sequence encoding the polypeptide having the amino acid sequence in SEQ ID NO:4, but lacking the N-terminal methionine; (c) a nucleotide sequence encoding the polypeptide having the amino acid sequence at positions from about 1 to about 326 in SEQ ID NO:4; (d) a nucleotide sequence encoding the polypeptide having the amino acid sequence encoded by the cDNA clone contained in ATCC Deposit No.75698; (e) a nucleotide sequence encoding the mature VEGF-2 polypeptide having the amino acid sequence encoded by the cDNA clone contained in ATCC Deposit No.75698; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a VEGF-2 polypeptide is intended that the nucleotide sequence of the polynucleotide is identical to the reference sequence except that the polynucleotide sequence may include up to five point mutations per each 100 nucleotides of the reference nucleotide sequence encoding the VEGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5N or 3N terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NOS:1 or 3, or to the nucleotides sequence of the deposited cDNA clone(s) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As described in detail below, the polypeptides of the present invention can be used to raise polyclonal and monoclonal antibodies, which are useful in diagnostic assays for detecting VEGF-2 protein expression as described below or as agonists and antagonists capable of enhancing or inhibiting VEGF-2 protein function. Further, such polypeptides can be used in the yeast two-hybrid system to "capture" VEGF-2 protein binding proteins which are also candidate agonist and antagonist according to the present invention. The yeast two hybrid system is described in Fields and Song, Nature 340:245–246 (1989).

In another aspect, the invention provides a peptide or polypeptide comprising an epitope-bearing portion of a polypeptide of the invention. As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate VEGF-2-specific antibodies include the following: a polypeptide comprising amino acid residues from about leu-37 to about glu-45 in SEQ ID NO:2, from about Tyr-58 to about Gly-66 in SEQ ID NO:2, from about Gln-73 to about Glu-81 in SEQ ID NO:2, from about Asp-100 to about Cys-108 in SEQ ID NO:2, from about Gly-140 to about Leu-148 in SEQ ID NO:2, from about Pro-168 to about Val-176 in SEQ ID NO:2, from about His-183 to about Lys-191 in SEQ ID NO:2, from about Ile-201 to about Thr-209 in SEQ ID NO:2, from about Ala-216 to about Tyr-224 in SEQ ID NO:2, from about Asp-244 to about His-254 in SEQ ID NO:2, from about Gly-258 to about Glu-266 in SEQ ID NO:2, from about Cys-272 to about Ser-280 in SEQ ID NO:2, from about Pro-283 to about Ser-291 in SEQ ID NO:2, from about Cys-296 to about Gln-304 in SEQ ID NO:2, from about Ala-307 to about Cys-316 in SEQ ID NO:2, from about Val-319 to about Cys-335 in SEQ ID NO:2, from about Cys-339 to about Leu-347 in SEQ ID NO:2, from about Cys-360 to about Glu-373 in SEQ ID NO:2, from about Tyr-378 to about Val-386 in SEQ ID NO:2, and from about Ser-388 to about Ser-396 in SEQ ID NO:2. These polypeptide fragments have been determined to bear antigenic epitopes of the VEGF-2 protein by the analysis of the Jameson-Wolf antigenic index.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide that acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al, supra; Chow, M. et al., Proc. Natl. Acad. Sci. USA 82:910–914; and Bittle, F. J. et al, J. Gen. Virol. 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 mg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a Amimotope) which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, VEGF-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)).

In accordance with the present invention, novel variants of VEGF-2 are also described. These can be produced by deleting or substituting one or more amino acids of VEGF-2. Natural mutations are called allelic variations. Allelic variations can be silent (no change in the encoded polypeptide) or may have altered amino acid sequence.

In order to attempt to improve or alter the characteristics of native VEGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

Amino Terminal and Carboxy Terminal Deletions

Figure 6:
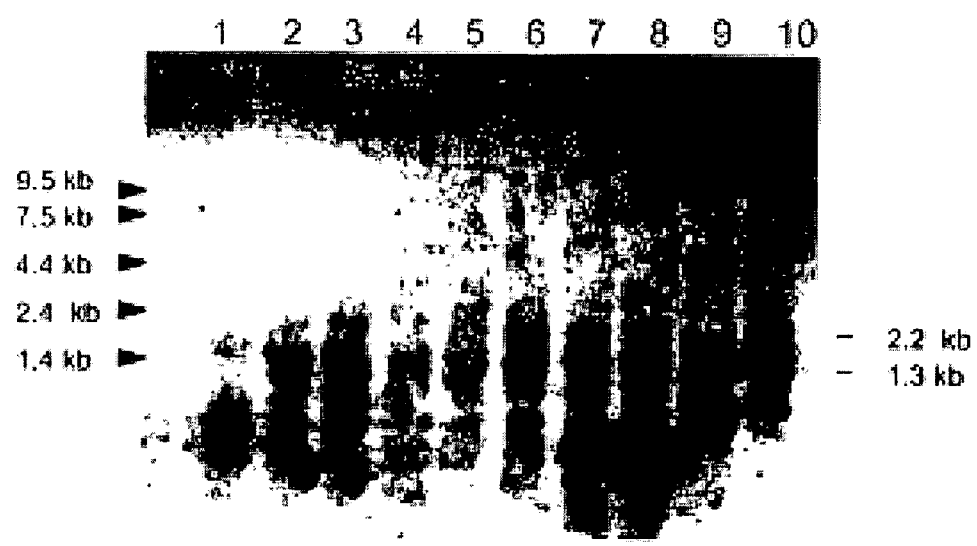
FIG. 6 depicts the results of a Northern blot analysis of VEGF-2 in human adult tissues.

Furthermore, VEGF-2 appears to be proteolytically cleaved upon expression resulting in polypeptide fragments of the following sizes when run on a SDS-PAGE gel (sizes are approximate) (See, FIGS. 6–8, for example): 80, 59, 45, 43, 41, 40, 39, 38, 37, 36, 31, 29, 21, and 15 kDa. These polypeptide fragments are the result of proteolytic cleavage at both the N-terminal and C-terminal portions of the protein. These proteolytically generated fragments appears to have activity, particularly the 21 kDa fragment.

In addition, protein engineering may be employed in order to improve or alter one or more characteristics of native VEGF-2. The deletion of carboxyterminal amino acids can enhance the activity of proteins. One example is interferon gamma that shows up to ten times higher activity by deleting ten amino acid residues from the carboxy terminus of the protein (Döbeli et al., *J. of Biotechnology* 7:199–216 (1988)). Thus, one aspect of the invention is to provide polypeptide analogs of VEGF-2 and nucleotide sequences encoding such analogs that exhibit enhanced stability (e.g., when exposed to typical pH, thermal conditions or other storage conditions) relative to the native VEGF-2 polypeptide.

Particular preferred VEGF-2 polypeptides are shown below (numbering starts with the first amino acid in the protein (Met) FIG. 1 (SEQ ID NO: 2)): Ala(residue 25) to Ser(residue 419); Pro(26) to Ser(419); Ala(27) to Ser(419); Ala(28) to Ser(419); Ala(29) to Ser(419); Ala(30) to Ser (419); Ala(31) to Ser(419); Phe(32) to Ser(419); Glu(33) to Ser(419); Ser(34) to Ser(419); Gly(35) to Ser(419); Leu(36) to Ser(419); Asp(37) to Ser(419); Leu(38) to (Ser(419); Ser(39) to Ser(419); Asp(40) to Ser(419); Ala(41) to Ser (419); Glu(42) to Ser(419); Pro(43) to Ser(419); Asp(44) to Ser(419); Ala(45) to Ser(419); Gly(46) to Ser(419); Glu(47) to Ser(419); Ala(48) to Ser(419); Thr(49) to Ser(419); Ala (50) to Ser(419); Tyr(51) to Ser(419); Ser(53) to Ser(419); Asp(55) to Ser(419); Val(63) to Ser(419); Val(66) to Ser (419); Met(1), Glu(24), or Ala(25) to Met(418); Met(1), Glu(24), or Ala(25) to Gln(417); Met(1), Glu(24), or Ala(25) to Pro(416); Met(1), Glu(24), or Ala(25) to Arg(415); Met (1), Glu(24), or Ala(25) to Gln(414); Met(1), Glu(24), or Ala(25) to Trp(413); Met(1), Glu(24), or Ala(25) to Tyr (412); Met(1), Glu(24), or Ala(25) to Ser(411); Met(1), Glu(24), or Ala(25) to Pro(410); Met(1), Glu(24), or Ala(25) to Val(409); Met(1), Glu(24), or Ala(25) to Cys(408); Met (1), Glu(24), or Ala(25) to Arg(407); Met(1), Glu(24), or Ala(25) to Cys(406); Met(1), Glu(24), or Ala(25) to Val (405); Met(1), Glu(24), or Ala(25) to Glu(404); Met(1), Glu(24), or Ala(25) to Glu(403); Met(1), Glu(24), or Ala(25) to Ser(402); Met(1), Glu(24), or Ala(25) to Gly(398); Met (1), Glu(24), or Ala(25) to Pro(397); Met(1), Glu(24), or Ala(25) to Lys(393); Met(1), Glu(24), or Ala(25) to Met (263); Met(1), Glu(24), or Ala(25) to Asp(311); Met(1), Glu(24), or Ala(25) to Pro(366); Met(1) to Ser(419); Met(1) to Ser(228); Glu(47) to Ser(419); Ala(111) to Lys(214); Ala(112) to Lys(214); His(113) to Lys(214); Tyr(114) to Lys(214); Asn(115) to Lys(214); Thr(116) to Lys(214); Thr(103) to Leu(215); Glu(104) to Leu(215); Glu(105) to Leu(215); Thr(106) to Leu(215); Ile(107) to Leu(215); Lys (108) to Leu(215); Phe(109) to Leu(215); Ala(110) to Leu (215); Ala(111) to Leu(215); Ala(112) to Leu(215); His(113) to Leu(215); Tyr(114) to Leu(215); Asn(115) to Leu(215); Thr(116) to Leu(215); Thr(103) to Ser(228); Glu(104) to Ser(228); Glu(105) to Ser(228); Thr(106) to Ser(228); Ile (107) to Ser(228); Lys(108) to Ser(228); Phe(109) to Ser (228); Ala(110) to Ser(228); Ala(111) to Ser(228); Ala(112) to Ser(228); His(113) to Ser(228); Tyr(114) to Ser(228); Asn(115) to Ser(228); Thr(116) to Ser(228); Thr(103) to Leu(229); Glu(104) to Leu(229); Thr(103) to Arg(227); Glu(104) to Arg(227); Glu(105) to Arg(227); Thr(106) to Arg(227); Ile(107) to Mg(227); Lys(108) to Arg(227); Phe (109) to Arg(227); Ala(110) to Arg(227); Ala(111) to Arg (227); Ala(112) to Arg(227); His(113) to Arg(227); Tyr(114) to Arg(227); Asn(115) to Arg(227); Thr(116) to Arg(227); Thr(103) to Ser(213); Glu(104) to Ser(213); Glu(105) to Ser(213); Thr(106) to Ser(213); Ile(107) to Ser(213); Lys (108) to Ser(213); Phe(109) to Ser(213); Ala(110) to Ser (213); Ala(111) to Ser(213); Ala(112) to Ser(213); His(113) to Ser(213); Tyr(114) to Ser(213); Asn(115) to Ser(213); Thr(116) to Ser(213); Thr(103) to Lys(214); Glu(104) to Lys(214); Glu(105) to Lys(214); Thr(106) to Lys(214); Ile(107) to Lys(214); Lys(108) to Lys(214); Phe(109) to Lys(214); Ala(110) to Lys(214); Glu(105) to Leu(229); Thr(106) to Leu(229); Ile(107) to Leu(229); Lys(108) to Leu(229); Phe(109) to Leu(229); Ala(110) to Leu(229); Ala(111) to Leu(229); Ala(112) to Leu(229); His(113) to Leu(229); Tyr(114) to Leu(229); Asn(115) to Leu(229); Thr(116) to Leu(229).

Preferred embodiments include the following deletion mutants: Thr(103)—Arg(227); Glu(104)—Arg(227); Ala (112)—Arg(227); Thr(103)—Ser(213); Glu(104)—Ser (213); Thr(103)—Leu(215); Glu(47)—Ser(419); Met(1), Glu(24), or Ala(25)—Met(263); Met(1), Glu(24), or Ala (25)—Asp(311); Met(1), Glu(24), or Ala(25)—Pro(366); Met(1)—Ser(419); and Met(1)—Ser(228) of(FIG. 1 (SEQ ID NO: 2)).

Also included by the present invention are deletion mutants having amino acids deleted from both the NB terminus and the C-terminus. Such mutants include all combinations of the N-terminal deletion mutants and C-terminal deletion mutants described above. Those combinations can be made using recombinant techniques known to those skilled in the art.

Particularly, N-terminal deletions of the VEGF-2 polypeptide can be described by the general formula m-396, where m is an integer from −23 to 388, where m corresponds to the position of the amino acid residue identified in SEQ ID NO:2. Preferably, N-terminal deletions retain the conserved boxed area of FIG. 3 (PXCVXXXRCXGCCN)(SEQ ID NO: 8), and include polypeptides comprising the amino acid sequence of residues: N-terminal deletions of the polypeptide of the invention shown as SEQ ID NO:2 include polypeptides comprising the amino acid sequence of residues: : E-24 to S-419; A-25 to S-419; P-26 to S-419; A-27 to S-419; A-28 to S-419; A-29 to S-419; A-30 to S-419; A-31 to S-419; F-32 to S-419; E-33 to S-419; S-34 to S-419; G-35 to S-419; L-36 to S-419; D-37 to S-419; L-38 to S-419; S-39 to S-419 D-40 to S-419; A-41 to S-419; E-42 to S-419; P-43 to S-419; D-44 to S-419; A-45 to S-419; G-46 to S-419; E-47 to S-419; A-48 to S-419; T-49 to S-419; A-50 to S-419; Y-51 to S-419; A-52 to S-419; S-53 to S-419; K-54 to S-419; D-55 to S-419; L-56 to S-419; E-57 to S-419; E-58 to S-419; Q-59 to S-419; L-60 to S-419; R-61 to S-419; S-62 to S-419; V-63 to S-419; S-64 to S-419; S-65 to S-419; V-66 to S-419; D-67 to S-419; E-68 to S-419; L-69 to S-419; M-70 to S-419; T-71 to S-419; V-72 to S-419; L-73 to S-419; Y-74 to S-419; P-75 to S-419; E-76 to S-419; Y-77 to S-419; W-78 to S-419; K-79 to S-419; M-80 to S-419; Y-81 to S-419; K-82 to S-419; C-83 to S-419; Q-84 to S-419; L-85 to S-419; R-86 to S-419; K-87 to S-419; G-88 to S-419; G-89 to S-419; W-90 to S-419; Q-91 to S-419; H-92 to S-419; N-93 to S-419; R-94 to S-419; E-95 to S-419; Q-96 to S-419; A-97 to S-419; N-98 to S-419; L-99 to S-419; N-100 to S-419; S-101 to S-419; R-102 to S-419; T-103 to S-419; E-104 to S-419; E-105 to S-419; T-106 to S-419; I-107 to S-419; K-108 to S-419; F-109 to S-419; A-110 to S-419; A-111 to S-419; A-112 to S-419; H-113 to S-419; Y-114 to S-419; N-115 to S-419; T-116 to S-419; E-117 to S-419; I-118 to S-419; L-119 to S-419; K-120 to S-419; S-121 to S-419; I-122 to S-419; D-123 to S-419; N-124 to S-419; E-125 to S-419; W-126 to S-419; R-127to S-419; K-128S-419; T-129to S-419; Q-130 to S-419; C-131 to S-419; M-132 to S-419; P-133 to S-419; R-134to S-419; E-135 to S-419; V-136 to S-419; C-137 to S-419; I-138 to S-419;

D-139 to S-419; V-140 to S-419; G-141 to S-419; K-142 to S-419; E-143 to S-419; F144 to S-419; G-145 to S-419; V-146 to S-419; A-147 to S-419; T-148 to S-419 N-149 to S-419; T-150 to S-419; F-151 to S-419; F-152 to S-419; K-153 to S-419; P-154 to S-419; P-155 to S-419; C-156 to S-419; V-157 to S-419; S-158 to S-419; V-159 to S-419; Y-160 to S-419; R-161 to S-419; C-162 to S-419; G-163to S-419; G-164 to S-419; C-165 to S-419; C-166 to S-419; N-167 to S-419; S-168 to S-419; E-169 to S-419; G-170 to S-419; L-171 to S-419; Q-172 to S-419; C-173 to S-419; M-174 to S-419; N-175 to S-419; T-176 to S-419; S-177 to S-419; T-178 to S-419; S-179 to S-419; Y-180 to S-419; L-181 to S-419; S-182 to S-419; K-183 to S-419; T-184 to S-419; L-185 to S-419; F-186 to S-419; E-187 to S-419; I-188 to S-419; T-189 to S-419; V-190 to S-419; P-191 to S-419; L-192 to S-419; S-193 to S-419; Q-194 to S-419; G-195 to S-419; P-196 to S-419; K-197to S-419; P-198 to S-419; V-199 to S-419; T-200to S-419; I-201 to S-419; S-202 to S-419; F-203 to S-419; A-204 to S-419; N-205 to S-419; H-206 to S-419; T-207 to S-419; S-208 to S-419; C-209 to S-419; R-210 to S-419; C-211 to S-419; M-212 to S-419; S-213 to S-419; K-214 to S-419; L-215 to S-419; D-216 to S-419; V-217 to S-419; Y-218 to S-419; R-219 to S-419; Q-220 to S-419; V-221 to S-419; H-222to S-419; S-223to S-419; I-224to S-419; I-225 to S-419; R-226 to S-419; R-227 to S-419; S-228 to S-419; L-229 to S-419; P-230 to S-419; A-231 to S-419; T-232 to S-419; L-233 to S-419; P-234 to S-419; Q-235 to S-419; C-236 to S-419; Q-237 to S-419; A-238 to S-419; A-239to S-419; N-240 to S-419; K-241 to S-419; T-242 to S-419; C-243 to S-419; P-244 to S-419; T-245 to S-419; N-246 to S-419; Y-247 to S-419; M-248 to S-419; W-249 to S-419; N-250 to S-419; N-251 to S-419; H-252 to S-419; I-253 to S-419; C-254 to S-419; R-255 to S-419; C-256 to S-419; L-257 to S-419; A-258 to S-419; Q-259 to S-419; E-260 to S-419; D-261 to S-419; F-262 to S-419; M-263 to S-419; F-264 to S-419; S-265 to S-419; S-266 to S-419; D-267 to S-419; A-268 to S-419; G-269 to S-419; D-270 to S-419; D-271 to S-419; S-272 to S-419; T-273 to S-419; D-274 to S-419; G-275 to S-419; F-276 to S-419; H-277 to S-419; D-278 to S-419; I-279 to S-419; C-280 to S-419; G-281 to S-419; P-282 to S-419; N-283 to S-419; K-284 to S-419; E-285 to S-419; L-286 to S-419; D-287 to S-419; E-288 to S-419; E-289 to S-419; T-290 to S-419; C-291 to S-419; Q-292 to S-419; C-293 to S-419; V-294 to S-419; C-295to S-419; R-296 to S-419; A-297 to S-419; G-298 to S-419; L-299 to S-419; R-300 to S-419; P-301 to S-419; A-302 to S-419; S-303 to S-419; C-304 to S-419; G-305 to S-419; P-306 to S-419; H-307 to S-419; K-308 to S-419; E-309 to S-419; L-310 to S-419; D-311 to S-419; R-312 to S-419; N-313 to S-419; S-314 to S-419; C-315 to S-419; Q-316to S-419; C-317 to S-419; V-318 to S-419; C-319 to S-419; K-320 to S-419; N-321 to S-419; K-322 to S-419; L-323 to S-419; F-324 to S-419; P-325 to S-419; S-326 to S-419; Q-327 to S-419; C-328 to S-419; G-329 to S-419; A-330 to S-419; N-331 to S-419; R-332 to S-419; E-333 to S-419; F-334 to S-419; D-335 to S-419; E-336 to S-419; N-337 to S-419; T-338 to S-419; C-339 to S-419; Q-340to S-419; C-341 to S-419; V-342 to S-419; C-343 to S-419; K-344 to S-419; R-345 to S-419; T-346 to S-419; C-347 to S-419; P-348 to S-419; R-349 to S-419; N-350 to S-419; Q-351 to S-419; P-352 to S-419; L-353 to S-419; N-354 to S-419; P-355 to S-419; G-356 to S-419; K-357 to S-419; C-358to S-419; A-359 to S-419; C-360 to S-419; E-361 to S-419; C-362 to S-419; T-363 to S-419; E-364 to S-419; S-365 to S-419; P-366 to S-419; Q-367 to S-419; K-368to S-419; C-369 to S-419; L-370 to S-419; L-371 to S-419; K-372 to S-419; G-373 to S-419; K-374 to S-419; K-375 to S-419; F-376 to S-419; H-377 to S-419; H-378 to S-419; Q-379 to S-419; T-380 to S-419; C-381 to S-419; S-382 to S-419; C-383 to S-419; Y-384 to S-419; R-385 to S-419; R-386 to S-419; P-387 to S-419; C-388 to S-419; T-389 to S-419; N-390 to S-419; R-391 to S-419; Q-392 to S-419; K-393 to S-419; A-394 to S-419; C-395 to S-419; E-396 to S-419; P-397 to S-419; G-398 to S-419; F-399 to S-419; S-400 to S-419; Y-401 to S-419; S-402 to S-419; E-403 to S-419; E-404 to S-419; V-405 to S-419; C-406 to S-419; R-407 to S-419; C-408 to S-419; V-409 to S-419; P-410 to S-419; S-411 to S-419; Y-412 to S-419; W-413 to S-419; Q-414 to S-419of SEQ ID NO:2. One preferred embodiment comprises amino acids S-223 to S-419; of SEQ ID NO:2. Also preferred are polynucleotides encoding these polypeptides.

Moreover, C-terminal deletions of the VEGF-2 polypeptide can also be described by the general formula –23–n, where n is an integer from –15 to 395 where n corresponds to the position of amino acid residue identified in SEQ ID NO:2. Preferably, C-terminal deletions retain the conserved boxed area of FIG. 3 (PXCVXXXRCXGCCN)(SEQ ID NO: 8), and include polypeptides comprising the amino acid sequence of residues: Likewise, C-terminal deletions of the polypeptide of the invention shown as SEQ ID NO:2 include polypeptides comprising the amino acid sequence of residues: E-24 to M-418; E-24 to Q-417; E-24 to P-416; E-24 to R-415 E-24 to Q-414; E-24 to W-413; E-24 to Y-412; E-24 to S-411; E-24 to P-410; E-24 to V-409; E-24 to C-408; E-24 to R-407; E-24 to C-406; E-24 to V-405; E-24 to E-404; E-24 to E-403; E-24 to S-402; E-24 to Y-401; E-24 to S-400; E-24 to F-399; E-24 to G-398; E-24 to P-397; E-24 to E-396; E-24 to C-395; E-24 to A-394; E-24 to K-393; E-24 to Q-392; E-24 to R-391; E-24 to N-390; E-24 to T-389; E-24 to C-388; E-24 to P-387; E-24 to R-386; E-24 to R-385; E-24 to Y-384; E-24 to C-383; E-24 to S-382; E-24 to C-381; E-24 to T-380; E-24 to Q-379; E-24 to H-378; E-24 to H-377; E-24 to F-376; E-24 to K-375; E-24 to K-374; E-24 to G-373; E-24 to K-372; E-24 to L-371; E-24 to L-370; E-24 to C-369; E-24 to K-368; E-24 to Q-367; E-24 to P-366; E-24 to S-365; E-24 to E-364; E-24 to T-363; E-24 to C-362; E-24 to E-361; E-24 to C-360; E-24 to A-359; E-24 to C-358; E-24 to K-357; E-24 to G-356; E-24 to P-355; E-24 to N-354; E-24 to L-353; E-24 to P-352; E-24 to Q-351; E-24 to N-350; E-24 to R-349; E-24 to P-348; E-24 to C-347; E-24 to T-346; E-24 to R-345; E-24 to K-344; E-24 to C-343; E-24 to V-342; E-24 to C-341; E-24 to Q-340; E-24 to C-339; E-24 to T-338; E-24 to N-337; E-24 to E-336; E-24 to D-335; E-24 to F-334; E-24 to E-333; E-24 to R-332; E-24 to N-331; E-24 to A-330; E-24 to G-329; E-24 to C-328; E-24 to Q-327; E-24 to S-326; E-24 to P-325; E-24 to F-324; E-24 to L-323; E-24 to K-322; E-24 to N-321; E-24 to K-320; E-24 to C-319; E-24 to V-318; E-24 to C-317; E-24 to Q-316; E-24 to C-315; E-24 to S-314; E-24 to N-313; E-24 to R-312; E-24 to D-311; E-24 to L-310; E-24 to E-309; E-24 to K-308; E-24 to H-307; E-24 to P-306; E-24 to G-305; E-24 to C-304; E-24 to S-303; E-24 to A-302; E-24 to P-301; E-24 to R-300; E-24 to L-299; E-24 to G-298; E-24 to A-297; E-24 to R-296; E-24 to C-295; E-24 to V-294; E-24 to C-293; E-24 to Q-292; E-24 to C-291; E-24 to T-290; E-24 to E-289; E-24 to E-288; E-24 to D-287; E-24 to L-286; E-24 to E-285; E-24 to K-284; E-24 to N-283; E-24 to P-282; E-24 to G-281; E-24 to C-280; E-24 to I-279; E-24 to D-278; E-24 to H-277; E-24 to F-276; E-24 to G-275; E-24 to D-274; E-24 to T-273; E-24 to S-272; E-24 to D-271; E-24 to D-270; E-24 to G-269; E-24 to A-268; E-24 to D-267; E-24 to S-266; E-24 to S-265; E-24 to F-264; E-24 to M-263;

E-24 to F-262; E-24 to D-261; E-24 to E-260; E-24 to Q-259; E-24 to A-258; E-24 to L-257; E-24 to C-256; E-24 to R-255; E-24 to C-254; E-24 to I-253; E-24 to H-252; E-24 to N-251; E-24 to N-250; E-24 to W-249; E-24 to M-248; E-24 to Y-247; E-24 to N-246; E-24 to T-245; E-24 to P-244; E-24 to C-243; E-24 to T-242; E-24 to K-241; E-24 to N-240; E-24 to A-239; E-24 to A-238; E-24 to Q-237; E-24 to C-236; E-24 to Q-235; E-24 to P-234; E-24 to L-233; E-24 to T-232; E-24 to A-231; E-24 to P-230; E-24 to L-229; E-24 to S-228; E-24 to R-227; E-24 to R-226; E-24 to I-225; E-24 to I-224; E-24 to S-223; E-24 to H-222; E-24 to V-221; E-24 to Q-220; E-24 to R-219; E-24 to Y-218; E-24 to V-217; E-24 to D-216; E-24 to L-215; E-24 to K-214; E-24 to S-213; E-24 to M-212; E-24 to C-211; E-24 to R-210; E-24 to C-209; E-24 to S-208; E-24 to T-207; E-24 to H-206; E-24 to N-205; E-24 to A-204; E-24 to F-203; E-24 to S-202; E-24 to I-201; E-24 to T-200; E-24 to V-199; E-24 to P-198; E-24 to K-197; E-24 to P-196; E-24 to G-195; E-24 to Q-194; E-24 to S-193; E-24 to L-192; E-24 to P-191; E-24 to V-190; E-24 to T-189; E-24 to I-188; E-24 to E-187; E-24 to F-186; E-24 to L-185; E-24 to T-184; E-24 to K-183; E-24 to S-182; E-24 to L-181; E-24 to Y-180; E-24 to S-179; E-24 to T-178; E-24 to S-177; E-24 to T-176; E-24 to N-175; E-24 to M-174; E-24 to C-173; E-24 to Q-172; E-24 to L-171; E-24 to G-170; E-24 to E-169; E-24 to S-168; E-24 to N-167; E-24 to C-166; E-24 to C-165; E-24 to G-164; E-24 to G-163; E-24 to C-162; E-24 to R-161; E-24 to Y-160; E-24 to V-159; E-24 to S-158; E-24 to V-157; E-24 to C-156; E-24 to P-155; E-24 to P-154; E-24 to K-153; E-24 to F-152; E-24 to F-151; E-24 to T-150; E-24 to N-149; E-24 to T-148; E-24 to A-147; E-24 to V-146; E-24 to G-145; E-24 to F-144; E-24 to E-143; E-24 to K-142; E-24 to G-141; E-24 to V-140; E-24 to D-139; E-24 to I-138; E-24 to C-137; E-24 to V-136; E-24 to E-135; E-24 to R-134; E-24 to P-133; E-24 to M-132; E-24 to C-131; E-24 to Q-130; E-24 to T-129; E-24 to K-128; E-24 to R-127; E-24 to W-126; E-24 to E-125; E-24 to N-124; E-24 to D-123; E-24 to I-122; E-24 to S-121; E-24 to K-120; E-24 to L-119; E-24 to I-118; E-24 to E-117; E-24 to T-116; E-24 to N-115; E-24 to Y-114; E-24 to H-113; E-24 to A-112; E-24 to A-111; E-24 to A-110; E-24 to F-109; E-24 to K-108; E-24 to I-107; E-24 to T-106; E-24 to E-105; E-24 to E-104; E-24 to T-103; E-24 to R-102; E-24 to S-101; E-24 to N-100; E-24 to L-99; E-24 to N-98; E-24 to A-97; E-24 to Q-96; E-24 to E-95; E-24 to R-94; E-24 to N-93; E-24 to H-92; E-24 to Q-91; E-24 to W-90; E-24 to G-89; E-24 to G-88; E-24 to K-87; E-24 to R-86; E-24 to L-85; E-24 to Q-84; E-24 to C-83; E-24 to K-82; E-24 to Y-81; E-24 to M-80; E-24 to K-79; E-24 to W-78; E-24 to Y-77; E-24 to E-76; E-24 to P-75; E-24 to Y-74; E-24 to L-73; E-24 to V-72; E-24 to T-71; E-24 to M-70; E-24 to L-69; E-24 to E-68; E-24 to D-67; E-24 to V-66; E-24 to S-65; E-24 to S-64; E-24 to V-63; E-24 to S-62; E-24 to R-61; E-24 to L-60; E-24 to Q-59; E-24 to E-58; E-24 to E-57; E-24 to L-56; E-24 to D-55; E-24 to K-54; E-24 to S-53; E-24 to A-52; E-24 to Y-51; E-24 to A-50; E-24 to T-49; E-24 to A-48; E-24 to E-47; E-24 to G-46; E-24 to A-45; E-24 to D-44; E-24 to P-43; E-24 to E-42; E-24 to A-41; E-24 to D-40; E-24 to S-39; E-24 to L-38; E-24 to D-37; E-24 to L-36; E-24 to G-35; E-24 to S-34; E-24 to E-33; E-24 to F-32; E-24 to A-31; E-24 to A-30 of SEQ ID NO:2. Also preferred are polynucleotides encoding these polypeptides.

Moreover, the invention also provides polypeptides having one or more amino acids deleted from both the amino and the carboxyl termini, which may be described generally as having residues m-n of SEQ ID NO:2, where n and m are integers as described above.

Likewise, also preferred are C-terminal deletions of the VEGF-2 polypeptide of the invention shown as SEQ ID NO:2 which include polypeptides comprising the amino acid sequence of residues: F-32 to M-418; F-32 to Q-417; F-32 to P-416; F-32 to R-415; F-32 to Q-414; F-32 to W-413; F-32 to Y-412; F-32 to S-411; F-32 to P-410; F-32 to V-409; F-32 to C-408; F-32 to R-407; F-32 to C-406; F-32 to V-405; F-32 to E-404; F-32 to E-403; F-32 to S-402; F-32 to Y-401; F-32 to S-400; F-32 to F-399; F-32 to G-398; F-32 to P-397; F-32 to E-396; F-32 to C-395; F-32 to A-394; F-32 K-393; F-32 to Q-392; F-32 to R-391; F-32 to N-390; F-32 to T-389; F-32 to C-388; F-32 to P-387; F-32 to R-386; F-32 to R-385; F-32 to Y-384; F-32 to C-383; F-32 to S-382; F-32 to C-381; F-32 to T-380; F-32 to Q-379; F-32 to H-378; F-32 to H-377; F-32 to F-376; F-32 to K-375; F-32 to K-374; F-32 to G-373; F-32 to K-372; F-32 to L-371; F-32 to L-370; F-32 to C-369; F-32 to K-368; F-32 to Q-367; F-32 to P-366; F-32 to S-365; F-32 to E-364; F-32 to T-363; F-32 to C-362; F-32 to E-361; F-32 to C-360; F-32 to A-359; F-32 to C-358; F-32 to K-357; F-32 to G-356; F-32 to P-355; F-32 to N-354; F-32 to L-353; F-32 to P-352; F-32 to Q-351; F-32 to N-350; F-32 to R-349; F-32 to P-348; F-32 to C-347; F-32 to T-346; F-32 to R-345; F-32 to K-344; F-32 to C-343; F-32 to V-342; F-32 to C-341; F-32 to Q-340; F-32 to C-339; F-32 to T-338; F-32 to N-337; F-32 to E-336; F-32 to D-335; F-32 to F-334; F-32 to E-333; F-32 to R-332; F-32 to N-331; F-32 to A-330; F-32 to G-329; F-32 to C-328; F-32 to Q-327; F-32 to S-326; F-32 to P-325; F-32 to F-324; F-32 to L-323; F-32 to K-322; F-32 to N-321; F-32 to K-320; F-32 to C-319; F-32 to V-318; F-32 to C-317; F-32 to Q-316; F-32 to C-315; F-32 to S-314; F-32 to N-313; F-32 to R-312; F-32 to D-311; F-32 to L-310; F-32 to E-309; F-32 to K-308; F-32 to H-307; F-32 to P-306; F-32 to G-305; F-32 to C-304; F-32 to S-303; F-32 to A-302; F-32 to P-301; F-32 to R-300; F-32 to L-299; F-32 to G-298; F-32 to A-297; F-32 to R-296; F-32 to C-295; F-32 to V-294; F-32 to C-293; F-32 to Q-292; F-32 to C-291; F-32 to T-290; F-32 to E-289; F-32 to E-288; F-32 to D-287; F-32 to L-286; F-32 to E-285; F-32 to K-284; F-32 to N-283; F-32 to P-282; F-32 to G-281; F-32 to C-280; F-32 to I-279; F-32 to D-278; F-32 to H-277; F-32 to F-276; F-32 to G-275; F-32 to D-274; F-32 to T-273; F-32 to S-272; F-32 to D-271; F-32 to D-270; F-32 to G-269; F-32 to A-268; F-32 to D-267; F-32 to S-266; F-32 to S-265; F-32 to F-264; F-32 to M-263; F-32 to F-262; F-32 to D-261; F-32 to E-260; F-32 to Q-259; F-32 to A-258; F-32 to L-257; F-32 to C-256; F-32 to R-255; F-32 to C-254; F-32 to I-253; F-32 to H-252; F-32 to N-251; F-32 to N-250; F-32 to W-249; F-32 to M-248; F-32 to Y-247; F-32 to N-246; F-32 to T-245; F-32 to P-244; F-32 to C-243; F-32 to T-242; F-32 to K-241; F-32 to N-240; F-32 to A-239; F-32 to A-238; F-32 to Q-237; F-32 to C-236; F-32 to Q-235; F-32 to P-234; F-32 to L-233; F-32 to T-232; F-32 to A-231; F-32 to P-230; F-32 to L-229; F-32 to S-228; F-32 to R-227; F-32 to R-226; F-32 to I-225; F-32 to I-224; F-32 to S-223; F-32 to H-222; F-32 to V-221; F-32 to Q-220; F-32 to R-219; F-32 to Y-218; F-32 to V-217; F-32 to D-216; F-32 to L-215; F-32 to K-214; F-32 to S-213; F-32 to M-212; F-32 to C-211; F-32 to R-210; F-32 to C-209; F-32 to S-208; F-32 to T-207; F-32 to H-206; F-32 to N-205; F-32 to A-204; F-32 to F-203; F-32 to S-202; F-32 to I-201; F-32 to T-200; F-32 to V-199; F-32 to P-198; F-32 to K-197; F-32 to P-196; F-32 to G-195; F-32 to Q-194; F-32 to S-193; F-32 to L-192; F-32 to P-191; F-32 to V-190; F-32 to T-189; F-32 to I-188; F-32 to E-187; F-32 to F-186; F-32 to L-185; F-32 to T-184; F-32 to K-183; F-32 to S-182; F-32 to L-181; F-32 to Y-180; F-32 to S-179; F-32 to T-178; F-32 to S-177; F-32 to T-176; F-32 to N-175; F-32 to M-174; F-32 to C-173; F-32 to Q-172; F-32 to L-171;

F-32 to G-170; F-32 to E-169; F-32 to S-168; F-32 to N-167; F-32 to C-166; F-32 to C-165; F-32 to G-164; F-32 to G-163; F-32 to C-162; F-32 to R-161; F-32 to Y-160; F-32 to V-159; F-32 to S-158; F-32 to V-157; F-32 to C-156; F-32 to P-155; F-32 to P-154; F-32 to K-153; F-32 to F-152; F-32 to F-151; F-32 to T-150; F-32 to N-149; F-32 to T-148; F-32 to A-147; F-32 to V-146; F-32 to G-145; F-32 to F-144; F-32 to E-143; F-32 to K-142; F-32 to G-141; F-32 to V-140; F-32 to D-139; F-32 to I-138; F-32 to C-137; F-32 to V-136; F-32 to B-135; F-32 to R-134; F-32 to P-133; F-32 to M-132; F-32 to C-131; F-32 to Q-130; F-32 to T-129; F-32 to K-128; F-32 to R-127; F-32 to W-126; F-32 to E-125; F-32 to N-124; F-32 to D-123; F-32 to I-122; F-32 to S-121; F-32 to K-120; F-32 to L-119; F-32 to I-118; F-32 to E-117; F-32 to T-116; F-32 to N-115; F-32 to Y-114; F-32 to H-113; F-32 to A-112; F-32 to A-111; F-32 to A-110; F-32 to F-109; F-32 to K-108; F-32 to I-107; F-32 to T-106; F-32 to E-105; F-32 to E-104; F-32 to T-103; F-32 to R-102; F-32 to S-101; F-32 to N-100; F-32 to L-99; F-32 to N-98; F-32 to A-97; F-32 to Q-96; F-32 to E-95; F-32 to R-94; F-32 to N-93; F-32 to H-92; F-32 to Q-91; F-32 to W-90; F-32 to G-89; F-32 to G-88; F-32 to K-87; F-32 to R-86; F-32 to L-85; F-32 to Q-84; F-32 to C-83; F-32 to K-82; F-32 to Y-81; F-32 to M-80; F-32 to K-79; F-32 to W-78; F-32 to Y-77; F-32 to E-76; F-32 to P-75; F-32 to Y-74; F-32 to L-73; F-32 to V-72; F-32 to T-71; F-32 to M-70; F-32 to L-69; F-32 to E-68; F-32 to D-67; F-32 to V-66; F-32 to S-65; F-32 to S-64; F-32 to V-63; F-32 to S-62; F-32 to R-61; F-32 to L-60; F-32 to Q-59; F-32 to E-58; F-32 to E-57; F-32 to L-56; F-32 to D-55; F-32 to K-54; F-32 to S-53; F-32 to A-52; F-32 to Y-28 51; F-32 to A-50; F-32 to T-49; F-32 to A-48; F-32 to E-47; F-32 to G-46; F-32 to A-45; F-32 to D-44; F-32 to P-43; F-32 to E-42; F-32 to A-41; F-32 to D-40; F-32 to S-39; F-32 to L-38; of SEQ ID NO:2. Specifically preferred is the polypeptide fragment comprising amino acid residues F-32 to R-226 of SEQ ID NO:2, as well as polynucleotides encoding this polypeptide. This F-32 to R-226 of SEQ ID NO:2 polypeptide preferably is associated with a S-228 to S-419 of SEQ ID NO:2 polypeptide. Association may be through disulfide, covalent or noncovalent interactions, by linkage via a linker (e.g. serine, glycine, proline linkages), or by an antibody.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1660 of SEQ ID NO:1, b is an integer of 15 to 1674, where both a and b correspond to the positions of nucleotide residues shown in SEQ ID NO: 1, and where the b is greater than or equal to a+14.

Thus, in one aspect, N-terminal deletion mutants are provided by the present invention. Such mutants include those comprising the amino acid sequence shown in FIG. 1 (SEQ ID NO: 2) except for a deletion of at least the first 24 N-terminal amino acid residues (i.e., a deletion of at least Met(1)—Glu(24)) but not more than the first 115 N-terminal amino acid residues of FIG. 1 (SEQ ID NO: 2). Alternatively, first 24 N-terminal amino acid residues (i.e., a deletion of at least Met(1)—Glu(24)) but not more than the first 103 N-terminal amino acid residues of FIG. 1 (SEQ ID NO: 2), etc.

In another aspect, C-terminal deletion mutants are provided by the present invention. Such mutants include those comprising the amino acid sequence shown in FIG. 1 (SEQ ID NO: 2) except for a deletion of at least the last C-terminal amino acid residue (Ser(419)) but not more than the last 220 C-terminal amino acid residues (i.e., a deletion of amino acid residues Val(199)–Ser(419)) of FIG. 1 (SEQ ID NO: 2). Alternatively, the deletion will include at least the last C-terminal amino acid residue but not more than the last 216 C-terminal amino acid residues of FIG. 1 (SEQ ID NO: 2). Alternatively, the deletion will include at least the last C-terminal amino acid residue but not more than the last 204 C-terminal amino acid residues of FIG. 1 (SEQ ID NO: 2). Alternatively, the deletion will include at least the last C-terminal amino acid residues but not more than the last 192 C-terminal amino acid residues of FIG. 1 (SEQ ID NO: 2). Alternatively, the deletion will include at least the last C-terminal amino acid residues but not more than the last 156 C-terminal amino acid residues of FIG. 1 (SEQ ID NO: 2). Alternatively, the deletion will include at least the last C-terminal amino acid residues but not more than the last 108 C-terminal amino acid residues of FIG. 1 (SEQ ID NO: 2). Alternatively, the deletion will include at least the last C-terminal amino acid residues but not more than the last 52 C-terminal amino acid residues of FIG. 1 (SEQ ID NO: 2).

In yet another aspect, also included by the present invention are deletion mutants having amino acids deleted from both the N-terminal and C-terminal residues. Such mutants include all combinations of the N-terminal deletion mutants and C-terminal deletion mutants described above.

The term "gene" means the segment of DNA involved in producing a polypeptide chain; it includes regions preceding and following the coding region (leader and trailer) as well as intervening sequences (introns) between individual coding segments (exons).

The present invention is further directed to fragments of the isolated nucleic acid molecules described herein. By a fragment of an isolated nucleic acid molecule having the nucleotide sequence of the deposited cDNA(s) or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650 or 1674 nt in length are also useful according to the present invention as are fragments corresponding to most, if not all, of the nucleotide sequence of the deposited cDNA(s) or as shown in SEQ ID NO:1 or SEQ ID NO:3. By a fragment at least 20 nt in length, for example, is intended fragments which include 20 or more contiguous bases from the nucleotide sequence of the deposited cDNA(s) or the nucleotide sequence as shown in SEQ ID NOS:1 or 3.

Moreover, representative examples of VEGF-2 polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, or 951 to the end of SEQ ID NO:1 or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

A VEGF-2 "polynucleotide" also includes those polynucleotides capable of hybridizing, under stringent hybridization conditions, to sequences contained in SEQ ID NO:1 or for instance, the cDNA clone(s) contained in ATCC Deposit Nos. 97149 or 75698, the complement thereof. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the VEGF-2 polynucleotides at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1). Of course, a polynucleotide which hybridizes only to a poly A sequence (such as the 3N terminal poly(A) tract of the VEGF-2 cDNA shown in SEQ ID NOS:1 or 3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The present application is directed to nucleic acid molecules at least 95%, 96%, 97%, 98% or 99% identical to the nucleic acid sequence shown in SEQ ID NOS:1 or 3 or to the nucleic acid sequence of the deposited cDNA(s), irrespective of whether they encode a polypeptide having VEGF-2 activity. This is because even where a particular nucleic acid molecule does not encode a polypeptide having VEGF-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having VEGF-2 activity include, inter alia, (1) isolating the VEGF-2 gene or allelic variants thereof in a cDNA library; (2) in situ hybridization (e.g., "FISH") to metaphase chromosomal spreads to provide precise chromosomal location of the VEGF-2 gene, as described in Verma et al., *Human Chromosomes: A Manual of Basic Techniques,* Pergamon Press, New York (1988); and Northern Blot analysis for detecting VEGF-2 mRNA expression in specific tissues.

Preferred, however, are nucleic acid molecules having sequences at least 95%, 96%, 97%, 98% or 99% identical to a nucleic acid sequence shown in SEQ ID NOS:1 or 3 or to a nucleic acid sequence of the deposited cDNA(s) which do, in fact, encode a polypeptide having VEGF-2 protein activity. By "a polypeptide having VEGF-2 activity" is intended polypeptides exhibiting VEGF-2 activity in a particular biological assay. For example, VEGF-2 protein activity can be measured using, for example, mitogenic assays and endothelial cell migration assays. See, e.g., Olofsson et al., *Proc. Natl. Acad. Sci. USA* 93:2576–2581 (1996) and Joukov et al., *EMBO J.* 5:290–298 (1996).

Of course, due to the degeneracy of the genetic code, one of ordinary skill in the art will immediately recognize that a large number of the nucleic acid molecules having a sequence at least 90%, 95%, 96%, 97%, 98%, or 99% identical to a nucleic acid sequence of the deposited cDNA(s) or the nucleic acid sequence shown in SEQ ID NO:1 or SEQ ID NO:3 will encode a polypeptide "having VEGF-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having VEGF-2 protein activity. This is because the skilled artisan is fully aware of amino acid substitutions that are either less likely or not likely to significantly effect protein function (e.g. replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Thus, the present invention is directed to polynucleotides having at least a 70% identity, preferably at least 90% and more preferably at least a 95%, 96%, 97%, or 98% identity to a polynucleotide which encodes the polypeptides of SEQ ID NOS:2 or 4, as well as fragments thereof, which fragments have at least 30 bases and preferably at least 50 bases and to polypeptides encoded by such polynucleotides.

"Identity" per se has an art-recognized meaning and can be calculated using published techniques. (See, e.g.: (COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991).) While there exists a number of methods to measure identity between two polynucleotide or polypeptide sequences, the term "identity" is well known to skilled artisans. (Carillo, H., and Lipton, D., *SIAM J. Applied Math.* 48:1073 (1988).) Methods commonly employed to determine identity or similarity between two sequences include, but are not limited to, those disclosed in "Guide to Huge Computers," Martin J. Bishop, ed., Academic Press, San Diego, (1994), and Carillo, H., and Lipton, D., *SIAM J. Applied Math.* 48:1073 (1988). Methods for aligning polynucleotides or polypeptides are codified in computer programs, including the GCG program package (Devereux, J., et al., *Nucleic Acids Research* 12(1):387 (1984)), BLASTP, BLASTN, FASTA (Atschul, S. F. et al., *J. Molec. Biol.* 215:403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, *Advances in Applied Mathematics* 2:482–489 (1981)). By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the VEGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence SEQ ID NO:1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-terminal of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

VEGF-2 Polypeptides

The present invention further relates to polypeptides which have the deduced amino acid sequence of FIG. 1 or 2, or which has the amino acid sequence encoded by the deposited cDNAs, as well as fragments, analogs, and derivatives of such polypeptides.

The terms "fragment," "derivative" and "analog" when referring to the polypeptide of FIG. 1 or 2 or that encoded by the deposited cDNA, means a polypeptide which retains the conserved motif of VEGF proteins as shown in FIG. 3 and essentially the same biological function or activity.

In the present invention, a "polypeptide fragment" refers to a short amino acid sequence contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, 161–180, 181–200, 201–220, 221–240, 241–260, 261–280, or 281 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted VEGF-2 protein as well as the mature form. Further preferred polypeptide fragments include the secreted VEGF-2 protein or the mature form having a continuous series of deleted residues from the amino or the carboxy terminus, or both. For example, any number of amino acids, ranging from 1–60, can be deleted from the amino terminus of either the secreted VEGF-2 polypeptide or the mature form. Similarly, any number of amino acids, ranging from 1–30, can be deleted from the carboxy terminus of the secreted VEGF-2 protein or mature form. Furthermore, any combination of the above amino and carboxy terminus deletions are preferred. Similarly, polynucleotide fragments encoding these VEGF-2 polypeptide fragments are also preferred.

Also preferred are VEGF-2 polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. (See FIG. 2.) Moreover, polynucleotide fragments encoding these domains are also contemplated.

Other preferred fragments are biologically active VEGF-2 fragments. Biologically active fragments are those exhibiting activity similar, but not necessarily identical, to an activity of the VEGF-2 polypeptide. The biological activity of the fragments may include an improved desired activity, or a decreased undesirable activity.

The polypeptides of the present invention may be recombinant polypeptides, natural polypeptides, or synthetic polypeptides, preferably recombinant polypeptides.

It will be recognized in the art that some amino acid sequences of the VEGF-2 polypeptide can be varied without significant effect of the structure or function of the protein. If such differences in sequence are contemplated, it should be remembered that there will be critical areas on the protein which determine activity.

Thus, the invention further includes variations of the VEGF-2 polypeptide which show substantial VEGF-2 polypeptide activity or which include regions of VEGF-2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragments, derivatives, or analogs of the polypeptides of FIG. 1 or 2, or that encoded by the deposited cDNAs may be: (1) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence; or (v) one in which comprises fewer amino acid residues shown in SEQ ID NOS: 2 or 4, and retains the conserved motif and yet still retains activity characteristics of the VEGF family of polypeptides. Such fragments, derivatives, and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the VEGF-2 protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-a to only one of the two known types of TNF receptors. Thus, the VEGF-2 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| | Alanine |
| Small | Serine |
| | Threonine |
| | Methionine |
| | Glycine |

Of course, the number of amino acid substitutions a skilled artisan would make depends on many factors, including those described above. Generally speaking, the number of substitutions for any given VEGF-2 polypeptide will not be more than 50, 40, 30, 25, 20, 15, 10, 5 or 3.

Amino acids in the VEGF-2 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of VEGF-2 coding sequence, but do not comprise all or a portion of any VEGF-2 intron. In another embodiment, the nucleic acid comprising VEGF-2 coding sequence does not contain coding sequences of a genomic flanking gene (i.e., 5' or 3' to the VEGF-2 gene in the genome).

The polypeptides of the present invention include the polypeptides of SEQ ID NOS:2 and 4 (in particular the mature polypeptide) as well as polypeptides which have at least 70% similarity (preferably at least 70% identity) to the polypeptides of SEQ ID NOS:2 and 4, and more preferably at least 90% similarity (more preferably at least 95% identity) to the polypeptides of SEQ ID NOS:2 and 4, and still more preferably at least 95% similarity (still more preferably at least 90% identity) to the polypeptides of SEQ ID NOS:2 and 4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The polypeptides of the present invention include the polypeptide encoded by the deposited cDNA including the leader; the mature polypeptide encoded by the deposited the cDNA minus the leader (i.e., the mature protein); a polypeptide comprising amino acids about −23 to about 396 in SEQ ID NO:2; a polypeptide comprising amino acids about −22 to about 396 in SEQ ID NO:2; a polypeptide comprising amino acids about 1 to about 396 in SEQ ID NO:2; as well as polypeptides which are at least 95% identical, and more preferably at least 96%, 97%, 98% or 99% identical to the polypeptides described above and also include portions of such polypeptides with at least 30 amino acids and more preferably at least 50 amino acids.

Fusion Proteins

Any VEGF-2 polypeptide can be used to generate fusion proteins. For example, the VEGF-2 polypeptide, when fused to a second protein, can be used as an antigenic tag. Antibodies raised against the VEGF-2 polypeptide can be used to indirectly detect the second protein by binding to the VEGF-2. Moreover, because secreted proteins target cellular locations based on trafficking signals, the VEGF-2 polypeptides can be used as a targeting molecule once fused to other proteins.

Examples of domains that can be fused to VEGF-2 polypeptides include not only heterologous signal sequences, but also other heterologous functional regions. The fusion does not necessarily need to be direct, but may occur through linker sequences.

Moreover, fusion proteins may also be engineered to improve characteristics of the VEGF-2 polypeptide. For instance, a region of additional amino acids, particularly charged amino acids, may be added to the N-terminus of the VEGF-2 polypeptide to improve stability and persistence during purification from the host cell or subsequent handling and storage. Also, peptide moieties may be added to the VEGF-2 polypeptide to facilitate purification. Such regions may be removed prior to final preparation of the VEGF-2 polypeptide. The addition of peptide moieties to facilitate handling of polypeptides are familiar and routine techniques in the art.

Moreover, VEGF-2 polypeptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-0 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the VEGF-2 polypeptides can be fused to marker sequences, such as a peptide which facilitates purification of VEGF-2. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the VEGF-2 polynucleotides or the polypeptides.

Biological Activities of VEGF-2

VEGF-2 polynucleotides and polypeptides can be used in assays to test for one or more biological activities. If VEGF-2 polynucleotides and polypeptides do exhibit activity in a particular assay, it is likely that VEGF-2 may be involved in the diseases associated with the biological activity. Therefore, VEGF-2 could be used to treat the associated disease.

Immune Activity

VEGF-2 polypeptides or polynucleotides may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, VEGF-2 polynucleotides or polypeptides can be used as a marker or detector of a particular immune system disease or disorder.

VEGF-2 polynucleotides or polypeptides may be useful in treating or detecting deficiencies or disorders of hematopoietic cells. VEGF-2 polypeptides or polynucleotides could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, VEGF-2 polypeptides or polynucleotides can also be used to modulate hemostatic (the stopping of bleeding) or thrombolytic activity (clot formation). For example, by increasing hemostatic or thrombolytic activity, VEGF-2 polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, VEGF-2 polynucleotides or polypeptides that can decrease hemostatic or thrombolytic activity could be used to inhibit or dissolve clotting, important in the treatment of heart attacks (infarction), strokes, or scarring.

VEGF-2 polynucleotides or polypeptides may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of VEGF-2 polypeptides or polynucleotides that can inhibit an immune response, particularly the proliferation, differentiation, or chemotaxis of T-cells, may be an effective therapy in preventing autoimmune disorders.

Examples of autoimmune disorders that can be treated or detected by VEGF-2 include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by VEGF-2 polypeptides or polynucleotides. Moreover, VEGF-2 can be used to treat anaphylaxis, hypersensitivity to an antigenic molecule, or blood group incompatibility.

VEGF-2 polynucleotides or polypeptides may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of VEGF-2 polypeptides or polynucleotides that inhibits an immune response, particularly the proliferation, differentiation, or chemotaxis of T-cells, may be an effective therapy in preventing organ rejection or GVHD. Similarly, VEGF-2 polypeptides or polynucleotides may also be used to modulate inflammation. For example, VEGF-2 polypeptides or polynucleotides may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

VEGF-2 polypeptides or polynucleotides can be used to treat or detect hyperproliferative disorders, including neoplasms. VEGF-2 antagonist polypeptides or polynucleotides may inhibit the proliferation of the disorder through direct or indirect interactions. Alternatively, VEGF-2 antagonist polypeptides or polynucleotides may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by VEGF-2 antagonist polynucleotides or polypeptides include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by VEGF-2 antagonist polynucleotides or polypeptides. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

VEGF-2 polypeptides or polynucleotides can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, VEGF-2 polypeptides or polynucleotides may also directly inhibit the infectious agent, without necessarily eliciting an immune response.

Viruses are one example of an infectious agent that can cause disease or symptoms that can be treated or detected by VEGF-2 polynucleotides or polypeptides. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. VEGF-2 polypeptides or polynucleotides can be used to treat or detect any of these symptoms or diseases.

Similarly, bacterial or fungal agents that can cause disease or symptoms and that can be treated or detected by VEGF-2 polynucleotides or polypeptides include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. VEGF-2 polypeptides or polynucleotides can be used to treat or detect any of these symptoms or diseases.

Moreover, parasitic agents causing disease or symptoms that can be treated or detected by VEGF-2 polynucleotides or polypeptides include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. VEGF-2 polypeptides or polynucleotides can be used to treat or detect any of these symptoms or diseases.

Preferably, treatment using VEGF-2 polypeptides or polynucleotides could either be by administering an effective amount of VEGF-2 polypeptide to the patient, or by removing cells from the patient, supplying the cells with VEGF-2 polynucleotide, and returning the engineered cells to the patient (ex vivo therapy). Moreover, the VEGF-2 polypeptide or polynucleotide can be used as an antigen in a vaccine to raise an immune response against infectious disease.

Regeneration

VEGF-2 polynucleotides or polypeptides can be used to differentiate, proliferate, and attract cells, leading to the regeneration of tissues. (See, *Science* 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), lymphatic (including lymphatic endothelium), nervous, hematopoietic, and skeletal (bone, cartilage, tendon, and ligament) tissue. Preferably, regeneration occurs without or decreased scarring. Regeneration also may include angiogenesis.

Moreover, VEGF-2 polynucleotides or polypeptides may increase regeneration of tissues difficult to heal. For example, increased tendon/ligament regeneration would quicken recovery time after damage. VEGF-2 polynucleotides or polypeptides of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using VEGF-2 polynucleotides or polypeptides to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the VEGF-2 polynucleotides or polypeptides.

Chemotaxis

VEGF-2 polynucleotides or polypeptides may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

VEGF-2 polynucleotides or polypeptides may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. As a chemotactic molecule, VEGF-2 could also attract fibroblasts, which can be used to treat wounds.

It is also contemplated that VEGF-2 polynucleotides or polypeptides may inhibit chemotactic activity. These molecules could also be used to treat disorders. Thus, VEGF-2 polynucleotides or polypeptides could be used as an inhibitor of chemotaxis.

Binding Activity

VEGF-2 polypeptides may be used to screen for molecules that bind to VEGF-2 or for molecules to which VEGF-2 binds. The binding of VEGF-2 and the molecule may activate (agonist), increase, inhibit (antagonist), or decrease activity of the VEGF-2 or the molecule bound. Examples of such molecules include antibodies, oligonucleotides, proteins (e.g., receptors), or small molecules.

Preferably, the molecule is closely related to the natural ligand of VEGF-2, e.g., a fragment of the ligand, or a natural substrate, a ligand, a structural or functional mimetic. (See, Coligan et al., *Current Protocols in Immunology* 1(2): Chapter 5 (1991).) Similarly, the molecule can be closely related to the natural receptor to which VEGF-2 binds (i.e., Flt-4), or at least, a fragment of the receptor capable of being bound by VEGF-2 (e.g., active site). In either case, the molecule can be rationally designed using known techniques. Preferably, the screening for these molecules involves producing appropriate cells which express VEGF-2, either as a secreted protein or on the cell membrane. Preferred cells include cells from mammals, yeast, *Drosophila*, or *E. coli*. Cells expressing VEGF-2(or cell membrane containing the expressed polypeptide) are then preferably contacted with a test compound potentially containing the molecule to observe binding, stimulation, or inhibition of activity of either VEGF-2 or the molecule.

The assay may simply test binding of a candidate compound to VEGF-2, wherein binding is detected by a label, or in an assay involving competition with a labeled competitor. Further, the assay may test whether the candidate compound results in a signal generated by binding to VEGF-2.

Alternatively, the assay can be carried out using cell-free preparations, polypeptide/molecule affixed to a solid support, chemical libraries, or natural product mixtures. The assay may also simply comprise the steps of mixing a candidate compound with a solution containing VEGF-2, measuring VEGF-2/molecule activity or binding, and comparing the VEGF-2/molecule activity or binding to a standard.

Preferably, an ELISA assay can measure VEGF-2 level or activity in a sample (e.g., biological sample) using a monoclonal or polyclonal antibody. The antibody can measure VEGF-2 level or activity by either binding, directly or indirectly, to VEGF-2 or by competing with VEGF-2 for a substrate.

All of these above assays can be used as diagnostic or prognostic markers. The molecules discovered using these assays can be used to treat disease or to bring about a particular result in a patient (e.g., blood vessel growth) by activating or inhibiting the VEGF-2/molecule. Moreover, the assays can discover agents which may inhibit or enhance the production of VEGF-2 from suitably manipulated cells or tissues.

Therefore, the invention includes a method of identifying compounds which bind to VEGF-2 comprising the steps of: (a) incubating a candidate binding compound with VEGF-2; and (b) determining if binding has occurred. Moreover, the invention includes a method of identifying agonists/antagonists comprising the steps of: (a) incubating a candidate compound with VEGF-2, (b) assaying a biological activity, and (b) determining if a biological activity of VEGF-2 has been altered.

Other Activities

VEGF-2 polypeptides or polynucleotides may also increase or decrease the differentiation or proliferation of embryonic stem cells, besides, as discussed above, hematopoietic lineage.

VEGF-2 polypeptides or polynucleotides may also be used to modulate mammalian characteristics, such as body height, weight, hair color, eye color, skin, percentage of adipose tissue, pigmentation, size, and shape (e.g., cosmetic surgery). Similarly, VEGF-2 polypeptides or polynucleotides may be used to modulate mammalian metabolism affecting catabolism, anabolism, processing, utilization, and storage of energy.

VEGF-2 polypeptides or polynucleotides may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

VEGF-2 polypeptides or polynucleotides may also be used as a food additive or preservative, such as to increase or decrease storage capabilities, fat content, lipid, protein, carbohydrate, vitamins, minerals, cofactors or other nutritional components.

Vectors, Host Cells, and Protein Production

The present invention also relates to recombinant vectors, which include the isolated nucleic acid molecules of the present invention, and to host cells containing the recombinant vectors, as well as to methods of making such vectors and host cells and for using them for production of VEGF-2 polypeptides or peptides by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the VEGF-2 genes of the invention. The culture conditions, such as temperature, pH and the like, are those previously used with the host cell selected for expression, and will be apparent to the skilled artisan.

The polynucleotides of the present invention may be employed for producing polypeptides by recombinant techniques. Thus, for example, the polynucleotide sequence may be included in any one of a variety of expression vectors for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively lined to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain at least one selectable marker gene to provide a phenotypic trait for selection of transformed host cells. Such markers include dihydrofolate reductase (DHFR) or neomycin resistance for eukaryotic cell culture, and tetracycline or ampicillin resistance for culturing in *E. coli* and other bacteria.

The vector containing the appropriate DNA sequence as herein above described, as well as an appropriate promoter or control sequence, may be employed to transform an appropriate host to permit the host to express the protein. Representative examples of appropriate hosts, include but are not limited to: bacterial cells, such as *E. coli, Salmonella typhimurium,* and *Streptomyces*; fungal cells, such as yeast; insect cells, such as *Drosophila* S2 and *Spodoptera* Sf19; animal cells such as CHO, COS, and Bowes melanoma; and plant cells. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example—bacterial: pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figure 28:
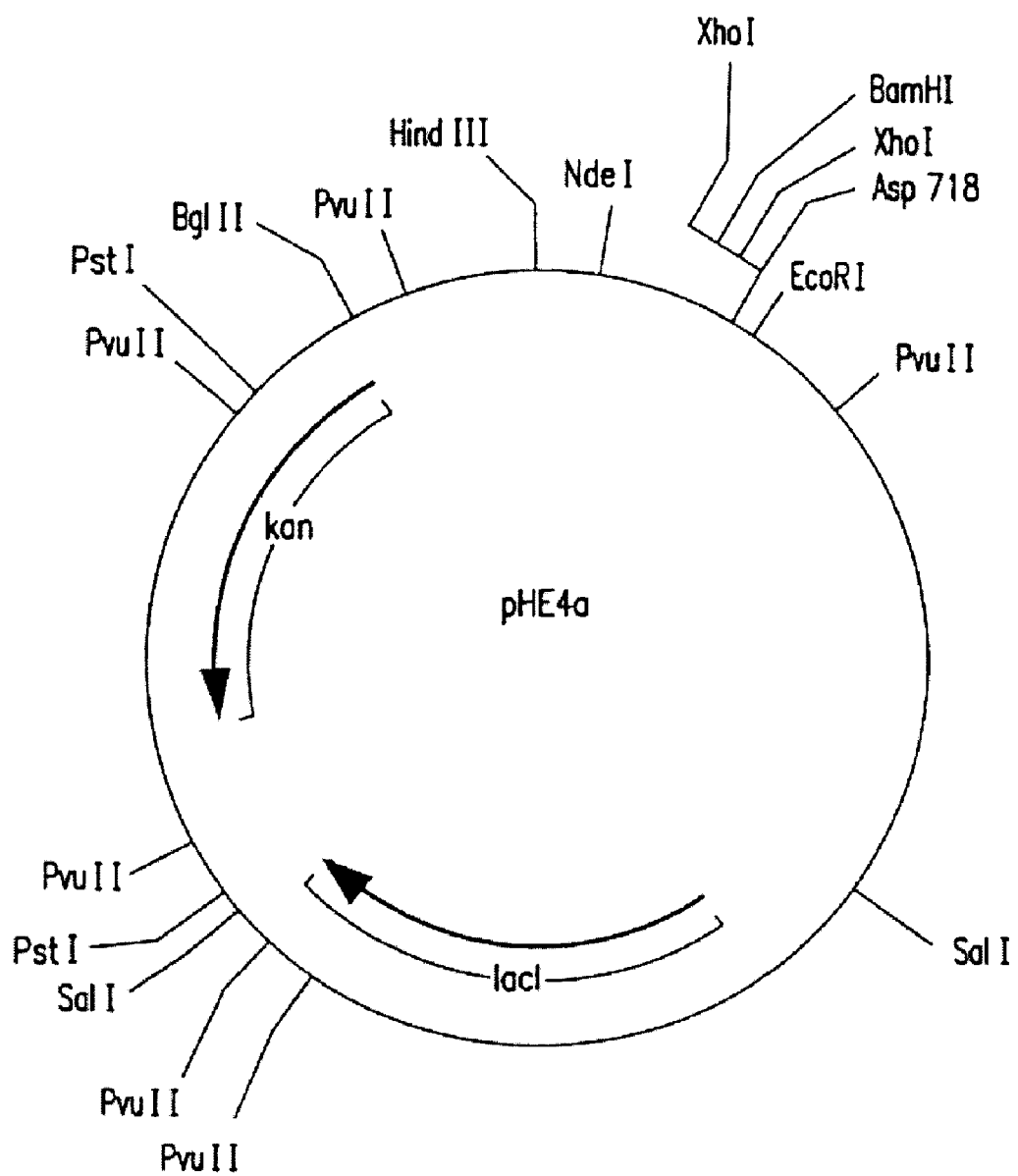
FIG. 28 shows a schematic representation of the pHE4a expression vector (SEQ ID NO:16). The locations of the kanamycin resistance marker gene, the multiple cloning site linker region, the oriC sequence, and the lacIq coding sequence are indicated.

As summarized in FIGS. 28 and 29, components of the pHE4a vector (SEQ ID NO:16) include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. The pHE4a vector was deposited with the ATCC on Feb. 25, 1998, and given accession number 209645.

A nucleotide sequence encoding VEGF-2 (SEQ ID NO:1), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding VEGF-2 (SEQ ID NO:1) having the appropriate restriction sites is generated, for example, according to the PCR protocol described in Example1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG).VEGF-2 thus is not produced in appreciable quantities in uninduced host cells containing the pHE4a vector. Induction of these host cells by the addition of an agent such as IPTG, however, results in the expression of the VEGF-2 coding sequence.

The promoter/operator sequences of the pHE4a vector (SEQ ID NO:17) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4a vector except for the VEGF-2 coding sequence. Features of the pHE4a vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO:16).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, electroporation, transduction, infection, or other methods (Davis, L., et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., *Molecular Cloning: A Laboratory Manual,* Second Edition, Cold Spring Harbor Laboratory, Cold Spring Harbor, N.Y. (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, well known to those skilled in the art, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., VEGF-2 sequence), and/or to include genetic material (e.g., heterologous promoters) that is operably associated with VEGF-2 sequence of the invention, and which activates, alters, and/or amplifies endogenous VEGF-2 polynucleotides. For example, techniques known in the art may be used to operably associate heterologous control regions and endogenous polynucleotide sequences (e.g. encoding VEGF-2) via homologous recombination (see, e.g., U.S. Pat. No. 5,641,670, issued Jun. 24, 1997; International Publication No. WO 96/29411, published Sep.

26, 1996; International Publication No. WO 94/12650, published Aug. 4, 1994; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the protein expressed.

The polypeptides can be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. It is preferred to have low concentrations (approximately 0.1–15 mM) of calcium ion present during purification (Price et al., *J. Biol. Chem.* 244:917 (1969)). Protein refolding steps can be used, as necessary, in completing configuration of the mature protein. Finally, high performance liquid chromatography (HPLC) can be employed for final purification steps. The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

In addition, polypeptides of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105–111). For example, a peptide corresponding to a fragment of the VEGF-2 polypeptides of the invention can be synthesized by use of a peptide synthesizer. Furthermore, if desired, nonclassical amino acids or chemical amino acid analogs can be introduced as a substitution or addition into the VEGF-2 polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses VEGF-2 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of VEGF-2 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The VEGF-2 polypeptides of the invention may be in monomers or multimers (i.e., dimers, trimers, tetramers and higher multimers). Accordingly, the present invention relates to monomers and multimers of the VEGF-2 polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only VEGF-2 polypeptides of the invention (including VEGF-2 fragments, variants, splice variants, and fusion proteins, as described herein). These homomers may contain VEGF-2 polypeptides having identical or different amino acid sequences. In a specific embodiment, a homomer of the invention is a multimer containing only VEGF-2 polypeptides having an identical amino acid sequence. In another specific embodiment, a homomer of the invention is a multimer containing VEGF-2 polypeptides having different amino acid sequences. In specific embodiments, the multimer of the invention is a homodimer (e.g., containing VEGF-2 polypeptides having identical or different amino acid sequences) or a homotrimer (e.g., containing VEGF-2 polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the VEGF-2 polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the VEGF-2 polypeptides of the invention. Such covalent associations may involve one or more amino acid residues contained in the polypeptide sequence (e.g., that recited in SEQ ID NO:2, or contained in the polypeptide encoded by the deposited clone.) In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a VEGF-2 fusion protein. In one example, covalent associations are between the heterologous sequence contained in a fusion protein of the invention (see, e.g., U.S. Pat. No. 5,478,925). In a specific example, the covalent associations are between the heterologous sequence contained in a VEGF-2-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Therapeutic Uses

Figure 12:
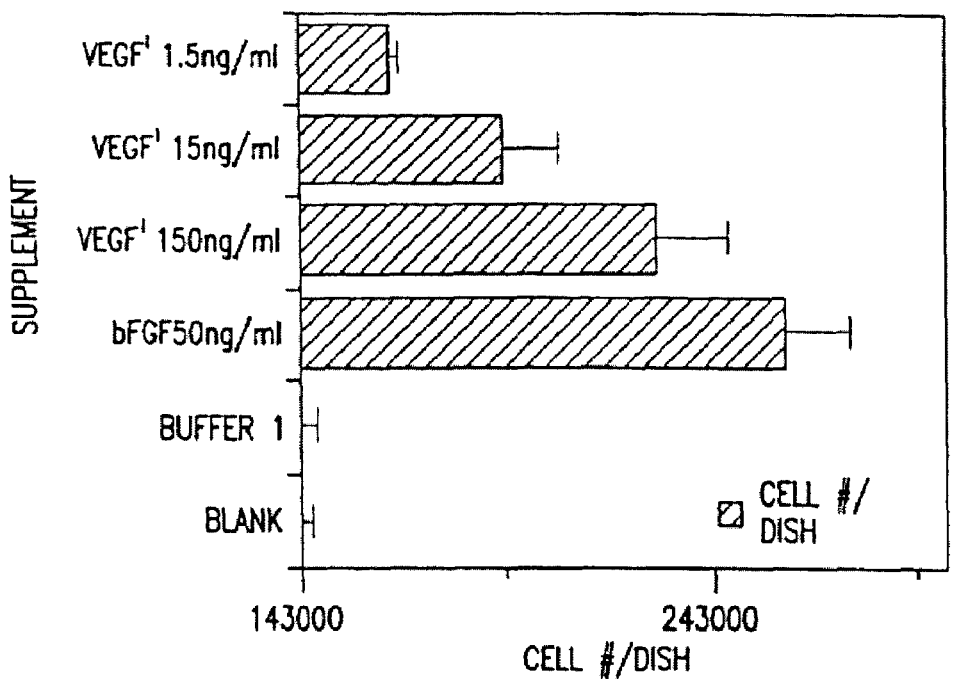
FIG. 12 is a bar graph illustrating the effect of partially-purified VEGF-2 protein on the growth of vascular endothelial cells in comparison to basic fibroblast growth factor.
Figure 13:
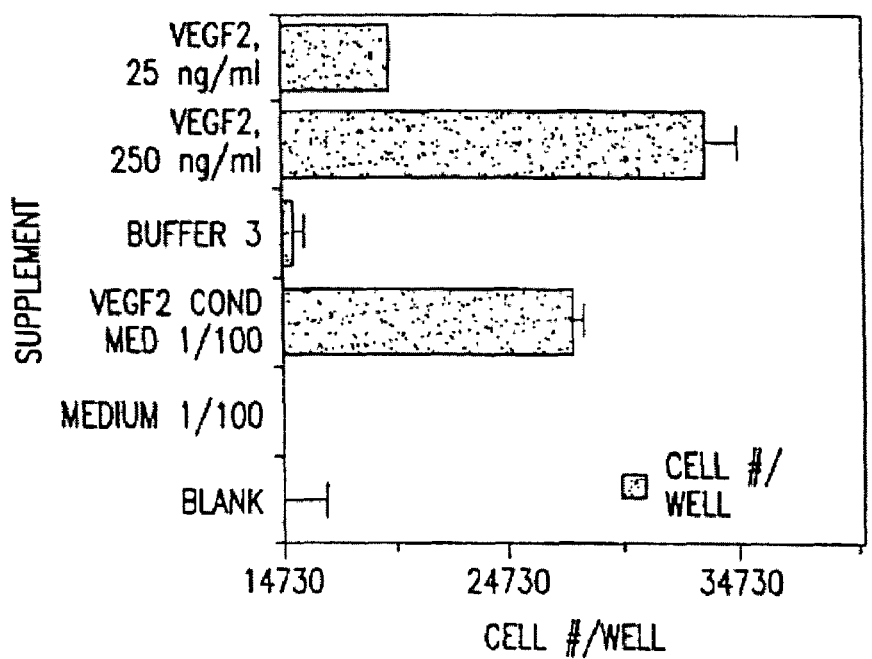
FIG. 13 is a bar graph illustrating the effect of purified VEGF-2 protein on the growth of vascular endothelial cells.

The VEGF-2 polypeptide of the present invention is a potent mitogen for vascular and lymphatic endothelial cells. As shown in FIGS. 12 and 13, the VEGF-2 polypeptide of SEQ ID NO:2, minus the initial 46 amino acids, is a potent mitogen for vascular endothelial cells and stimulates their growth and proliferation. The results of a Northern blot analysis performed for the VEGF-2 nucleic acid sequence encoding this polypeptide wherein 20 mg of RNA from several human tissues were probed with $^{32}$P-VEGF-2, illustrates that this protein is actively expressed in the heart and lung which is further evidence of mitogenic activity.

Accordingly, VEGF-2, or biologically active portions thereof, may be employed to treat vascular trauma by promoting angiogenesis. For example, to stimulate the growth of transplanted tissue where coronary bypass surgery is performed. VEGF-2, or biologically active portions thereof, may also be employed to promote wound healing, particularly to re-vascularize damaged tissues or stimulate collateral blood flow during ischemia and where new capillary angiogenesis is desired. VEGF-2, or biologically active portions thereof, may be employed to treat full-thickness wounds such as dermal ulcers, including pressure sores, venous ulcers, and diabetic ulcers. In addition, VEGF-2, or biologically active portions thereof, may be employed to treat full-thickness burns and injuries where a skin graft or flap is used to repair such burns and injuries. VEGF-2, or biologically active portions thereof, may also be employed for use in plastic surgery, for example, for the repair of lacerations, burns, or other trauma. In addition, VEGF-2 can be used to promote healing of wounds and injuries to the eye as well as to treat eye diseases.

Along these same lines, VEGF-2, or biologically active portions thereof, may also be employed to induce the growth of damaged bone, periodontium or ligament tissue. VEGF-2, or biologically active portions thereof, may also be employed for regenerating supporting tissues of the teeth, including cementum and periodontal ligament, that have been damaged by, e.g., periodontal disease or trauma.

Since angiogenesis is important in keeping wounds clean and non-infected, VEGF-2, or biologically active portions thereof, may be employed in association with surgery and following the repair of incisions and cuts. VEGF-2, or biologically active portions thereof, may also be employed for the treatment of abdominal wounds where there is a high risk of infection.

VEGF-2, or biologically active portions thereof, may be employed for the promotion of endothelialization in vascular graft surgery. In the case of vascular grafts using either transplanted or synthetic material, VEGF-2, or biologically active portions thereof, can be applied to the surface of the graft or at the junction to promote the growth of vascular endothelial cells. VEGF-2, or biologically active portions thereof, may also be employed to repair damage of myocardial tissue as a result of myocardial infarction. VEGF-2, or biologically active portions thereof, may also be employed to repair the cardiac vascular system after ischemia. VEGF-2, or biologically active portions thereof, may also be employed to treat damaged vascular tissue as a result of coronary artery disease and peripheral and CNS vascular disease.

VEGF-2, or biologically active portions thereof, may also be employed to coat artificial prostheses or natural organs which are to be transplanted in the body to minimize rejection of the transplanted material and to stimulate vascularization of the transplanted materials.

VEGF-2, or biologically active portions thereof, may also be employed for vascular tissue repair of injuries resulting from trauma, for example, that occurring during arteriosclerosis and required following balloon angioplasty where vascular tissues are damaged.

VEGF-2, or biologically active portions thereof, may also be used to treat peripheral arterial disease. Accordingly, in a further aspect, there is provided a process for utilizing VEGF-2 polypeptides to treat peripheral arterial disease. Preferably, a VEGF-2 polypeptide is administered to an individual for the purpose of alleviating or treating peripheral arterial disease. Suitable doses, formulations, and administration routes are described below.

VEGF-2, or biologically active portions thereof, may also to promote the endothelial function of lymphatic tissues and vessels, such as to treat the loss of lymphatic vessels, occlusions of lymphatic vessels, and lymphangiomas. VEGF-2 may also be used to stimulate lymphocyte production.

VEGF-2, or biologically active portions thereof, may also be used to treat hemangioma in newborns. Accordingly, in a further aspect, there is provided a process for utilizing VEGF-2 polypeptides to treat hemangioma in newborns. Preferably, a VEGF-2 polypeptide is administered to an individual for the purpose of alleviating or treating hemangioma in newborns. Suitable doses, formulations, and administration routes are described below.

VEGF-2, or biologically active portions thereof, may also be used to prevent or treat abnormal retinal development in premature newborns. Accordingly, in a further aspect, there is provided a process for utilizing VEGF-2 polypeptides to treat abnormal retinal development in premature newborns. Preferably, a VEGF-2 polypeptide is administered to an individual for the purpose of alleviating or treating abnormal retinal development in premature newborns. Suitable doses, formulations, and administration routes are described below.

VEGF-2, or biologically active portions thereof, may be used to treat primary (idiopathic) lymphademas, including Milroy's disease and Lymphedema praecox. Accordingly, in a further aspect, there is provided a process for utilizing VEGF-2 polypeptides to treat primary (idiopathic) lymphademas, including Milroy's disease and Lymphedema praecox. Preferably, a VEGF-2 polypeptide is administered to an individual for the purpose of alleviating or treating primary (idiopathic) lymphademas, including Milroy's disease and Lymphedema praecox. VEGF-2 or biologically active portions thereof, may also be used to treat edema as well as to effect blood pressure in an animal. Suitable doses, formulations, and administration routes are described below.

VEGF-2, or biologically active portions thereof, may also be used to treat secondary (obstructive) lifetimes including those that result from (I) the removal of lymph nodes and vessels, (ii) radiotherapy and surgery in the treatment of cancer, and (iii) trauma and infection. Accordingly, in a further aspect, there is provided a process for utilizing VEGF-2 polypeptides to treat secondary (obstructive) lifetimes including those that result from (I) the removal of lymph nodes and vessels, (ii) radiotherapy and surgery in the treatment of cancer, and (iii) trauma and infection. Preferably, a VEGF-2 polypeptide is administered to an individual for the purpose of secondary (obstructive) lifetimes including those that result from (I) the removal of lymph nodes and vessels, (ii) radiotherapy and surgery in the treatment of cancer, and (iii) trauma and infection. Suitable doses, formulations, and administration routes are described below.

VEGF-2, or biologically active portions thereof, may also be used to treat Kaposi's Sarcoma. Accordingly, in a further aspect, there is provided a process for utilizing VEGF-2 polypeptides to treat Kaposi's Sarcoma. Preferably, a VEGF-2 polypeptide is administered to an individual for the purpose of alleviating or treating Kaposi's Sarcoma. Suitable doses, formulations, and administration routes are described below.

VEGF-2 antagonists can be used to treat cancer by inhibiting the angiogenesis necessary to support cancer and tumor growth.

Cardiovascular Disorders

The present inventors have shown that VEGF-2 stimulates the growth of vascular endothelial cells, stimulates endothelial cell migration, stimulates angiogenesis in the CAM assay, decreases blood pressure in spontaneously hypertensive rats, and increases blood flow to ischemic limbs in rabbits. Accordingly, VEGF-2 polypeptides or polynucleotides encoding VEGF-2 may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, post-pericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lowin-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneulysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

VEGF-2 polypeptides or polynucleotides are especially effective for the treatment of critical limb ischemia and coronary disease. As shown in Example 18, administration of VEGF-2 polynucleotides and polypeptides to an experimentally induced ischemia rabbit hindlimb restored blood pressure ratio, blood flow, angiographic score, and capillary density.

VEGF-2 polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. VEGF-2 polypeptides may be administered as part of a pharmaceutical composition, described in more detail below. Methods of delivering VEGF-2 polynucleotides are described in more detail below.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the VEGF-2 polypeptide of the present invention. This method requires a polynucleotide which codes for a VEGF-2 polypeptide operatively linked to a promoter and any other genetic elements necessary for the expression of the polypeptide by the target tissue. Such gene therapy and delivery techniques are known in the art, see, for example, WO 90/11092, which is herein incorporated by reference.

Thus, for example, cells from a patient may be engineered with a polynucleotide (DNA or RNA) comprising a promoter operably linked to a VEGF-2 polynucleotide ex vivo, with the engineered cells then being provided to a patient to be treated with the polypeptide. Such methods are well-known in the art. For example, see Belldegrun, A., et al., *J. Natl. Cancer Inst.* 85: 207–216 (1993); Ferrantini, M. et al., *Cancer Research* 53: 1107–1112 (1993); Ferrantini, M. et al., *J. Immunology* 153: 4604–4615 (1994); Kaido, T., et al., *Int. J. Cancer* 60: 221–229 (1995); Ogura, H., et al., *Cancer Research* 50: 5102–5106 (1990); Santodonato, L., et al., *Human Gene Therapy* 7:1–10 (1996); Santodonato, L., et al., *Gene Therapy* 4:1246–1255 (1997); and Zhang, J.-F. et al., *Cancer Gene Therapy* 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the VEGF-2 polynucleotide constructs can be delivered by any method that delivers injectable materials to the cells of an animal, such as, injection into the interstitial space of tissues (heart, muscle, skin, lung, liver, and the like). The VEGF-2 polynucleotide constructs may be delivered in a pharmaceutically acceptable liquid or aqueous carrier.

In one embodiment, the VEGF-2 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the VEGF-2 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The VEGF-2 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, pRc/CMV2 available from Invitrogen, and the vector containing the VEGF-2 polynucleotide, pVGI.1, deposited as ATCC Deposit Number PTA-2185. Other suitable vectors will be readily apparent to the skilled artisan.

Any strong promoter known to those skilled in the art can be used for driving the expression of VEGF-2 DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for VEGF-2.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The VEGF-2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

For myocardium delivery, multiple doses of pVGI.1 (VEGF-2) can be administered to a patient, at various dose levels such as, for example, 200, 800, and 2000 μg. One way to deliver the dose could be through direct injection into the myocardium using, for example, a minimally invasive thoracotomy. If necessary, multiple injection sites can be selected according to the areas of ischemia identified by a baseline myocardial profusion study such as SPECT (single photon emission computed tomography) imaging.

For limb delivery, multiple doses of pVGI.1 (VEGF-2) can be administered to the limb of a patient, at various dose levels such as, for example, 2, 4, and 8 mg. One way to deliver the dose could be through intramuscular injection.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked VEGF-2 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced by Example 18, naked VEGF-2 nucleic acid sequences can be administered in vivo results in the successful expression of VEGF-2 polypeptide in the femoral arteries of rabbits. The constructs may also be delivered with delivery vehicles such as viral sequences, viral particles, liposome formulations, lipofectin, precipitating agents, etc. Such methods of delivery are known in the art.

In certain embodiments, the VEGF-2 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* (1987) 84:7413–7416, which is herein incorporated by reference); mRNA (Malone et al., *Proc. Natl. Acad. Sci. USA* (1989) 86:6077–6081, which is herein incorporated by reference); and purified transcription factors (Debs et al., *J. Biol. Chem.* (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl. Acad. Sci. USA* (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology* (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* (1975) 394:483; Wilson et al., *Cell* (1979) 17:77); ether injection (Deamer, D. and Bangham, A., *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); detergent dialysis (Enoch, H. and Strittmatter, P., *Proc. Natl. Acad. Sci. USA* (1979) 76:145); and reverse-phase evaporation (REV) (Fraley et al., *J. Biol. Chem.* (1980) 255:10431; Szoka, F. and Papahadjopoulos, D., *Proc. Natl. Acad. Sci. USA* (1978) 75:145; Schaefer-Ridder et al., *Science* (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589, 466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding VEGF-2. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include polynucleotide encoding VEGF-2. Such retroviral vector particles then may be employed, to transduce eukaryotic cells, either in vitro or in vivo. The transduced eukaryotic cells will express VEGF-2.

In certain other embodiments, cells are engineered, ex vivo or in vivo, with VEGF-2 polynucleotide contained in an adenovirus vector. Adenovirus can be manipulated such that it encodes and expresses VEGF-2, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109: 233–238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252: 431–434; Rosenfeld et al., (1992) *Cell* 68:143–155). Furthermore, extensive studies to attempt to establish adenovirus as a causative agent in human cancer were uniformly negative (Green, M. et al. (1979) *Proc. Natl. Acad. Sci. USA* 76:6606).

Suitable adenoviral vectors useful in the present invention are described, for example, in Kozarsky and Wilson, *Curr. Opin. Genet. Devel.* 3:499–503 (1993); Rosenfeld et al., *Cell* 68:143–155 (1992); Engelhardt et al., *Human Genet. Ther.* 4:759–769 (1993); Yang et al., *Nature Genet.* 7:362–369 (1994); Wilson et al., *Nature* 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenovintses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., *Curr. Topics in Microbiol. Immunol.* 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The VEGF-2 polynucleotide construct is inserted into the AAV vector using standard cloning methods, such as those found in Sambrook et al., *Molecular Cloning: A Laboratory Manual,* Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the VEGF-2 polynucleotide construct. These viral particles are then used to transduce eukaryotic cells, either ex vivo or in vivo. The transduced cells will contain the VEGF-2 polynucleotide construct integrated into its genome, and will express VEGF-2.

Another method of gene therapy involves operably associating heterologous control regions and endogenous polynucleotide sequences (e.g. encoding VEGF-2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the VEGF-2 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous VEGF-2 sequence is placed under the control of the promoter. The promoter then drives the expression of the endogenous VEGF-2 sequence.

The polynucleotides encoding VEGF-2 may be administered along with other polynucleotides encoding other angiongenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding VEGF-2 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constricts can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189: 11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Nucleic Acid Utilities

VEGF-2 nucleic acid sequences and VEGF-2 polypeptides may also be employed for in vitro purposes related to scientific research, synthesis of DNA and manufacture of DNA vectors, and for the production of diagnostics and therapeutics to treat human disease. For example, VEGF-2 may be employed for in vitro culturing of vascular endothelial cells, where it is added to the conditional medium in a concentration from 10 pg/ml to 10 ng/ml.

Fragments of the full length VEGF-2 gene may be used as a hybridization probe for a cDNA library to isolate other genes which have a high sequence similarity to the gene or similar biological activity. Probes of this type generally have at least 50 base pairs, although they may have a greater number of bases. The probe may also be used to identify a cDNA clone corresponding to a full length transcript and a genomic clone or clones that contain the complete VEGF-2 gene including regulatory and promoter regions, exons, and introns. An example of a screen comprises isolating the coding region of the VEGF-2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides methods for identification of VEGF-2 receptors. The gene encoding the receptor can be identified by numerous methods known to those of skill in the art, for example, ligand panning and FACS sorting (Coligan et al., Current Protocols in Immun., 1(2), Chapter 5, (1991)). Preferably, expression cloning is employed wherein polyadenylated RNA is prepared from a cell responsive to VEGF-2, and a cDNA library created from this RNA is divided into pools and used to transfect COS cells or other cells that are not responsive to VEGF-2. Transfected cells which are grown on glass slides are exposed to labeled VEGF-2. VEGF-2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VEGF-2 can be photoaffinity linked with cell membrane or extract preparations that express the receptor molecule. Cross-linked material is resolved by PAGE and exposed to X-ray film. The labeled complex containing VEGF-2 is then excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

VEGF-2 Agonist and Antagonists

This invention is also related to a method of screening compounds to identify those which are VEGF-2 agonists or antagonists. An example of such a method takes advantage of the ability of VEGF-2 to significantly stimulate the proliferation of human endothelial cells in the presence of the comitogen Con A. Endothelial cells are obtained and cultured in 96-well flat-bottomed culture plates (Costar, Cambridge, Mass.) in a reaction mixture supplemented with Con-A (Calbiochem, La Jolla, Calif.). Con-A, polypeptides of the present invention and the compound to be screened are added. After incubation at 37EC, cultures are pulsed with 1 FCi of $^3$[H]thymidine (5 Ci/mmol; 1 Ci=37 BGq; NEN) for a sufficient time to incorporate the $^3$[H] and harvested onto glass fiber filters (Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]thymidine incorporation, as compared to a control assay where the compound is excluded, indicates stimulation of endothelial cell proliferation.

To assay for antagonists, the assay described above is performed and the ability of the compound to inhibit $^3$[H] thymidine incorporation in the presence of VEGF-2 indicates that the compound is an antagonist to VEGF-2. Alternatively, VEGF-2 antagonists may be detected by combining VEGF-2 and a potential antagonist with membrane-bound VEGF-2 receptors or recombinant receptors under appropriate conditions for a competitive inhibition assay. VEGF-2 can be labeled, such as by radioactivity, such that the number of VEGF-2 molecules bound to the receptor can determine the effectiveness of the potential antagonist.

Alternatively, the response of a known second messenger system following interaction of VEGF-2 and receptor would be measured and compared in the presence or absence of the compound. Such second messenger systems include but are not limited to, cAMP guanylate cyclase, ion channels or phosphoinositide hydrolysis. In another method, a mammalian cell or membrane preparation expressing the VEGF-2 receptor is incubated with labeled VEGF-2 in the presence of the compound. The ability of the compound to enhance or block this interaction could then be measured.

Potential VEGF-2 antagonists include an antibody, or in some cases, an oligonucleotide, which bind to the polypeptide and effectively eliminate VEGF-2 function. Alternatively, a potential antagonist may be a closely related protein which binds to VEGF-2 receptors, however, they are inactive forms of the polypeptide and thereby prevent the action of VEGF-2. Examples of these antagonists include a negative dominant mutant of the VEGF-2 polypeptide, for example, one chain of the hetero-dimeric form of VEGF-2 may be dominant and may be mutated such that biological activity is not retained. An example of a negative dominant mutant includes truncated versions of a dimeric VEGF-2 which is capable of interacting with another dimer to form wild type VEGF-2, however, the resulting homo-dimer is inactive and fails to exhibit characteristic VEGF activity.

Another potential VEGF-2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)), thereby preventing transcription and the production of VEGF-2. The antisense RNA oligonucleotide hybridizes to the mRNA in vivo and blocks translation of the mRNA molecule into the VEGF-2 polypeptide (Antisense—Okano, J. Neurochem. 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of VEGF-2.

Potential VEGF-2 antagonists also include small molecules which bind to and occupy the active site of the polypeptide thereby making the catalytic site inaccessible to substrate such that normal biological activity is prevented. Examples of small molecules include but are not limited to small peptides or peptide-like molecules.

The antagonists may be employed to limit angiogenesis necessary for solid tumor metastasis. The identification of VEGF-2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF-2 is extremely low in normal tissues including breast, it can be found expressed at moderate levels in at least two breast tumor cell lines that are derived from malignant tumors. It is, therefore, possible that VEGF-2 is involved in tumor angiogenesis and growth.

Gliomas are also a type of neoplasia which may be treated with the antagonists of the present invention.

The antagonists may also be used to treat chronic inflammation caused by increased vascular permeability. In addition to these disorders, the antagonists may also be employed to treat retinopathy associated with diabetes, rheumatoid arthritis and psoriasis.

The antagonists may be employed in a composition with a pharmaceutically acceptable carrier, e.g. as hereinafter described.

Pharmaceutical Compositions

The VEGF-2 polypeptides, polynucleotides and agonists and antagonists may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the pharmaceutical compositions are administered in an amount of at least about 10 mg/kg body weight and in most cases they will be administered in an amount not in excess of about 8 mg/Kg body weight per day. In most cases, the dosage is from about 10 mg/kg to about 1 mg/kg body weight daily, taking into account the routes of administration, symptoms, etc.

The VEGF-2 polypeptides, and agonists or antagonists which are polypeptides may also be employed in accordance with the present invention by expression of such polypeptide in vivo, which is often referred to as "gene therapy," described above.

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of a polypeptide in vivo, for example, by procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques* 7:980–990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-14X, VT-19-17-H2, yCRE, yCRIP, GP+E-86, GP+en-vAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Diagnostic Assays

This invention is also related to the use of the VEGF-2 gene as part of a diagnostic assay for detecting diseases or susceptibility to diseases related to the presence of mutations in VEGF-2 nucleic acid sequences.

Individuals carrying mutations in the VEGF-2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature* 324:163–166 (1986)) prior to analysis. RNA or cDNA may also be used for the same purpose. As an example, PCR primers complementary to the nucleic acid encoding VEGF-2 can be used to identify and analyze VEGF-2 mutations. For example, deletions and insertions can be detected by a change in size of the amplified product in comparison to the normal genotype. Point mutations can be identified by hybridizing amplified DNA to radiolabeled VEGF-2 RNA or alternatively, radiolabeled VEGF-2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations may also be revealed by nuclease protection assays, such as RNase and S1 protection or the chemical cleavage method (e.g., Cotton et al., *PNAS, USA* 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of VEGF-2 protein in various tissues since an over-expression of the proteins compared to normal control tissue samples may detect the presence of a disease or susceptibility to a disease, for example, abnormal cellular differentiation. Assays used to detect levels of VEGF-2 protein in a sample derived from a host are well-known to those of skill in the art and include radioimmunoassays, competitive-binding assays, Western Blot analysis, ELISA assays and "sandwich" assay. An ELISA assay (Coligan et al., *Current Protocols in Immunology* 1(2), Chapter 6, (1991)) initially comprises preparing an antibody specific to the VEGF-2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, such as, bovine serum albumen. Next, the monoclonal antibody is incubated in the dish during which time the monoclonal antibodies attach to any VEGF-2 proteins attached to the polystyrene dish. All unbound monoclonal antibody is washed out with buffer. The reporter antibody linked to horseradish peroxidase is placed in the dish resulting in binding of the reporter antibody to any monoclonal antibody bound to VEGF-2. Unattached reporter antibody is then washed out. Peroxidase substrates are then added to the dish and the amount of color developed in a given time period is a measurement of the amount of VEGF-2 protein present in a given volume of patient sample when compared against a standard curve.

A competition assay may be employed wherein antibodies specific to VEGF-2 are attached to a solid support. Polypeptides of the present invention are then labeled, for example, by radioactivity, and a sample derived from the host are passed over the solid support and the amount of label detected, for example by liquid scintillation chromatography, can be correlated to a quantity of VEGF-2 in the sample.

A "sandwich" assay is similar to an ELISA assay. In a "sandwich" assay VEGF-2 is passed over a solid support and binds to antibody attached to a solid support. A second antibody is then bound to the VEGF-2. A third antibody which is labeled and specific to the second antibody is then passed over the solid support and binds to the second antibody and an amount can then be quantified.

Chromosome Identification

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes.

Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with probes from the cDNA as short as 50 or 60 base pairs. For a review of this technique, see Verma et al., *Human Chromosomes: a Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

Antisense

The present invention is further directed to inhibiting VEGF-2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al., *Nucl. Acids Res.* 6:3073 (1979); Cooney et al., *Science* 241:456 (1988); and Dervan et al. *Science,* 251:1360 (1991), thereby preventing transcription and the production of VEGF-2. The antisense RNA oligonucleotide hybridizes to the mRNA in vivo and blocks translation of an mRNA molecule into the VEGF-2 (antisense—Okano, *J. Neurochem.* 56:560 (1991); *Oligodeoxynucleotides as Antisense Inhibitors of Gene Expression,* CRC Press, Boca Raton, Fla. (1988)).

Alternatively, the oligonucleotides described above can be delivered to cells by procedures in the art such that the anti-sense RNA or DNA may be expressed in vivo to inhibit production of VEGF-2 in the manner described above.

Antisense constructs to VEGF-2, therefore, may inhibit the angiogenic activity of the VEGF-2 and prevent the further growth or even regress solid tumors, since angiogenesis and neovascularization are essential steps in solid tumor growth. These antisense constructs may also be used to treat rheumatoid arthritis, psoriasis, diabetic retinopathy and Kaposi's sarcoma which are all characterized by abnormal angiogenesis.

Epitope-Bearing Portions

In another aspect, the invention provides peptides and polypeptides comprising epitope-bearing portions of the polypeptides of the present invention.

These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998–4002. However, antibodies can be made to any antigenic epitope, regardless of whether it is an immunogenic epitope, by using methods such as phage display. See e.g., Petersen G. et al. (1995) Mol. Gen. Genet. 249:425–431. Therefore, included in the present invention are both immunogenic epitopes and antigenic epitopes.

It is particularly pointed out that the immunogenic epitopes comprises predicted critical amino acid residues determined by the Jameson-Wolf analysis. Thus, additional flanking residues on either the N-terminal, C-terminal, or both N- and C-terminal ends may be added to these sequences to generate an epitope-bearing polypeptide of the present invention. Therefore, the immunogenic epitopes may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347–2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84–86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958–3964. Nucleic acids encoding the above epitopes can also be recombined with a gene of interest as an epitope tag to aid in detection and purification of the expressed polypeptide.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) J. Immunol. 147:60–69; U.S. Pat. Nos.

5,573,920, 4,474,893, 5,601,819, 4,714,681, 4,925,648; Kostelny, S. A. et al. (1992) J. Immunol. 148:1547–1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $5\times10^{-10}$M, $5\times10^{-11}$M, $10^{-11}$M, $5\times10^{-12}$M, $10^{-12}$M, $10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide of techniques known in the art including the use of hybridoma and recombinant technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 187 9–18; Burton, D. R. et al. (1994) Advances in Immunology 57:191–280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) BioTechniques 12(6):864–869; and Sawai, H. et al. (1995) AJRI 34:26–34; and Better, M. et al. (1988) Science 240:1041–1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46–88; Shu, L. et al. (1993) PNAS 90:7995–7999; and Skerra, A. et al. (1988) Science 240:1038–1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191–202; and U.S. Pat. No. 5,807, 715. Antibodies can be humanized using a variety of techniques including CDR-grafting (EP 0 239 400; WO 91/09967; U.S. Pat. No. 5,530,101; and 5,585,089), veneering or resurfacing (EP 0 592 106; EP 0 519 596; Padlan E. A., (1991) Molecular Immunology 28(4/5):489–498; Studnicka G. M. et al. (1994) Protein Engineering 7(6):805–814; Roguska M. A. et al. (1994) PNAS 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91–99; U.S. Pat. No. 5,474,981; Gillies, S. O. et al. (1992) PNAS 89:1428–1432; Fell, H. P. et al. (1991) J. Immunol. 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535–10539; Zheng, X. X. et al. (1995) J. Immunol. 154:5590–5600; and Vil, H. et al. (1992) PNAS 89:11337–11341 (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981–1988; Chen, Z. et al. (1998) Cancer Res. 58(16): 3668–3678; Harrop, J. A. et al. (1998) J. Immunol. 161(4): 1786–1794; Zhu, Z. et al. (1998) Cancer Res. 58(15): 3209–3214; Yoon, D. Y. et al. (1998) J. Immunol. 160(7): 3170–3179; Prat, M. et al. (1998) J. Cell. Sci. 111(Pt2): 237–247; Pitard, V. et al. (1997) J. Immunol. Methods 205(2):177–190; Liautard, J. et al. (1997) Cytokinde 9(4): 233–241; Carlson, N. G. et al. (1997) J. Biol. Chem. 272(17):11295–11301; Taryman, R. E. et al. (1995) Neuron 14(4):755–762; Muller, Y. A. et al. (1998) Structure 6(9): 1153–1167; Bartunek, P. et al. (1996) Cytokine 8(1):14–20 (said references incorporated by reference in their entireties).

Antibodies may further be used in an immunoassay to detect the presence of tumors in certain individuals. Enzyme immunoassay can be performed from the blood sample of an individual. Elevated levels of VEGF-2 can be considered diagnostic of cancer.

Truncated versions of VEGF-2 can also be produced that are capable of interacting with wild type VEGF-2 to form dimers that fail to activate endothelial cell growth, therefore inactivating the endogenous VEGF-2. Or, mutant forms of VEGF-2 form dimers themselves and occupy the ligand binding domain of the proper tyrosine kinase receptors on the target cell surface, but fail to activate cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF-2 since receptor sites are occupied. In these ways, the action of the VEGF-2 is prevented and the antagonist/inhibitors may be used therapeutically as an anti-tumor drug by occupying the receptor sites of tumors which are recognized by VEGF-2 or by inactivating VEGF-2 itself. The antagonist/inhibitors may also be used to prevent inflammation due to the increased vascular permeability action of VEGF-2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 Fl of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37EC are ordinarily used, but may vary in accordance with the supplier's instructions. After digestion the reaction is electrophoresed directly on a poly-acrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refer to either a single stranded polydeoxynucleotide or two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook et al., *Molecular Cloning: A Laboratory Manual,* Second Edition, Cold Spring Harbor Laboratory, Cold Spring Harbor, N.Y. (1989), p. 146). Unless otherwise provided, ligation may be accomplished using known buffers and conditions with 10 units of T4 DNA ligase ("ligase") per 0.5 mg of approximately equimolar amounts of the DNA fragments to be ligated.

Unless otherwise stated, transformation was performed as described by the method of Graham, F. and Van der Eb, A., *Virology* 52:456–457 (1973).

EXAMPLES

Example 1

Expression Pattern of VEGF-2 in Human Tissues and Breast Cancer Cell Lines

Northern blot analysis was carried out to examine the levels of expression of VEGF-2 in human tissues and breast cancer cell lines in human tissues. Total cellular RNA samples were isolated with RNAzol™ B system (Biotecx Laboratories, Inc.). About 10 mg of total RNA isolated from each breast tissue and cell line specified was separated on 1% agarose gel and blotted onto a nylon filter, (Sambrook et al., *Molecular Cloning: A Laboratory Manual,* Second Edition, Cold Spring Harbor Laboratory, Cold Spring Harbor, N.Y. (1989)). The labeling reaction was done according to the Stratagene Prime-It kit with 50 ng DNA fragment. The labeled DNA was purified with a Select-G-50 column from 5 Prime÷3 Prime, Inc (Boulder, Colo.). The filter was then hybridized with a radioactive labeled full length VEGF-2 gene at 1,000,000 cpm/ml in 0.5 M $NaPO_4$ and 7% SDS overnight at 65° C. After washing twice at room temperature and twice at 60° C. with 0.5×SSC, 0.1% SDS, the filters were then exposed at −70° C. overnight with an intensifying screen. A message of 1.6 Kd was observed in 2 breast cancer cell lines. FIG. 5, lane #4 represents a very tumorigenic cell line that is estrogen independent for growth.

Also, 10 mg of total RNA from 10 human adult tissues were separated on an agarose gel and blotted onto a nylon filter. The filter was then hybridized with radioactively labeled VEGF-2 probe in 7% SDS, 0.5 M NaPO4, pH 7.2; 1% BSA overnight at 65° C. Following washing in 0.2×SSC at 65° C., the filter was exposed to film for 24 days at −70° C. with intensifying screen. See FIG. 6.

Example 2

Expression of the Truncated Form of VEGF-2 (SEQ ID NO:4) by In Vitro Transcription and Translation The VEGF-2 cDNA was transcribed and translated in vitro to determine the size of the translatable polypeptide encoded by the truncated form of VEGF-2 and a partial VEGF-2 cDNA. The two inserts of VEGF-2 in the pBluescript SK vector were amplified by PCR with three pairs of primers, 1) M13-reverse and forward primers; 2) M13-reverse primer and VEGF primer F4; and 3) M13-reverse primer and VEGF primer F5. The sequence of these primers are as follows.

M13-2 reverse primer: 5'-ATGCTTCCGGCTCGTATG-3' (SEQ ID NO:9) This sequence is located upstream of the 5' end of the VEGF-2 cDNA insert in the pbluescript vector and is in an anti-sense orientation as the cDNA. A T3 promoter sequence is located between this primer and the VEGF-2 cDNA. M13-2 forward primer: 5'GGGTTTTC-CCAGTCACGAC-3' (SEQ ID NO:10) This sequence is located downstream of the 3' end of the VEGF-2 cDNA insert in the pBluescript vector and is in an anti-sense orientation as the cDNA insert. VEGF primer F4: 5'-CCA-CATGGTTCAGGAAAGACA-3' (SEQ ID NO:11) This sequence is located within the VEGF-2 cDNA in an anti-sense orientation from bp 1259–1239, which is about 169 bp away from the 3' end of the stop codon and about 266 bp before the last nucleotide of the cDNA.

PCR reaction with all three pairs of primers produce amplified products with T3 promoter sequence in front of the cDNA insert. The first and third pairs of primers produce PCR products that encode the polypeptide of VEGF-2 shown in SEQ ID NO:4. The second pair of primers produce PCR product that misses 36 amino acids coding sequence at the C-terminus of the VEGF-2 polypeptide.

Approximately 0.5 mg of PCR product from first pair of primers, 1 mg from second pair of primers, 1 mg from third pair of primers were used for in vitro transcription/translation. The in vitro transcription/translation reaction was performed in a 25 Fl of volume, using the $T_NTJ$ Coupled Reticulocyte Lysate Systems (Promega, CAT# L4950). Specifically, the reaction contains 12.5 Fl of $T_NT$ rabbit reticulocyte lysate 2 Fl of $T_NT$ reaction buffer, 1 Fl of T3 polymerase, 1 Fl of 1 mM amino acid mixture (minus methionine), 4 Fl of $^{35}S$-methionine (>1000 Ci/mmol, 10 mCi/ml), 1 Fl of 40 U/µl; RNasin ribonuclease inhibitor, 0.5 or 1 mg of PCR products. Nuclease-free $H_2O$ was added to bring the volume to 25 Fl. The reaction was incubated at 30° C. for 2 hours. Five microliters of the reaction product was analyzed on a 4–20% gradient SDS-PAGE gel. After fixing in 25% isopropanol and 10% acetic acid, the gel was dried and exposed to an X-ray film overnight at 70° C.

Figure 7:
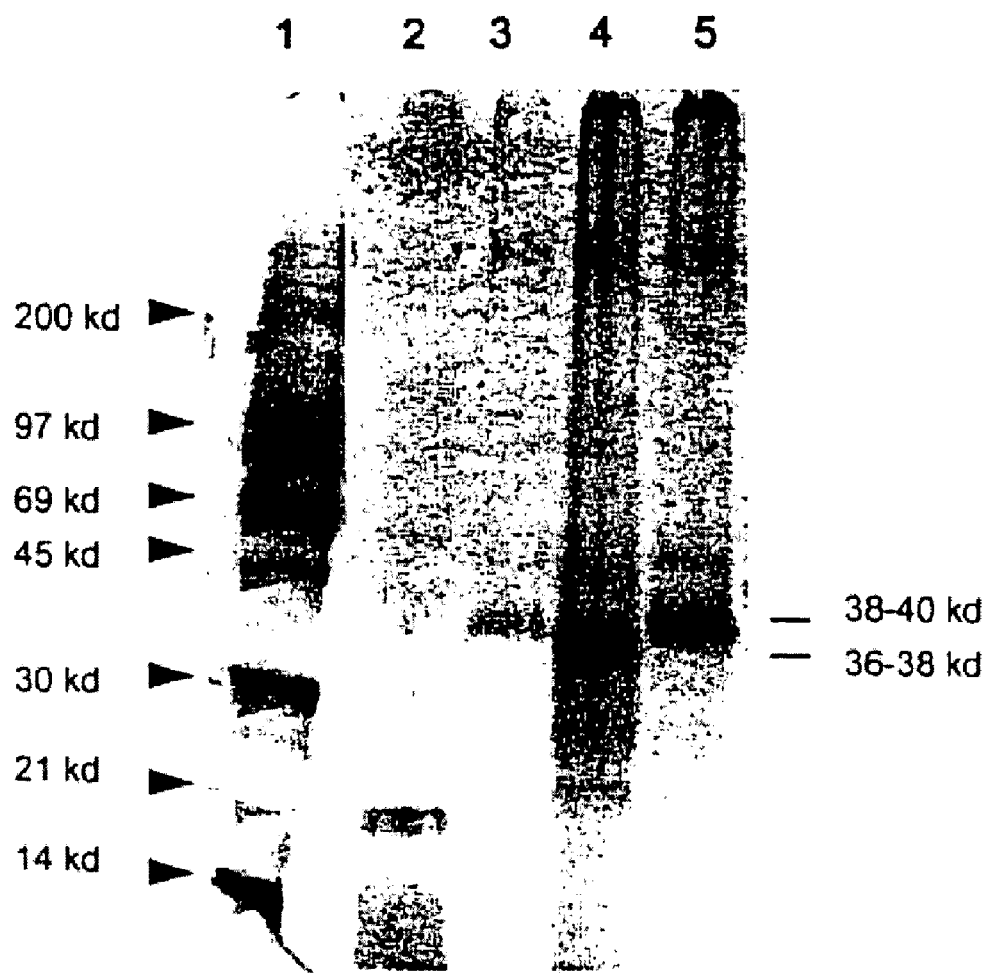
FIG. 7 shows a photograph of an SDS-PAGE gel after in vitro transcription, translation and electrophoresis of the polypeptide of the present invention. Lane 1: $^{14}C$ and rainbow M. W. marker; Lane 2: FGF control; Lane 3: VEGF-2 produced by M13-reverse and forward primers; Lane 4: VEGF-2 produced by M13 reverse and VEGF-F4 primers; Lane 5: VEGF-2 produced by M13 reverse and VEGF-F5 primers.
Figure 8A:
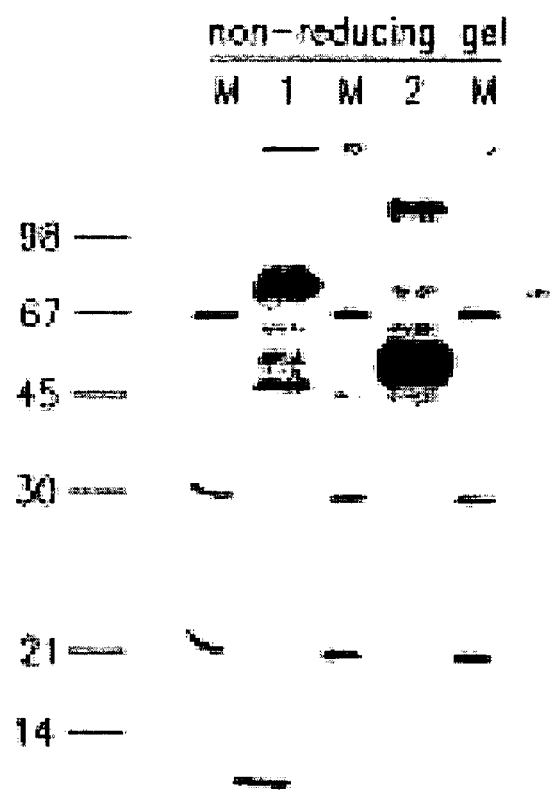
FIGS. 8A and 8B depict photographs of SDS-PAGE gels. VEGF-2 polypeptide was expressed in a baculovirus system consisting of Sf9 cells. Protein from the medium and cytoplasm of cells were analyzed by SDS-PAGE under non-reducing (FIG. 8A) and reducing (FIG. 8B) conditions.
Figure 8B:
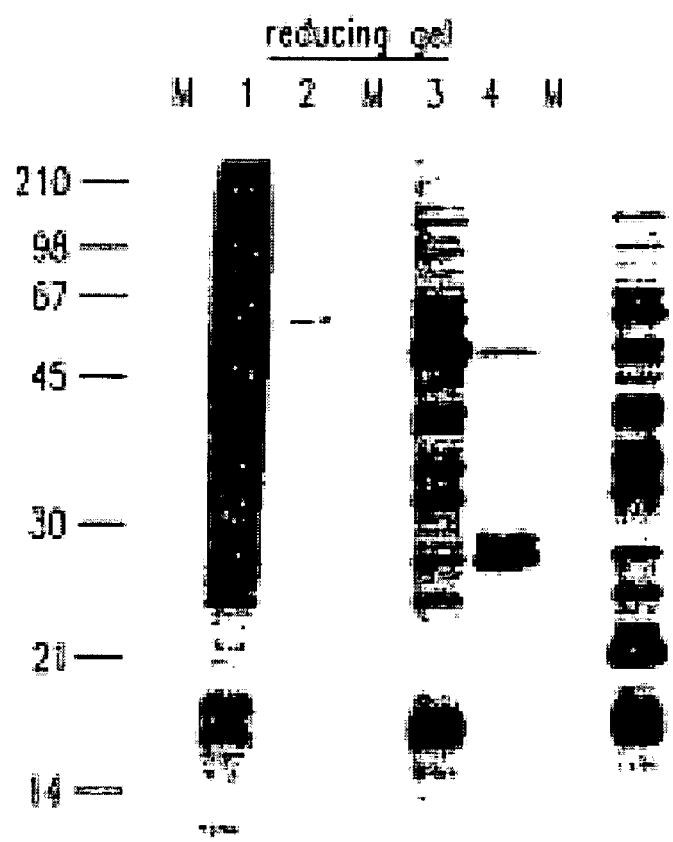

As shown in FIG. 7, PCR products containing the truncated VEGF-2 cDNA (i.e., as depicted in SEQ ID NO:3) and the cDNA missing 266 bp in the 3' un-translated region (3'-UTR) produced the same length of translated products, whose molecular weights are estimated to be 38–40 dk (lanes 1 and 3). The cDNA missing all the 3'UTR and missing sequence encoding the C-terminal 36 amino acids was translated into a polypeptide with an estimated molecular weight of 36–38 kd (lane 2).

Example 3

Cloning and Expression of VEGF-2 Using the Baculovirus Expression System

The DNA sequence encoding the VEGF-2 protein without 46 amino acids at the N-terminus, see ATCC No. 97149, was amplified using PCR oligonucleotide primers corresponding to the 5' and 3' sequences of the gene:

The 5' primer has the sequence TGT AAT ACG ACT CAC TAT AGG GAT CCC GCC ATG GAG GCC ACG GCT TAT GC (SEQ ID NO:12) and contains a BamH1 restriction enzyme site (in bold) and 17 nucleotide sequence complementary to the 5' sequence of VEGF-2 (nt. 150–166).

The 3' primer has the sequence GATC TCT AGA TTA GCT CAT TTG TGG TCT (SEQ ID NO:13) and contains the cleavage site for the restriction enzyme XbaI and 18 nucleotides complementary to the 3' sequence of VEGF-2, including the stop codon and 15 nt sequence before stop codon.

The amplified sequences were isolated from a 1% agarose gel using a commercially available kit ("Geneclean," BIO 101, Inc., La Jolla, Calif.). The fragment was then digested with the endonuclease BamH1 and XbaI and then purified again on a 1% agarose gel. This fragment was ligated to pAcGP67A baculovirus transfer vector (Pharmingen) at the BamH1 and XbaI sites. Through this ligation, VEGF-2 cDNA was cloned in frame with the signal sequence of baculovirus gp67 gene and was located at the 3' end of the signal sequence in the vector. This is designated pAcGP67A-VEGF-2.

To clone VEGF-2 with the signal sequence of gp67 gene to the pRG1 vector for expression, VEGF-2 with the signal sequence and some upstream sequence were excised from the pAcGP67A-VEGF-2 plasmid at the Xho restriction endonuclease site located upstream of the VEGF-2 cDNA and at the XbaI restriction endonuclease site by XhoI and XbaI restriction enzyme. This fragment was separated from the rest of vector on a 1% agarose gel and was purified using "Geneclean" kit. It was designated F2.

The PRG1 vector (modification of pVL941 vector) is used for the expression of the VEGF-2 protein using the baculovirus expression system (for review see: Summers, M. D. and Smith, G. E., "A Manual of Methods for Baculovirus Vectors and Insect Cell Culture Procedures," Texas Agricultural Experimental Station Bulletin No. 1555, (1987)). This expression vector contains the strong polyhedrin promoter of the Autographa californica nuclear polyhedrosis virus (AcMNPV) followed by the recognition sites for the restriction endonucleases BamH1, Sma1, XbaI, BglII and Asp718. A site for restriction endonuclease Xho1 is located upstream of BamH1 site. The sequence between Xho1 and BamH1 is the same as that in PAcGp67A (static on tape) vector. The polyadenylation site of the simian virus (SV)40 is used for efficient polyadenylation. For an easy selection of recombinant virus the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology 170:31–39 (1989).

The plasmid was digested with the restriction enzymes XboI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E. coli HB101 cells were then transformed and bacteria identified that contained the plasmid (pBac gp67-VEGF-2) with the VEGF-2 gene using the enzymes BamH1 and XbaI. The sequence of the cloned fragment was confirmed by DNA sequencing.

5 mg of the plasmid pBac gp67-VEGF-2 was cotransfected with 1.0 mg of a commercially available linearized baculovirus ("BaculoGoldJ baculovirus DNA", Pharmingen, San Diego, Calif.) using the lipofectin method (Felgner et al., Proc. Natl. Acad. Sci. USA 84:7413–7417 (1987)).

1 mg of BaculoGoldJ virus DNA and 5 mg of the plasmid pBac gp67-VEGF-2 were mixed in a sterile well of a microtiter plate containing 50 ml of serum free Grace's medium (Life Technologies Inc., Gaithersburg, Md.). Afterwards 10 ml Lipofectin plus 90 ml Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith, supra. As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells, blue stained plaques were picked with the tip of an Eppendorf pipette. The agar containing the recombinant viruses was then resuspended in an Eppendorf tube containing 200 ml of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-gp67-VEGF-2 at a multiplicity of infection (MOI) of 1. Six hours later the medium was removed and replaced with SF900 II medium minus methionine and cysteine (Life Technologies Inc., Gaithersburg). 42 hours later 5 mCi of $^{35}$S-methionine and 5 mCi 35S cysteine (Amersham) were added. The cells were further incubated for 16 hours before they were harvested by centrifugation and the labelled proteins visualized by SDS-PAGE and autoradiography.

Figure 9:
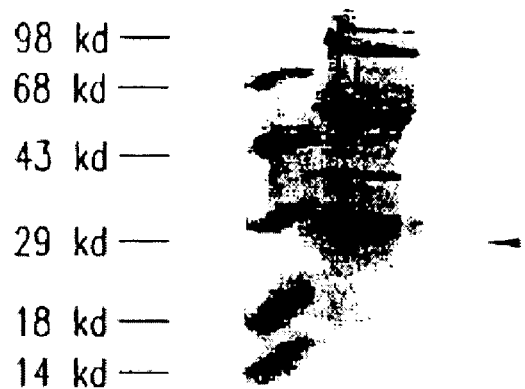
FIG. 9 depicts a photograph of an SDS-PAGE gel. The medium from Sf9 cells infected with a nucleic acid sequence of the present invention was precipitated. The resuspended precipitate was analyzed by SDS-PAGE and stained with Coomassie brilliant blue.

Protein from the medium and cytoplasm of the Sf9 cells was analyzed by SDS-PAGE under non-reducing and reducing conditions. See FIGS. 8A and 8B, respectively. The medium was dialyzed against 50 mM MES, pH 5.8. Precpitates were obtained after dialysis and resuspended in 100 mM NaCitrate, pH 5.0. The resuspended precipitate was analyzed again by SDS-PAGE and was stained with Coomassie Brilliant Blue. See FIG. 9.

Figure 10:
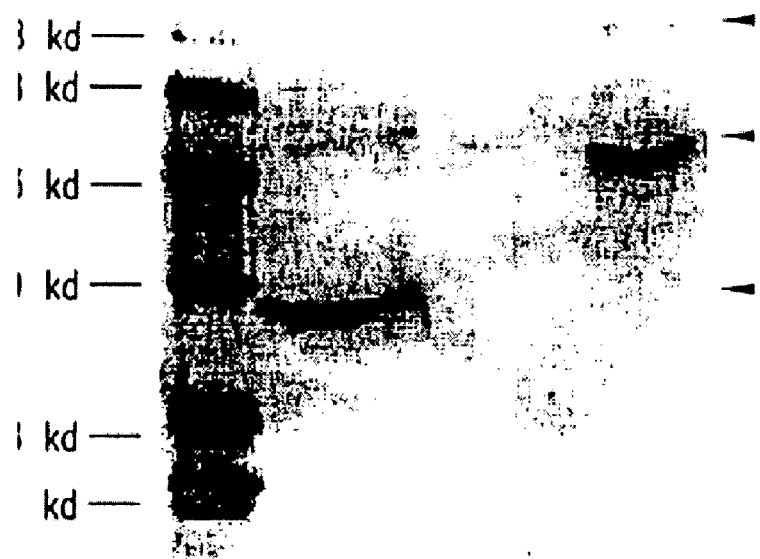
FIG. 10 depicts a photograph of an SDS-PAGE gel. VEGF-2 was purified from the medium supernatant and analyzed by SDS-PAGE in the presence or absence of the reducing agent b-mercaptoethanol and stained by Coomassie brilliant blue.
Figure 11:
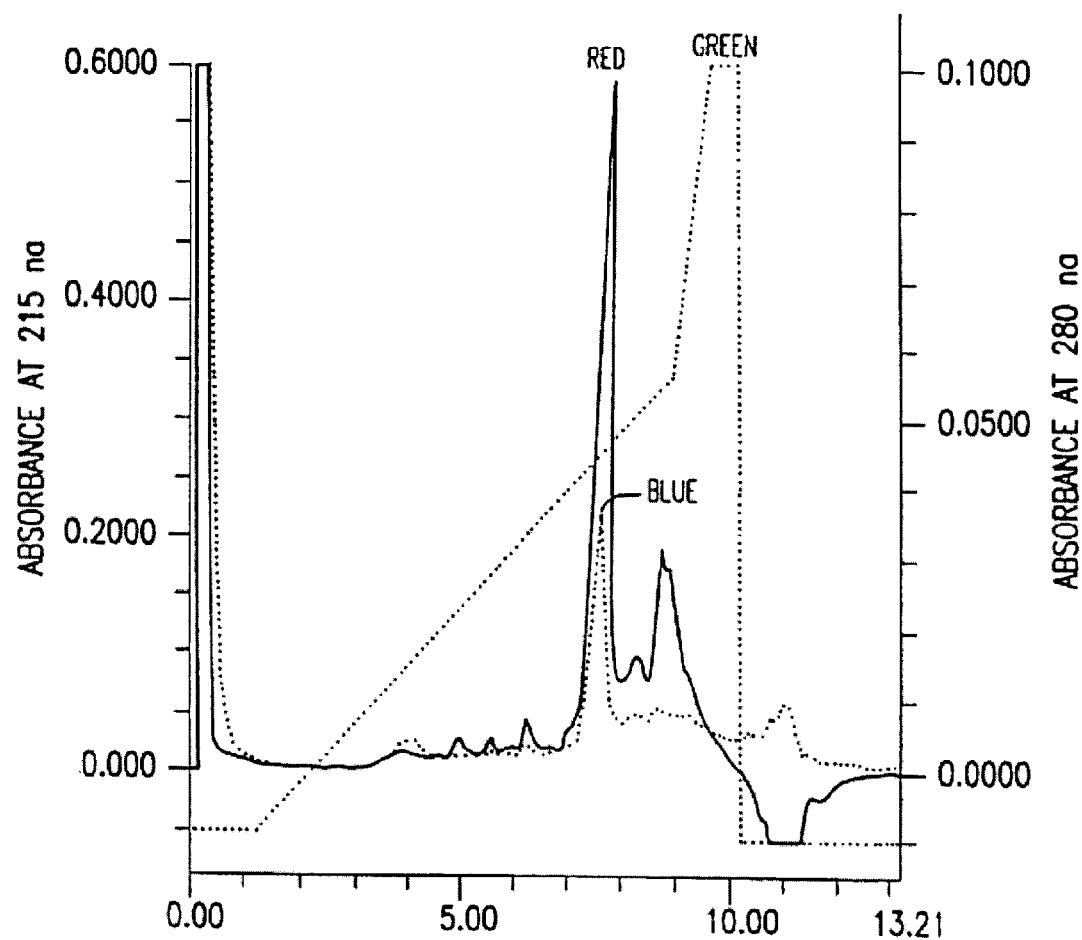
FIG. 11 depicts reverse phase HPLC analysis of purified VEGF-2 using a RP-300 column (0.21×3 cm, Applied Biosystems, Inc.). The column was equilibrated with 0.1% trifluoroacetic acid (Solvent A) and the proteins eluted with a 7.5 min gradient from 0 to 60% Solvent B, composed of acetonitrile containing 0.07% TFA. The protein elution was monitored by absorbance at 215 nm ("red" line) and 280 nm ("blue" line). The percentage of Solvent B is shown by the "green" line.

The medium supernatant was also diluted 1:10 in 50 mM MES, pH 5.8 and applied to an SP-650M column (1.0×6.6 cm, Toyopearl) at a flow rate of 1 ml/min. Protein was eluted with step gradients at 200, 300 and 500 mM NaCl. The VEGF-2 was obtained using the elution at 500 mM. The eluate was analyzed by SDS-PAGE in the presence or absence of reducing agent, b-mercaptoethanol and stained by Coomassie Brilliant Blue. See FIG. 10.

Example 4

Expression of Recombinant VEGF-2 in COS Cells

The expression of plasmid, VEGF-2-HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron and polyadenylation site. A DNA fragment encoding the entire VEGF-2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (Wilson et al., *Cell* 37:767 (1984)). The infusion of HA tag to the target protein allows easy detection of the recombinant protein with an antibody that recognizes the HA epitope.

The plasmid construction strategy is described as follows: The DNA sequence encoding VEGF-2, ATCC No. 97149, was constructed by PCR using two primers: the 5' primer (CGC GGA TCC ATG ACT GTA CTC TAC CCA) (SEQ ID NO:14) contains a BamH1 site followed by 18 nucleotides of VEGF-2 coding sequence starting from the initiation codon; the 3' sequence (CGC TCT AGA TCA AGC GTA GTC TGG GAC GTC GTA TGG GTA CTC GAG GCT CAT TTG TGG TCT 3') (SEQ ID NO:15) contains complementary sequences to an XbaI site, HA tag, XhoI site, and the last 15 nucleotides of the VEGF-2 coding sequence (not including the stop codon). Therefore, the PCR product contains a BamHI site, coding sequence followed by an XhoI restriction endonuclease site and HA tag fused in frame, a translation termination stop codon next to the HA tag, and an XbaI site. The PCR amplified DNA fragment and the vector, pcDNAI/Amp, were digested with BamH1 and XbaI restriction enzyme and ligated. The ligation mixture was transformed into E. coli strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant VEGF-2, COS cells were transfected with the expression vector by DEAE-DEXTRAN method (J. Sambrook, E. Fritsch, T. Maniatis, *Molecular Cloning: A Laboratory Manual*, Cold Spring Laboratory Press, (1989)). The expression of the VEGF-2-HA protein was detected by radiolabelling and immunoprecipitation method (E. Harlow and D. Lane, *Antibodies: A Laboratory Manual*, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson et al., *Cell* 37:767 (1984)). Both cell lysate and culture media were precipitated with an HA specific monoclonal antibody. Proteins precipitated were analyzed on 15% SDS-PAGE gels.

Example 5

The Effect of Partially Purified VEGF-2 Protein on the Growth of Vascular Endothelial Cells On day 1, human umbilical vein endothelial cells (HUVEC) were seeded at 2–5×10$^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium was replaced with M199 containing 10% FBS, 8 units/ml heparin. VEGF-2 protein of SEQ ID NO. 2 minus the initial 45 amino acid residues, (VEGF) and basic FGF (bFGF) were added, at the concentration shown. On days 4 and 6, the medium was replaced. On day 8, cell number was determined with a Coulter Counter (See FIG. 12).

Example 6

The Effect of Purified VEGF-2 Protein on the Growth of Vascular Endothelial Cells On day 1, human umbilical vein endothelial cells (HUVEC) were seeded at 2–5×10$^4$ cells/35 mm dish density in M199 medium containing 4% fetal bovine serum (FBS), 16 units/ml heparin, 50 units/ml endothelial cell growth supplements (ECGS, Biotechnique, Inc.). On day 2, the medium was replaced with M199 containing 10% FBS, 8 units/ml heparin. Purified VEGF-2 protein of SEQ ID NO:2 minus initial 45 amino acid residues was added to the medium at this point. On days 4 and 6, the medium was replaced with fresh medium and supplements. On day 8, cell number was determined with a Coulter Counter (See FIG. 13).

Example 7

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added.

This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219–225 (1988)) flanked by the long terminal repeats of the Moloney murine sarcoma virus, is digested with EcoRi and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 8

Expression of VEGF-2 mRNA in Human Fetal and Adult Tissues

Experimental Design

Northern blot analysis was carried out to examine the levels of expression of VEGF-2 mRNA in human fetal and adult tissues. A cDNA probe containing the entire nucleotide sequence of the VEGF-2 protein was labeled with 32p using the rediprime° DNA labeling system (Amersham Life Science), according to the manufacturer's instructions. After labeling, the probe was purified using a CHROMA SPIN-100* column (Clontech Laboratories, Inc.), according to manufacturer's protocol number PT1200-1. The purified labeled probe was then used to examine various human tissues for VEGF-2 mRNA.

A Multiple Tissue Northern (MTN) blot containing various human tissues (Fetal Kidney, Fetal Lung, Fetal Liver, Brain, Kidney, Lung, Liver, Spleen, Thymus, Bone Marrow, Testes, Placenta, and Skeletal Muscle) was obtained from Clontech. The MTN blot was examined with the labeled probe using ExpressHyb* hybridization solution (Clontech) according to manufacturer's protocol number PT1190-1. Following hybridization and washing, the blot was exposed to film at −70° C. overnight with an intensifying screen and developed according to standard procedures.

Results

Figure 14A:
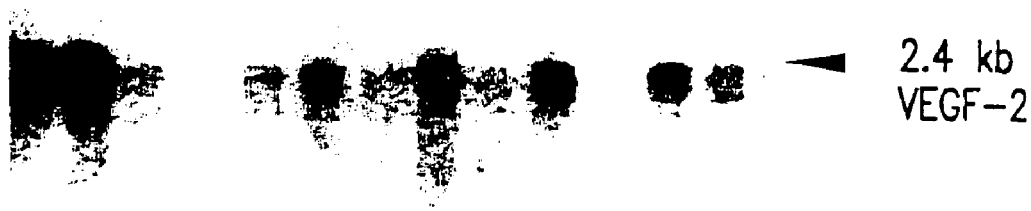
FIG. 14(A–B) depicts expression of VEGF-2 mRNA in human fetal and adult tissues.
Figure 14B:

Expression of VEGF-2 mRNA is abundant in vascular smooth muscle and several highly vascularized tissues. VEGF-2 is expressed at significantly higher levels in tissues associated with hematopoetic or angiogenic activities, i.e. fetal kidney, fetal lung, bone marrow, placental, spleen and lung tissue. The expression level of VEGF-2 is low in adult kidney, fetal liver, adult liver, testes; and is almost undetectable in fetal brain, and adult brain (See FIG. 14).

Figure 15:
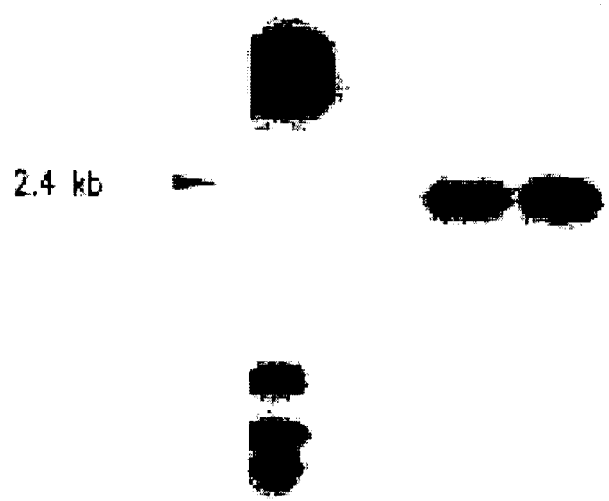
FIG. 15 depicts expression of VEGF-2 mRNA in human primary culture cells.

In primary cultured cells, the expression of VEGF-2 mRNA is abundant in vascular smooth muscle cells and dermal fibroblast cells, but much lower in human umbilical vein endothelial cells (see FIG. 15). This mRNA distribution pattern is very similar to that of VEGF.

Example 9

Construction of Amino Terminal and Carboxy Terminal Deletion Mutants

In order to identify and analyze biologically active VEGF-2 polypeptides, a panel of deletion mutants of VEGF-2 was constructed using the expression vector pHE4a.

1. Construction of VEGF-2 T103–L215 in pHE4

To permit Polymerase Chain Reaction directed amplification and sub-cloning of VEGF-2 T103–L215 (amino acids 103 to 215 in FIG. 1 or SEQ ID NO:18) into the *E. coli* protein expression vector, pHE4, two oligonucleotide primers complementary to the desired region of VEGF-2 were synthesized with the following base sequence:

```
5' Primer
(Nde I/START and 18 nt of coding sequence):
                            (SEQ ID NO:19)
5'-GCA GCA CAT ATG ACA GAA GAG ACT ATA AAA-3'

3' Primer
(Asp718, STOP, and 15 nt of coding sequence):
                            (SEQ ID NO:20)
5'-GCA GCA GGT ACC TCA CAG TTT AGA CAT GCA-3'
```

The above described 5' primer (SEQ ID NO: 19), incorporates an NdeI restriction site and the above described 3' Primer (SEQ ID NO:20), incorporates an Asp718 restriction site. The 5' primer (SEQ ID NO:19) also contains an ATG sequence adjacent and in frame with the VEGF-2 coding region to allow translation of the cloned fragment in *E. coli*, while the 3' primer (SEQ ID NO:20) contains one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24–419 in SEQ ID NO: 2) as, for example, constructed in Example 3 as template. The resulting amplicon was restriction digested with NdeI and Asp718 and subcloned into NdeI/Asp718 digested pHE-4a expression vector.

2. Construction of VEGF-2 T103–R227 in pHE4

To permit Polymerase Chain Reaction directed amplification and sub-cloning of VEGF-2 T103–R227 (amino acids 103 to 227 in FIG. 1 or SEQ ID NO:18) into the E. coli protein expression vector, pHE4, two oligonucleotide primers complementary to the desired region of VEGF-2 were synthesized with the following base sequence:

```
5' Primer
(Nde I/START and 18 nt of coding sequence):
                                  (SEQ ID NO:19)
5'-GCA GCA CAT ATG ACA GAA GAG ACT ATA AAA-3'

3' Primer
(Asp 718, STOP, and 15 nt of coding sequence):
                                  (SEQ ID NO:21)
5'-GCA GCA GGT ACC TCA ACG TCT AAT AAT GGA-3'
```

In the case of the above described primers, an NdeI or Asp718 restriction site was incorporated he 5' primer and 3' primer, respectively. The 5'primer (SEQ ID NO:19) also contains an ATG sequence adjacent and in frame with the VEGF-2 coding region to allow translation of the cloned fragment in *E. coli,* while the 3' Primer (SEQ ID NO:21) contains one stop codon (preferentially utilized in *E. coli*) adjacent and in frame with the VEGF-2 coding region which ensures correct translational termination in *E. coli.*

The Polymerase Chain Reaction was performed using standard conditions well known to those skilled in the art and the nucleotide sequence for the mature VEGF-2 (aa 24–419 in SEQ ID NO: 2) as, for example, constructed in Example 3, as template. The resulting amplicon was restriction digested with NdeI and Asp718 and subcloned into NdeI/Asp718 digested pHE-4a protein expression vector.

3. Construction of VEGF-2 T103–L215 in pA2GP

In this illustrative example, the plasmid shuttle vector pA2 GP is used to insert the cloned DNA encoding the N-terminal and C-terminal deleted VEGF-2 protein (amino acids 103–215 in FIG. 1 or SEQ ID NO:18), into a baculovirus to express the N-terminal and C-terminal deleted VEGF-2 protein, using a baculovirus leader and standard methods as described in Summers et al., *A Manual of Methods for Baculovirus Vectors and Insect Cell Culture Procedures,* Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the VEGF-2 protein without 102 amino acids at the N-terminus and without 204 amino acids at the C-terminus in FIG. 1, was amplified using PCR oligonucleotide primers corresponding to the 5' and 3' sequences of the gene.

The 5' primer has the sequence 5'-GCA GCA GGA TCC CAC AGA AGA GAC TAT AAA-3' (SEQ ID NO:22) containing the BamHI restriction enzyme site (in bold) followed by 1 spacer nt to stay in-frame with the vector-supplied signal peptide, and 17 nt of coding sequence bases of VEGF-2 protein. The 3' primer has the sequence 5N-GCA GCA TCT AGA TCA CAG TTT AGA CAT GCA-3' (SEQ ID NO:23) containing the XbaI restriction site (in bold) followed by a stop codon and 17 nucleotides complementary to the 3' coding sequence of VEGF-2.

The amplified sequences were isolated from a 1% agarose gel using a commercially available kit ("Geneclean," BIO 101, Inc., La Jolla, Calif.). The fragment was then digested with the endonuclease BamH1 and XbaI and then purified again on a 1% agarose gel. This fragment was ligated to pA2 GP baculovirus transfer vector (Supplier) at the BamH1 and XbaI sites. Through this ligation, VEGF-2 cDNA representing the N-terminal and C-terminal deleted VEGF-2 protein (amino acids 103–215 in FIG. 1 or SEQ ID NO:18) was cloned in frame with the signal sequence of baculovirus GP gene and was located at the 3' end of the signal sequence in the vector. This is designated pA2GPVEGF-2.T103–L215.

4. Construction of VEGF-2 T103–R227 in pA2GP

The cDNA sequence encoding the VEGF-2 protein without 102 amino acids at the N-terminus and without 192 amino acids at the C-terminus in FIG. 1 (i.e., amino acids 103–227 of SEQ ID NO: 2) was amplified using PCR oligonucleotide primers corresponding to the 5' and 3' sequences of the gene.

The 5'-GCA GCA GGA TCC CAC AGA AGA GAC TAT AAA ATT TGC TGC-3' primer has the sequence (SEQ ID NO:24) containing the BamHI restriction enzyme site (in bold) followed by 1 spacer nt to stay in-frame with the vector-supplied signal peptide, and 26 nt of coding sequence bases of VEGF-2 protein. The 3' primer has the sequence 5N-GCA GCA TCT AGA TCA ACG TCT AAT AAT GGA ATG AAC-3' (SEQ ID NO:25) containing the XbaI restriction site (in bold) followed by a stop codon and 21 nucleotides complementary to the 3' coding sequence of VEGF-2.

The amplified sequences were isolated from a 1% agarose gel using a commercially available kit ("Geneclean," BIO 101, Inc., La Jolla, Calif.). The fragment was then digested with the endonuclease BamH1 and XbaI and then purified again on a 1% agarose gel. This fragment was ligated to pA2 GP baculovirus transfer vector (Supplier) at the BamH1 and XbaI sites. Through this ligation, VEGF-2 cDNA representing the N-terminal and C-terminal deleted VEGF-2 protein (amino acids 103–227 in FIG. 1 or SEQ ID NO:18) was cloned in frame with the signal sequence of baculovirus GP gene and was located at the 3' end of the signal sequence in the vector. This construct is designated pA2GPVEGF-2.T103–R227.

5. Construction of VEGF-2 in pC1

The expression vectors pC1 and pC4 contain the strong promoter (LTR) of the Rous Sarcoma Virus (Cullen et al., *Molecular and Cellular Biology,* 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3N intron, the polyadenylation and termination signal of the rat preproinsulin gene.

The vector pC1 is used for the expression of VEGF-2 protein. Plasmid pC1 is a derivative of the plasmid pSV2-dhfr [ATCC Accession No. 37146]. Both plasmids contain the mouse DHFR gene under control of the SV40 early promoter. Chinese hamster ovary—or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., *Molecular and Cellular Biology,* March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3N intron and the polyadenylation site of the rat preproinsulin gene. Other high efficient promoters can also be used for the expression, e.g., the human b-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

codon; the 3' primer (5'-GCA GGG TAC GGA TCC TAG ATT AGC TCA TTT GTG GTC TTT-3' (SEQ ID NO:27)) contains a BamHI site and 16 nt of VEGF-2 coding sequence not including the stop codon.

The PCR amplified DNA fragment is isolated from a 1% agarose gel as described above and then digested with the endonuclease BamHI and then purified again on a 1% agarose gel. The isolated fragment and the dephosphorylated vector are then ligated with T4 DNA ligase. *E. coli* HB101 cells are then transformed and bacteria identified that contained the plasmid pC1. The sequence and orientation of the inserted gene is confirmed by DNA sequencing. This construct is designated pC1VEGF-2.

6. Construction of pC4SigVEGF-2 T103–L215

Plasmid pC4Sig is plasmid pC4 (Accession No. 209646) containing a human IgG Fe portion as well as a protein signal sequence.

To permit Polymerase Chain Reaction directed amplification and sub-cloning of VEGF-2 T103–L215 (amino acids 103 to 215 in FIG. 1 or SEQ ID NO:18) into pC4Sig, two oligonucleotide primers complementary to the desired region of VEGF-2 were synthesized with the following base sequence:

5' Primer (Bam HI and 26 nt of coding sequence):

5'-GCA GCA GGA TCC ACA GAA GAG ACT ATA AAA TTT GCT GC-3' (SEQ ID NO:34)

3' Primer (Xba I, STOP, and 15 nt of coding sequence):

5'-CGT CGT TCT AGA TCA CAG TTT AGA CAT GCA TCG GCA G-3' (SEQ ID NO:35)

The Polymerase Chain Reaction was performed using standard conditions well known to those skilled in the art and the nucleotide sequence for the mature VEGF-2 (aa 24–419) as, for example, constructed in Example 3, as template. The resulting amplicon was restriction digested with BamHI and XbaI and subcloned into BamHI/XbaI digested pC4Sig vector.

7. Construction of pC4SigVEGF-2 T103–R227

To permit Polymerase Chain Reaction directed amplification and sub-cloning of VEGF-2 T103–L215 (amino acids 103 to 227 in FIG. 1 or SEQ ID NO: 18) into pC4Sig, two oligonucleotide primers complementary to the desired region of VEGF-2 were synthesized with the following base sequence:

```
5' Primer (Barn HI and 26 nt of coding sequence):
5'-GCA GCA GGA TCC ACA GAA GAG ACT ATA AAA TTT GCT GC-3'   (SEQ ID NO:34)

3' Primer (Xba I, STOP, and 21 nt of coding sequence):
5'-GCA GCA TCT AGA TCA ACG TCT AAT AAT GGA ATG AAC-3'      (SEQ ID NO:25)
```

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding VEGF-2, ATCC Accession No. 97149, was constructed by PCR using two primers corresponding to the 5' and 3'ends of the VEGF-2 gene: the 5' Primer (5'-GAT CGA TCC ATC ATG CAC TCG CTG GGC TTC TTC TCT GTG GCG TGT TCT CTG CTC G-3' (SEQ ID NO:26)) contains a Klenow-filled BamHI site and 40 nt of VEGF-2 coding sequence starting from the initiation The Polymerase Chain Reaction was performed using standard conditions well known to those skilled in the art and the nucleotide sequence for the mature VEGF-2 (aa 24–419) as, for example, constructed in Example 3, as template. The resulting amplicon was restriction digested with BamHI and XbaI and subcloned into BamHI/XbaI digested pC4Sig vector.

8. Construction of pC4VEGF-2 M1–M263

The expression vector pC4 contains the strong promoter (LTR) of the Rous Sarcoma Virus (Cullen et al., *Molecular and Cellular Biology,* 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vector contains in addition the 3N intron, the polyadenylation and termination signal of the rat preproinsulin gene.

In this illustrative example, the cloned DNA encoding the C-terminal deleted VEGF-2 M1–M263 protein (amino acids 1–263 in FIG. 1 or SEQ ID NO: 2) is inserted into the plasmid vector pC-4 to express the C-terminal deleted VEGF-2 protein.

To permit Polymerase Chain Reaction directed amplification and sub-cloning of VEGF-2 M1–M263 into the expression vector, pC4, two oligonucleotide primers complementary to the desired region of VEGF-2 were synthesized with the following base sequence:

```
5' Primer
5'-GAC TGG ATC CGC CAC CAT GCA CTC    (SEQ ID NO:28)
GCT GGG CTT CTT CTC-3'

3' Primer
5'-GAC TGG TAC CTT ATC ACA TAA AAT    (SEQ ID NO:29)
CTT CCT GAG CC-3'
```

In the case of the above described 5' primer, an BamH1 restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in E. coli, while the 3' primer contains 2 nt, 20 nt of VEGF-2 coding sequence, and one stop codon (preferentially utilized in E. coli) adjacent and in frame with the VEGF-2 coding region which ensures correct translational termination in E. coli.

The Polymerase Chain Reaction was performed using standard conditions well known to those skilled in the art and the nucleotide sequence for the mature VEGF-2 (aa 24–419) as constructed, for example, in Example 3 as template. The resulting amplicon was restriction digested with BamH1 and Asp718 and subcloned into BamH1/Asp718 digested pC4 protein expression vector. This construct is designated pC4VEGF-2 M1–M263.

9. Construction of pC4VEGF-2 M1–D311

In this illustrative example, the cloned DNA encoding the C-terminal deleted VEGF-2 M1–D311 protein (amino acids 1–311 in FIG. 1 or SEQ ID NO: 2) is inserted into the plasmid vector pC4 to express the C-terminal deleted VEGF-2 protein.

To permit Polymerase Chain Reaction directed amplification and sub-cloning of VEGF-2 M1–D311 into the expression vector, pC4, two oligonucleotide primers complementary to the desired region of VEGF-2 were synthesized with the following base sequence:

```
5' Primer
5'-GAC TGG ATC CGC CAC CAT GCA CTC    (SEQ ID NO:30)
GCT GGG CTT CTT CTC-3'

3' Primer
5'-GAC TGG TAC CTT ATC AGT CTA GTT    (SEQ ID NO:31)
CTT TGT GGG G-3'
```

In the case of the above described 5' primer, an BamH1 restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in E. coli, while the 3' primer contains 2 nt, 20 nt of VEGF-2 coding sequence, and one stop codon (preferentially utilized in E. coli) adjacent and in frame with the VEGF-2 coding region which ensures correct translational termination in E. coli.

The Polymerase Chain Reaction was performed using standard conditions well known to those skilled in the art and the nucleotide sequence for the mature VEGF-2 (aa 24–419) as constructed, for example, in Example 3 as template. The resulting amplicon was restriction digested with BamH1 and Asp718 and subcloned into BamH1/Asp718 digested pC4 protein expression vector.

10. Construction of pC4VEGF-2 M1–Q367

In this illustrative example, the cloned DNA encoding the C-terminal deleted VEGF-2 M1–D-311 protein (amino acids 1–311 in SEQ ID NO: 2) is inserted into the plasmid vector pC4 to express the C-terminal deleted VEGF-2 protein.

To permit Polymerase Chain Reaction directed amplification and sub-cloning of VEGF-2 M1–D311 into the expression vector, pC4, two oligonucleotide primers complementary to the desired region of VEGF-2 were synthesized with the following base sequence:

```
5' Primer
5'-GAC TGG ATC CGC CAC CAT GCA CTC    (SEQ ID NO:32)
GCT GGG CTT CTT CTC-3'

3' Primer
5'-GAC TGG TAC CTC ATT ACT GTG GAC    (SEQ ID NO:33)
TTT CTG TAC ATT C-3'
```

In the case of the above described 5' primer, an BamH1 restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in E. coli, while the 3' primer contains 2 nt, 20 nt of VEGF-2 coding sequence, and one stop codon (preferentially utilized in E. coli) adjacent and in frame with the VEGF-2 coding region which ensures correct translational termination in E. coli.

The Polymerase Chain Reaction was performed using standard conditions well known to those skilled in the art and the nucleotide sequence for the mature VEGF-2 (aa 24–419) as constructed, for example, in Example 3 as template. The resulting amplicon was restriction digested with BamH1 and Asp718 and subcloned into BamH1/Asp718 digested pC4 protein expression vector. This construct is designated pC4VEGF-2 M1–Q367.

Example 10

Transient Expression of VEGF-2 Protein in COS-7 Cells

Experimental Design

Expression of the VEGF-2-HA fusion protein from the construct made in Example 4, for example, was detected by radiolabeling and immunoprecipitation, using methods described in, for example Harlow and colleagues (Antibodies: A Laboratory Manual, 2nd Ed.; Cold Spring Harbor Laboratory Press, Cold Spring Harbor, N.Y. (1988)). To this end, two days after transfection, the cells were labeled by incubation in media containing 35S-cysteine for 8 hours. The cells and the media were collected, and the cells were washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins were precipitated from the cell lysate and from the culture media using an HA-specific monoclonal antibody. The precipitated proteins then were analyzed by SDS-PAGE and autoradiography.

Results

Figure 16A:
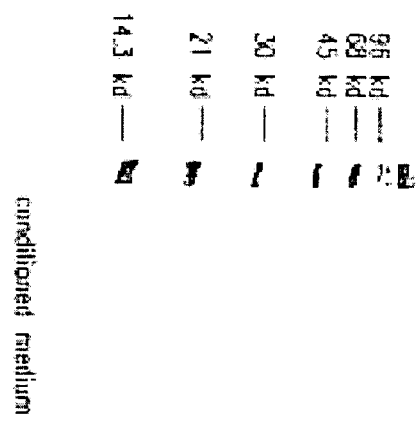
FIG. 16(A–B) depicts transient expression of VEGF-2 protein in COS-7 cells.
Figure 16B:
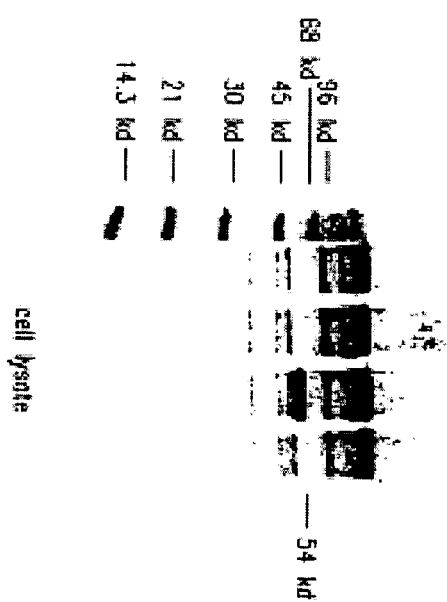

As shown in FIG. 16, cells transfected with pcDNA1 VEGF-2HA secreted a 56 kd and a 30 kd protein. The 56 kd protein, but not the 30 kd protein, could also be detected in the cell lysate but is note detected in controls. This suggests the 30 kd protein is likely to result from cleavage of the 56 kd protein. Since the HA-tag is on the C-terminus of VEGF-2, the 30 kd protein must represent the C-terminal portion of the cleaved protein, whereas the N-terminal portion of the cleaved protein would not be detected by immunoprecipitation. These data indicate that VEGF-2 protein expressed in mammalian cells is secreted and processed.

Example 11

Stimulatory Effect of VEGF-2 on Proliferation of Vascular Endothelial Cells

Experimental Design

Expression of VEGF-2 is abundant in highly vascularized tissues. Therefore the role of VEGF-2 in regulating proliferation of several types of endothelial cells was examined.

Endothelial Cell Proliferation Assay

For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells were seeded in a 96-well plate (5,000 cells/well) in 0.1 mL serum-supplemented medium and allowed to attach overnight. After serum-starvation for 12 hours in 0.5% FBS, conditions (bFGF, $VEGF_{165}$ or VEGF-2 in 0.5% FBS) with or without Heparin (8 U/ml) were added to wells for 48 hours. 20 mg of MTS/PMS mixture (1:0.05) were added per well and allowed to incubate for 1 hour at 37° C. before measuring the absorbance at 490 nm in an ELISA plate reader. Background absorbance from control wells (some media, no cells) was subtracted, and seven wells were performed in parallel for each condition. See, Leak et al. *In Vitro Cell. Dev. Biol.* 30A:512–518 (1994)

Results

Figure 17:
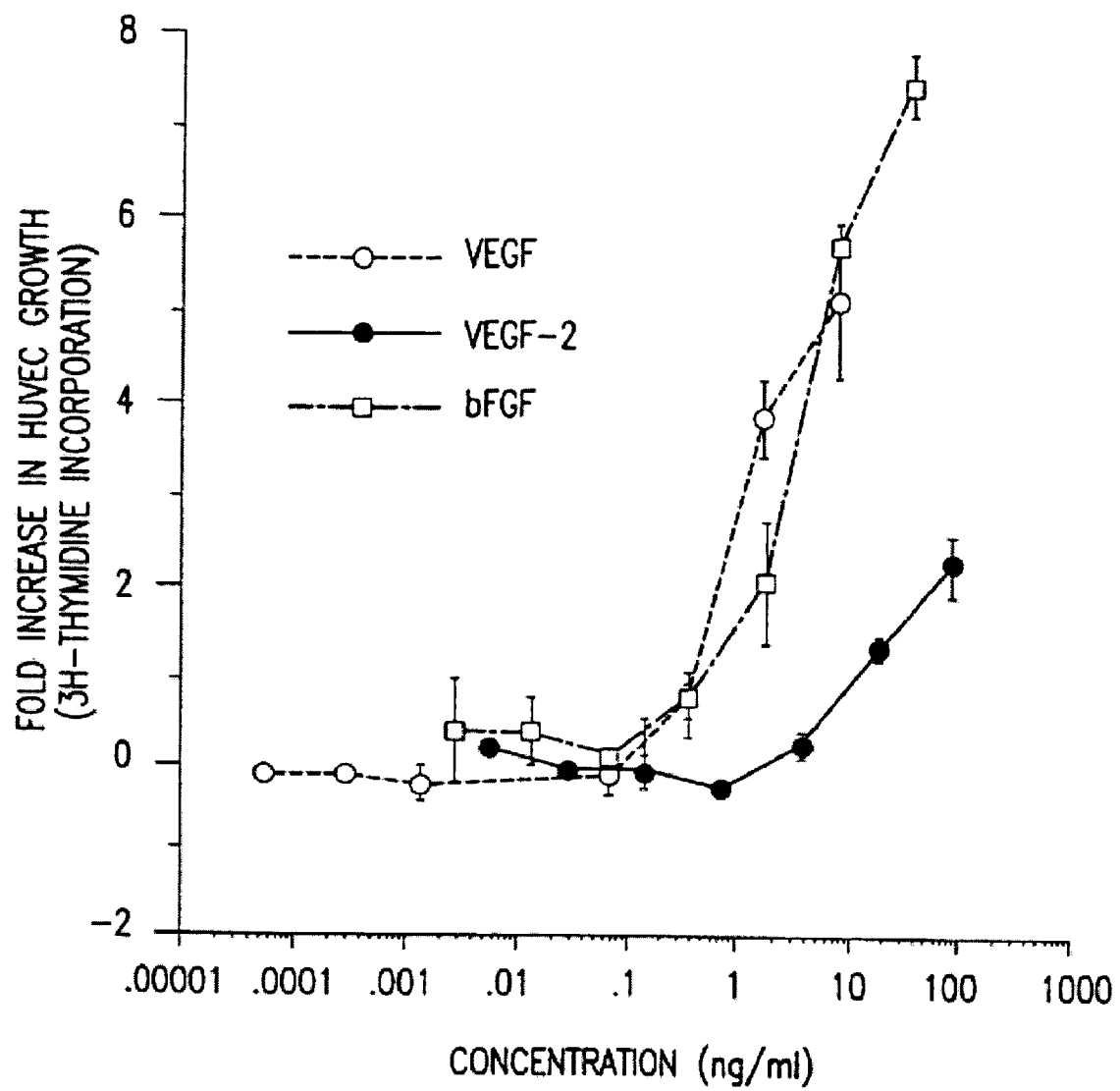
FIG. 17 depicts VEGF-2 stimulated proliferation of human umbilical vein endothelial cells (HUVEC).
Figure 18:
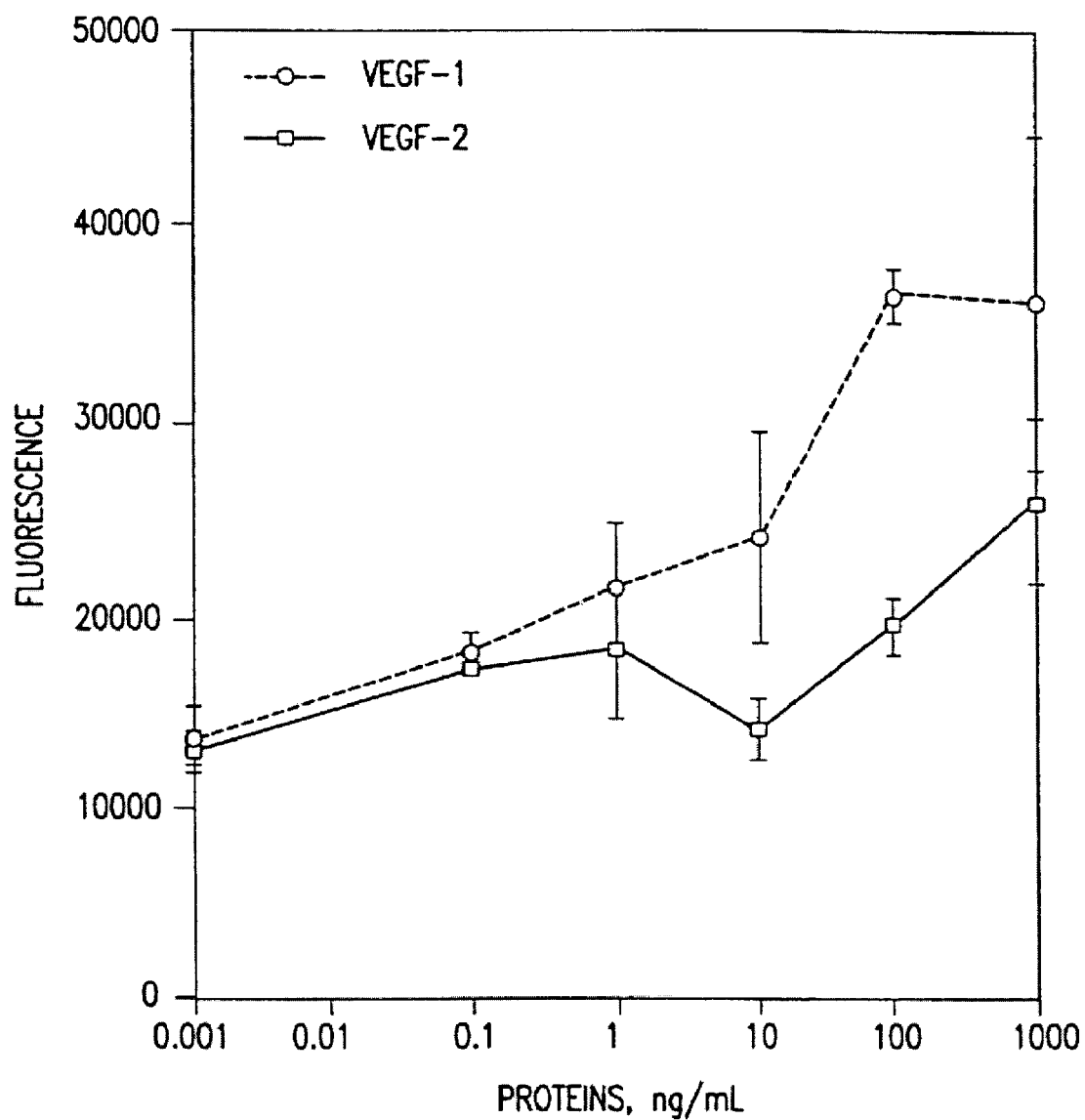
FIG. 18 depicts VEGF-2 stimulated proliferation of dermal microvascular endothelial cells.
Figure 19:
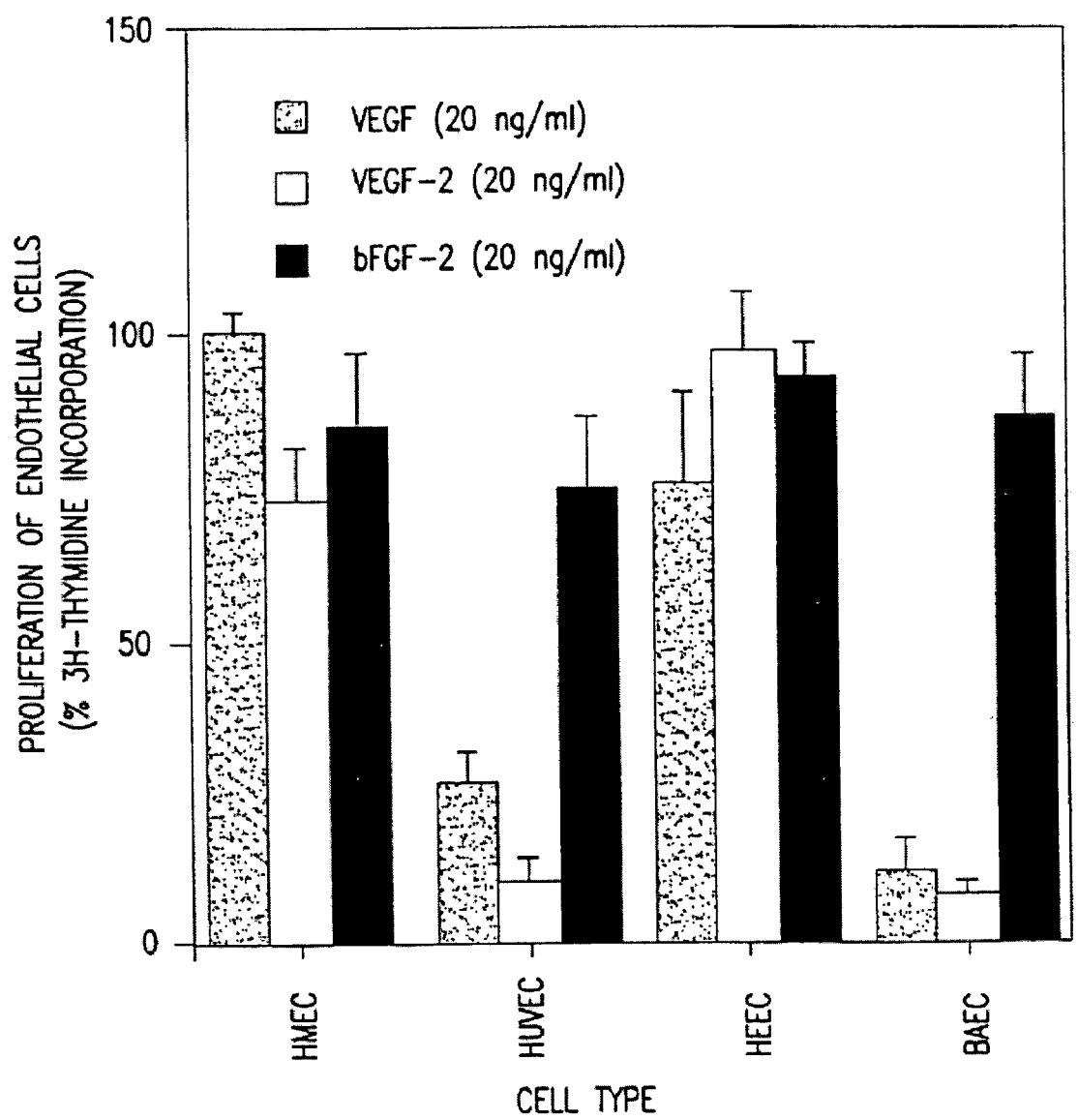
FIG. 19 depicts the stimulatory effect of VEGF-2 on proliferation of microvascular, umbilical cord, endometrial, and bovine aortic endothelial cells.

VEGF-2 stimulated proliferation of human umbilical vein endothelial cells (HUVEC) and dermal microvascular endothelial cells slightly (FIGS. 17 and 18). The stimulatory effect of VEGF-2 is more pronounced on proliferation of endometrial and microvascular endothelial cells (FIG. 19). Endometrial endothelial cells (HEEC) demonstrated the greatest response to VEGF-2 (96% of the effect of VEGF on microvascular endothelial cells). The response of microvascular endothelial cells (HMEC) to VEGF-2 was 73% compared to VEGF. The response of HUVEC and BAEC (bovine aortic endothelial cells) to VEGF-2 was substantially lower at 10% and 7%, respectively. The activity of VEGF-2 protein has varied between different purification runs with the stimulatory effect of certain batches on HUVEC proliferation being significantly higher than that of other batches.

Example 12

Inhibition of PDGF-induced Vascular Smooth Muscle Cell Proliferation

VEGF-2 expression is high in vascular smooth muscle cells. Smooth muscle is an important therapeutic target for vascular diseases, such as restenosis. To evaluate the potential effects of VEGF-2 on smooth muscle cells, the effect of VEGF-2 on human aortic smooth muscle cell (HAOSMC) proliferation was examined.

Experimental Design

HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after exposing to denaturing solution and then with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6;271(36):21985–21992 (1996).

Results

Figure 20A:
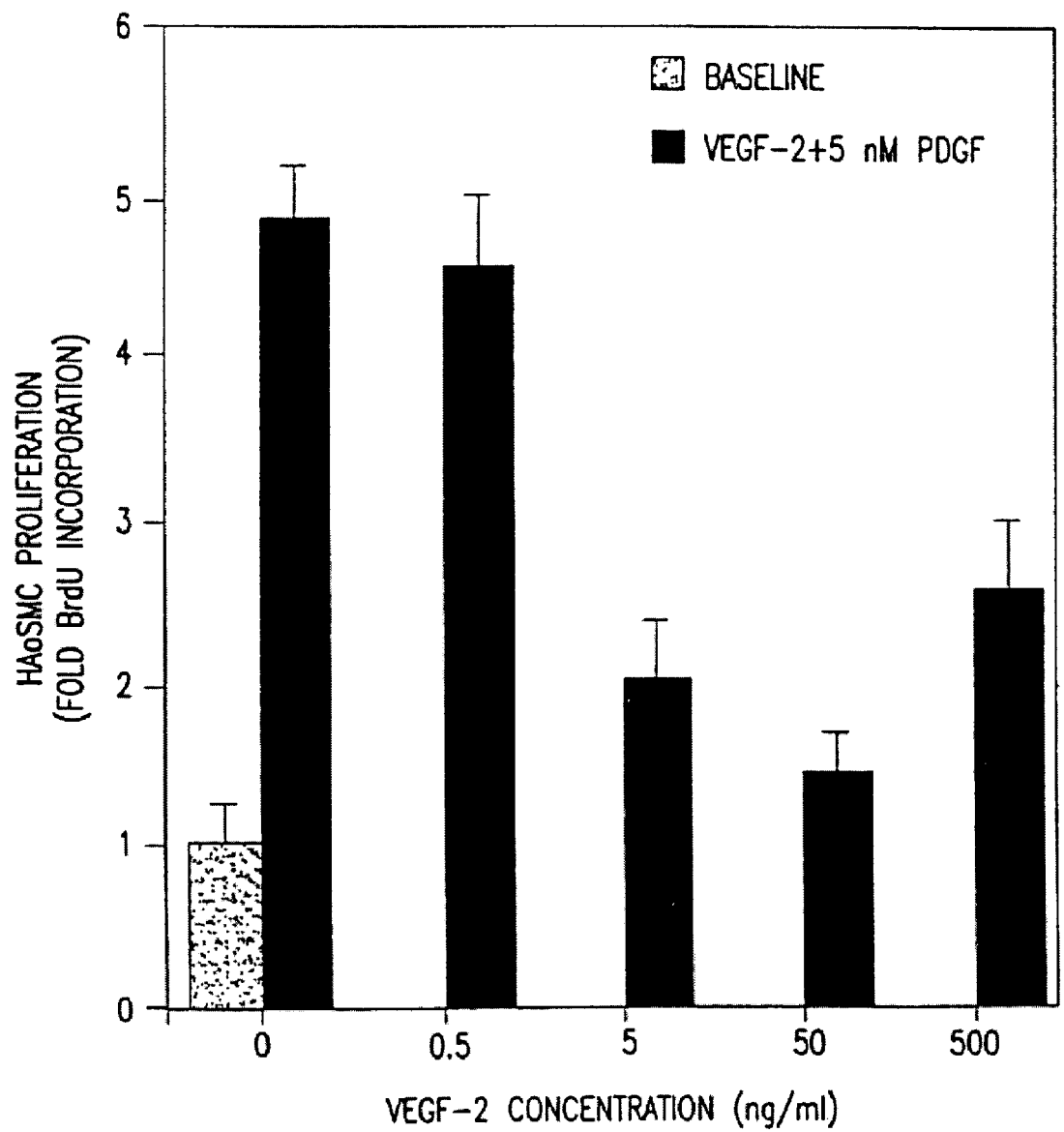
FIG. 20(A–B) depicts inhibition of PDGF-induced vascular (human aortic) smooth muscle cell proliferation.
Figure 20B:
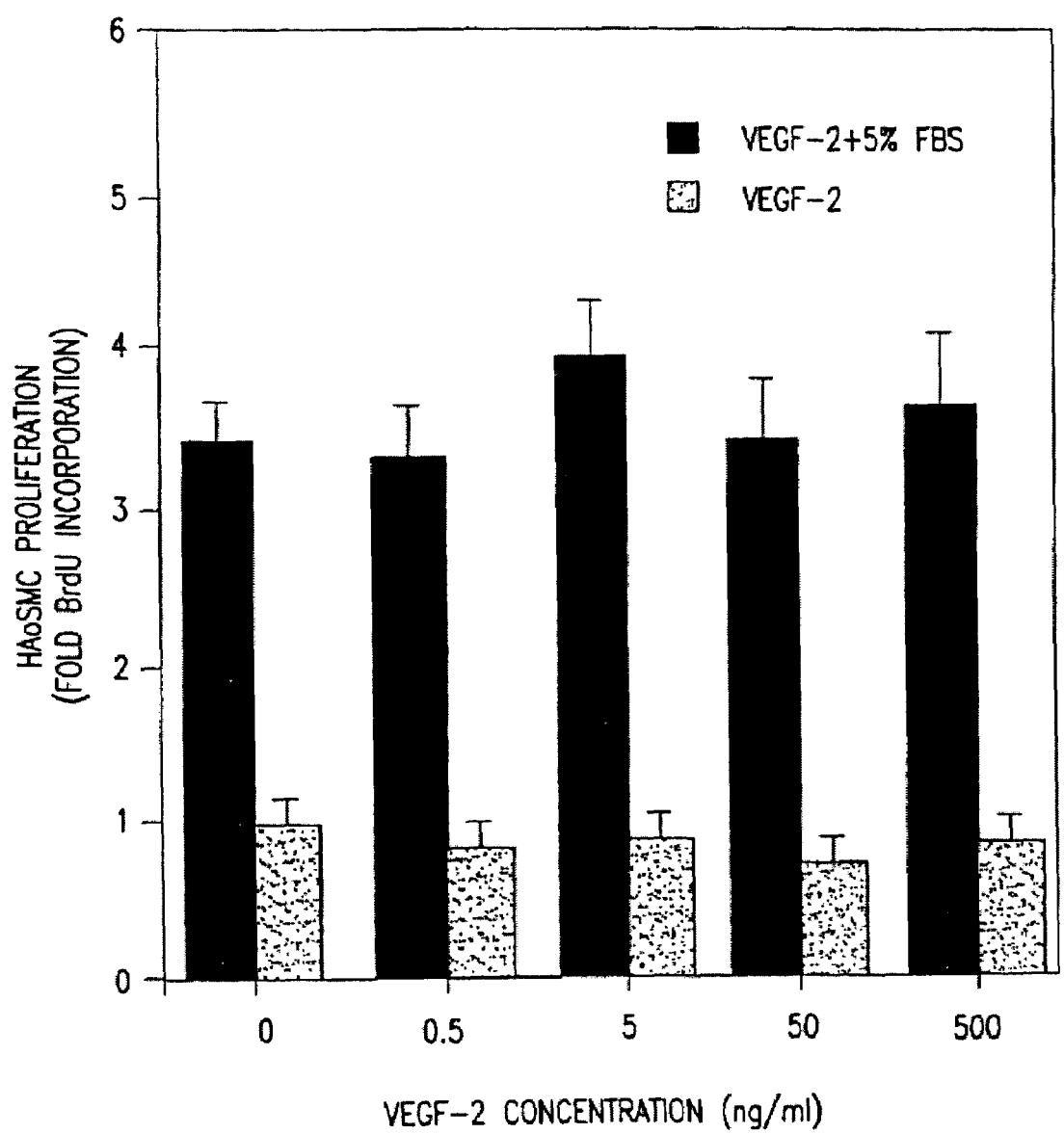

VEGF-2 has an inhibitory effect on proliferation of vascular smooth muscle cells induced by PDGF, but not by Fetal Bovine Serum (FBS) (FIG. 20).

Example 13

Stimulation of Endothelial Cell Migration

Endothelial cell migration is an important step involved in angiogenesis.

Experimental Design

This example will be used to explore the possibility that VEGF-2 may stimulate lymphatic endothelial cell migration. Currently, there are no published reports of such a model. However, we will be adapting a model of vascular endothelial cell migration for use with lymphatic endothelial cells essentially as follows:

Endothelial cell migration assays are performed using a 48 well microchemotaxis chamber (Neuroprobe Inc., Cabin John, M D; Falk, W., Goodwin, R. H. J., and Leonard, E. J. "A 48 well micro chemotaxis assembly for rapid and accurate measurement of leukocyte migration." *J. Immunological Methods* 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

Results

Figure 21A:
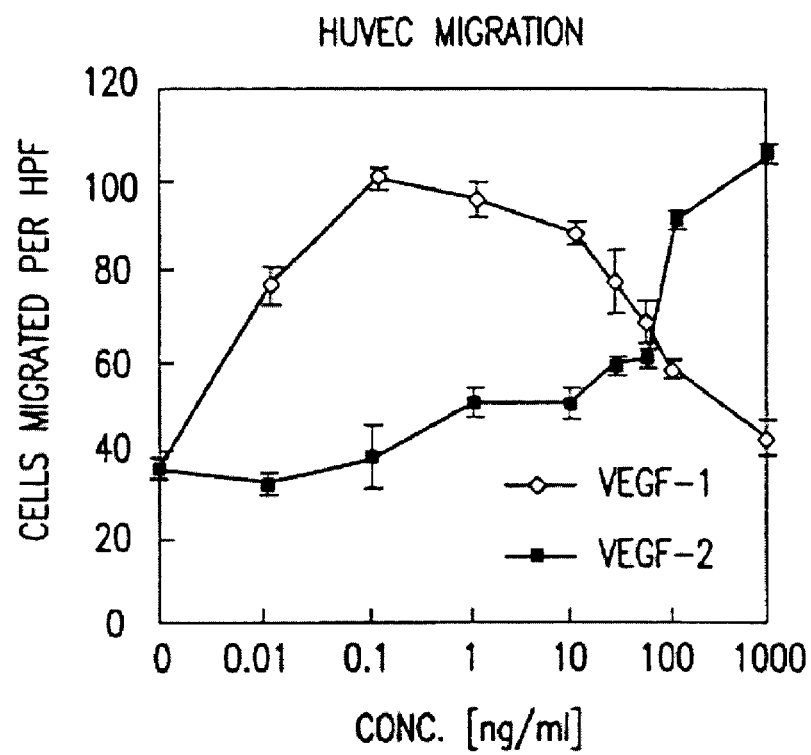
FIG. 21(A–B) depicts stimulation of migration of HUVEC and bovine microvascular endothelial cells (BMEC) by VEGF-2.
Figure 21B:
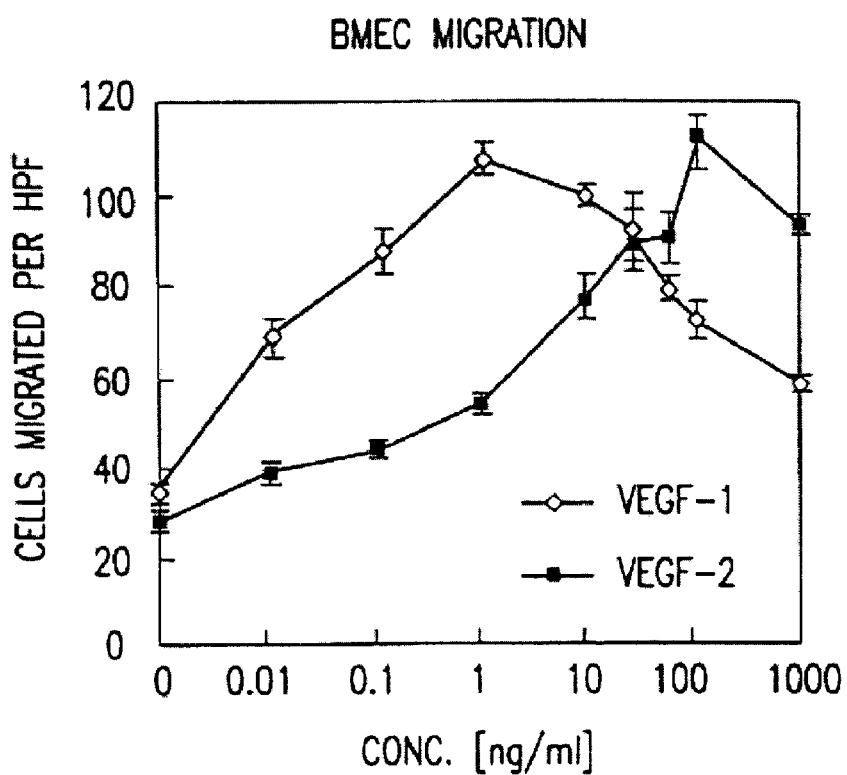

In an assay examining HUVEC migration using a 43-well microchemotaxis chamber, VEGF-2 was able to stimulate migration of HUVEC (FIG. 21).

Example 14

Stimulation of Nitric Oxide Production by Endothelial Cells

Nitric oxide released by the vascular endothelium is believed to be a mediator of vascular endothelium relaxation. VEGF-1 has been demonstrated to induce nitric oxide production by endothelial cells in response to VEGF-1. As a result, VEGF-2 activity can be assayed by determining nitric oxide production by endothelial cells in response to VEGF-2.

Experimental Design

Nitric oxide is measured in 96-well plates of confluent microvascular endothelial cells after 24 hours starvation and a subsequent 4 hr exposure to various levels of VEGF-1 and VEGF-2. Nitric oxide in the medium is determined by use of the Griess reagent to measure total nitrite after reduction of nitric oxide-derived nitrate by nitrate reductase. The effect of VEGF-2 on nitric oxide release was examined on HUVEC.

Briefly, NO release from cultured HUVEC monolayer was measured with a NO-specific polarographic electrode connected to a NO meter (Iso-NO, World Precision Instruments Inc.) (1049). Calibration of the NO elements was performed according to the following equation:

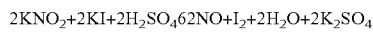

$$2KNO_2 + 2KI + 2H_2SO_4 \rightarrow 2NO + I_2 + 2H_2O + 2K_2SO_4$$

The standard calibration curve was obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO was previously determined by measurement of NO from authentic NO gas (1050). The culture medium was removed and HUVECs were washed twice with Dulbecco's phosphate buffered saline. The cells were then bathed in 5 ml of filtered Krebs-Henseleit solution in 6-well plates, and the cell plates were kept on a slide warmer (Lab Line Instruments Inc.) To maintain the temperature at 37° C. The NO sensor probe was inserted vertically into the wells, keeping the tip of the electrode 2 mm under the surface of the solution, before addition of the different conditions. S-nitroso acetyl penicillamin (SNAP) was used as a positive control. The amount of released NO was expressed as picomoles per $1 \times 10^6$ endothelial cells. All values reported were means of four to six measurements in each group (number of cell culture wells). See, Leak et al. *Biochem. and Biophys. Res. Comm.* 217:96–105 (1995).

Results

Figure 22:
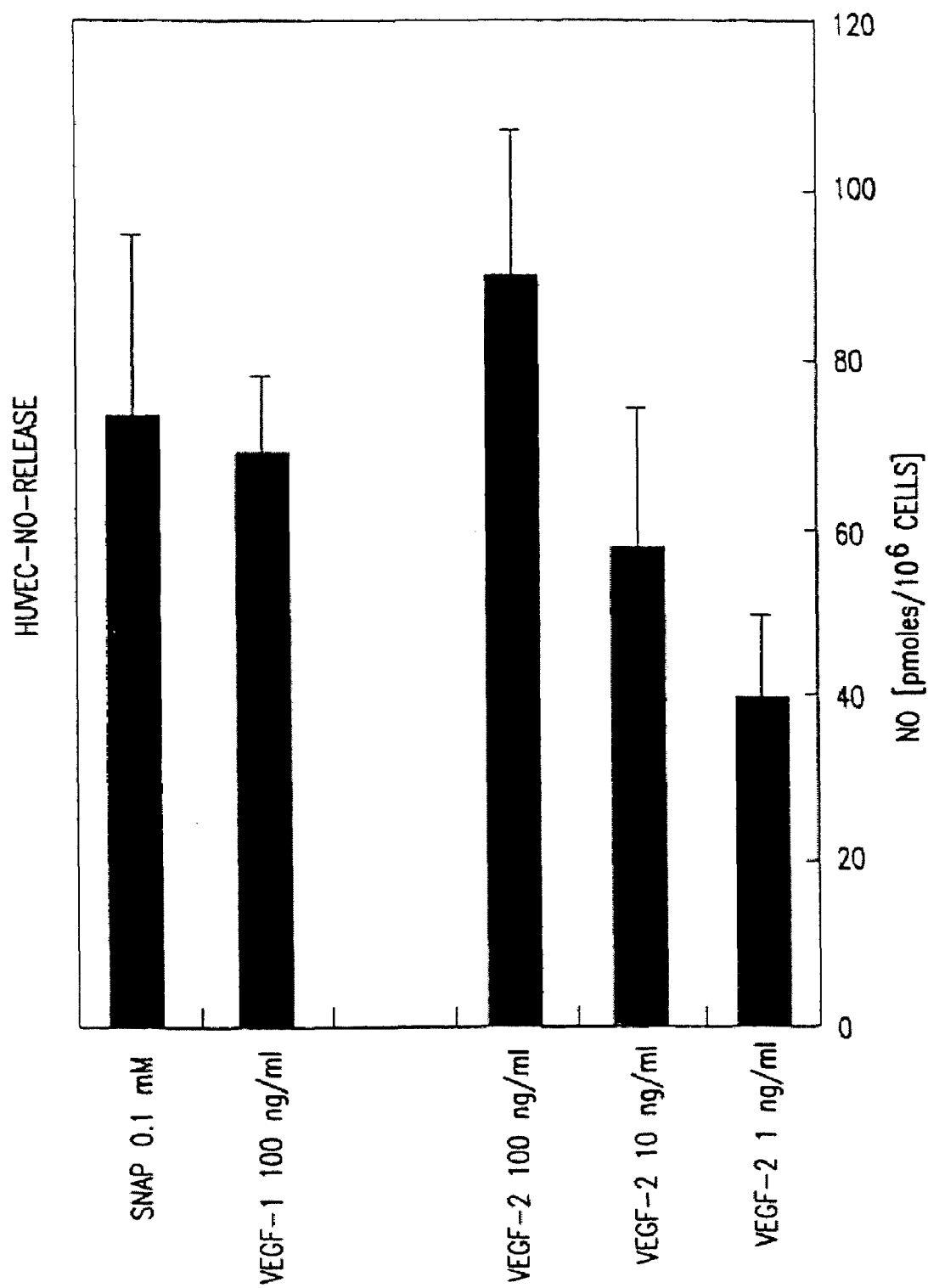
FIG. 22 depicts stimulation of nitric oxide release of HUVEC by VEGF-2 and VEGF-1.

VEGF-2 was capable of stimulating nitric oxide release on HUVEC (FIG. 22) to a higher level than VEGF. This suggested that VEGF-2 may modify vascular permeability and vessel dilation.

Example 15

Effect of VEGF-2 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

Experimental Design

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or HGS protein (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

Results

Figure 23:
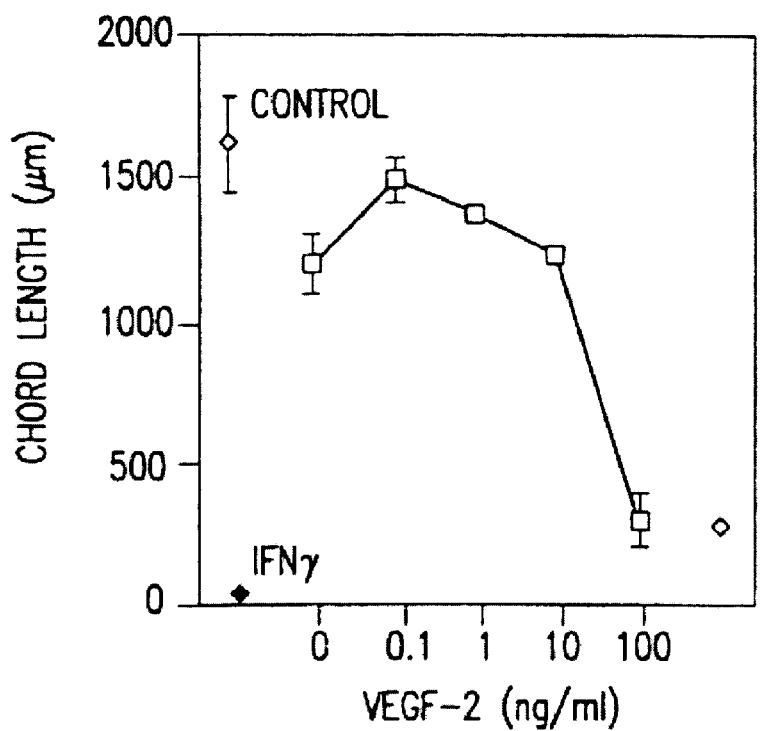
FIG. 23 depicts inhibition of cord formation of microvascular endothelial cells (CADMEC) by VEGF-2.

It has been observed that VEGF-2 inhibits cord formation similar to IFNa which also stimulates endothelial cell proliferation (FIG. 23). This inhibitory effect may be a secondary effect of endothelial proliferation which is mutually exclusive with the cord formation process.

Example 16

Angiogenic Effect on Chick Chorioallantoic Membrane

Chick chorioallantoic membrane (CAM) is a well-established system to examine angiogenesis. Blood vessel formation on CAM is easily visible and quantifiable. The ability of VEGF-2 to stimulate angiogenesis in CAM was examined.

Experimental Design

Embryos

Fertilized eggs of the White Leghorn chick (*Gallus gallus*) and the Japanese qual (*Coturnix coturnix*) were incubated at 37.8° C. and 80% humidity. Differentiated CAM of 16-day-old chick and 13-day-old qual embryos was studied with the following methods.

CAM Assay

On Day 4 of development, a window was made into the egg shell of chick eggs. The embryos were checked for normal development and the eggs sealed with cellotape.

They were further incubated until Day 13. Thermanox coverslips (Nunc, Naperville, Ill.) were cut into disks of about 5 mm in diameter. Sterile and salt-free growth factors were dissolved in distilled water and about 3.3 mg/5 ml was pipetted on the disks. After air-drying, the inverted disks were applied on CAM. After 3 days, the specimens were fixed in 3% glutaraldehyde and 2% formaldehyde and rinsed in 0.12 M sodium cacodylate buffer. They were photographed with a stereo microscope [Wild M8] and embedded for semi- and ultrathin sectioning as described above. Controls were performed with carrier disks alone.

Results

Figure 24:
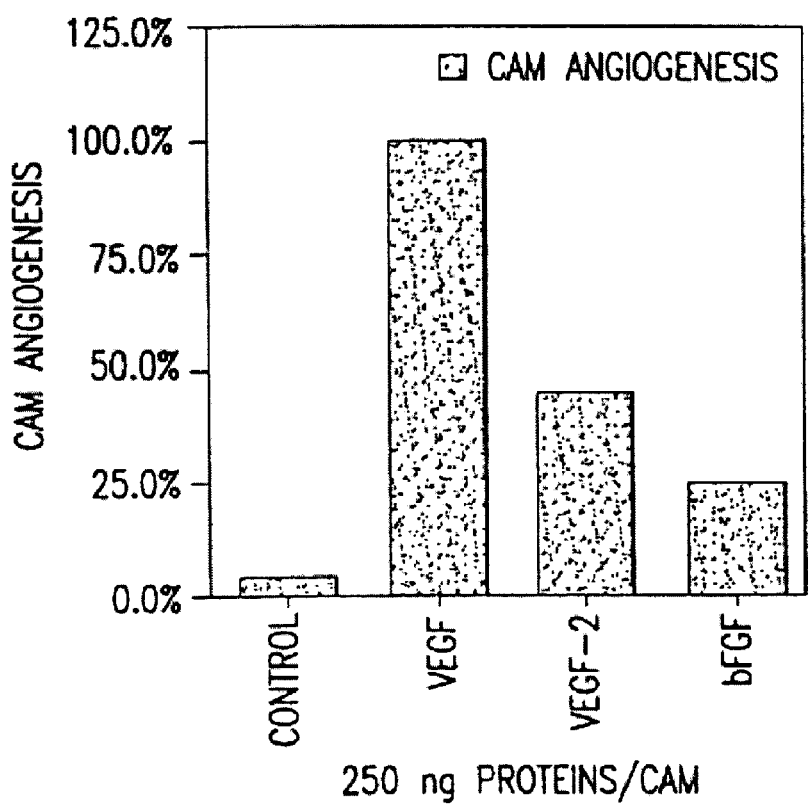
FIG. 24 depicts stimulation of angiogenesis by VEGF, VEGF-2, and bFGF in the CAM assay.

This data demonstrates that VEGF-2 can stimulate angiogenesis in the CAM assay nine-fold compared to the untreated control. However, this stimulation is only 45% of the level of VEGF stimulation (FIG. 24).

Example 17

Angiogenesis Assay Using a Matrigel Implant in Mouse

Experimental Design

In order to establish an in vivo model for angiogenesis to test protein activities, mice and rats have been implanted subcutaneously with methylcellulose disks containing either 20 mg of BSA (negative control) and 1 mg of bFGF and 0.5 mg of VEGF-1 (positive control).

It appeared as though the BSA disks contained little vascularization, while the positive control disks showed signs of vessel formation. At day 9, one mouse showed a clear response to the bFGF.

Results

Both VEGF proteins appeared to enhance Matrigel cellularity by a factor of approximately 2 by visual estimation.

An additional 30 mice were implanted with disks containing BSA, bFGF, and varying amounts of VEGF-1, VEGF-2-B8, and VEGF-2-C4. Each mouse received two identical disks, rather than one control and one experimental disk.

Samples of all the disks recovered were immunostained with Von Willebrand's factor to detect for the presence of endothelial cells in the disks, and flk-1 and flt-4 to distinguish between vascular and lymphatic endothelial cells. However, definitive histochemical analysis of neovascularization and lymphangiogenesis could not be determined.

Example 18

Rescue of Ischemia in Rabbit Lower Limb Model

Experimental Design

To study the in vivo effects of VEGF-2 on ischemia, a rabbit hindlimb ischemia model was created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147: 1649–1660 (1995)). An interval of 10 days was allowed for post-operative recovery of rabbits and development of endogenous collateral vessels. At 10 day post-operatively (day 0), after performing a baseline angiogram, the internal iliac artery of the ischemic limb was transfected with 500 mg naked VEGF-2 expression plasmid by arterial gene transfer technology using a hydrogel-coated balloon catheter as described (Riessen, R. et al. *Hum Gene Ther.* 4:749–758 (1993); Leclerc, G. et al. *J. Clin. Invest.* 90: 936–944 (1992)). When VEGF-2 was used in the treatment, a single bolus of 500 mg VEGF-2 protein or control was delivered into the internal iliac artery of the ischemic limb over a period of 1 min. through an infusion catheter. On day 30, various parameters were measured in these rabbits.

Results

Figure 25A:
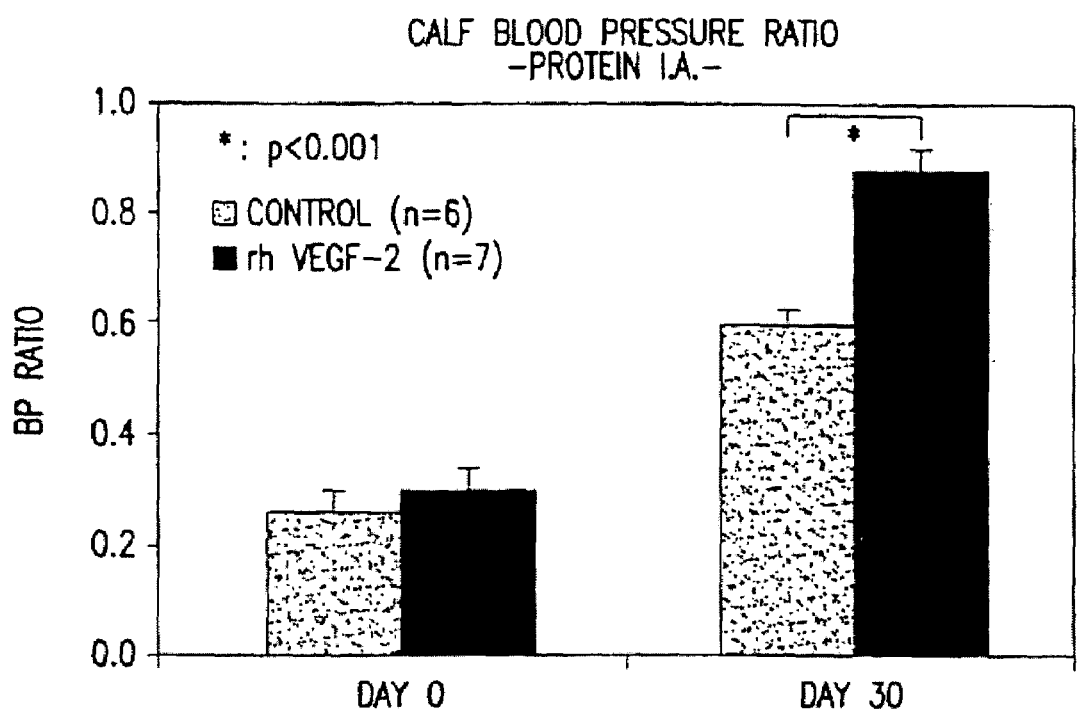
FIGS. 25A–25O depict restoration of certain parameters in the ischemic limb by VEGF2 protein (FIGS. 25A, C, D, E, H, I, J, L, M, O) and naked expression plasmid (FIGS. 25B, C, F, G, H, I, K, L, M, O): BP ratio (FIGS. 25A–25C); Blood Flow and Flow Reserve (FIGS. 25D–25I); Angiographic Score (FIGS. 25J–25L); Capillary density (FIGS. 25M–25O).
Figure 25B:
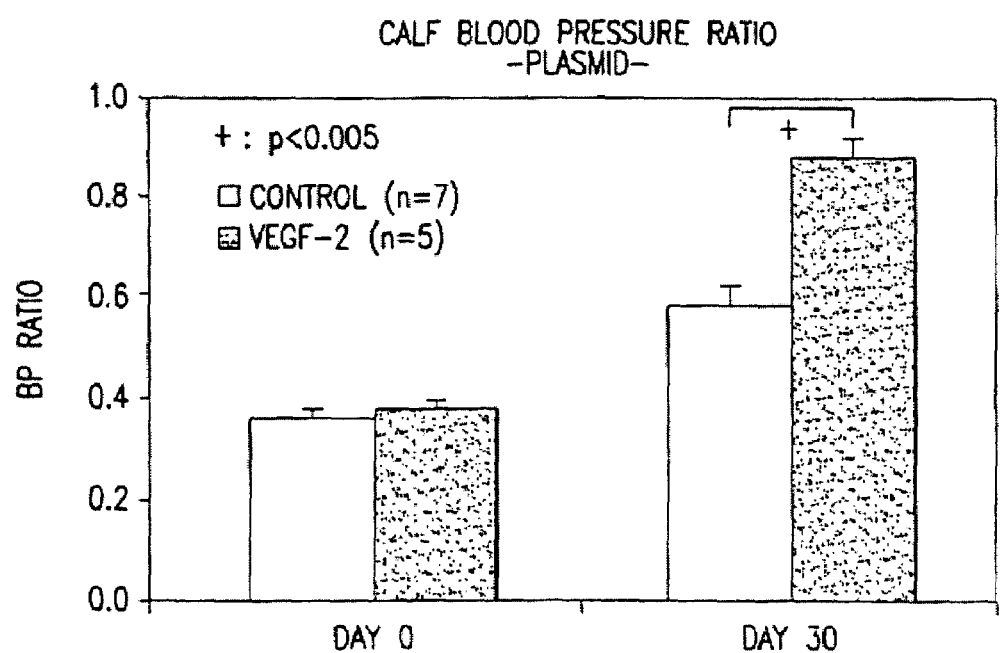
Figure 25C:
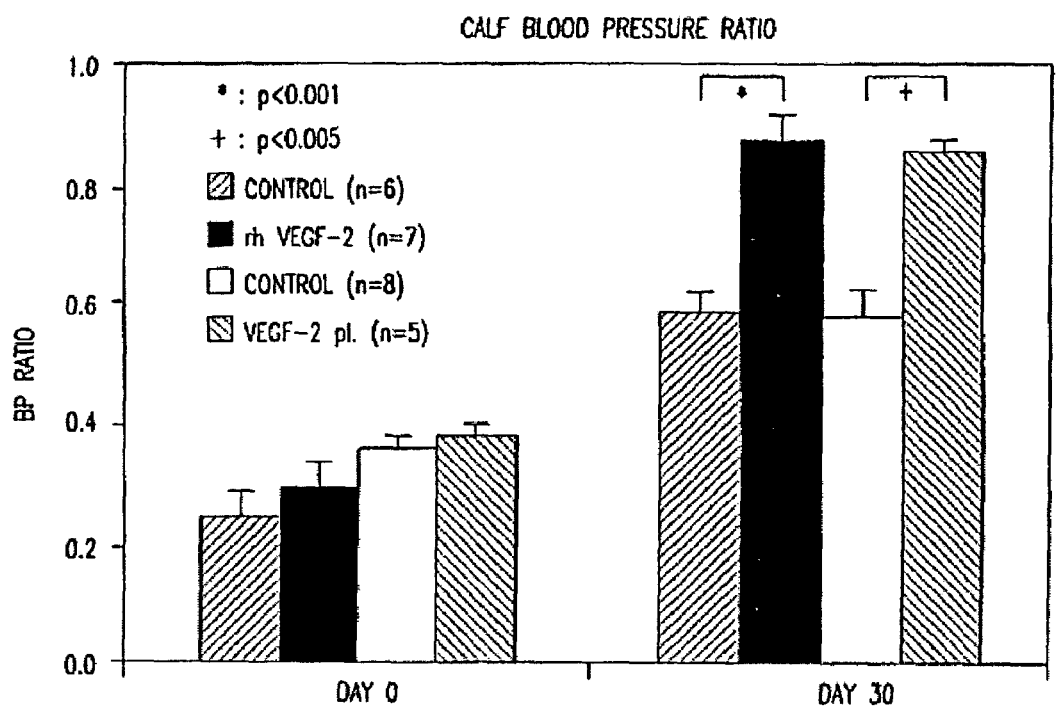
Figure 25D:
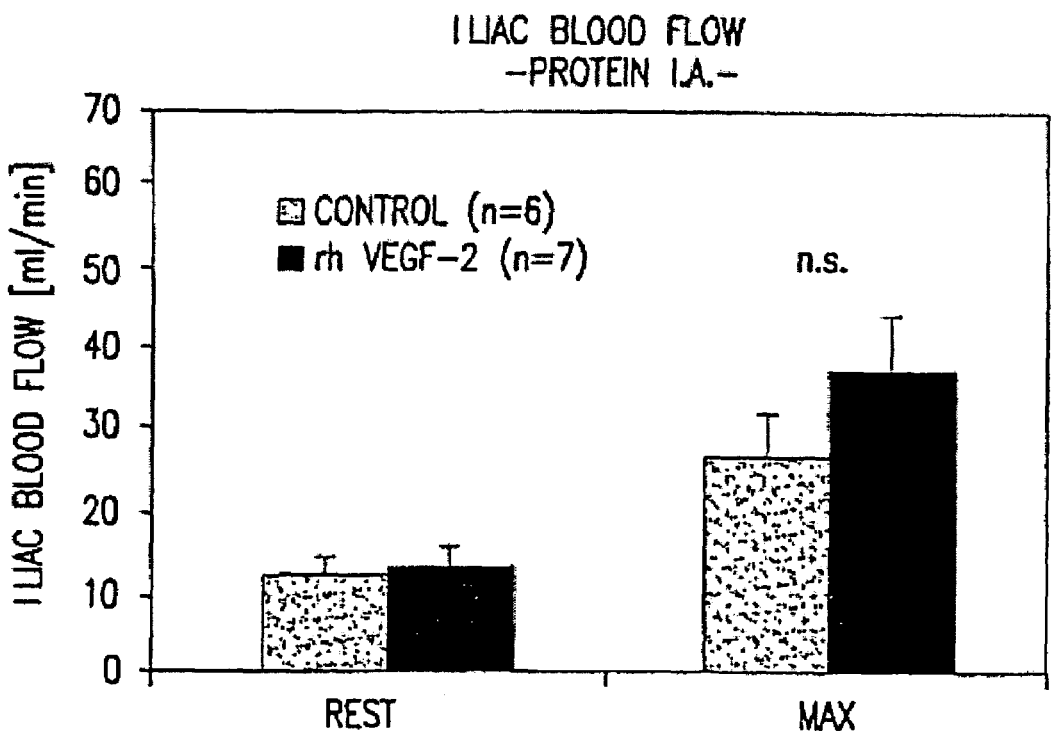
Figure 25E:
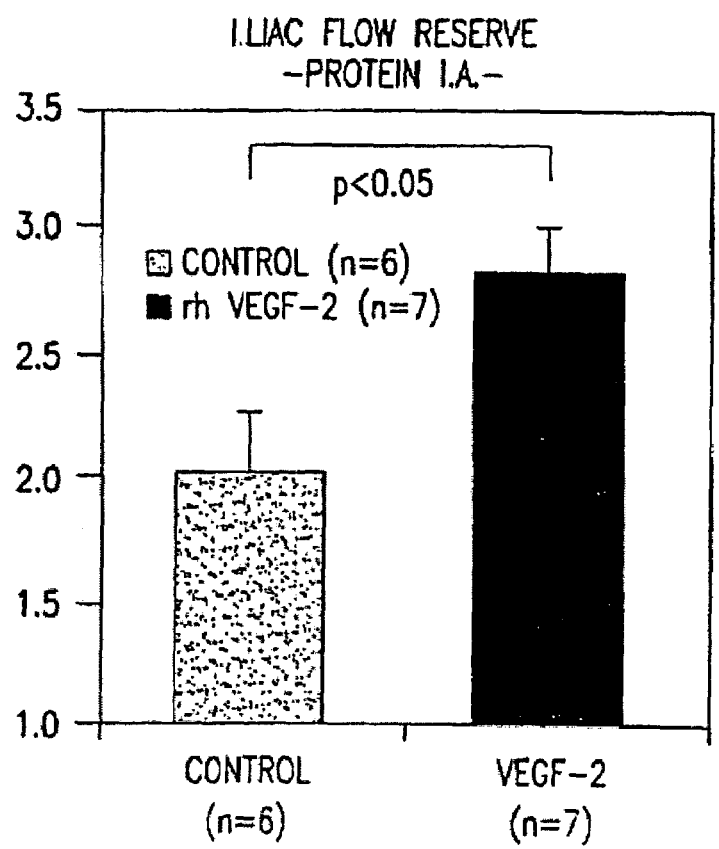
Figure 25F:
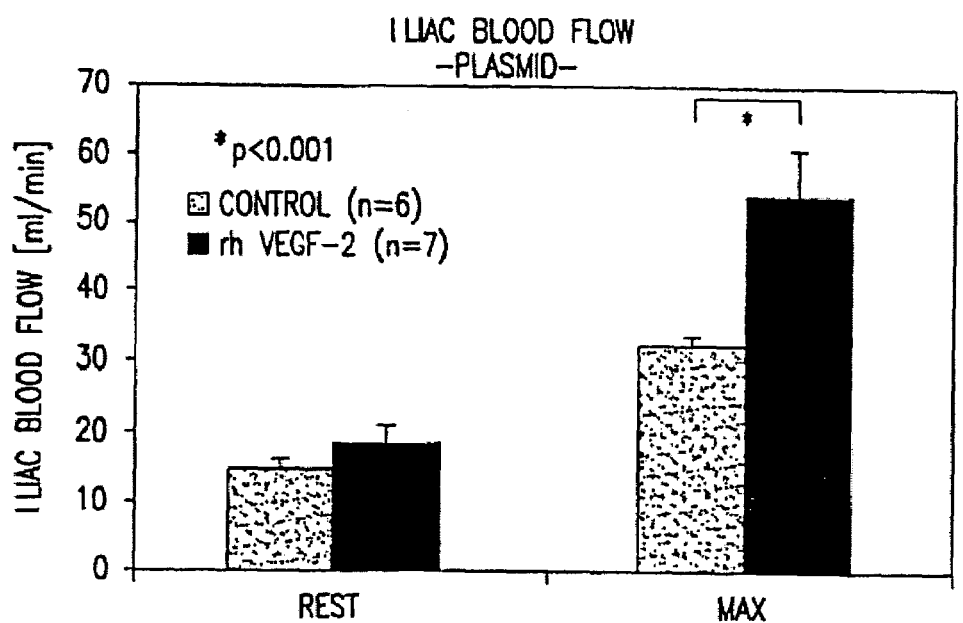
Figure 25G:
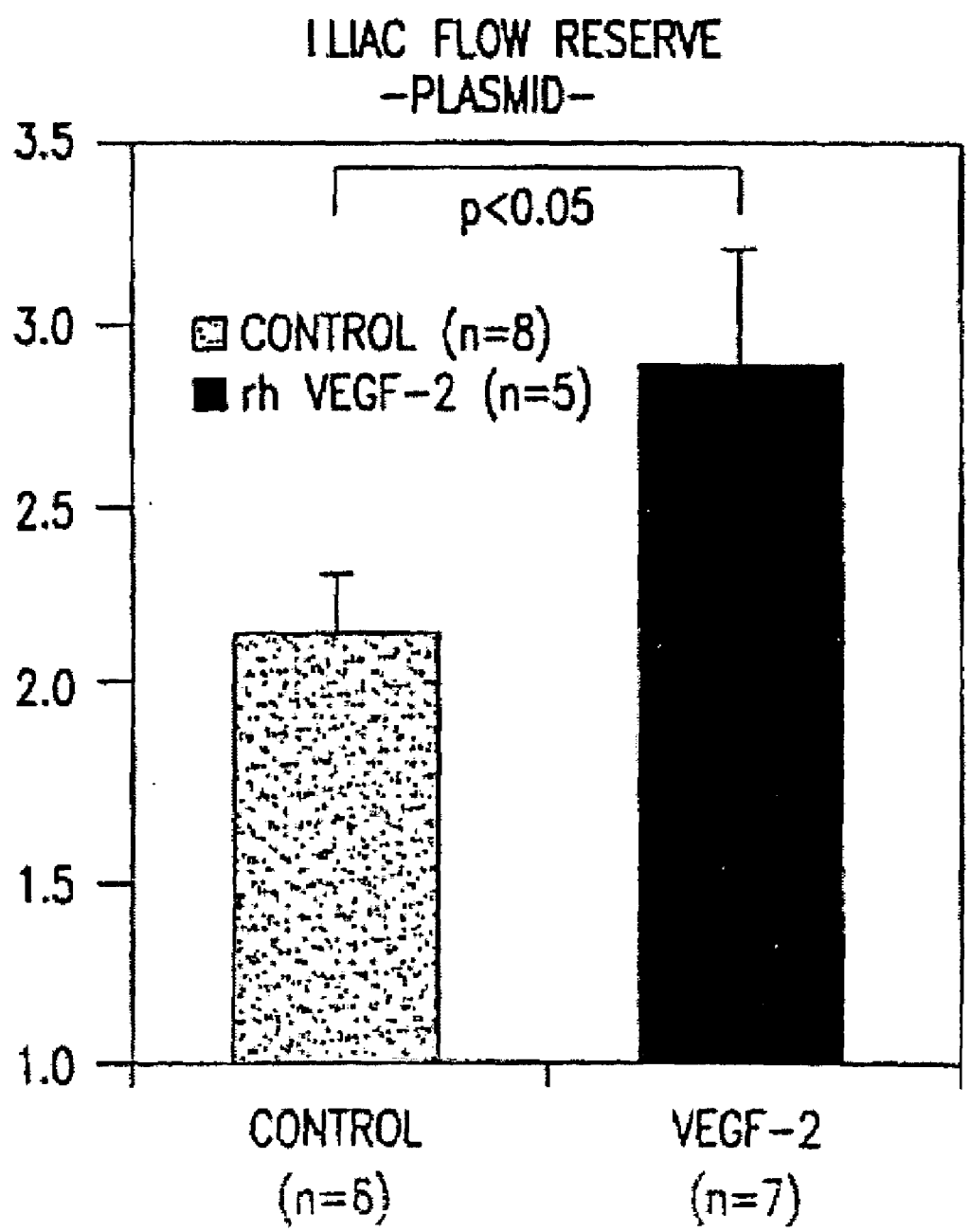
Figure 25H:
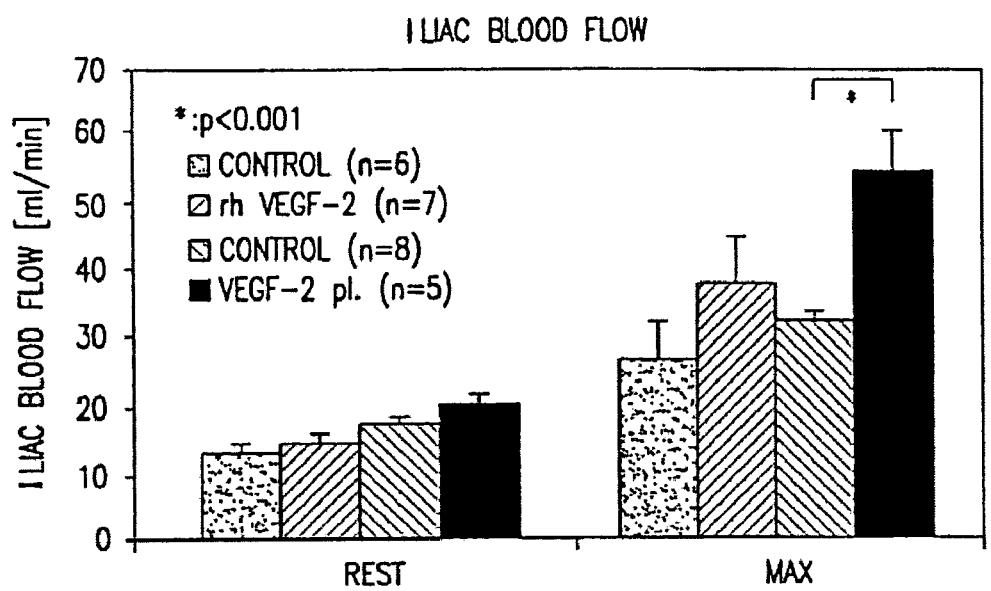
Figure 25I:
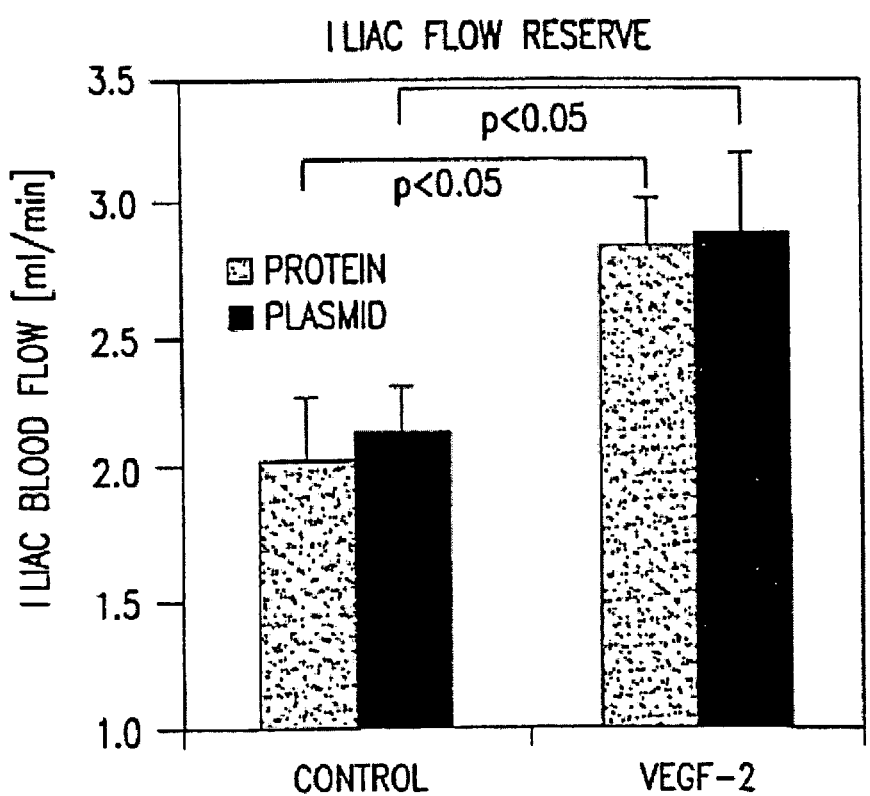

Both VEGF-2 protein (FIGS. 25A, C, D, E, H, I, J, L, M, O) and naked expression plasmid (FIGS. 25B, C, F, G, H, I, K, L, M, O) were able to restore the following parameters in the ischemic limb. Restoration of blood flow, angiographic score seem to be slightly more by administration of 500 mg plasmid compared with by 500 mg protein (FIGS. 25H, I, L). The extent of the restoration is comparable with that by VEGF in separate experiments (data not shown). A vessel dilator was not able to achieve the same effect, suggesting that the blood flow restoration is not simply due to a vascular dilation effect.

a. BP Ratio (FIGS. 25A–25C)

The blood pressure ratio of systolic pressure of the ischemic limb to that of normal limb.

b. Blood Flow and Flow Reserve (FIGS. 25D–25I)

Resting FL: the blood flow during un-dilated condition

Max FL: the blood flow during fully dilated condition (also an indirect measure of the blood vessel amount)

Figure 25J:
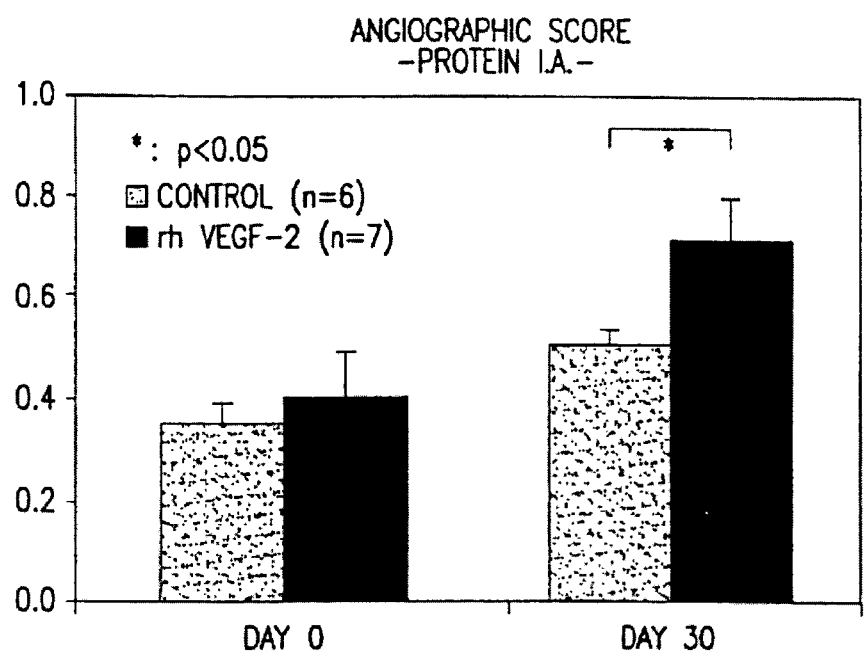
Figure 25K:
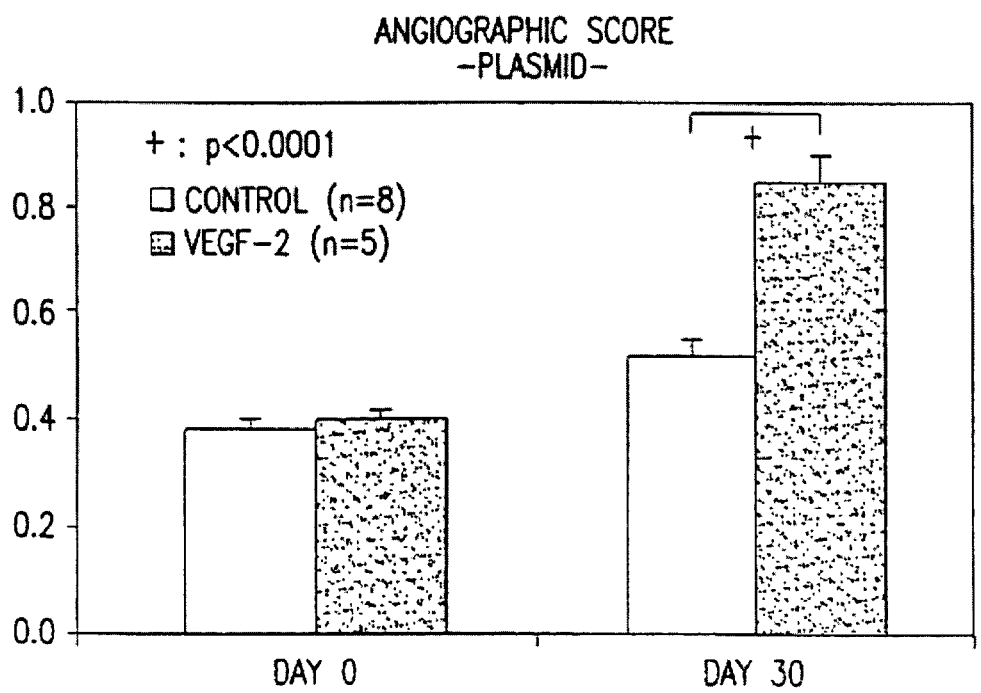
Figure 25L:
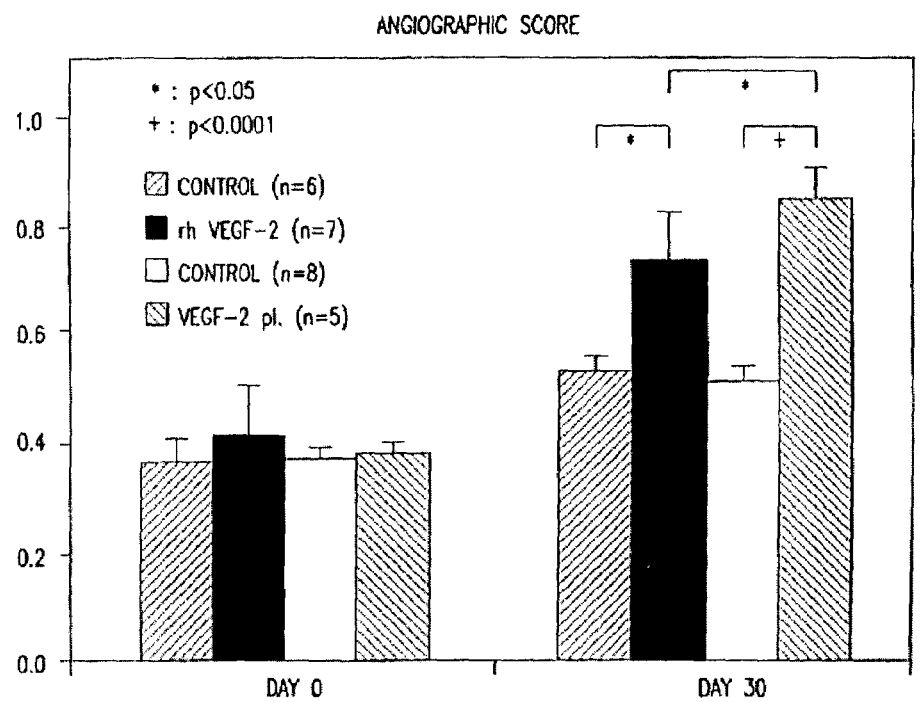

Flow Reserve is reflected by the ratio of max FL: resting FL.

c. Angiographic Score (FIGS. 25J–25L)

Figure 25M:
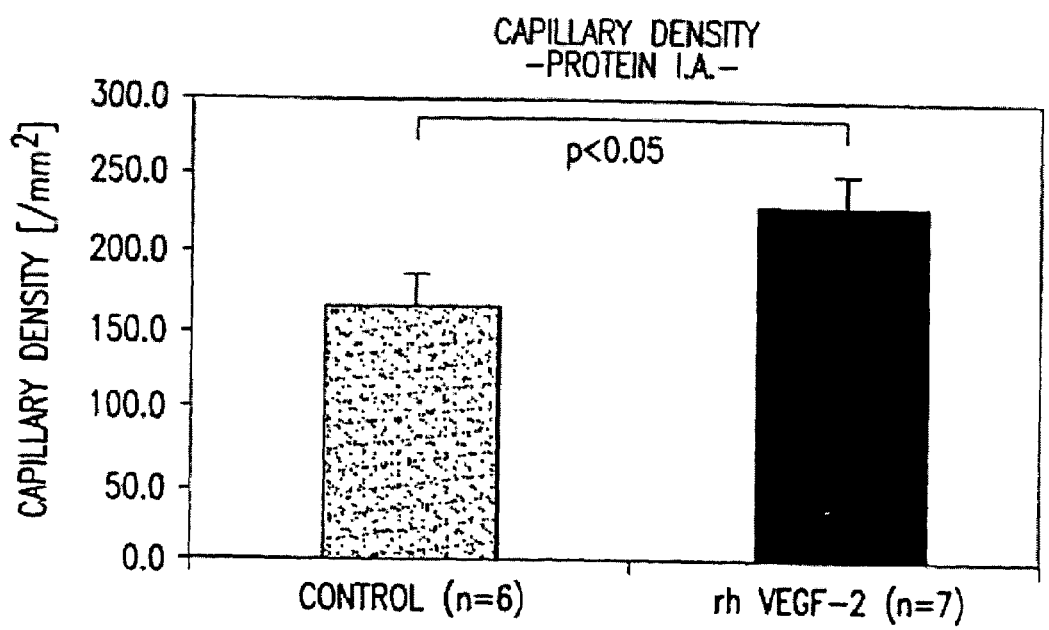
Figure 25N:
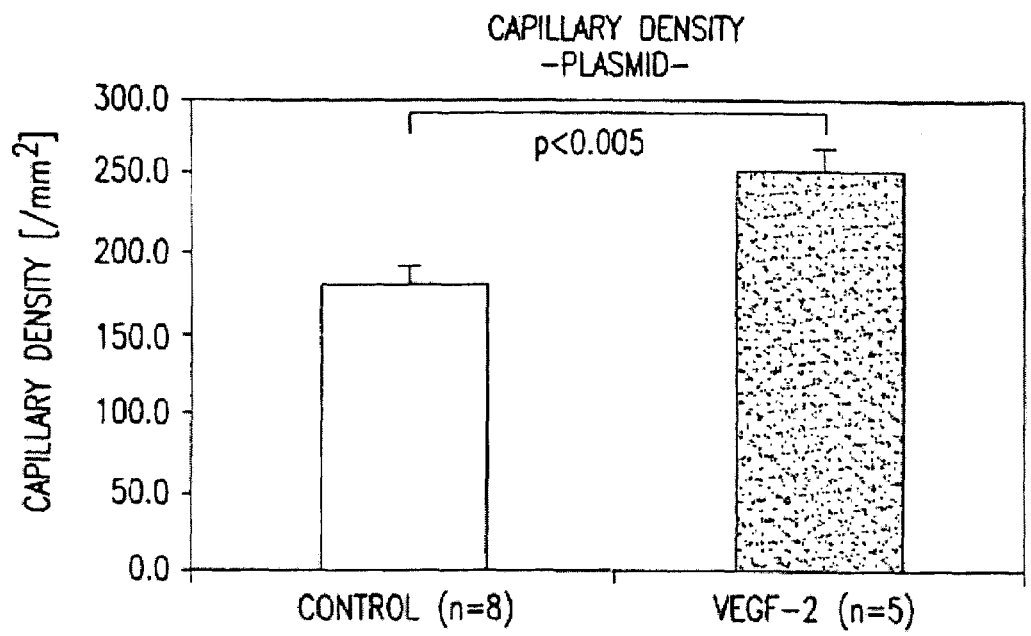
Figure 25O:
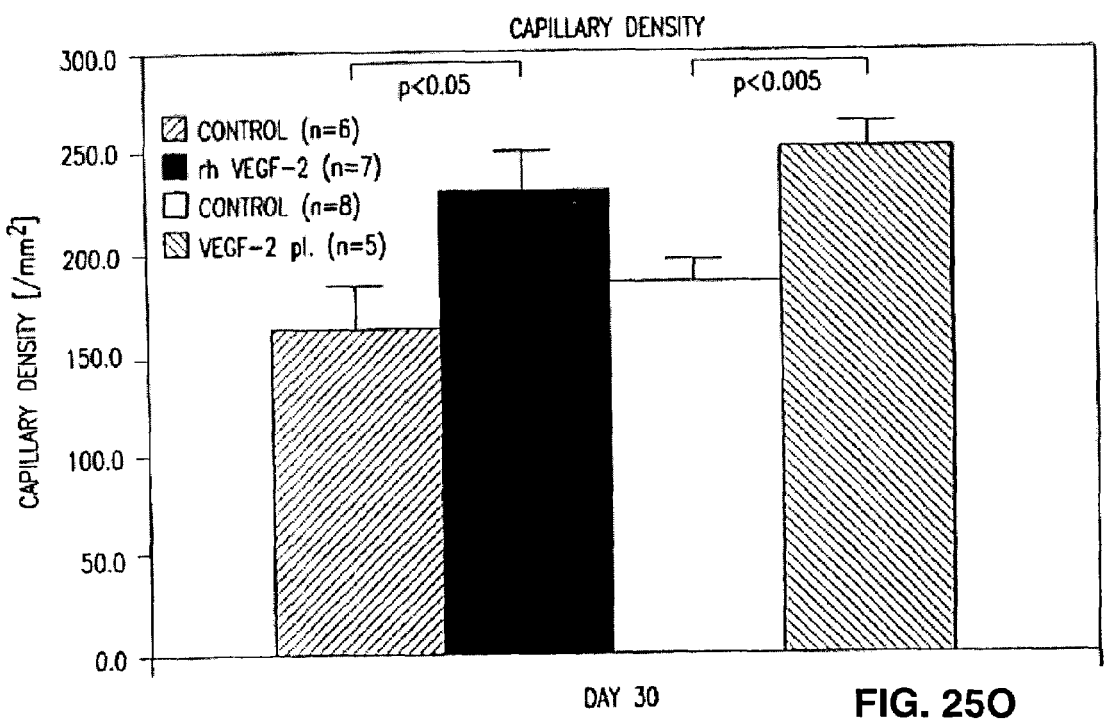

This is measured by the angiogram of collateral vessels. A score was determined by the percentage of circles in an overlaying grid that with crossing opacified arteries divided by the total number m the rabbit thigh.

d. Capillary Density (FIGS. 25M–25O)

The number of collateral capillaries determined in light microscopic sections taken from hindlimbs.

Example 19

Effect of VEGF-2 on Vasodilation

Figure 26A:
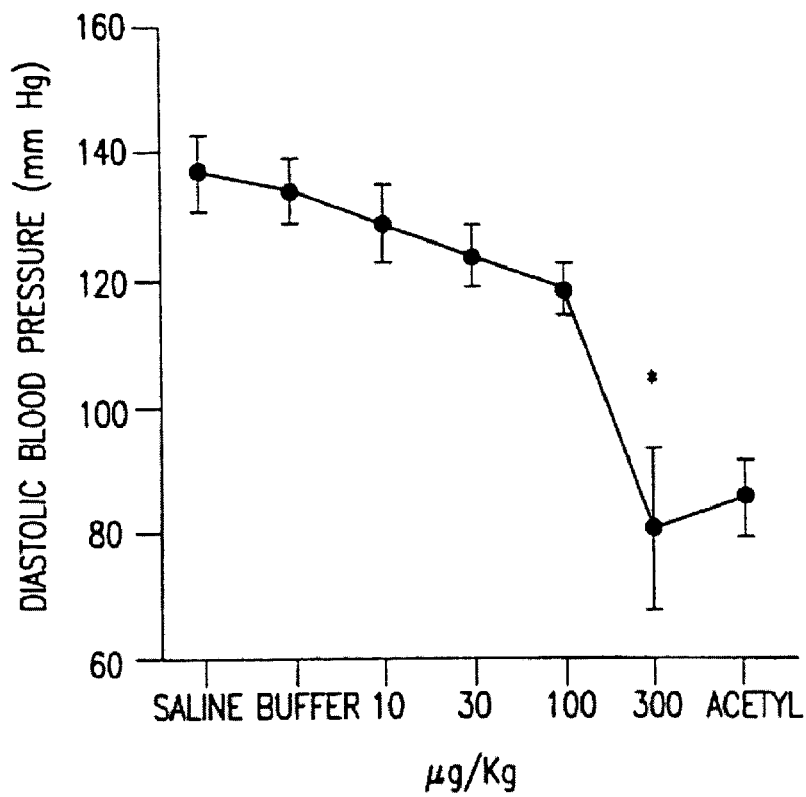
FIGS. 26A–26G depicts the ability of VEGF2 to affect the diastolic blood pressure in spontaneously hypertensive rats (SHR), FIGS. 26a and b depict the dose-dependent decrease in diastolic blood pressure achieved with VEGF-2.
Figure 26B:
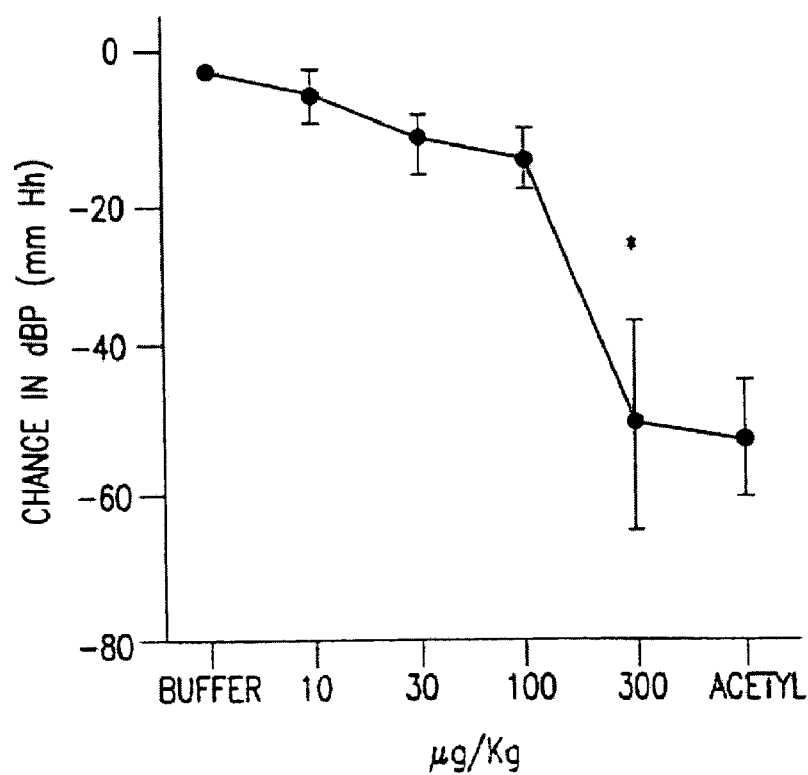
Figure 26C:
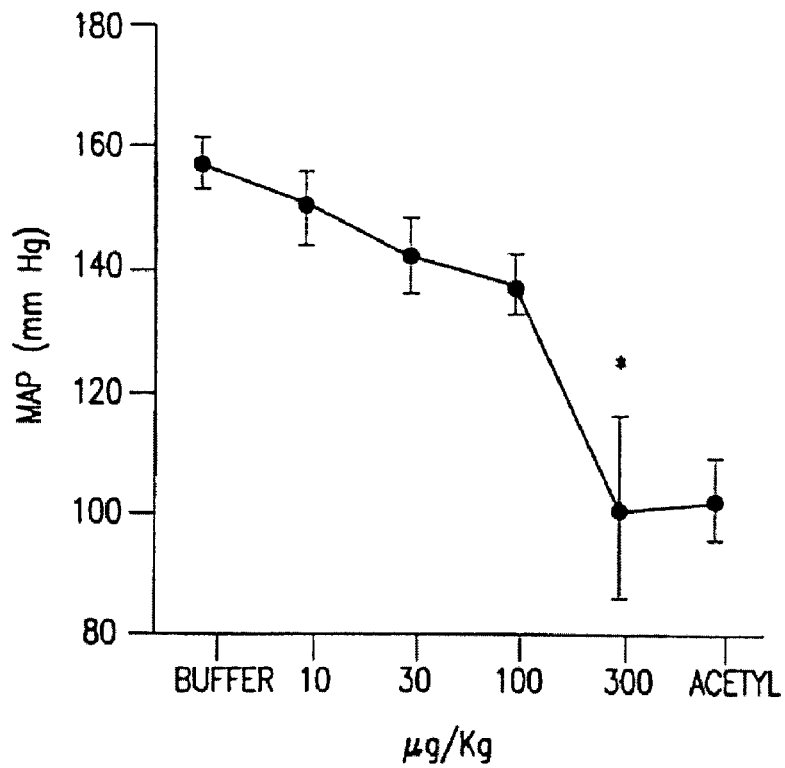
Figure 26D:
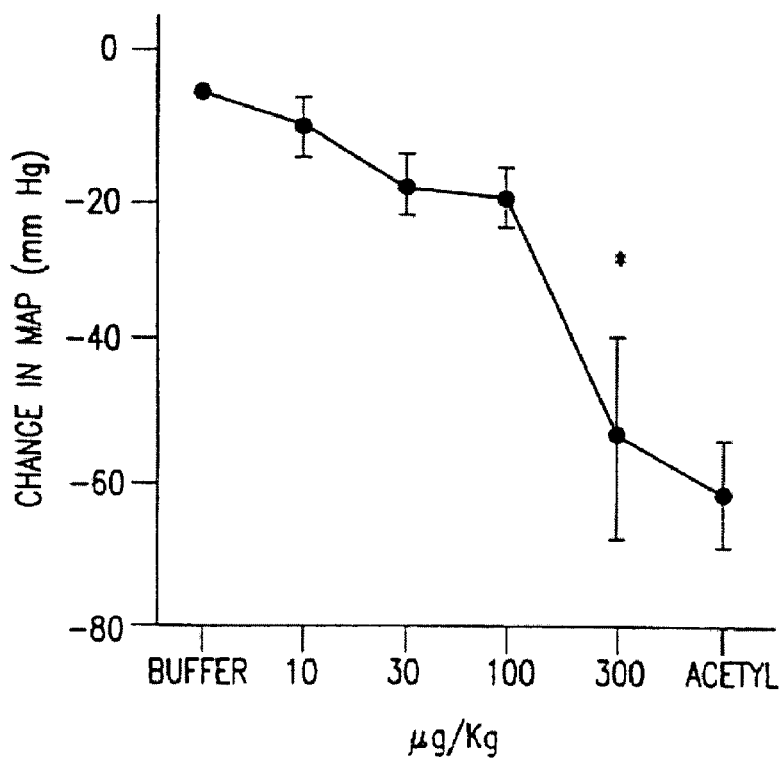
Figure 26E:
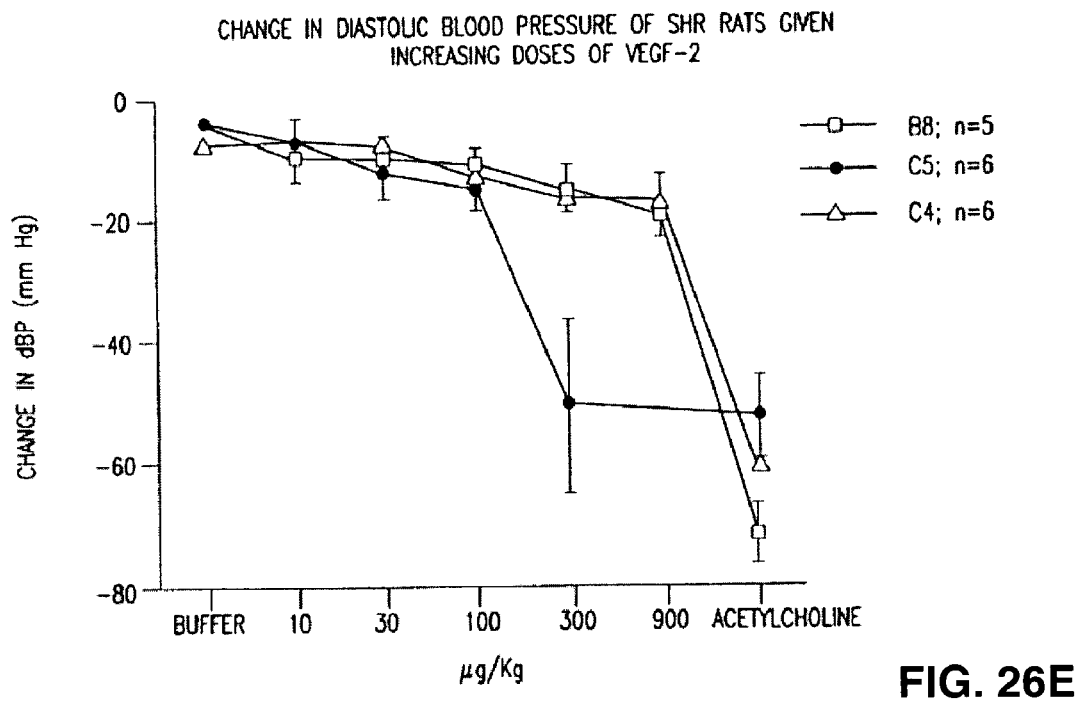
Figure 26F:
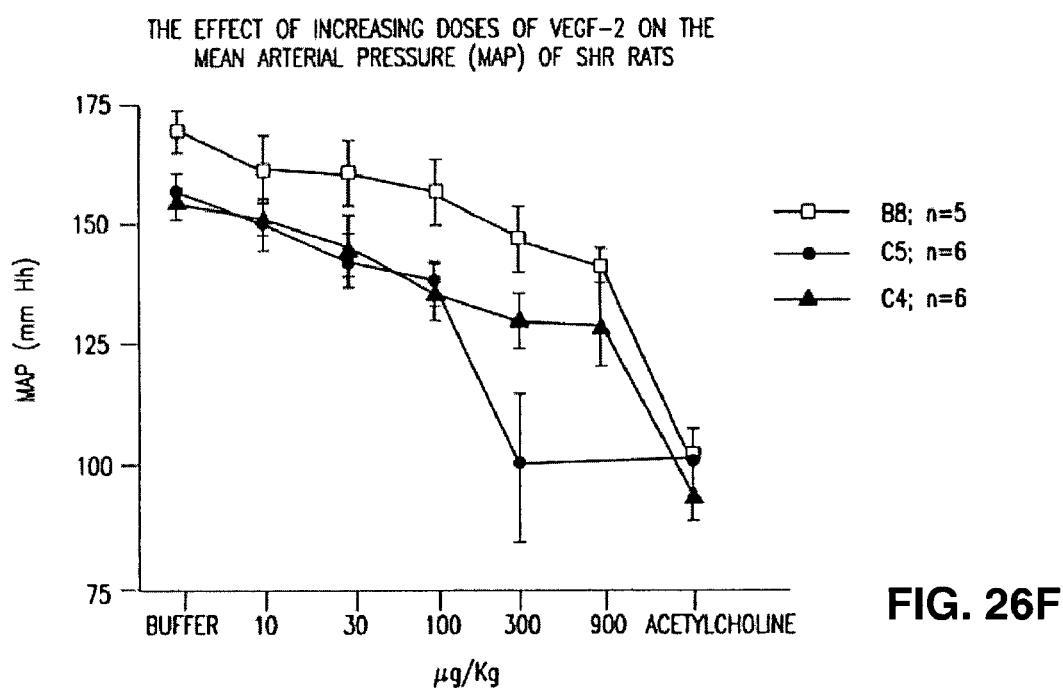
Figure 26G:
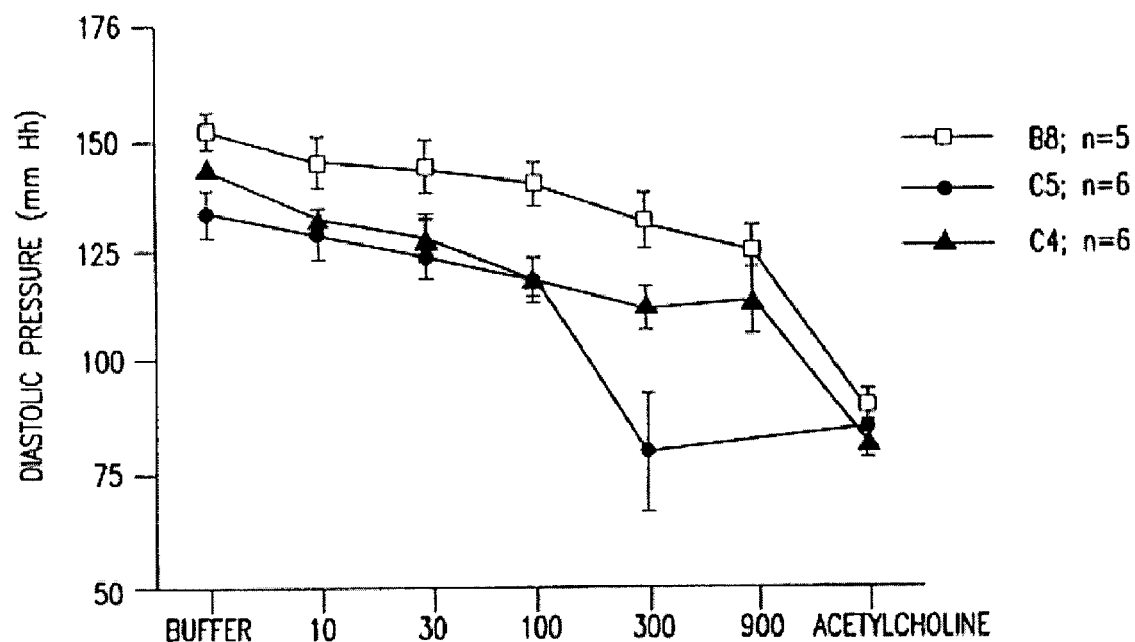
Figure 27:
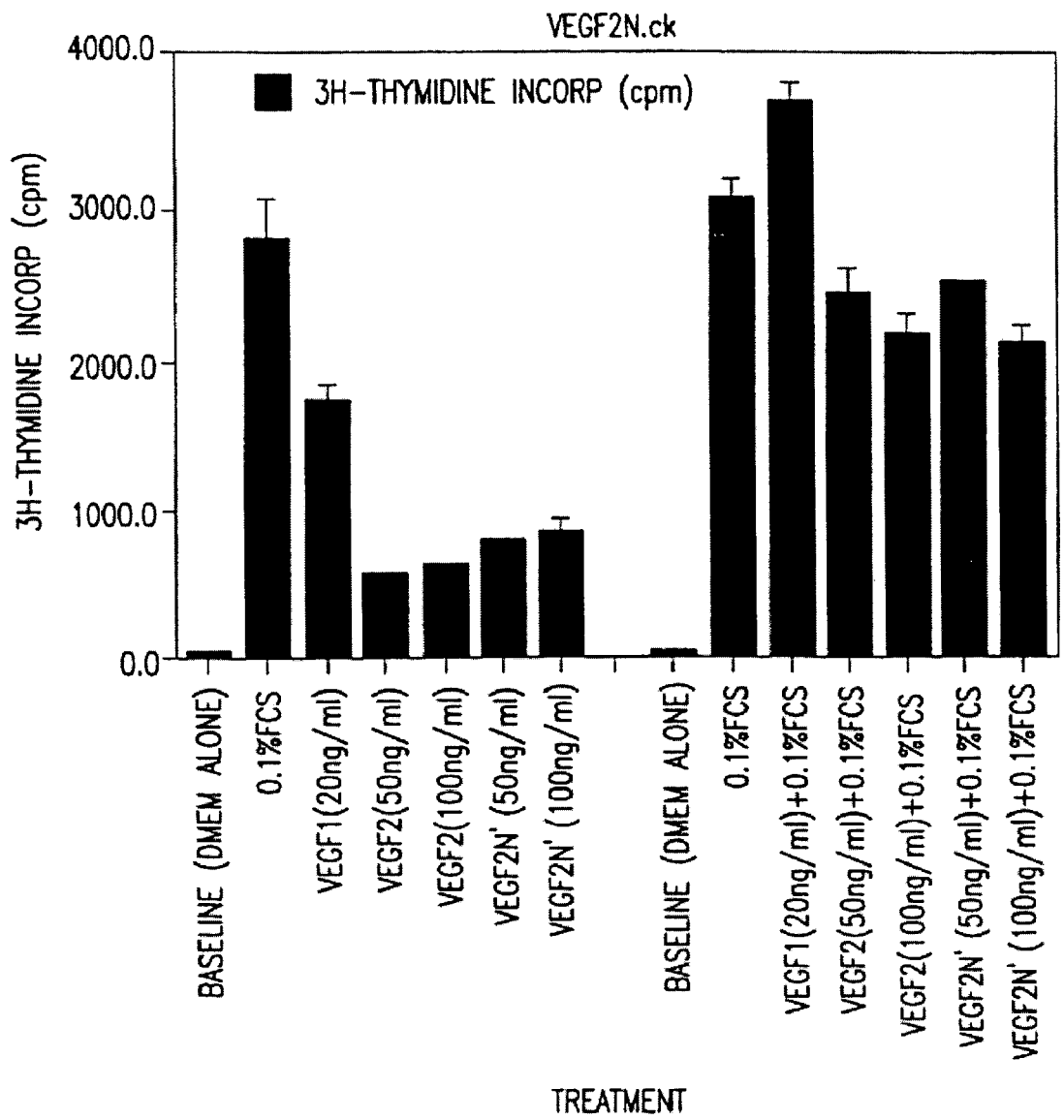
FIG. 27 depicts inhibition of VEGF-2N= and VEGF-2-induced proliferation.

As described above, VEGF-2 can stimulate NO release, a mediator of vascular endothelium dilation. Since dilation of vascular endothelium is important in reducing blood pressure, the ability of VEGF-2 to affect the blood pressure in spontaneously hypertensive rats (SHR) was examined. VEGF-2 caused a dose-dependent decrease in diastolic blood pressure (FIGS. 26a and b). There was a steady decline in diastolic blood pressure with increasing doses of VEGF-2 which attained statistical significance when a dose of 300 mg/kg was administered. The changes observed at this dose were not different than those seen with acetylcholine (0.5 mg/kg). Decreased mean arterial pressure (MAP) was observed as well (FIGS. 26c and d). VEGF-2 (300 mg/kg) and acetylcholine reduced the MAP of these SHR animals to normal levels.

Additionally, increasing doses (0, 10, 30, 100, 300, and 900 mg/kg) of the B8, C5, and C4 preps of VEGF-2 were administered to 13–14 week old spontaneously hypertensive rats (SHR). Data are expressed as the mean+/−SEM. Statistical analysis was performed with a paired t-test and statistical significance was defined as $p<0.05$ vs. the response to buffer alone.

Studies with VEGF-2 (C5 prep) revealed that although it significantly decreased the blood pressure, the magnitude of the response was not as great as that seen with VEGF-2 (B8 prep) even when used at a dose of 900 mg/kg.

Studies with VEGF-2 (C4 preparation) revealed that this CHO expressed protein preparation yielded similar results to that seen with C5 (i.e. statistically significant but of far less magnitude than seen with the B8 preparation) (see FIGS. 26A–D).

As a control and since the C4 and C5 batches of VEGF-2 yielded minor, but statistically significant, changes in blood pressure, experiments were performed experiments with another CHO-expressed protein, M-CIF. Administration of M-CIF at doses ranging from 10–900 mg/kg produced no significant changes in diastolic blood pressure. A minor statistically significant reduction in mean arterial blood pressure was observed at doses of 100 and 900 mg/kg but no dose response was noted. These results suggest that the reductions in blood pressure observed with the C4 and C5 batches of VEGF-2 were specific, i.e. VEGF-2 related.

Example 20

Rat Ischemic Skin Flap Model

Experimental Design

The evaluation parameters include skin blood flow, skin temperature, and factor VIII immunohistochemistry or endothelial alkaline phosphatase reaction. VEGF-2 expression, during the skin ischemia, is studied using in situ hybridization.

The study in this model is divided into three parts as follows:
a) Ischemic skin
b) Ischemic skin wounds
c) Normal wounds The experimental protocol includes:
a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with VEGF-2 of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

Example 21

Peripheral Arterial Disease Model

Angiogenic therapy using VEGF-2 has been developed as a novel therapeutic strategy to obtain restoration of blood flow around the ischemia in case of peripheral arterial diseases.

Experimental Design

The experimental protocol includes:
a) One side of the femoral artery is ligated to create ischemic muscle of the hindlimb, the other side of hindlimb serves as a control.
b) VEGF-2 protein, in a dosage range of 20 mg–500 mg, is delivered intravenously and/or intramuscularly 3 times (perhaps more) per week for 2–3 weeks.
c) The ischemic muscle tissue is collected after ligation of the femoral artery at 1, 2, and 3 weeks for the analysis of VEGF-2 expression and histology. Biopsy is also performed on the other side of normal muscle of the contralateral hindlimb.

Example 22

Ischemic Myocardial Disease Model

VEGF-2 is evaluated as a potent mitogen capable of stimulating the development of collateral vessels, and restructuring new vessels after coronary artery occlusion. Alteration of VEGF-2 expression is investigated in situ.

Experimental Design

The experimental protocol includes:
a) The heart is exposed through a left-side thoracotomy in the rat. Immediately, the left coronary artery is occluded with a thin suture (6–0) and the thorax is closed.
b) VEGF-2 protein, in a dosage range of 20 mg–500 mg, is delivered intravenously and/or intramuscularly 3 times (perhaps more) per week for 2–4 weeks.
c) Thirty days after the surgery, the heart is removed and cross-sectioned for morphometric and in situ analyzes.

Example 23

Rat Corneal Wound Healing Model

This animal model shows the effect of VEGF-2 on neovascularization.

Experimental Design

The experimental protocol includes:
a) Making a 1–1.5 mm long incision from the center of cornea into the stromal layer.
b) Inserting a spatula below the lip of the incision facing the outer corner of the eye.
c) Making a pocket (its base is 1–1.5 mm form the edge of the eye).
d) Positioning a pellet, containing 50 mg–500 mg VEGF-2, within the pocket.
e) VEGF-2 treatment can also be applied topically to the corneal wounds in a dosage range of 20 mg–500 mg (daily treatment for five days).

Example 24

Diabetic Mouse and Glucocorticoid-Impaired Wound Healing Models

Experimental Design

The experimental protocol includes:

1. Diabetic db+/db+ mouse model.

To demonstrate that VEGF-2 accelerates the healing process, the genetically diabetic mouse model of wound healing iss used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al, *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (Suppl):1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Animals

Genetically diabetic female C57BL/KsJ (db+/db+) mice and their non-diabetic (db+/+m) heterozygous littermates were used in this study (Jackson Laboratories). The animals were purchased at 6 weeks of age and were 8 weeks old at the beginning of the study. Animals were individually housed and received food and water ad libitum. All manipulations were performed using aseptic techniques. The experiments were conducted according to the rules and guidelines of Human Genome Sciences, Inc. Institutional Animal Care and Use Committee and the Guidelines for the Care and Use of Laboratory Animals.

Surgical Wounding

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

VEGF-2 is administered using at a range different doses of VEGF-2, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Experimental Design

Three groups of 10 animals each (5 diabetic and 5 non-diabetic controls) were evaluated: 1) Vehicle placebo control, 2) VEGF-2.

Measurement of Wound Area and Closure

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 was 64 mm$^2$, the corresponding size of the dermal punch. Calculations were made using the following formula:

[Open area on day 8]–[Open area on day 1]/[Open area on day 1]

Histology

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with KGF-2. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Immunohistochemistry

Re-epithelialization

Tissue sections are stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Cell Proliferation Marker

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Statistical Analysis

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that VEGF-2 can accelerate the healing process, the effects of multiple topical applications of VEGF-2 on full thickness excisional skin wounds in rats in which healing has been impaired by the systemic administration of methylprednisolone is assessed.

Animals

Young adult male Sprague Dawley rats weighing 250–300 g (Charles River Laboratories) are used in this example. The animals are purchased at 8 weeks of age and were 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

Surgical Wounding

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8 for Figure. Wounds are measured horizontally and vertically using a calibrated Jameson caliper. Wounds are considered healed if granulation tissue was no longer visible and the wound is covered by a continuous epithelium.

VEGF-2 is administered using at a range different doses of VEGF-2, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Experimental Design

Four groups of 10 animals each (5 with methylprednisolone and 5 without glucocorticoid) were evaluated: 1) Untreated group 2) Vehicle placebo control 3) VEGF-2 treated groups.

Measurement of Wound Area and Closure

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 was 64 $mm^2$, the corresponding size of the dermal punch. Calculations were made using the following formula:

[Open area on day 8]−[Open area on day 1]/[Open area on day 1]

Histology

Specimens are fixed in 10% buffered formalin and paraffin embedded blocks are sectioned perpendicular to the wound surface (5 mm) and cut using an Olympus microtome. Routine hematoxylin-eosin (H&E) staining was performed on cross-sections of bisected wounds. Histologic examination of the wounds allows assessment of whether the healing process and the morphologic appearance of the repaired skin was improved by treatment with VEGF-2. A calibrated lens micrometer was used by a blinded observer to determine the distance of the wound gap.

Statistical Analysis

Experimental data are analyzed using an unpaired t test. A p value of <0.05 is considered significant.

Example 25

Specific Peptide Fragments to Generate VEGF-2 Monoclonal Antibodies

Four specific peptides (designated SP-40, SP-41, SP-42 and SP-43) have been generated. These will be used to generate monoclonal antibodies to analyze VEGF-2 processing. The peptides are shown below:

1. "SP-40":MTVLYPEYWKMY (amino acids 70–81 in SEQ ID NO:2)

2. "SP-41":KSIDNEWRKTQSMPREV (amino acids 120–136(note C->S mutation at position 131) in SEQ ID NO:18)

-continued

3. "SP-42":MSKLDVYRQVHSIIRR (amino acids 212–227 in SEQ ID NO:18)

4. "SP-43":MFSSDAGDDSTDGFHDI (amino acids 263–279 in SEQ ID NO:18)

Example 26

Lymphadema Animal Model

The purpose of this experimental approach is to create an appropriate and consistent lymphedema model for testing the therapeutic effects of VEGF-2 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Experimental Procedure

Prior to beginning surgery, blood sample was drawn for protein concentration analysis. Male rats weighing approximately 350g are dosed with Pentobarbital. Subsequently, the right legs were shaved from knee to hip. The shaved area is swabbed with gauze soaked in 70% EtOH. Blood is drawn for serum total protein testing. Circumference and volumetric measurements were made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care was taken to control any mild bleeding resulting from this procedure. After lymphatics were occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals were checked daily through the optimal edematous peak, which typically occurred by day 5–7. The plateau edematous peak was then observed. To evaluate the intensity of the lymhedema, we measured the circumference and volumes of 2 designated places on each paw before operation and daily for 7 days. The effect plasma proteins have on lymphedema and determined if protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and $Ca^{2+}$ comparison.

Limb Weight Comparison: After drawing blood, the animal is prepared for tissue collection. The limbs were amputated using a quillitine, then both experimental and control legs were cut at the ligature and weighed. A second weighing is done as the tibio-cacaneal joint was disarticulated and the foot was weighed.

Histological Preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle was observed under fluorescent microscopy for lymphatics. Other immuno/histological methods are currently being evaluated.

Example 27

Method of Treatment Using Gene Therapy for Production of VEGF-2 Polypeptide—In Vivo Another aspect of the present invention is using in vivo gene therapy methods to treat disorders, diseases and conditions. The gene therapy method relates to the introduction of naked nucleic acid (DNA, RNA, and antisense DNA or RNA) comprising VEGF-2 operably linked to a promoter into an animal to increase the expression of VEGF-2. Such gene therapy and delivery techniques and methods are known in the art, see, for example, WO 90/11092, WO 98/11779; U.S. Pat. Nos. 5,693,622, 5,705,151, 5580859; Tabata H. et al. (1997) *Cardiovasc. Res.* 35(3):470–479, Chao, J et al. (1997) *Pharmacol. Res.* 35(6):517–522, Wolff, J. A. (1997) *Neuromuscul. Disord.* 7(5):314–318, Schwartz, B. et al. (1996) *Gene Ther.* 3(5):405–411, Tsurumi, Y. et al. (1996) *Circulation* 94(12):3281–3290 (incorporated herein by reference).

The VEGF-2 polynucleotide constructs may be delivered by any method that delivers injectable materials to the cells of an animal, such as, injection into the interstitial space of tissues (heart, muscle, skin, lung, liver, intestine and the like). The VEGF-2 polynucleotide constructs may also be delivered directly into arteries. The VEGF-2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the VEGF-2 polynucleotide may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The VEGF-2 vector constructs used in the gene therapy method are preferably constructs that will not integrate into the host genome nor will they contain sequences that allow for replication. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

Figure 30:
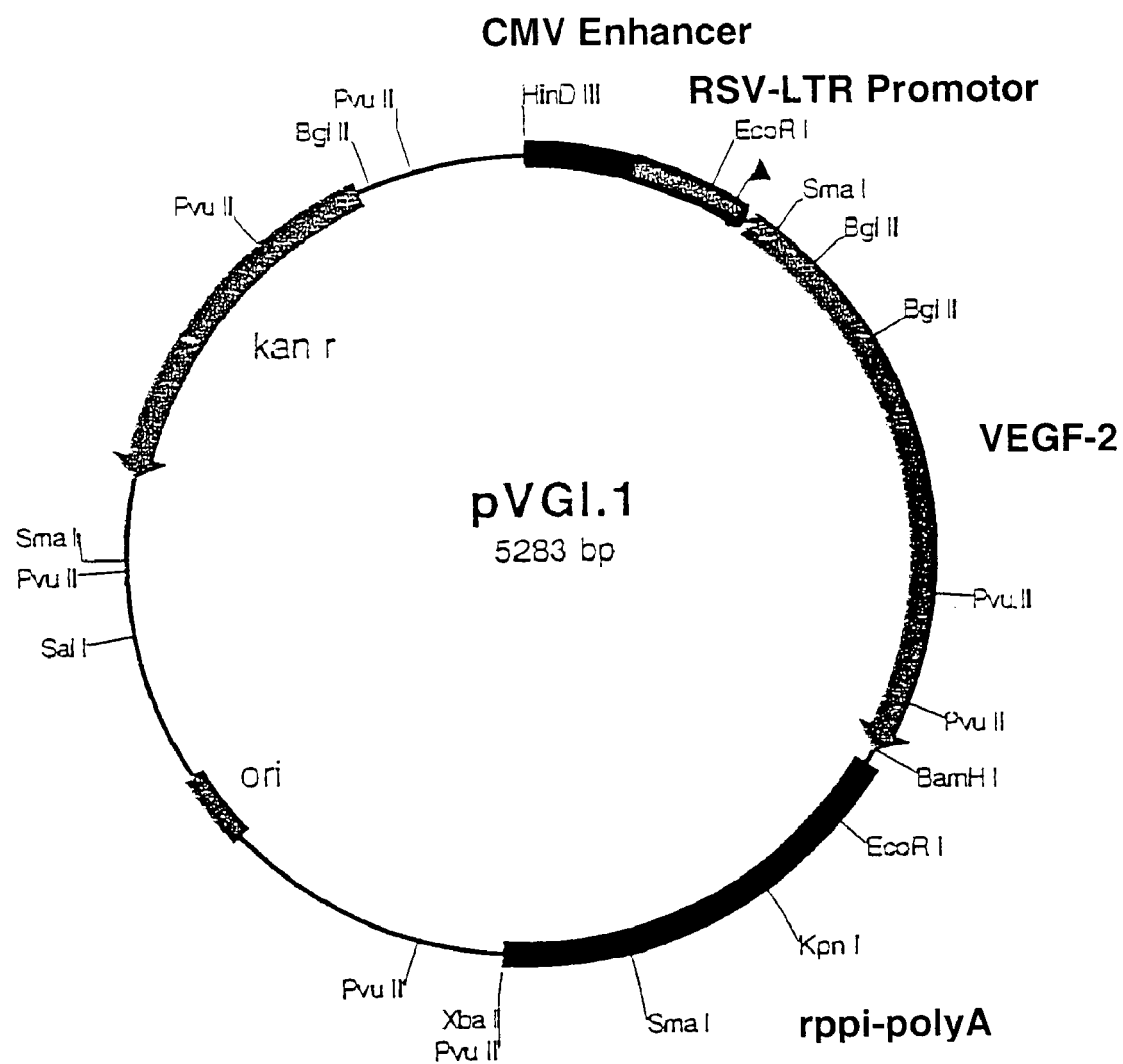
FIG. 30 shows a schematic representation of the pVGI.1 expression vector construct containing a polynucleotide encoding VEGF-2.
Figure 31B:
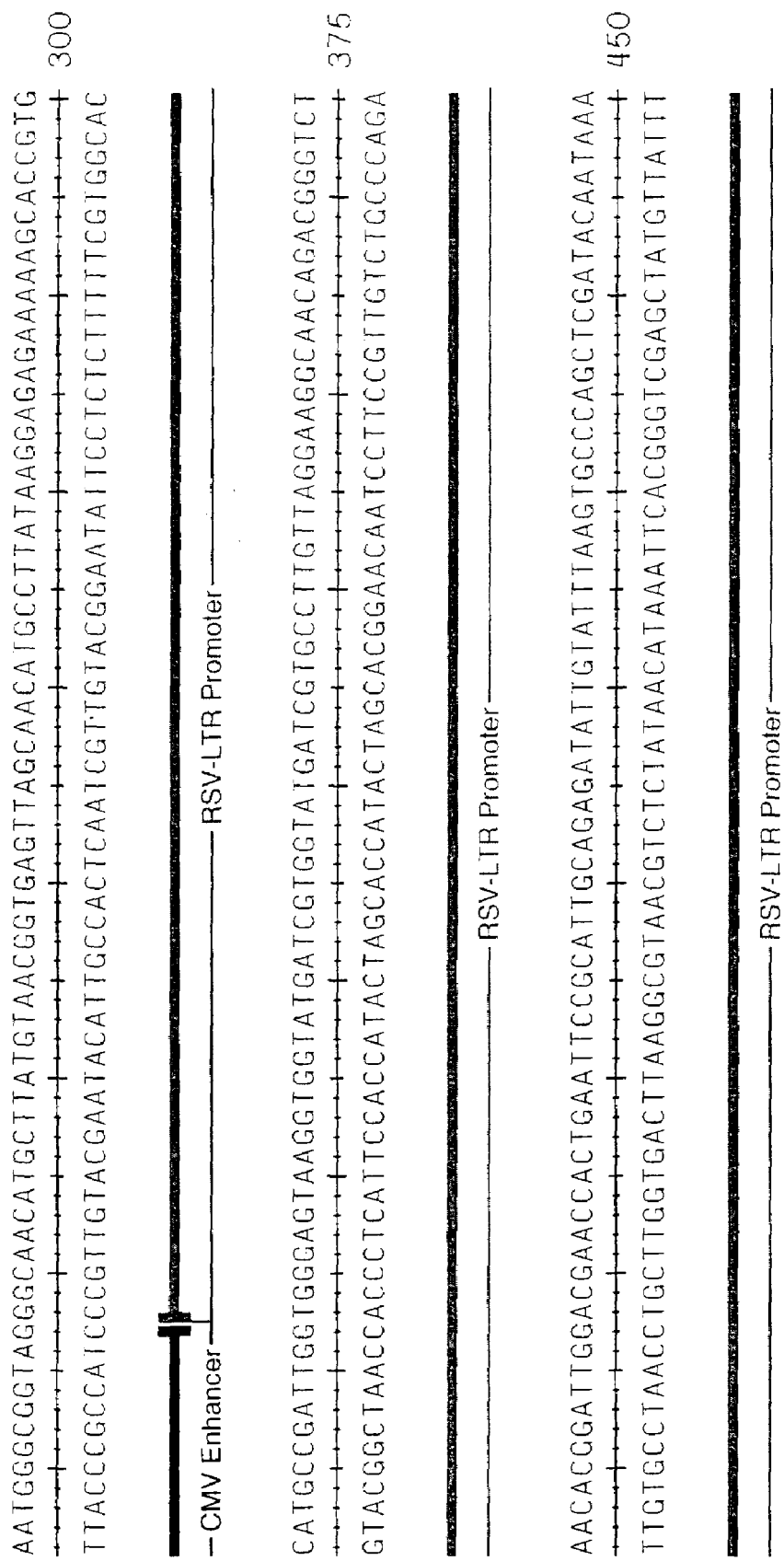
FIG. 31A–U shows the nucleotide sequence of the pVGI.1 vector construct containing the VEGF-2 insert (SEQ ID NO:36).
Figure 31C:
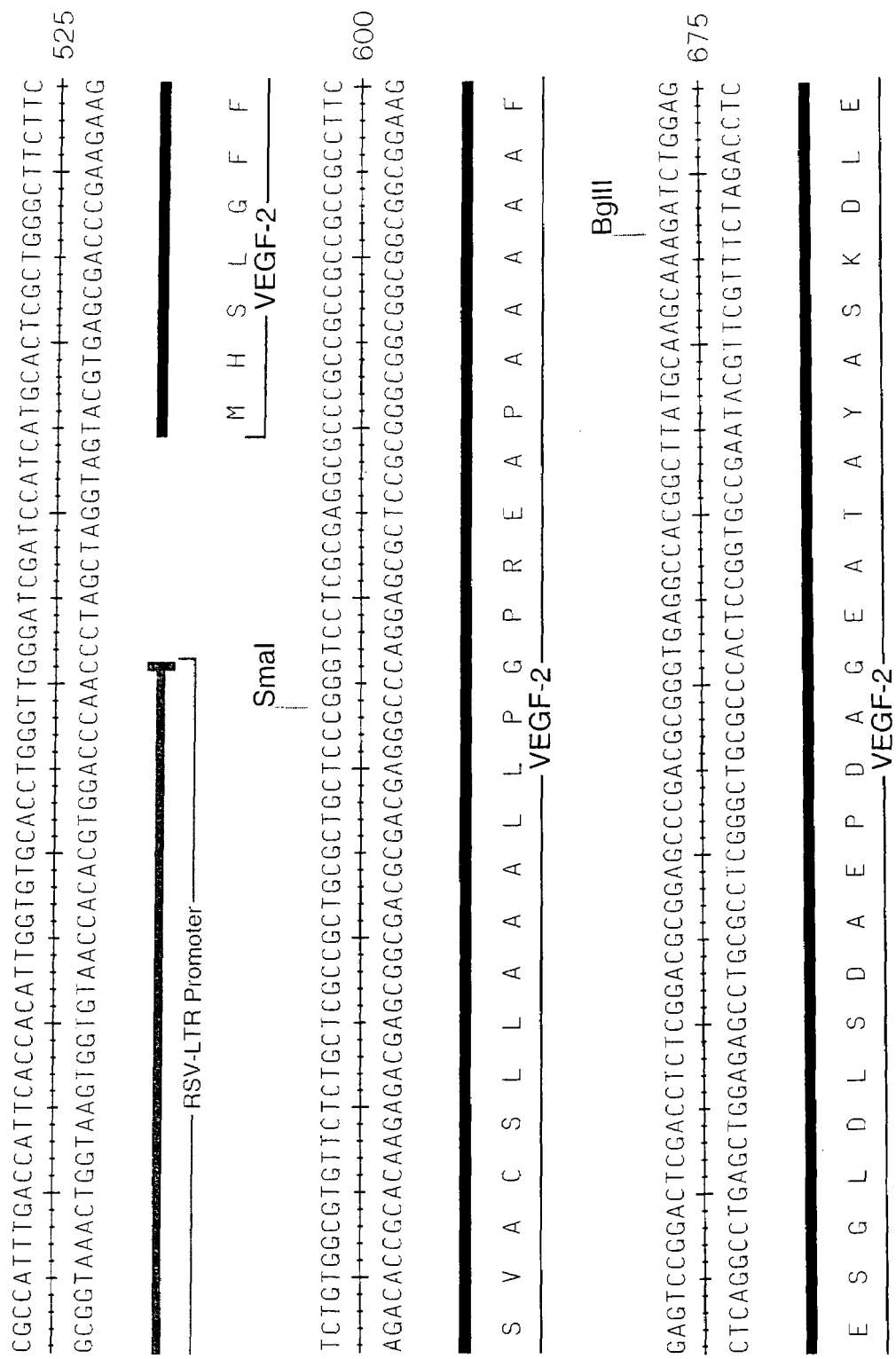
Figure 31G:
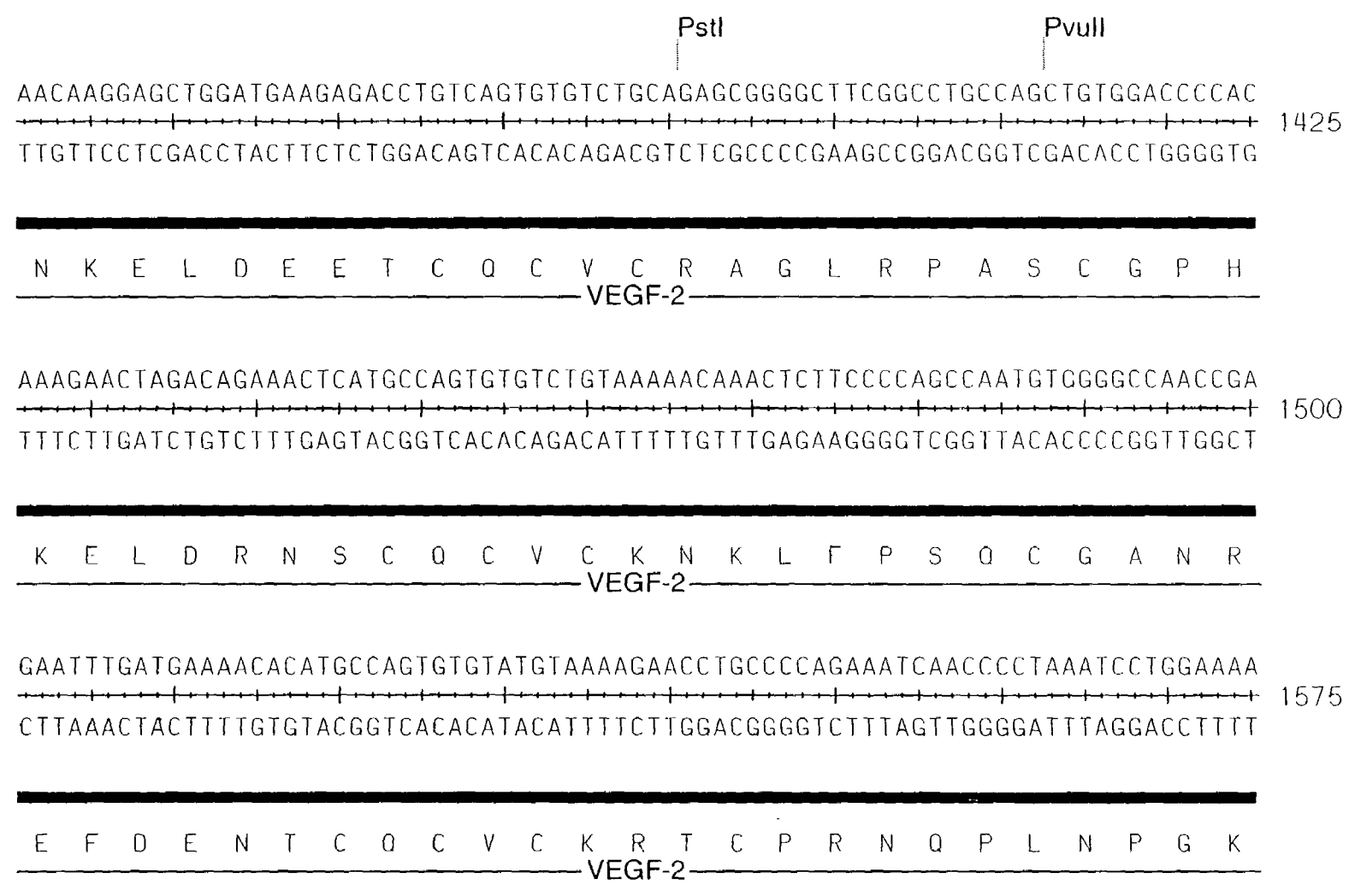
Figure 31H:
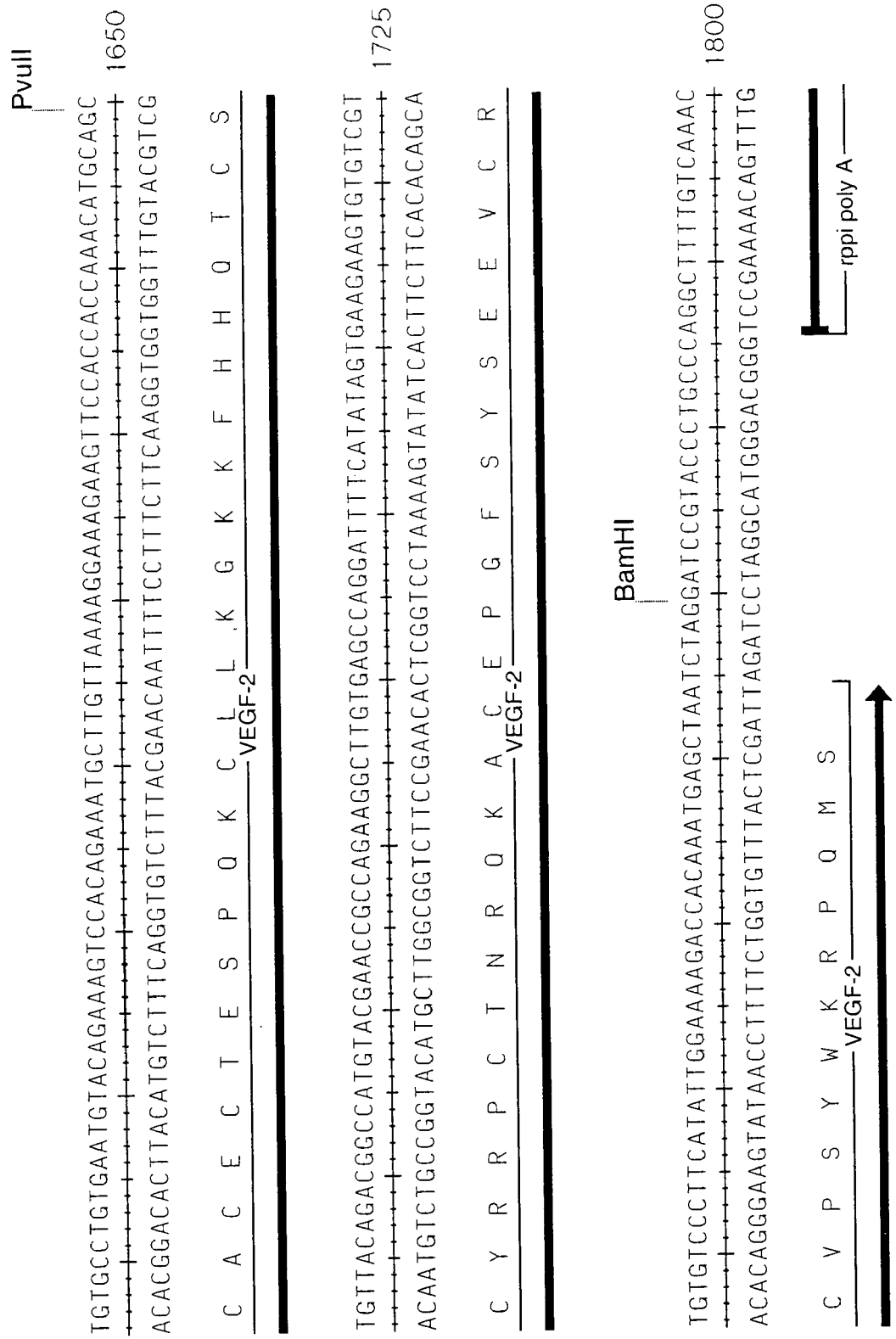
Figure 31K:
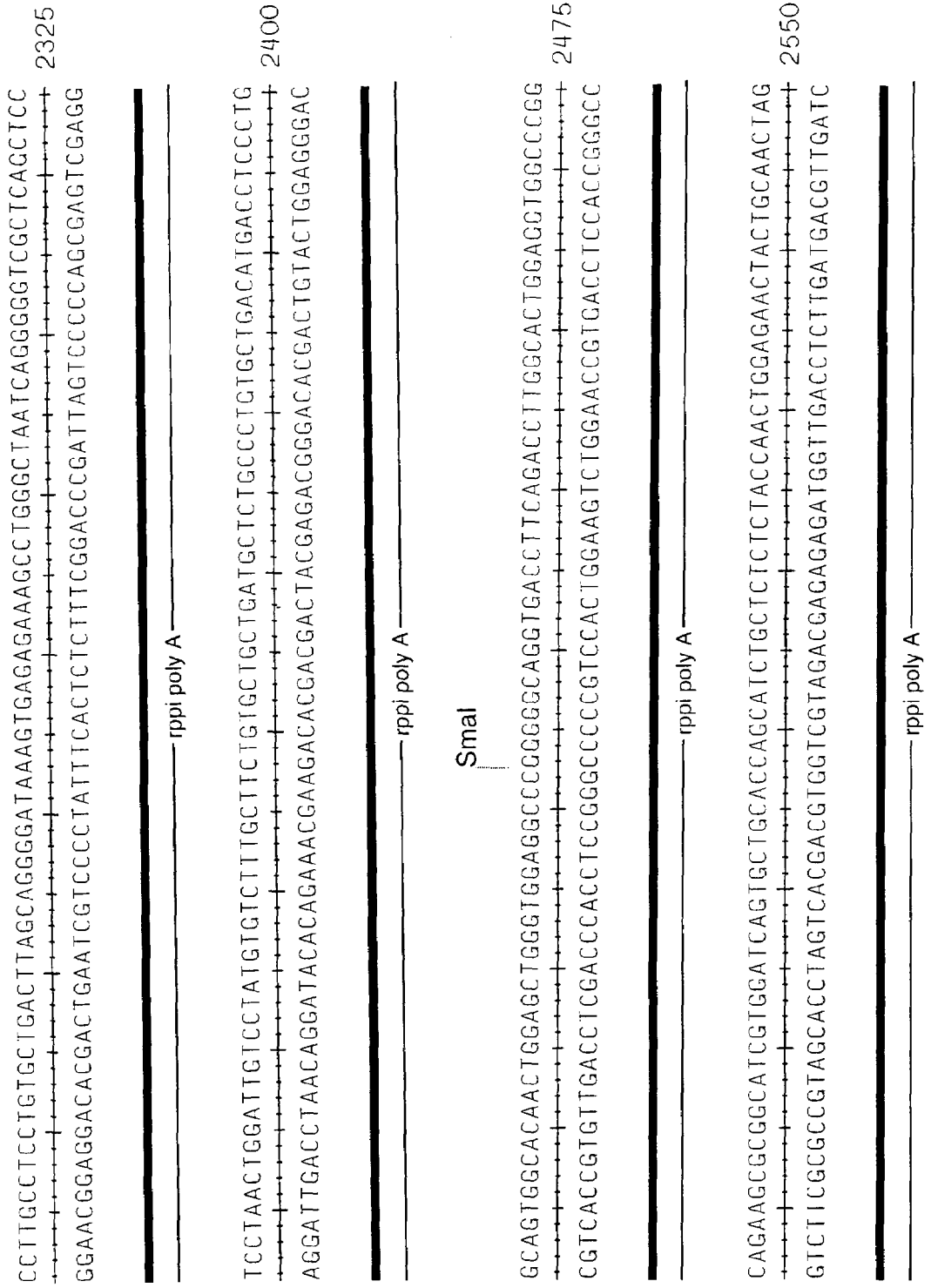

Preferably, the VEGF-2 construct will comprise a VEGF-2 polynucleotide operably inserted into the pVGI.1 plasmid, as illustrated in FIG. 30. The pVGI.1 plasmid construct, the sequence of which is shown in FIG. 31A-G, was deposited on Jul. 3, 2000 at the American Type Tissue Collection (ATCC), 10801 University Boulevard, Manassas, Va. 20110-2209, and given ATCC Deposit Number PTA-2185. This VEGF-2 polynucleotide vector construct can be delivered to tissues, by methods know in the art and described above, preferably by direct injection using naked polynucleotide, for therapeutic applications. Such uses include the promotion of angiogenesis in the treatment of a number of diseases and conditions, as described in "Therapeutic Uses" above, and elsewhere herein. Preferred uses of this construct include the treatment of critical limb ischemia and coronary artery disease.

The VEGF-2 construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. Preferably, they are delivered by direct injection into the artery.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues, or directly into arteries. However, other parenteral routes may also be used, such as, inhalation of an aerosol formulation particularly for delivery to lungs or bronchial tissues, throat or mucous membranes of the nose. In addition, naked VEGF-2 constructs can be delivered to arteries during angioplasty by the catheter used in the procedure.

The dose response effects of injected VEGF-2 polynucleotide construct in arteries in vivo is determined as follows. Suitable template DNA for production of mRNA coding for VEGF-2 is prepared in accordance with a standard recombinant DNA methodology. The template DNA, which may be either circular or linear, is either used as naked DNA or complexed with liposomes. The arteries of rabbits are then injected with various amounts of the template DNA.

Hindlimb ischemia in rabbits is surgically induced, as described in Example 18. Immediately following this, five different sites in the adductor (2 sites), medial large (2 sites), and semimembranous muscles (1 site) are injected directly with plasmid DNA encoding VEGF-2 using a 3 ml syringe and 2-gauge needle advanced through a small skin incision. The skin is then closed using 4.0 nylon.

The ability to rescue hindlimb ischemia is determined by measuring the number of capillaries in light microsopic sections taken from the treated hindlimbs, compared to ischemic hindlimbs from untreated rabbits, measurement of calf blood pressure, and intra-arterial Doppler guidewire measurement of flow velocity (Takeshita et al., J. Clin. Invest. 93:662–670 (1994)). The results of the above experimentation in rabbits can be use to extrapolate proper dosages and other treatment parameters in humans and other animals using VEGF-2 polynucleotide naked DNA.

Example 28

Method of Treatment Using Gene Therapy—Ex Vivo

One method of gene therapy transplants fibroblasts, which are capable of expressing VEGF-2 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding VEGF-2 can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted VEGF-2.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the VEGF-2 gene is then added to the media and the packaging cells transduced with the vector. The packaging cells now produce infectious viral particles containing the VEGF-2 gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether VEGF-2 protein is produced.

The engineered fibroblasts are then transplanted onto the host, either alone or after having been grown to confluence on cytodex 3 microcarrier beads

Example 29

Method of Treatment Using Gene Therapy Homologous Recombination

Another method of gene therapy according to the present invention involves operably associating the endogenous VEGF-2 sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous VEGF-2, flanking the promoter. The targeting sequence will be sufficiently near the 5' end of VEGF-2 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous VEGF-2 sequence. This results in the expression of VEGF-2 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. To construct a plasmid for targeting to the VEGF-2 locus, plasmid pUC18 (MBI Fermentas, Amherst, N.Y.) is digested with HindIII. The CMV promoter is amplified by PCR with an XbaI site on the 5' end and a BamHI site on the 3'end. Two VEGF-2 non-coding sequences are amplified via PCR: one VEGF-2 non-coding sequence (VEGF-2 fragment 1) is amplified with a HindIII site at the 5' end and an Xba site at the 3'end; the other VEGF-2 non-coding sequence (VEGF-2 fragment 2) is amplified with a BamHI site at the 5'end and a HindIII site at the 3'end. The CMV promoter and VEGF-2 fragments are digested with the appropriate enzymes (CMV promoter—XbaI and BamHI; VEGF-2 fragment 1—XbaI; VEGF-2 fragment 2—BamHI) and ligated together. The resulting ligation product is digested with HindIII, and ligated with the HindIII-digested pUC 18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37EC. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product.

Example 30

VEGF-2 Transgenic Animals

The VEGF-2 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of VEGF-2 polypeptides, studying conditions and/or disorders associated with aberrant VEGF-2 expression, and in screening for compounds effective in ameliorating such conditions and/or disorders.

Example 31

VEGF-2 Knock-Out Animals

Endogenous VEGF-2 gene expression can also be reduced by inactivating or "knocking out" the VEGF-2 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the VEGF-2 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of VEGF-2 polypeptides, studying conditions and/or disorders associated with aberrant VEGF-2 expression, and in screening for compounds effective in ameliorating such conditions and/or disorders.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

Additionally, the Sequence Listing submitted in Provisional Application Ser. No. 60/223,276, filed Aug. 4, 2000, whether in computer, microfiche, CD-R, and/or paper forms, is hereby incorporated by reference in its entirety.

---

What is claimed is:

1. An isolated nucleic acid molecule comprising the nucleic acid sequence of the pVGI.1 expression vector construct depicted in FIG. 31 (SEQ ID NO:36).

2. A method of producing a host cell in vitro comprising transducing, transforming or transfecting a cell with the nucleic acid molecule of claim 1 to produce a genetically engineered host cell.

3. A host cell comprising the nucleic acid molecule of claim 1.

4. An isolated nucleic acid molecule comprising the pVGI.1 expression vector construct contained in ATCC Deposit No. PTA-2185.

5. A method of producing a host cell in vitro comprising transducing, transforming or transfecting a cell with the nucleic acid molecule of claim 4 to produce a genetically engineered host cell.

6. A host cell comprising the nucleic acid molecule of claim 4.

* * * * *

SEQUENCE LISTING

<160> NUMBER OF SEQ ID NOS: 36

<210> SEQ ID NO 1
<211> LENGTH: 1674
<212> TYPE: DNA
<213> ORGANISM: homo sapiens

<400> SEQUENCE: 1

```
gtccttccac catgcactcg ctgggcttct tctctgtggc gtgttctctg ctcgccgctg      60
cgctgctccc gggtcctcgc gaggcgcccg ccgccgccgc cgccttcgag tccggactcg     120
acctctcgga cgcggagccc gacgcgggcg aggccacggc ttatgcaagc aaagatctgg     180
aggagcagtt acggtctgtg tccagtgtag atgaactcat gactgtactc tacccagaat     240
```

```
attggaaaat gtacaagtgt cagctaagga aaggaggctg gcaacataac agagaacagg    300
ccaacctcaa ctcaaggaca gaagagacta taaaatttgc tgcagcacat tataatacag    360
agatcttgaa aagtattgat aatgagtgga gaaagactca atgcatgcca cgggaggtgt    420
gtatagatgt ggggaaggag tttggagtcg cgacaaacac cttctttaaa cctccatgtg    480
tgtccgtcta cagatgtggg ggttgctgca atagtgaggg gctgcagtgc atgaacacca    540
gcacgagcta cctcagcaag acgttatttg aaattacagt gcctctctct caaggcccca    600
aaccagtaac aatcagtttt gccaatcaca cttcctgccg atgcatgtct aaactggatg    660
tttacagaca agttcattcc attattagac gttccctgcc agcaacacta ccacagtgtc    720
aggcagcgaa caagacctgc cccaccaatt acatgtggaa taatcacatc tgcagatgcc    780
tggctcagga agatttttatg ttttcctcgg atgctggaga tgactcaaca gatggattcc    840 atgcacatctg tggaccaaac aaggagctgg atgaagagac ctgtcagtgt gtctgcagag    900
cggggcttcg gcctgccagc tgtggacccc acaaagaact agacagaaac tcatgccagt    960
gtgtctgtaa aaacaaactc ttccccagcc aatgtgggc caaccgagaa tttgatgaaa    1020
acacatgcca gtgtgtatgt aaaagaacct gccccagaaa tcaaccccta aatcctggaa    1080
aatgtgcctg tgaatgtaca gaaagtccac agaaatgctt gttaaaagga agaagttcc    1140 accaccaaac atgcagctgt tacagacggc catgtacgaa ccgccagaag gcttgtgagc    1200
caggattttc atatagtgaa gaagtgtgtc gttgtgtccc ttcatattgg caaagaccac    1260 aaaatgagcta agattgtact gttttccagt tcatcgattt tctattatgg aaaactgtgt    1320
tgccacagta gaactgtctg tgaacagaga gacccttgtg ggtccatgct aacaaagaca    1380
aaagtctgtc tttcctgaac catgtggata actttacaga aatggactgg agctcatctg    1440
caaaaggcct cttgtaaaga ctggtttttct gccaatgacc aaacagccaa gattttcctc    1500
ttgtgatttc tttaaaagaa tgactatata atttatttcc actaaaaata ttgtttctgc    1560 attcatttttt atagcaacaa caattggtaa aactcactgt gatcaatatt tttatatcat    1620
gcaaaatatg tttaaaataa aatgaaaatt gtatttataa aaaaaaaaa aaaa          1674
```

<210> SEQ ID NO 2
<211> LENGTH: 419
<212> TYPE: PRT
<213> ORGANISM: homo sapiens

<400> SEQUENCE: 2

```
Met His Ser Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
```

```
            115                 120                 125
Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Gln Arg Pro
                405                 410                 415

Gln Met Ser

<210> SEQ ID NO 3
<211> LENGTH: 1526
<212> TYPE: DNA
<213> ORGANISM: homo sapiens

<400> SEQUENCE: 3
cgaggccacg gcttatgcaa gcaaagatct ggaggagcag ttacggtctg tgtccagtgt      60
agatgaactc atgactgtac tctacccaga atattggaaa atgtacaagt gtcagctaag     120
gaaaggaggc tggcaacata acagagaaca ggccaacctc aactcaagga cagaagagac     180
tataaaattt gctgcagcac attataatac agagatcttg aaaagtattg ataatgagtg     240
gagaaagact caatgcatgc cacgggaggt gtgtatagat gtggggaagg agtttggagt     300
cgcgacaaac accttcttta aacctccatg tgtgtccgtc tacagatgtg ggggttgctg     360
caatagtgag gggctgcagt gcatgaacac cagcacgagc tacctcagca agacgttatt     420
```

-continued

```
tgaaattaca gtgcctctct ctcaaggccc caaaccagta acaatcagtt ttgccaatca    480
cacttcctgc cgatgcatgt ctaaactgga tgtttacaga caagttcatt ccattattag    540
acgttccctg ccagcaacac taccacagtg tcaggcagcg aacaagacct gccccaccaa    600
ttacatgtgg aataatcaca tctgcagatg cctggctcag gaagatttta tgttttcctc    660
ggatgctgga gatgactcaa cagatggatt ccatgacatc tgtggaccaa caaggagct     720
ggatgaagag acctgtcagt gtgtctgcag agcggggctt cggcctgcca gctgtggacc    780
ccacaaagaa ctagacagaa actcatgcca gtgtgtctgt aaaaacaaac tcttccccag    840
ccaatgtggg gccaaccgag aatttgatga aaacacatgc cagtgtgtat gtaaaagaac    900
ctgccccaga aatcaacccc taaatcctgg aaaatgtgcc tgtgaatgta cagaaagtcc    960
acagaaatgc ttgttaaaag gaagaagtt ccaccaccaa acatgcagct gttacagacg    1020
gccatgtacg aaccgccaga aggcttgtga gccaggatt tcatatagtg aagaagtgtg     1080
tcgttgtgtc ccttcatatt ggcaaagacc acaaatgagc taagattgta ctgttttcca    1140
gttcatcgat tttctattat ggaaaactgt gttgccacag tagaactgtc tgtgaacaga    1200
gagacccttg tgggtccatg ctaacaaaga caaaagtctg tctttcctga accatgtgga    1260
taactttaca gaaatggact ggagctcatc tgcaaaaggc ctcttgtaaa gactggtttt    1320
ctgccaatga ccaaacagcc aagatttttcc tcttgtgatt tctttaaaag aatgactata    1380
taatttattt ccactaaaaa tattgtttct gcattcattt ttatagcaac aacaattggt    1440
aaaactcact gtgatcaata tttttatatc atgcaaaata tgtttaaaat aaaatgaaaa    1500
ttgtatttat aaaaaaaaaa aaaaaa                                         1526
```

<210> SEQ ID NO 4
<211> LENGTH: 350
<212> TYPE: PRT
<213> ORGANISM: homo sapiens

<400> SEQUENCE: 4

```
Met Thr Val Leu Tyr Pro Glu Tyr Trp Lys Met Tyr Lys Cys Gln Leu
1               5                   10                  15
Arg Lys Gly Gly Trp Gln His Asn Arg Glu Gln Ala Asn Leu Asn Ser
            20                  25                  30
Arg Thr Glu Glu Thr Ile Lys Phe Ala Ala Ala His Tyr Asn Thr Glu
        35                  40                  45
Ile Leu Lys Ser Ile Asp Asn Glu Trp Arg Lys Thr Gln Cys Met Pro
    50                  55                  60
Arg Glu Val Cys Ile Asp Val Gly Lys Glu Phe Gly Val Ala Thr Asn
65                  70                  75                  80
Thr Phe Phe Lys Pro Pro Cys Val Ser Val Tyr Arg Cys Gly Gly Cys
                85                  90                  95
Cys Asn Ser Glu Gly Leu Gln Cys Met Asn Thr Ser Thr Ser Tyr Leu
            100                 105                 110
Ser Lys Thr Leu Phe Glu Ile Thr Val Pro Leu Ser Gln Gly Pro Lys
        115                 120                 125
Pro Val Thr Ile Ser Phe Ala Asn His Thr Ser Cys Arg Cys Met Ser
    130                 135                 140
Lys Leu Asp Val Tyr Arg Gln Val His Ser Ile Ile Arg Arg Ser Leu
145                 150                 155                 160
Pro Ala Thr Leu Pro Gln Cys Gln Ala Ala Asn Lys Thr Cys Pro Thr
                165                 170                 175
```

```
Asn Tyr Met Trp Asn Asn His Ile Cys Arg Cys Leu Ala Gln Glu Asp
            180                 185                 190

Phe Met Phe Ser Ser Asp Ala Gly Asp Asp Ser Thr Asp Gly Phe His
        195                 200                 205

Asp Ile Cys Gly Pro Asn Lys Glu Leu Asp Glu Glu Thr Cys Gln Cys
    210                 215                 220

Val Cys Arg Ala Gly Leu Arg Pro Ala Ser Cys Gly Pro His Lys Glu
225                 230                 235                 240

Leu Asp Arg Asn Ser Cys Gln Cys Val Cys Lys Asn Lys Leu Phe Pro
                245                 250                 255

Ser Gln Cys Gly Ala Asn Arg Glu Phe Asp Glu Asn Thr Cys Gln Cys
            260                 265                 270

Val Cys Lys Arg Thr Cys Pro Arg Asn Gln Pro Leu Asn Pro Gly Lys
        275                 280                 285

Cys Ala Cys Glu Cys Thr Glu Ser Pro Gln Lys Cys Leu Leu Lys Gly
    290                 295                 300

Lys Lys Phe His His Gln Thr Cys Ser Cys Tyr Arg Arg Pro Cys Thr
305                 310                 315                 320

Asn Arg Gln Lys Ala Cys Glu Pro Gly Phe Ser Tyr Ser Glu Glu Val
                325                 330                 335

Cys Arg Cys Val Pro Ser Tyr Trp Gln Arg Pro Gln Met Ser
            340                 345                 350

<210> SEQ ID NO 5
<211> LENGTH: 211
<212> TYPE: PRT
<213> ORGANISM: homo sapiens

<400> SEQUENCE: 5

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
```

```
            195                 200                 205
Lys Pro Thr
    210

<210> SEQ ID NO 6
<211> LENGTH: 241
<212> TYPE: PRT
<213> ORGANISM: homo sapiens

<400> SEQUENCE: 6

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 7
<211> LENGTH: 190
<212> TYPE: PRT
<213> ORGANISM: homo sapiens

<400> SEQUENCE: 7

Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
            20                  25                  30

Glu Gln Lys Ala His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60
```

```
Pro Asp Glu Ile Glu Tyr Ile Phe Lys Pro Ser Cys Val Pro Leu Met
 65                  70                  75                  80

Arg Cys Ala Gly Cys Cys Asn Asp Glu Ala Leu Glu Cys Val Pro Thr
                 85                  90                  95

Ser Glu Ser Asn Val Thr Met Gln Ile Met Arg Ile Lys Pro His Gln
             100                 105                 110

Ser Gln His Ile Gly Glu Met Ser Phe Leu Gln His Ser Arg Cys Glu
         115                 120                 125

Cys Arg Pro Lys Lys Asp Arg Thr Lys Pro Glu Asn His Cys Glu Pro
     130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                 165                 170                 175

Glu Leu Asn Glu Arg Thr Cys Arg Cys Asp Lys Pro Arg Arg
            180                 185                 190

<210> SEQ ID NO 8
<211> LENGTH: 14
<212> TYPE: PRT
<213> ORGANISM: homo sapiens
<220> FEATURE:
<221> NAME/KEY: SITE
<222> LOCATION: (2)..(2)
<223> OTHER INFORMATION: Xaa equals any amino acid.
<221> NAME/KEY: SITE
<222> LOCATION: (5)..(5)
<223> OTHER INFORMATION: Xaa equals any amino acid.
<221> NAME/KEY: SITE
<222> LOCATION: (6)..(6)
<223> OTHER INFORMATION: Xaa equals any amino acid.
<221> NAME/KEY: SITE
<222> LOCATION: (7)..(7)
<223> OTHER INFORMATION: Xaa equals any amino acid.
<221> NAME/KEY: SITE
<222> LOCATION: (10)..(10)
<223> OTHER INFORMATION: Xaa equals any amino acid.

<400> SEQUENCE: 8

Pro Xaa Cys Val Xaa Xaa Xaa Arg Cys Xaa Gly Cys Cys Asn
1               5                   10

<210> SEQ ID NO 9
<211> LENGTH: 18
<212> TYPE: DNA
<213> ORGANISM: artificial sequence
<220> FEATURE:
<221> NAME/KEY: primer_bind
<222> LOCATION: (1)..(18)
<223> OTHER INFORMATION: M13-2 reverse primer

<400> SEQUENCE: 9
atgcttccgg ctcgtatg                                                 18

<210> SEQ ID NO 10
<211> LENGTH: 19
<212> TYPE: DNA
<213> ORGANISM: artificial sequence
<220> FEATURE:
<221> NAME/KEY: primer_bind
<222> LOCATION: (1)..(19)
<223> OTHER INFORMATION: M13-2 forward primer

<400> SEQUENCE: 10
gggttttccc agtcacgac                                                19
```

<210> SEQ ID NO 11
<211> LENGTH: 21
<212> TYPE: DNA
<213> ORGANISM: artificial sequence
<220> FEATURE:
<221> NAME/KEY: primer_bind
<222> LOCATION: (1)..(21)
<223> OTHER INFORMATION: VEGF primer F4

<400> SEQUENCE: 11
ccacatggtt caggaaagac a                                        21

<210> SEQ ID NO 12
<211> LENGTH: 50
<212> TYPE: DNA
<213> ORGANISM: artificial sequence
<220> FEATURE:
<221> NAME/KEY: primer_bind
<222> LOCATION: (1)..(50)
<223> OTHER INFORMATION: 5' PCR oligonucleotide primer.

<400> SEQUENCE: 12
tgtaatacga ctcactatag ggatcccgcc atggaggcca cggcttatgc          50

<210> SEQ ID NO 13
<211> LENGTH: 28
<212> TYPE: DNA
<213> ORGANISM: artificial sequence
<220> FEATURE:
<221> NAME/KEY: primer_bind
<222> LOCATION: (1)..(28)
<223> OTHER INFORMATION: 3' PCR oligonucleotide primer.

<400> SEQUENCE: 13
gatctctaga ttagctcatt tgtggtct                                 28

<210> SEQ ID NO 14
<211> LENGTH: 27
<212> TYPE: DNA
<213> ORGANISM: artificial sequence
<220> FEATURE:
<221> NAME/KEY: primer_bind
<222> LOCATION: (1)..(27)
<223> OTHER INFORMATION: 5' PCR oligonucleotide primer containing a
      BamHI site.

<400> SEQUENCE: 14
cgcggatcca tgactgtact ctaccca                                  27

<210> SEQ ID NO 15
<211> LENGTH: 60
<212> TYPE: DNA
<213> ORGANISM: artificial sequence
<220> FEATURE:
<221> NAME/KEY: primer_bind
<222> LOCATION: (1)..(60)
<223> OTHER INFORMATION: 3' PCR oligonucleotide primer containing
      complementary sequeces to an XbaI site, HA tag, and XhoI site.

<400> SEQUENCE: 15
cgctctagat caagcgtagt ctgggacgtc gtatgggtac tcgaggctca tttgtggtct  60

<210> SEQ ID NO 16
<211> LENGTH: 3974
<212> TYPE: DNA
<213> ORGANISM: Escherichia coli

<400> SEQUENCE: 16

```
ggtacctaag tgagtagggc gtccgatcga cggacgcctt ttttttgaat tcgtaatcat    60
ggtcatagct gtttcctgtg tgaaattgtt atccgctcac aattccacac aacatacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900
gaagaacagt atttggtatc tgcgctctgc tgaagccagt taccttcgga aaaagagttg   960
gtagctcttg atccggcaaa caaaccaccg ctggtagcgg tggttttttt gtttgcaagc  1020
agcagattac gcgcagaaaa aaaggatctc aagaagatcc tttgatcttt tctacggggt  1080
ctgacgctca gtggaacgaa aactcacgtt aagggatttt ggtcatgaga ttatcgtcga  1140
caattcgcgc gcgaaggcga agcggcatgc atttacgttg acaccatcga atggtgcaaa  1200
acctttcgcg gtatggcatg atagcgcccg gaagagagtc aattcagggt ggtgaatgtg  1260
aaaccagtaa cgttatacga tgtcgcagag tatgccggtg tctcttatca gaccgtttcc  1320
cgcgtggtga accaggccag ccacgtttct gcgaaaacgc gggaaaaagt ggaagcggcg  1380
atggcggagc tgaattacat tcccaaccgc gtggcacaac aactggcggg caaacagtcg  1440
ttgctgattg gcgttgccac ctccagtctg gccctgcacg cgccgtcgca aattgtcgcg  1500
gcgattaaat ctcgcgccga tcaactgggt gccagcgtgg tggtgtcgat ggtagaacga  1560
agcggcgtcg aagcctgtaa agcggcggtg cacaatcttc tcgcgcaacg cgtcagtggg  1620
ctgatcatta actatccgct ggatgaccag gatgccattg ctgtggaagc tgcctgcact  1680
aatgttccgg cgttatttct tgatgtctct gaccagacac ccatcaacag tattattttc  1740
tcccatgaag acggtacgcg actgggcgtg gagcatctgg tcgcattggg tcaccagcaa  1800
atcgcgctgt tagcgggccc attaagttct gtctcggcgc gtctgcgtct ggctggctgg  1860
cataaatatc tcactcgcaa tcaaattcag ccgatagcgg aacgggaagg cgactggagt  1920
gccatgtccg gttttcaaca aaccatgcaa atgctgaatg agggcatcgt tcccactgcg  1980
atgctggttg ccaacgatca gatggcgctg ggcgcaatgc gcgccattac cgagtccggg  2040
ctgcgcgttg gtgcggatat ctcggtagtg gatacgacg ataccgaaga cagctcatgt  2100
tatatcccgc cgttaaccac catcaaacag gattttcgcc tgctggggca aaccagcgtg  2160
gaccgcttgc tgcaactctc tcagggccag gcggtgaagg gcaatcagct gttgcccgtc  2220
tcactggtga aaagaaaaac cacccctggcg cccaatacgc aaaccgcctc tccccgcgcg  2280
ttggccgatt cattaatgca gctggcacga caggtttccc gactggaaag cgggcagtga  2340
```

```
gcgcaacgca attaatgtaa gttagcgcga attgtcgacc aaagcggcca tcgtgcctcc    2400
ccactcctgc agttcggggg catggatgcg cggatagccg ctgctggttt cctggatgcc    2460
gacggatttg cactgccggt agaactccgc gaggtcgtcc agcctcaggc agcagctgaa    2520
ccaactcgcg aggggatcga gcccggggtg ggcgaagaac tccagcatga atccccgcg    2580 ctggaggatc atccagccgg cgtcccggaa aacgattccg aagcccaacc tttcatagaa    2640
ggcggcggtg gaatcgaaat ctcgtgatgg caggttgggc gtcgcttggt cggtcatttc    2700
gaacccagaa gtcccgctca gaagaactcg tcaagaaggc gatagaaggc gatgcgctgc    2760
gaatcgggag cggcgatacc gtaaagcacg aggaagcggt cagcccattc gccgccaagc    2820
tcttcagcaa tatcacgggt agccaacgct atgtcctgat agcggtccgc cacacccagc    2880
cggccacagt cgatgaatcc agaaaagcgg ccattttcca ccatgatatt cggcaagcag    2940
gcatcgccat gggtcacgac gagatcctcg ccgtcgggca tgcgcgcctt gagcctggcg    3000
aacagttcgg ctggcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aagaaccgg gcgcccctgc gctgacagcc ggaacacggc ggcatcagag    3420
cagccgattg tctgttgtgc ccagtcatag ccgaatagcc tctccaccca gcgccgga    3480 gaacctgcgt gcaatccatc ttgttcaatc atgcgaaacg atcctcatcc tgtctcttga    3540
tcagatcttg atcccctgcg ccatcagatc cttggcggca agaaagccat ccagtttact    3600
ttgcagggct tcccaacctt accagagggc gccccagctg gcaattccgg ttcgcttgct    3660
gtccataaaa ccgcccagtc tagctatcgc catgtaagcc cactgcaagc tacctgcttt    3720
ctctttgcgc ttgcgttttc ccttgtccag atagcccagt agctgacatt catccggggt    3780
cagcaccgtt tctgcggact ggctttctac gtgttccgct tcctttagca gcccttgcgc    3840
cctgagtgct tgcggcagcg tgaagcttaa aaaactgcaa aaaatagttt gacttgtgag    3900
cggataacaa ttaagatgta cccaattgtg agcggataac aatttcacac attaaagagg    3960
agaaattaca tatg                                                     3974
```

<210> SEQ ID NO 17
<211> LENGTH: 112
<212> TYPE: DNA
<213> ORGANISM: artificial sequence
<220> FEATURE:
<221> NAME/KEY: promoter
<222> LOCATION: (1)..(112)
<223> OTHER INFORMATION: pHE4a promotor

<400> SEQUENCE: 17

```
aagcttaaaa aactgcaaaa aatagtttga cttgtgagcg gataagaatt aagatgtacc    60
caattgtgag cggataacaa tttcacacat taaagaggag aaattacata tg           112
```

<210> SEQ ID NO 18
<211> LENGTH: 113
<212> TYPE: PRT
<213> ORGANISM: Homo sapiens

<400> SEQUENCE: 18

```
Thr Glu Glu Thr Ile Lys Phe Ala Ala Ala His Tyr Asn Thr Glu Ile
1               5                   10                  15

Leu Lys Ser Ile Asp Asn Glu Trp Arg Lys Thr Gln Cys Met Pro Arg
            20                  25                  30

Glu Val Cys Ile Asp Val Gly Lys Glu Phe Gly Val Ala Thr Asn Thr
        35                  40                  45

Phe Phe Lys Pro Pro Cys Val Ser Val Tyr Arg Cys Gly Gly Cys Cys
    50                  55                  60

Asn Ser Glu Gly Leu Gln Cys Met Asn Thr Ser Thr Ser Tyr Leu Ser
65                  70                  75                  80

Lys Thr Leu Phe Glu Ile Thr Val Pro Leu Ser Gln Gly Pro Lys Pro
                85                  90                  95

Val Thr Ile Ser Phe Ala Asn His Thr Ser Cys Arg Cys Met Ser Lys
            100                 105                 110

Leu
```

<210> SEQ ID NO 19
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: 5' PCR oligonucleotide primer containing an Nde I site.

<400> SEQUENCE: 19
gcagcacata tgacagaaga gactataaaa                                    30

<210> SEQ ID NO 20
<211> LENGTH: 30
<212> TYPE: DNA
<213> ORGANISM: artificialsequence
<220> FEATURE:
<221> NAME/KEY: primer_bind
<222> LOCATION: (1)..(30)
<223> OTHER INFORMATION: 3' PCR oligonucleotide primer containing an Asp718 site.

<400> SEQUENCE: 20
gcagcaggta cctcacagtt tagacatgca                                    30

<210> SEQ ID NO 21
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: 5' PCR oligonucleotide primer containing an Asp 718I site.

<400> SEQUENCE: 21
gcagcaggta cctcaacgtc taataatgga                                    30

<210> SEQ ID NO 22
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: 5' PCR oligonucleotide primer containing an BamHI site.

<400> SEQUENCE: 22
gcagcaggat cccacagaag agactataaa                                           30

<210> SEQ ID NO 23
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: 3' PCR oligonucleotide primer containing an
      XbaI site.

<400> SEQUENCE: 23
gcagcatcta gatcacagtt tagacatgca                                           30

<210> SEQ ID NO 24
<211> LENGTH: 39
<212> TYPE: DNA
<213> ORGANISM: artificial sequence
<220> FEATURE:
<221> NAME/KEY: protein_bind
<222> LOCATION: (1)..(39)
<223> OTHER INFORMATION: 5' PCR oligonucleotide primer containing an
      BamHI site.

<400> SEQUENCE: 24
gcagcaggat cccacagaag agactataaa atttgctgc                                 39

<210> SEQ ID NO 25
<211> LENGTH: 36
<212> TYPE: DNA
<213> ORGANISM: artificial sequence
<220> FEATURE:
<221> NAME/KEY: primer_bind
<222> LOCATION: (1)..(36)
<223> OTHER INFORMATION: 3' PCR oligonucleotide primer containing an XbaI
      site.

<400> SEQUENCE: 25
gcagcatcta gatcaacgtc taataatgga atgaac                                    36

<210> SEQ ID NO 26
<211> LENGTH: 55
<212> TYPE: DNA
<213> ORGANISM: artificial sequence
<220> FEATURE:
<221> NAME/KEY: primer_bind
<222> LOCATION: (1)..(55)
<223> OTHER INFORMATION: 5' PCR oligonucleotide primer containing a
      Klenow-filled BamHI site

<400> SEQUENCE: 26
gatcgatcca tcatgcactc gctgggcttc ttctctgtgg cgtgttctct gctcg              55

<210> SEQ ID NO 27
<211> LENGTH: 39
<212> TYPE: DNA
<213> ORGANISM: artificial sequence
<220> FEATURE:
<221> NAME/KEY: primer_bind
<222> LOCATION: (1)..(39)
<223> OTHER INFORMATION: 3' PCR oligonucleotide primer containing a
      BamHI site.

<400> SEQUENCE: 27

-continued gcagggtacg gatcctagat tagctcattt gtggtcttt        39

<210> SEQ ID NO 28
<211> LENGTH: 39
<212> TYPE: DNA
<213> ORGANISM: artificial sequence
<220> FEATURE:
<221> NAME/KEY: primer_bind
<222> LOCATION: (1)..(39)
<223> OTHER INFORMATION: 5' PCR oligonucleotide primer.

<400> SEQUENCE: 28
gactggatcc gccaccatgc actcgctggg cttcttctc        39

<210> SEQ ID NO 29
<211> LENGTH: 35
<212> TYPE: DNA
<213> ORGANISM: artificial sequence
<220> FEATURE:
<221> NAME/KEY: primer_bind
<222> LOCATION: (1)..(35)
<223> OTHER INFORMATION: 3' PCR oligonucleotide primer.

<400> SEQUENCE: 29
gactggtacc ttatcacata aaatcttcct gagcc        35

<210> SEQ ID NO 30
<211> LENGTH: 39
<212> TYPE: DNA
<213> ORGANISM: artificial sequence
<220> FEATURE:
<221> NAME/KEY: primer_bind
<222> LOCATION: (1)..(39)
<223> OTHER INFORMATION: 5' PCR oligonucleotide primer.

<400> SEQUENCE: 30
gactggatcc gccaccatgc actcgctggg cttcttctc        39

<210> SEQ ID NO 31
<211> LENGTH: 34
<212> TYPE: DNA
<213> ORGANISM: artificial sequence
<220> FEATURE:
<221> NAME/KEY: primer_bind
<222> LOCATION: (1)..(34)
<223> OTHER INFORMATION: 3' PCR oligonucleotide primer.

<400> SEQUENCE: 31
gactggtacc ttatcagtct agttctttgt gggg        34

<210> SEQ ID NO 32
<211> LENGTH: 39
<212> TYPE: DNA
<213> ORGANISM: artificial sequence
<220> FEATURE:
<221> NAME/KEY: primer_bind
<222> LOCATION: (1)..(39)
<223> OTHER INFORMATION: 5' PCR oligonucleotide primer.

<400> SEQUENCE: 32
gactggatcc gccaccatgc actcgctggg cttcttctc        39

<210> SEQ ID NO 33
<211> LENGTH: 37
<212> TYPE: DNA
<213> ORGANISM: artificial sequence
<220> FEATURE:
<221> NAME/KEY: primer_bind

```
<222> LOCATION: (1)..(37)
<223> OTHER INFORMATION: 3' PCR oligonucleotide primer.

<400> SEQUENCE: 33
gactggtacc tcattactgt ggactttctg tacattc                              37

<210> SEQ ID NO 34
<211> LENGTH: 38
<212> TYPE: DNA
<213> ORGANISM: artificial sequence
<220> FEATURE:
<221> NAME/KEY: primer_bind
<222> LOCATION: (1)..(38)
<223> OTHER INFORMATION: 5' PCR oligonucleotide primer containing a
      BamHI site.

<400> SEQUENCE: 34
gcagcaggat ccacagaaga gactataaaa tttgctgc                             38

<210> SEQ ID NO 35
<211> LENGTH: 36
<212> TYPE: DNA
<213> ORGANISM: artificial sequence
<220> FEATURE:
<221> NAME/KEY: primer_bind
<222> LOCATION: (1)..(36)
<223> OTHER INFORMATION: 3' PCR oligonucleotide primer containing an
      XbaI site.

<400> SEQUENCE: 35
cgtcgttcta gatcacagtt tagacatgca tcggca                               36

<210> SEQ ID NO 36
<211> LENGTH: 5283
<212> TYPE: DNA
<213> ORGANISM: homo sapiens

<400> SEQUENCE: 36
aagcttgacc ttatgcgact ttcctacttg gcagtacatc tacgtattag tcatcgctat     60
taccatggtg atgcggtttt ggcagtacat caatgggcgt ggatagcggt ttgactcacg    120
gggatttcca gtctccaccc cactgacgt caatgggagt ttgttttggc accaaaatca     180
acgagacttt ccaaaatgtc gtaacaactc cgccccattg acgcaaatgg gcggtagggc    240
aacatgctta tgtaacggtg agttagcaac atgccttata aggagagaaa agcaccgtg     300 catgccgatt ggtgggagta aggtggtatg atcgtggtat gatcgtgcct tgttaggaag    360
gcaacagacg ggtctaacac ggattggacg aaccactgaa ttccgcattg cagagatatt    420
gtatttaagt gcccagctcg atacaataaa cgccatttga ccattcacca cattggtgtg    480
cacctgggtt gggatcgatc catcatgcac tcgctgggct tcttctctgt ggcgtgttct    540
ctgctcgccg ctgcgctgct cccgggtcct cgcgaggcgc ccgccgccgc cgccgccttc    600
gagtccggac tcgacctctc ggacgcggag cccgacgcgg gtgaggccac ggcttatgca    660
agcaaagatc tggaggagca gttacggtct gtgtccagtg tagatgaact catgactgta    720
ctctacccag aatattggaa aatgtacaag tgtcagctaa ggaaaggagg ctggcaacat    780
aacagagaac aggccaacct caactcaagg acagaagaga ctataaaatt tgctgcagca    840
cattataata cagagatctt gaaaagtatt gataatgagt ggagaaagac tcaatgcatg    900
ccacgggagg tgtgtataga tgtggggaag gagtttggag tcgcgacaaa caccttcttt    960
aaacctccat gtgtgtccgt ctacagatgt ggggttgct gcaatagtga ggggctgcag   1020
```

```
tgcatgaaca ccagcacgag ctacctcagc aagacgttat ttgaaattac agtgcctctc    1080
tctcaaggcc ccaaaccagt aacaatcagt tttgccaatc acacttcctg ccgatgcatg    1140
tctaaactgg atgtttacag acaagttcat tccattatta gacgttccct gccagcaaca    1200
ctaccacagt gtcaggcagc gaacaagacc tgccccacca attacatgtg gaataatcac    1260
atctgcagat gcctggctca ggaagatttt atgttttcct cggatgctgg agatgactca    1320
acagatggat tccatgacat ctgtggacca acaaggagc tggatgaaga gacctgtcag     1380
tgtgtctgca gagcgggct tcggcctgcc agctgtggac cccacaaaga actagacaga    1440
aactcatgcc agtgtgtctg taaaaacaaa ctcttcccca gccaatgtgg ggccaaccga    1500
gaatttgatg aaaacacatg ccagtgtgta tgtaaaagaa cctgccccag aaatcaaccc    1560
ctaaatcctg gaaatgtgc ctgtgaatgt acagaaagtc cacagaaatg cttgttaaaa     1620
ggaaagaagt tccaccacca acatgcagc tgttacagac ggccatgtac gaaccgccag     1680
aaggcttgtg agccaggatt tcatatagt gaagaagtgt gtcgttgtgt cccttcatat     1740
tggaaaagac cacaaatgag ctaatctagg atccgtaccc tgcccaggct tttgtcaaac    1800
agcacctttg tggttctcac ttggtggaag ctctctacct ggtgtgtggg gagcgtggat    1860
tcttctacac acccatgtcc cgccgcgaag tggaggaccc acaaggtaag ctctgctcct    1920
gaattctatc ccaagtgcta actaccctgt ttgtctttca cccttgagac cttgtaaatt    1980
gtgccctagg tgtggagggt ctcaggctaa ccagtggggg gcacatttct gtgggcagct    2040
agacatatgt aaacatggta gctgccagga aggagtgaga atccttcctt aagtctccta    2100
ggtggtgacg ggtggctagg ccccaggata ggtacctatt tggggacccc atagagcact    2160
gcactgactg agggatggta acaggatgtg taggttttgg aggcccatat gtccattcat    2220
gaccagtgac ttgtctcaca gccatgcaac ccttgcctcc tgtgctgact tagcagggga    2280
taaagtgaga gaaagcctgg gctaatcagg gggtcgctca gctcctccta actggattgt    2340
cctatgtgtc tttgcttctg tgctgctgat gctctgccct gtgctgacat gacctccctg    2400
gcagtggcac aactggagct gggtggaggc ccggggcag gtgaccttca gaccttggca     2460
ctggaggtgg cccggcagaa gcgcggcatc gtggatcagt gctgcaccag catctgctct    2520
ctctaccaac tggagaacta ctgcaactag gcccaccact accctgtcca cccctctgca    2580
atgaataaaa cctttgaaag agcactacaa gttgtgtgta catgcgtgca tgtgcatatg    2640
tggtgcgggg ggaacatgag tggggctggc tggagtggtc gcggcttaat ctatctggca    2700
gctgtctaga cgtaatcatg gtcatagctg tttcctgtgt gaaattgtta tccgctcaca    2760
attccacaca acatacgagc cggaagcata aagtgtaaag cctggggtgc ctaatgagtg    2820
agctaactca cattaattgc gttgcgctca ctgcccgctt ccagtcggg aaacctgtcg     2880 tgccagctgc attaatgaat cggccaacgc gcggggagag gcggtttgcg tattgggcgc    2940
tcttccgctt cctcgctcac tgactcgctg cgctcggtcg ttcggctgcg gcgagcggta    3000
tcagctcact caaaggcggt aatacggtta tccacagaat caggggataa cgcaggaaag    3060
aacatgtgag caaaaggcca gcaaaggcc aggaaccgta aaaaggccgc gttgctggcg     3120 ttttccata ggctccgccc ccctgacgag catcacaaaa atcgacgctc aagtcagagg     3180
tggcgaaacc cgacaggact ataaagatac caggcgtttc ccctggaag ctccctcgtg     3240 cgctctcctg ttccgaccct gccgcttacc ggatacctgt ccgcctttct cccttcggga    3300
agcgtggcgc tttctcatag ctcacgctgt aggtatctca gttcggtgta ggtcgttcgc    3360
tccaagctgg gctgtgtgca cgaaccccc gttcagcccg accgctgcgc cttatccggt     3420
```

```
aactatcgtc ttgagtccaa cccggtaaga cacgacttat cgccactggc agcagccact    3480
ggtaacagga ttagcagagc gaggtatgta ggcggtgcta cagagttctt gaagtggtgg    3540
cctaactacg gctacactag aagaacagta tttggtatct gcgctctgct gaagccagtt    3600
accttcggaa aaagagttgg tagctcttga tccggcaaac aaaccaccgc tggtagcggt    3660 ggttttttg tttgcaagca gcagattacg cgcagaaaaa aaggatctca agaagatcct    3720
ttgatctttt ctacggggtc tgacgctcag tggaacgaaa actcacgtta agggattttg    3780
gtcatgagat tatcgtcgac caaagcggcc atcgtgcctc cccactcctg cagttcgggg    3840
gcatggatgc gcggatagcc gctgctggtt tcctggatgc cgacggattt gcactgccgg    3900
tagaactccg cgaggtcgtc cagcctcagg cagcagctga accaactcgc gaggggatcg    3960 agcccgggt gggcgaagaa ctccagcatg agatccccgc gctggaggat catccagccg    4020
gcgtcccgga aaacgattcc gaagcccaac ctttcataga aggcggcggt ggaatcgaaa    4080
tctcgtgatg gcaggttggg cgtcgcttgg tcggtcattt cgaaccccag agtcccgctc    4140
agaagaactc gtcaagaagg cgatagaagg cgatgcgctg cgaatcggga gcggcgatac    4200
cgtaaagcac gaggaagcgg tcagcccatt cgccgccaag ctcttcagca atatcacggg    4260
tagccaacgc tatgtcctga tagcggtccg ccacacccag ccggccacag tcgatgaatc    4320
cagaaaagcg gccatttttcc accatgatat tcggcaagca ggcatcgcca tgggtcacga    4380
cgagatcctc gccgtcgggc atgcgcgcct tgagcctggc gaacagttcg gctggcgcga    4440
gcccctgatg ctcttcgtcc agatcatcct gatcgacaag accggcttcc atccgagtac    4500
gtgctcgctc gatgcgatgt ttcgcttggt ggtcgaatgg gcaggtagcc ggatcaagcg    4560
tatgcagccg ccgcattgca tcagccatga tggatacttt ctcggcagga gcaaggtgag    4620
atgacaggag atcctgcccc ggcacttcgc ccaatagcag ccagtccctt cccgcttcag    4680
tgacaacgtc gagcacagct gcgcaaggaa cgcccgtcgt ggccagccac gatagccgcg    4740
ctgcctcgtc ctgcagttca ttcagggcac cggacaggtc ggtcttgaca aaaagaaccg    4800
ggcgcccctg cgctgacagc cggaacacgg cggcatcaga gcagccgatt gtctgttgtg    4860
cccagtcata gccgaatagc ctctccaccc aagcggccgg agaacctgcg tgcaatccat    4920
cttgttcaat catgcgaaac gatcctcatc ctgtctcttg atcagatctt gatccctgc    4980 gccatcagat ccttggcggc aagaaagcca tccagtttac tttgcagggc ttcccaacct    5040
taccagaggg cgccccagct ggcaattccg gttcgcttgc tgtccataaa accgcccagt    5100
ctagctatcg ccatgtaagc ccactgcaag ctacctgctt tctctttgcg cttgcgtttt    5160
cccttgtcca gatagcccag tagctgacat tcatccgggg tcagcaccgt ttctgcggac    5220
tggctttcta cgtgttccgc ttcctttagc agcccttgcg ccctgagtgc ttgcggcagc    5280
gtg                                                                  5283
```